(12) United States Patent
Inoue et al.

(10) Patent No.: US 11,643,417 B2
(45) Date of Patent: May 9, 2023

(54) TETRAHYDROBENZOFURODIAZEPINONE COMPOUND AND PHARMACEUTICAL USE THEREOF

(71) Applicant: Japan Tobacco Inc., Tokyo (JP)

(72) Inventors: Masafumi Inoue, Takatsuki (JP); Yosuke Ogoshi, Takatsuki (JP); Takayuki Furukawa, Takatsuki (JP); Takuya Machida, Takatsuki (JP); Ikuo Mitani, Takatsuki (JP); Kazuhito Harada, Takatsuki (JP); Yuichi Nakagawa, Takatsuki (JP); Nobutaka Yamaoka, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 17/493,528

(22) Filed: Oct. 4, 2021

(65) Prior Publication Data

US 2022/0162220 A1    May 26, 2022

(30) Foreign Application Priority Data

Oct. 5, 2020 (JP) .............................. JP2020-168596

(51) Int. Cl.
| | | |
|---|---|---|
| *C07D 491/048* | (2006.01) | |
| *C07D 491/107* | (2006.01) | |
| *C07D 519/00* | (2006.01) | |
| *A61K 31/551* | (2006.01) | |
| *A61P 9/12* | (2006.01) | |
| *A61P 11/00* | (2006.01) | |
| *A61P 17/06* | (2006.01) | |
| *A61P 35/00* | (2006.01) | |
| *A61P 43/00* | (2006.01) | |

(52) U.S. Cl.
CPC ................. *C07D 491/048* (2013.01)

(58) Field of Classification Search
CPC ............ C07D 491/048; C07D 491/107; C07D 519/00; A61K 31/551; A61P 9/12; A61P 11/00; A61P 17/06; A61P 35/00; A61P 43/00
See application file for complete search history.

(56) References Cited

U.S. PATENT DOCUMENTS

| | | |
|---|---|---|
| 2004/0116410 A1 | 6/2004 | Cho et al. |
| 2005/0250765 A1 | 11/2005 | Cho et al. |
| 2009/0247559 A1 | 10/2009 | Brown et al. |

FOREIGN PATENT DOCUMENTS

| | | |
|---|---|---|
| WO | WO2002014324 | 2/2002 |
| WO | WO2009086264 | 7/2009 |

OTHER PUBLICATIONS

Li et al., "More than just a GPCR ligand: A structure-based discovery of thioridazine derivatives as Pim-1 kinase inhibitors", MedChemComm, 2014, 5(4):507-511.
PCT International Search Report in International Appln. No. PCT/JP2021/036553, dated Nov. 2, 2021, 3 pages.
Tsuhako et al., "The design, synthesis and biological evaluation of PIM kinase inhibitors" Bioorganic & Medicinal Chemistry Letters, 2012, 22(11):3732-3738.

*Primary Examiner* — Bruck Kifle
(74) *Attorney, Agent, or Firm* — Fish & Richardson P.C.

(57) ABSTRACT

The present invention provides a compound having a Pim-1 inhibitory activity.
The present invention provides a compound of Formula [I] or a pharmaceutically acceptable salt thereof, a pharmaceutical composition containing the same, and a pharmaceutical use thereof, and the like.

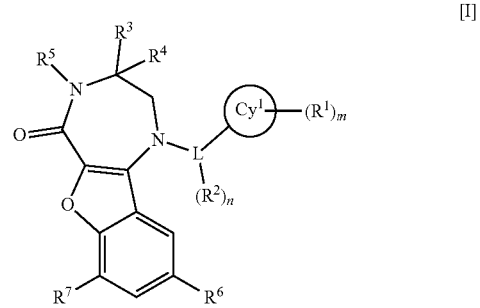

wherein each symbol is as defined in the description.

40 Claims, No Drawings

TETRAHYDROBENZOFURODIAZEPINONE COMPOUND AND PHARMACEUTICAL USE THEREOF

CROSS REFERENCE TO RELATED APPLICATIONS

This application claims the benefit of Japanese Application No. 2020-168596, filed on Oct. 5, 2020. The disclosure of the prior application is incorporated herein by reference.

TECHNICAL FIELD

The present invention relates to a tetrahydrobenzofurodiazepinone compound having a Pim-1 inhibitory activity or a pharmaceutically acceptable salt thereof, a pharmaceutical composition containing the same, and a pharmaceutical use thereof.

BACKGROUND ART

Pim-1 (Proviral Integration site for Moloney murine leukemia virus-1) is one of Pim family belonging to proto-oncogene serine/threonine kinase. Pim-1 exists downstream of receptors of cytokine Interleukin (IL)-2, 3, 5, 6, 7, 12, 15, 22, a hematopoietic stimulating factor GM-CFS (Granulocyte Macrophage colony-stimulating Factor), growth-derived factors VEGF (Vascular Endothelial Growth Factor) and PDGF (Platelet-Derived Growth Factor), and the like. When a ligand binds to these receptors, Pim-1 expression is induced via PI3K-AKT, JAK/STAT and NF-kB signals, and the downstream signal is constitutively activated. It is known that Pim-1 suppresses apoptosis through phosphorylations of BAD (Bcl-2 Associated Death promotor) and ASK1 (Apoptosis signal-regulating kinase 1), and promotes cell proliferation through phosphorylations of p21, p27, cdc25 and c-Myc (Non-Patent Documents 1 and 2). Therefore, Pim-1 inhibitors can be expected to be effective against diseases associated with apoptosis and cell proliferation.

The uses of the Pim-1 inhibitor will be described below.
(1) Pulmonary Arterial Hypertension (PAH)

It has been reported that, in an observational study, Pim-1 expression in plasma was increased in PAH patients as compared with healthy subjects, and that the expression level correlated with the 6-minute walking distance and pulmonary vascular resistance, which are indicators of pathological conditions (Non-Patent Document 3). Furthermore, it has also been reported that increased expression of Pim-1 was observed in pulmonary artery smooth muscle cells (PASMC) isolated from PAH patients, and cell proliferation, which have been increased as compared with PASMC derived from healthy subjects, was suppressed by knockdown of Pim-1. Moreover, it has also been reported that, in a non-clinical study using a rat PAH model, knockdown of Pim-1 suppressed increase in pulmonary arterial pressure and medial wall thickening in pulmonary arteries which are characteristic pathologies in PAH (Non-Patent Document 4). From these findings, Pim-1 inhibitors are expected to improve the pathological condition of PAH by suppressing medial wall thickening through suppression of proliferation of pulmonary artery smooth muscle cells.
(2) Cancer In clinical studies, cancers for which increased Pim-1 expression levels are reported include hematological cancers (acute lymphocytic leukemia, acute myeloid leukemia, diffuse large B-cell lymphoma, multiple myeloma) (Non-Patent Document 5), colon cancer (Non-Patent Document 6), pancreatic cancer (Non-Patent Document 7), prostate cancer (Non-Patent Document 8), bladder cancer (Non-Patent Document 9), osteosarcoma (Non-Patent Document 10), breast cancer (Non-Patent Document 11), and the like. It has been reported that, among them, acute myeloid leukemia, colon cancer, pancreatic cancer, osteosarcoma and breast cancer have a correlation between the expression level of Pim-1 and the prognosis of life, and the cell proliferation is suppressed by knocking down Pim-1 in the cell line (Non-Patent Documents 6, 12, 7, 10, 11, 14). Therefore, the Pim-1 inhibitor is particularly expected to show a therapeutic effect on the above-mentioned cancers.

It has also been reported that the Pim-1 inhibitor SMI-4a exhibits an growth inhibitory and apoptosis-inducing effects on cells derived from chronic myelogenous leukemia (Non-Patent Document 15), and the pan-Pim-1 inhibitor INCB053914 exhibits growth inhibitory effects on various blood cancer cells such as acute myeloid leukemia, multiple myeloma, diffuse large B-cell lymphoma and myeloproliferative neoplasm, and a tumor growth inhibitory effect in a mouse cancer-bearing model (Non-Patent Documents 16 and 17). Therefore, the Pim-1 inhibitor is also expected to show a therapeutic effect on the above-mentioned cancers.
(3) Psoriasis It is known that in psoriasis, inflammatory cells infiltrate the epidermis and dermis with remodeling of dermal blood vessels, which causes inflammation. Increased expression of Pim-1 is observed in the dermal blood vessels of human psoriasis patients, and Pim-1 is considered to be involved in their remodeling. It has been reported that, in non-clinical studies, epidermal thickness and inflammatory cell infiltration observed in IL-22-induced psoriasis-like skin inflammation model animals are suppressed by knockdown of Pim-1 (Non-Patent Document 13). From the above findings, the Pim-1 inhibitor is expected to show a therapeutic effect on psoriasis through suppression of remodeling of dermal blood vessels.
(4) Systemic Lupus Erythematosus (SLE)

Lupus nephritis (LN) is glomerulonephritis caused by SLE. Increased expression of Pim-1 is observed in Peripheral Blood Mononuclear Cells (PBMC) of human SLE patients and the kidneys of LN patients. In a study using human podocytes, knockdown of Pim-1 was found to reduce inflammation-related signals NFATc1 and IL-1β. In a non-clinical study using mouse LN model animals, the Pim-1 inhibitor SMI-4a was found to reduce glomerular damage, reduce urinary albumin/creatinine ratio, and improve mortality (Non-Patent Document 18). From the above findings, the Pim-1 inhibitor is expected to show a therapeutic effect on LN with SLE through suppression of inflammation.

DOCUMENT LIST

Non-Patent Document

[Non-Patent Document 1] Laurent Brault, Christelle Gasser, Franz Bracher, Kilian Huber, Stefan Knapp, and Juerg Schwaller1: PIM serine/threonine kinases in the pathogenesis and therapy of hematologic malignancies and solid cancers. Haematologica. 2010 June; 95(6):1004-15.

[Non-Patent Document 2] Patrizia Mondello, Salvatore Cuzzocrea and Michael Mian: Pim kinases in hematological malignancies: where are we now and where are we going? J Hematol Oncol. 2014 Dec. 10; 7:95.

[Non-Patent Document 3] Se'bastien Renard, Roxane Paulin, Sandra Breuils-Bonnet, Serge Simard, Philippe Pibarot, Se'bastien Bonnet, and Steeve Provencher: Pim- 1: A new biomarker in pulmonary arterial hypertension. Pulm Circ. 2013 January; 3(1):74-81.

[Non-Patent Document 4] Roxane Paulin, MSc; Audrey Courboulin, MSc; Jolyane Meloche, BSc; Vincent Mainguy, MSc; Eric Dumas de la Roque, MD; Nehme' Saksouk, PhD; Jacques Coˆte', PhD; Steeve Provencher, MD; Mark A. Sussman, PhD; Se'bastien Bonnet, PhD: Signal Transducers and Activators of Transcription-3/Pim1 Axis Plays a Critical Role in the Pathogenesis of Human Pulmonary Arterial Hypertension. Circulation. 2011 Mar. 22; 123(11):1205-15.

[Non-Patent Document 5] Pablo D. Garcia, John L. Langowski, Yingyun Wang, Min Chen, Joseph Castillo, Christie Fanton, Marjorie Ison, Tatiana Zavorotinskaya, Yumin Dai, Jing Lu, Xiao-Hong Niu, Stephen Basham, Julie Chan, Jianjun Yu, Michael Doyle, Paul Feucht, Robert Warne, Jamie Narberes, Tiffany Tsang, Christine Fritsch, Audrey Kauffmann, Estelle Pfister, Peter Drueckes, Joerg Trappe, Christopher Wilson, Wooseok Han, Jiong Lan, Gisele Nishiguchi, Mika Lindvall, Cornelia Bellamacina, J. Alex Aycinena, Richard Zang, Jocelyn Holash and Matthew T. Burger: Pan-PIM Kinase Inhibition Provides a Novel Therapy for Treating Hematologic Cancers. Clin Cancer Res. 2014 Apr. 1; 20(7): 1834-45.

[Non-Patent Document 6] Yong-hai Peng, Jian-jun Li, Fangwei Xie, Jian-fang Chen, Ying-hao Yu, Xue-nong Ouyang, Houjie Liang: Expression of pim-1 in Tumors, Tumor Stroma and Tumor-Adjacent Mucosa Co-Determines the Prognosis of Colon Cancer Patients. PLoS One. 2013 Oct. 7; 8(10):e76693.

[Non-Patent Document 7] Jianwei Xu, Guangbing Xiong, Zhe Cao, Hua Huang, Tianxiao Wang, Lei You, Li Zhou, Lianfang Zheng, Ya Hu, Taiping Zhang and Yupei Zhao: PIM-1 contributes to the malignancy of pancreatic cancer and displays diagnostic and prognostic value. J Exp Clin Cancer Res. 2016 Sep. 5; 35(1):133.

[Non-Patent Document 8] T L Cibull, T D Jones, L Li, J N Eble, L Ann Baldridge, S R Malott, Y Luo, L Cheng: Overexpression of Pim-1 during progression of prostatic adenocarcinoma. J Clin Pathol. 2006 March; 59(3):285-8

[Non-Patent Document 9] Shengjie Guo, Xiaopeng Mao, Junxing Chen, Bin Huang, Chu Jin, Zhenbo Xu, Shaopeng Qiu: Overexpression of Pim-1 in bladder cancer. J Exp Clin Cancer Res. 2010 Dec. 11; 29:161.

[Non-Patent Document 10] Yunfei Liao Yong Feng Jacson Shen Yan Gao Gregory Cote Edwin Choy David Harmon Henry Mankin Francis Hornicek Zhenfeng Duan: Clinical and biological significance of PIM1 kinase in osteosarcoma. J Orthop Res. 2016 July; 34(7):1185-94.

[Non-Patent Document 11] Horiuchi D, Camarda R, Zhou A Y, Yau C, Momcilovic O, Balakrishnan S, Corella A N, Eyob H, Kessenbrock K, Lawson D A, Marsh L A, Anderton B N, Rohrberg J, Kunder R, Bazarov A V, Yaswen P, McManus M T, Rugo H S, Werb Z, Goga A: PIM1 kinase inhibition as a targeted therapy against triple-negative breast tumors with elevated MYC expression. Nat Med. 2016 November; 22(11):1321-1329.

[Non-Patent Document 12] Ulrike Weirauch, Nadine Beckmann, Maren Thomas, Arnold Grünweller, Kilian Huber, Franz Bracher, Roland K. Hartmann and Achim Aigner: Functional Role and Therapeutic Potential of the Pim-1 Kinase in Colon Carcinoma. Neoplasia. 2013 July; 15(7): 783-94.

[Non-Patent Document 13] Perera G K, Ainali C, Semenova E, Hundhausen C, Barinaga G, Kassen D, Williams A E, Mirza M M, Balazs M, Wang X, Rodriguez R S, Alendar A, Barker J, Tsoka S, Ouyang W, Nestle F O: Integrative biology approach identifies cytokine targeting strategies for psoriasis. Sci Transl Med. 2014 Feb. 12; 6(223): 223ra22.

[Non-Patent Document 14] Hui Cheng, Chongmei Huang, Xiaoqiau Xu, Xiaoxia Hu, Shenglan Gong, Gusheng Tang, Xianimn Song, Weiping Zhang, Jianmin Wang, Li Chen and Jianmin Yang: PIM-1 mRNA expression is a potential prognostic biomarker in acute myeloid leukemia. J Transl Med. 2017; 15:179.

[Non-Patent Document 15] Rui-Fang Fan, Ying Lu, Zhi-Gang Fang, Xiao-Yan Guo, Yu-Xin Chen, Yi-Chuan Xu, Ya-Mei Lei, Ke-Fang Liu, Dong-Jun Lin, Ling-Ling Liu, Xiang-Fu Liu: PIM-1 kinase inhibitor SMI-4a exerts antitumor effects in chronic myeloid leukemia cells by enhancing the activity of glycogen synthase kinase 3β. Mol Med Rep. 2017 October; 16(4):4603-4612.

[Non-Patent Document 16] Holly Koblish, Yun-long Li, Niu Shin, Lesile Hall, Qian Wang, Kathy Wang, Maryanne Coveington, Cindy Marando, Kevin Bowman, Jason Boer, Krista Burke, Richard Wynn, Alex Margulis, Gary W. Reuther, Que T. Lambert, Varerie Dostalik Roman, Ke Zhang, Hao Feng, Chu-Biao Xue, Sharon Diamond, Greg Hollis, Swamy Yeleswaram, Wenqing Yao, Reid Huber, Kris Vaddi, Peggy Scherle: Preclinical characterization of INCB053914, a novel pan-PIM Kinase inhibitor, alone and in combination with anticancer agents, in models of hematologic malignancies. PLoS One. 2018 Jun. 21; 13(6):e0199108.

[Non-Patent Document 17] Lucia Mazzacurati, Robert J. Collins, Garima Pandey, Que T. Lambert-Showers, Narmin E. Amin, Ling Zhang, Matthew C. Stubbs, Pearlie K. Epling-Burnette, Holly K. Koblish, Gary W. Reuther: The pan-PIM inhibitor INCB053914 displays potent synergy in combination with ruxolitinib in models of MPN. Blood Adv. 2019 Nov. 26; 3(22):3503-3514.

[Non-Patent Document 18] Rong Fu M D, PhD, Yong Xia MD, PhD, Meirong Li BS, Renxiang Mao MD, Chaohuan Guo MD, Mianjing Zhou MD, Hechang Tan MD, PhD, Meiling Liu BS, Shuang Wang MD, PhD, Niansheng Yang MD, PhD, Jijun Zhao MD, PhD: Pim-1 as a Therapeutic Target in Lupus Nephritis. Arthritis Rheumatol. 2019 August; 71(8):1308-1318.

SUMMARY OF THE INVENTION

The present invention provides a tetrahydrobenzofurodiazepinone compound having a Pim-1 inhibitory activity or a pharmaceutically acceptable salt thereof, a pharmaceutical composition containing the same, a pharmaceutical use thereof, and the like. Accordingly, the present invention encompasses the embodiments exemplified below.

[Item 1]

A compound of Formula [I], or a pharmaceutically acceptable salt thereof:

[I]

wherein
$Cy^1$ is
(1) $C_{3-7}$ cycloalkyl, (2) 4 to 7-membered heterocycloalkyl containing one or two heteroatoms independently selected from the group consisting of oxygen and sulfur atoms (the sulfur atom may be oxidized), as a ring constituting atom besides carbon atom(s),
(3) $C_{5-8}$ bridged cycloalkyl,
(4) 7 to 9-membered bridged heterocycloalkyl containing one oxygen atom as a ring constituting atom besides carbon atom(s),
(5) $C_{7-11}$ spirocycloalkyl, or
(6) 7 to 11-membered spiroheterocycloalkyl containing one to three oxygen atoms as a ring constituting atom besides carbon atom(s);
$R^1$ in the number of m are each independently
(1) halogen,
(2) hydroxy,
(3) $C_{1-6}$ alkyl wherein the alkyl is optionally substituted by
  (a) hydroxy,
  (b) $C_{1-4}$ alkoxy,
  (c) cyano,
  (d) $OCOR^{11}$ wherein $R^{11}$ is phenyl, or
  (e) $SO_2R^{12}$ wherein $R^{12}$ is $C_{1-4}$ alkyl,
(4) $C_{1-4}$ haloalkyl wherein the haloalkyl is optionally substituted by hydroxy,
(5) $C_{1-4}$ alkoxy wherein the alkoxy is optionally substituted by 1 to 3 halogen,
(6) $COR^{13}$ wherein $R^3$ is
  (a) hydroxy, or
  (b) $NR^{14}R^{15}$ wherein $R^{14}$ and $R^{15}$ are each independently hydrogen or $C_{1-4}$ alkyl,
(7) cyano,
(8) $SO_2R^{16}$ wherein $R^{16}$ is $C_{1-4}$ alkyl,
(9) $C_{3-4}$ cycloalkyl wherein the cycloalkyl is optionally substituted by hydroxy, or
(10) triazolyl, or
two R1 bonded to the same carbon atom are taken together to form oxo;
$R^2$ in the number of n are each independently
(1) halogen, or
(2) $C_{1-4}$ alkoxy, or
two $R^2$ bonded to the same carbon atom are taken together to form $C_{3-4}$ cycloalkane with the carbon atom to which they are bonded;
$R^3$ and $R^4$ are each independently
(1) hydrogen, or
(2) $C_{1-4}$ alkyl, or
$R^3$ and $R^4$ are taken together to form $C_{3-4}$ cycloalkane with the carbon atom to which they are bonded;
$R^5$ is hydrogen or $C_{1-4}$ alkyl;
$R^6$ is $C_{1-4}$ haloalkyl;
$R^7$ is hydrogen or halogen;
L is linear $C_{1-4}$ alkylene;
m is 0, 1, 2, 3 or 4; and
n is 0, 1, 2 or 3.
[Item 2]
The compound according to Item 1 or a pharmaceutically acceptable salt thereof, wherein $R^5$ is hydrogen.
[Item 3]
The compound according to Item 1 or 2 or a pharmaceutically acceptable salt thereof, wherein L is ethylene or trimethylene.
[Item 4]
The compound according to any one of Items 1 to 3 or a pharmaceutically acceptable salt thereof, wherein $R^7$ is hydrogen.

[Item 5]
The compound according to any one of Items 1 to 4 or a pharmaceutically acceptable salt thereof, wherein $R^2$ in the number of n are each independently halogen, or two $R^2$ bonded to the same carbon atom are taken together to form $C_{3-4}$ cycloalkane with the carbon atom to which they are bonded.
[Item 6]
The compound according to Item 1 or a pharmaceutically acceptable salt thereof, which is represented by Formula [III]:

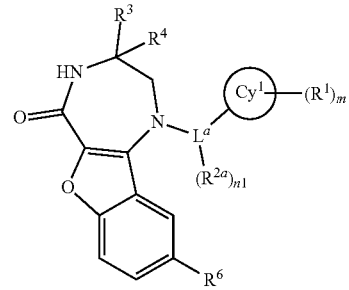

[III]

wherein
$R^{2a}$ in the number of n1 are each independently halogen;
$L^a$ is ethylene or trimethylene;
n1 is 0, 1 or 2; and
$Cy^1$, $R^1$, $R^3$, $R^4$, $R^6$ and m are as defined in Item 1.
[Item 7]
The compound according to any one of Items 1 to 6 or a pharmaceutically acceptable salt thereof, wherein $Cy^1$ is
(1) $C_{3-7}$ cycloalkyl,
(2) 4 to 7-membered heterocycloalkyl containing one or two heteroatoms independently selected from the group consisting of oxygen and sulfur atoms (the sulfur atom may be oxidized), as a ring constituting atom besides carbon atom(s),
(3) $C_{7-11}$ spirocycloalkyl, or
(4) 7 to 11-membered spiroheterocycloalkyl containing one to three oxygen atoms as a ring constituting atom besides carbon atom(s).
[Item 8]
The compound according to any one of Items 1 to 7 or a pharmaceutically acceptable salt thereof, wherein $R^6$ is
(1) monofluoromethyl,
(2) difluoromethyl, or
(3) trifluoromethyl.
[Item 9]
The compound according to any one of Items 1 to 8 or a pharmaceutically acceptable salt thereof, wherein $R^3$ and $R^4$ are each independently
(1) hydrogen, or
(2) methyl, or
$R^3$ and $R^4$ are taken together to form cyclopropane with the carbon atom to which they are bonded.
[Item 10]
The compound according to any one of Items 1 to 9 or a pharmaceutically acceptable salt thereof, wherein $R^1$ in the number of m are each independently
(1) halogen,
(2) hydroxy,
(3) $C_{1-6}$ alkyl wherein the alkyl is optionally substituted by
  (a) hydroxy, (b) $C_{1-4}$ alkoxy,
(c) cyano, or
(d) $SO_2R^{12}$ wherein $R^{12}$ is $C_{1-4}$ alkyl,
(4) $C_{1-4}$ haloalkyl wherein the haloalkyl is optionally substituted by hydroxy,
(5) $C_{1-4}$ alkoxy wherein the alkoxy is optionally substituted by 1 to 3 halogen,
(6) $COR^{13}$ wherein $R^{13}$ is
 (a) hydroxy, or
 (b) $NR^{14}R^{15}$ wherein $R^{14}$ and $R^{15}$ are each independently hydrogen or $C_{1-4}$ alkyl,
(7) cyano,
(8) $SO_2R^{16}$ wherein $R^{16}$ is $C_{1-4}$ alkyl, or
(9) $C_{3-4}$ cycloalkyl wherein the cycloalkyl is optionally substituted by hydroxy, or
two $R^1$ bonded to the same carbon atom are taken together to form oxo.

[Item 11]

A compound selected from compounds of the following formulas:

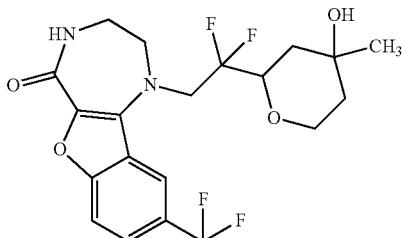

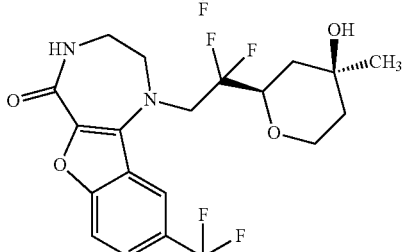

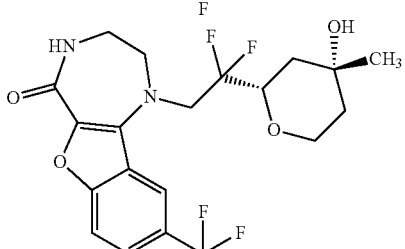

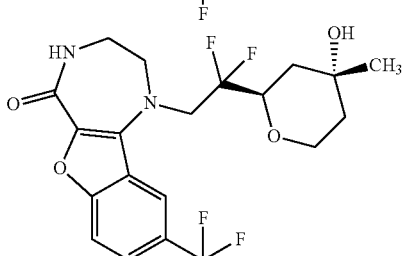

-continued

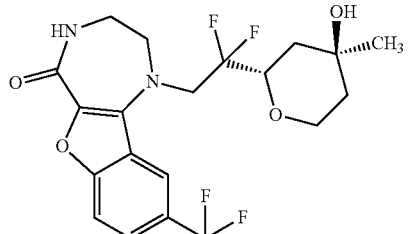

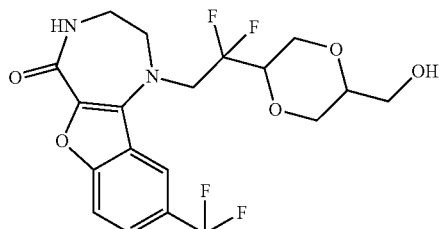

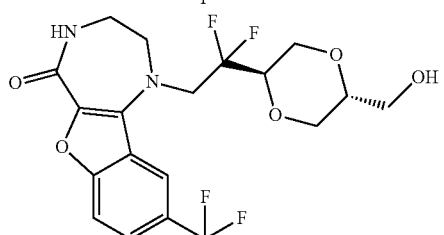

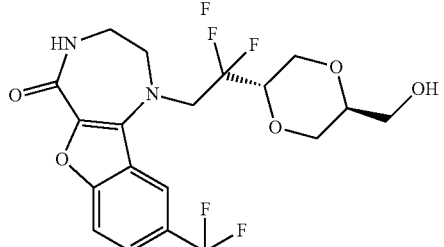

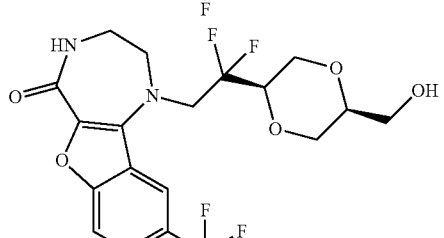

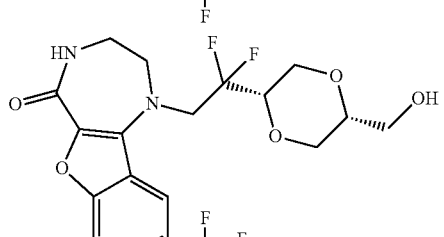

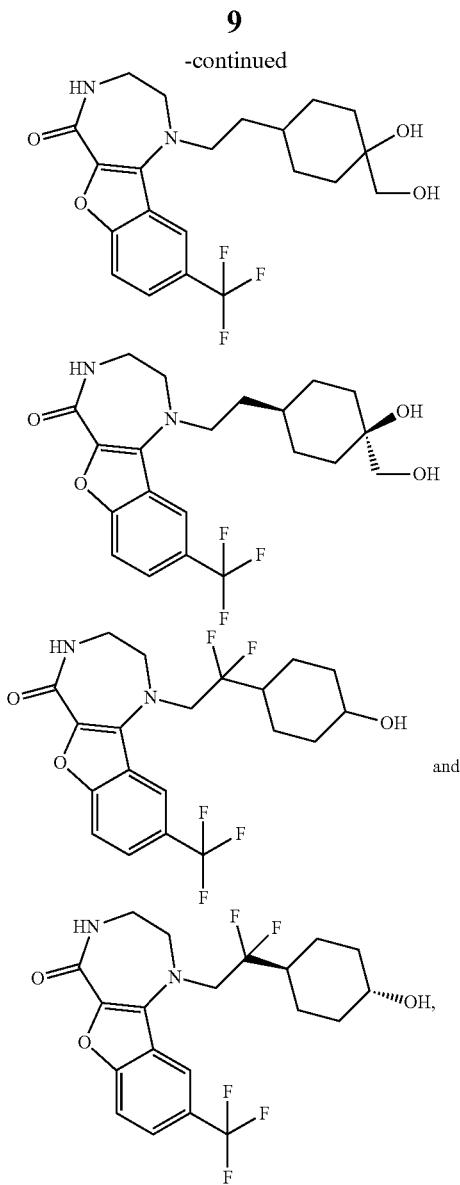

or a pharmaceutically acceptable salt thereof.

[Item 12]
A pharmaceutical composition comprising the compound according to any one of Items 1 to 11 or a pharmaceutically acceptable salt thereof, and a pharmaceutically acceptable carrier.

[Item 13]
A Pim-1 inhibitor comprising the compound according to any one of Items 1 to 11 or a pharmaceutically acceptable salt thereof.

[Item 14]
An agent for the treatment or prophylaxis of a disease selected from the group consisting of pulmonary arterial hypertension, cancer, psoriasis and systemic lupus erythematosus, which comprises the compound according to any one of Items 1 to 11 or a pharmaceutically acceptable salt thereof.

[Item 15]
A method for inhibiting Pim-1 in a mammal, which comprises administering a therapeutically effective amount of the compound according to any one of Items 1 to 11 or a pharmaceutically acceptable salt thereof to the mammal.

[Item 16]
A method for treating or preventing a disease selected from the group consisting of pulmonary arterial hypertension, cancer, psoriasis and systemic lupus erythematosus in a mammal, which comprises administering a therapeutically effective amount of the compound according to any one of Items 1 to 11 or a pharmaceutically acceptable salt thereof to the mammal.

[Item 17]
Use of the compound according to any one of Items 1 to 11 or a pharmaceutically acceptable salt thereof for the manufacture of a Pim-1 inhibitor.

[Item 18]
Use of the compound according to any one of Items 1 to 11 or a pharmaceutically acceptable salt thereof for the manufacture of an agent for the treatment or prophylaxis of a disease selected from the group consisting of pulmonary arterial hypertension, cancer, psoriasis and systemic lupus erythematosus.

[Item 19]
The compound according to any one of Items 1 to 11 or a pharmaceutically acceptable salt thereof, for use in the inhibition of Pim-1.

[Item 20]
The compound according to any one of Items 1 to 11 or a pharmaceutically acceptable salt thereof, for use in the treatment or prophylaxis of a disease selected from the group consisting of pulmonary arterial hypertension, cancer, psoriasis and systemic lupus erythematosus.

Embodiments of the Invention

The definitions of the terms used herein are as follows.
Examples of the "halogen" include fluorine, chlorine, bromine and iodine. The preferred "halogen" is fluorine.

The "$C_{1-6}$ alkyl" means a linear or branched saturated hydrocarbon group having 1 to 6 carbon atoms. Examples of the "$C_{1-6}$ alkyl" include methyl, ethyl, n-propyl, isopropyl, n-butyl, isobutyl, sec-butyl, tert-butyl, n-pentyl, isopentyl, neo-pentyl, 1,1-dimethylpropyl, 1-ethylpropyl, n-hexyl, isohexyl, 1,1-dimethylbutyl, 2,2-dimethylbutyl, 3,3-dimethylbutyl and 2-ethylbutyl. The preferred "$C_{1-6}$ alkyl" are methyl, ethyl and isopropyl.

The "$C_{1-4}$ alkyl" means a linear or branched saturated hydrocarbon group having 1 to 4 carbon atoms. Examples of the "$C_{1-4}$ alkyl" include methyl, ethyl, n-propyl, isopropyl, n-butyl, isobutyl, sec-butyl and tert-butyl. The preferred "$C_{1-4}$ alkyl" are methyl, ethyl and isopropyl.

The "linear $C_{1-4}$ alkylene" means a bivalent group derived from a linear saturated hydrocarbon having 1 to 4 carbon atoms. Examples of the "linear $C_{1-4}$ alkylene" include methylene, ethylene, trimethylene and tetramethylene. The preferred "linear $C_{1-4}$ alkylene" are methylene, ethylene and trimethylene.

The "$C_{1-4}$ haloalkyl" means the above-mentioned "$C_{1-4}$ alkyl" substituted by 1 to 5 halogen independently selected from the group consisting of the above-mentioned "halogen". Examples of the "$C_{1-4}$ haloalkyl" include monofluoromethyl, monochloromethyl, difluoromethyl, trifluoromethyl, 2-fluoroethyl, 1,1-difluoroethyl, 2,2-difluoroethyl, 2,2,2-trifluoroethyl, pentafluoroethyl, 3-fluoropropyl, 3-chloropropyl, 1,1-difluoropropyl, 3,3,3-trifluoropropyl and 4-fluorobutyl. The preferred "$C_{1-4}$ haloalkyl" are monofluoromethyl, difluoromethyl, trifluoromethyl and 1,1-difluoroethyl.

The "$C_{3-7}$ cycloalkyl" means a 3 to 7-membered monocyclic saturated hydrocarbon group. Examples of the "$C_{3-7}$ cycloalkyl" include cyclopropyl, cyclobutyl, cyclopentyl, cyclohexyl and cycloheptyl. The preferred "$C_{3-7}$ cycloalkyl" are cyclopropyl, cyclobutyl and cyclohexyl.

The "$C_{3-4}$ cycloalkyl" means a 3 to 4-membered monocyclic saturated hydrocarbon group. Examples of the "$C_{3-4}$ cycloalkyl" include cyclopropyl and cyclobutyl. The preferred "$C_{3-4}$ cycloalkyl" are cyclopropyl and cyclobutyl.

The "$C_{3-4}$ cycloalkane" means a 3 to 4-membered monocyclic saturated hydrocarbon. Examples of the "$C_{3-4}$ cycloalkane" include cyclopropane and cyclobutane. The preferred "$C_{2-4}$ cycloalkane" is cyclopropane.

The "$C_{5-8}$ bridged cycloalkyl" means a 5 to 8-membered bridged type saturated cyclic hydrocarbon group. Examples of the "$C_{5-8}$ bridged cycloalkyl" include bicyclo[1.1.1]pentyl, bicyclo[2.2.1]heptyl and bicyclo[2.2.2]octyl. The preferred "$C_{5-8}$ bridged cycloalkyl" is bicyclo[1.1.1]pentyl.

The "$C_{7-11}$ spirocycloalkyl" means a 7 to 11-membered spiro type saturated cyclic hydrocarbon group. Examples of the "$C_{7-11}$ spirocycloalkyl" include spiro[3.3]heptyl, spiro[4.5]decyl and spiro[5.5]undecyl. The preferred "$C_{7-11}$ spirocycloalkyl" is spiro[3.3]heptyl.

The "$C_{1-4}$ alkoxy" means a group wherein the above-mentioned "$C_{1-4}$ alkyl" is bonded to an oxygen atom. Examples of the "$C_{1-4}$ alkoxy" include methoxy, ethoxy, propoxy, isopropoxy, butoxy, isobutoxy, sec-butoxy and tert-butoxy. The preferred "$C_{1-4}$ alkoxy" is methoxy.

The "4 to 7-membered heterocycloalkyl containing one or two heteroatoms independently selected from the group consisting of oxygen and sulfur atoms (the sulfur atom may be oxidized), as a ring constituting atom besides carbon atom(s)" means a 4 to 7-membered monocyclic saturated heterocyclic group which contains one or two heteroatoms independently selected from the group consisting of oxygen and sulfur atoms as a ring constituting atom besides carbon atom(s). The sulfur atom may be oxidized. Examples of the "4 to 7-membered heterocycloalkyl containing one or two heteroatoms independently selected from the group consisting of oxygen and sulfur atoms (the sulfur atom may be oxidized), as a ring constituting atom besides carbon atom(s)" include oxetanyl, tetrahydrofuryl, tetrahydrothienyl, tetrahydropyranyl, 1,3-dioxanyl, 1,4-dioxanyl, tetrahydrothiopyranyl, 1,1-dioxidotetrahydrothiopyranyl and oxepanyl. The preferred "4 to 7-membered heterocycloalkyl containing one or two heteroatoms independently selected from the group consisting of oxygen and sulfur atoms (the sulfur atom may be oxidized), as a ring constituting atom besides carbon atom(s)" are oxetanyl, tetrahydrofuryl, tetrahydropyranyl, 1,3-dioxanyl, 1,4-dioxanyl, 1,1-dioxidotetrahydrothiopyranyl and oxepanyl.

The "7 to 9-membered bridged heterocycloalkyl containing one oxygen atom as a ring constituting atom besides carbon atom(s)" means a 7 to 9-membered bridged type saturated heterocyclic group which contains one oxygen atom as a ring constituting atom besides carbon atom(s). Examples of the "7 to 9-membered bridged heterocycloalkyl containing one oxygen atom as a ring constituting atom besides carbon atom(s)" include 7-oxabicyclo[2.2.1]heptyl, 8-oxabicyclo[3.2.1]octyl and 2-oxabicyclo[3.2.2]nonyl. The preferred "7 to 9-membered bridged heterocycloalkyl containing one oxygen atom as a ring constituting atom besides carbon atom(s)" is 8-oxabicyclo[3.2.1]octyl.

The "7 to 11-membered spiroheterocycloalkyl containing one to three oxygen atoms as a ring constituting atom besides carbon atom(s)" means a 7 to 11-membered spiro type saturated heterocyclic group which contains one to three oxygen atoms as a ring constituting atom besides carbon atom(s). Examples of the "7 to 11-membered spiroheterocycloalkyl containing one to three oxygen atoms as a ring constituting atom besides carbon atom(s)" include 2-oxaspiro[3.3]heptyl, 2,6-dioxaspiro[3.4]octyl, 2,7-dioxaspiro[3.5]nonyl, 1,3-dioxaspiro[4.5]decyl, 1,4-dioxaspiro[4.5]decyl, 1,4,8-trioxaspiro[4.5]decyl and 3-oxaspiro[5.5]undecyl. The preferred "7 to 11-membered spiroheterocycloalkyl containing one to three oxygen atoms as a ring constituting atom besides carbon atom(s)" are 2-oxaspiro[3.3]heptyl, 2,7-dioxaspiro[3.5]nonyl, 1,3-dioxaspiro[4.5]decyl, 1,4-dioxaspiro[4.5]decyl and 1,4,8-trioxaspiro[4.5]decyl.

The expression that Substituent A is "optionally substituted" by Substituent B means that Substituent A is unsubstituted, or substituted by Substituent B at any substitutable position thereof (any hydrogen is replaced with Substituent B). For example, the "$C_{1-4}$ alkyl optionally substituted by hydroxy" means that $C_{1-4}$ alkyl is unsubstituted, or substituted by hydroxy at any substitutable position thereof.

Specific embodiments of each group of the compound of Formula [I] (hereinafter, also to be referred to as "Compound [I]") are exemplified below, which should not be construed as limitative. Compound [I] also encompasses combinations of two or more embodiments selected appropriately from the specific embodiments of each group.

$Cy^1$ is preferably
(1) $C_{3-7}$ cycloalkyl,
(2) 4 to 7-membered heterocycloalkyl containing one or two heteroatoms independently selected from the group consisting of oxygen and sulfur atoms (the sulfur atom may be oxidized), as a ring constituting atom besides carbon atom(s),
(3) $C_{7-11}$ spirocycloalkyl, or
(4) 7 to 11-membered spiroheterocycloalkyl containing one to three oxygen atoms as a ring constituting atom besides carbon atom(s).

$Cy^1$ is more preferably
(1) $C_{3-7}$ cycloalkyl,
(2) 4 to 7-membered heterocycloalkyl containing one or two heteroatoms independently selected from the group consisting of oxygen and sulfur atoms (the sulfur atom may be oxidized), as a ring constituting atom besides carbon atom(s), or
(3) 7 to 11-membered spiroheterocycloalkyl containing one to three oxygen atoms as a ring constituting atom besides carbon atom(s).

$Cy^1$ is further more preferably
(1) $C_{3-7}$ cycloalkyl, or
(2) 4 to 7-membered heterocycloalkyl containing one or two heteroatoms independently selected from the group consisting of oxygen and sulfur atoms (the sulfur atom may be oxidized), as a ring constituting atom besides carbon atom(s).

$Cy^1$ is still more preferably
(1) cyclohexyl,
(2) tetrahydropyranyl, or
(3) 1,4-dioxanyl.

As a specific embodiment, $Cy^1$ is a group represented by the formula:

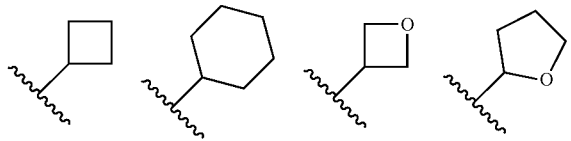

wherein the wavy line indicates a binding site to L.

$R^1$ in the number of m are preferably each independently
(1) halogen,
(2) hydroxy,
(3) $C_{1-6}$ alkyl wherein the alkyl is optionally substituted by
  (a) hydroxy,
  (b) $C_{1-4}$ alkoxy,
  (c) cyano, or
  (d) $SO_2R^{12}$ wherein $R^{12}$ is $C_{1-4}$ alkyl,
(4) $C_{1-4}$ haloalkyl wherein the haloalkyl is optionally substituted by hydroxy,
(5) $C_{1-4}$ alkoxy wherein the alkoxy is optionally substituted by 1 to 3 halogen,
(6) $COR^{13}$ wherein $R^{13}$ is
  (a) hydroxy, or
  (b) $NR^{14}R^{15}$ wherein $R^{14}$ and $R^{15}$ are each independently hydrogen or $C_{1-4}$ alkyl,
(7) cyano,
(8) $SO_2R^{16}$ wherein $R^{16}$ is $C_{1-4}$ alkyl, or
(9) $C_{3-4}$ cycloalkyl wherein the cycloalkyl is optionally substituted by hydroxy, or
two $R^1$ bonded to the same carbon atom are taken together to form oxo.

$R^1$ in the number of m are more preferably each independently
(1) halogen,
(2) hydroxy,
(3) $C_{1-6}$ alkyl wherein the alkyl is optionally substituted by
  (a) hydroxy, or
  (b) $SO_2R^{12}$ wherein $R^{12}$ is $C_{1-4}$ alkyl,
(4) $C_{1-4}$ haloalkyl wherein the haloalkyl is optionally substituted by hydroxy,
(5) $C_{1-4}$ alkoxy wherein the alkoxy is optionally substituted by 1 to 3 halogen,
(6) cyano, or
(7) $C_{3-4}$ cycloalkyl wherein the cycloalkyl is optionally substituted by hydroxy, or
two $R^1$ bonded to the same carbon atom are taken together to form oxo.

$R^1$ in the number of m are further more preferably each independently
(1) fluorine,
(2) hydroxy,
(3) $C_{1-4}$ alkyl wherein the alkyl is optionally substituted by
  (a) hydroxy, or
  (b) $SO_2R^{12}$ wherein $R^{12}$ is methyl,
(4) $C_{1-4}$ haloalkyl wherein the haloalkyl is optionally substituted by hydroxy,
(5) methoxy wherein the methoxy optionally substituted by 1 to 3 fluorine,
(6) cyano, or
(7) cyclopropyl wherein the cyclopropyl is optionally substituted by hydroxy, or
two $R^1$ bonded to the same carbon atom are taken together to form oxo.

As a specific embodiment, $R^1$ in the number of m are each independently fluorine, hydroxy, methyl, hydroxymethyl, 2-hydroxyethyl, 2-hydroxypropan-2-yl, methoxymethyl, cyanomethyl, (benzoyloxy)methyl, (methylsulfonyl)methyl, fluoromethyl, difluoromethyl, trifluoromethyl, 1,1-difluoro-2-hydroxyethyl, methoxy, difluoromethoxy, carboxy, carbamoyl, methylcarbamoyl, dimethylcarbamoyl, cyano, methylsulfonyl, 1-hydroxycyclopropyl, or 1H-1,2,4-triazol-5-yl, or two $R^1$ bonded to the same carbon atom are taken together to form oxo.

$R^2$ in the number of n are preferably each independently halogen, or two $R^2$ bonded to the same carbon atom are taken together to form $C_{3-4}$ cycloalkane with the carbon atom to which they are bonded.

$R^2$ in the number of n are more preferably each independently halogen.

$R^2$ in the number of n are further more preferably fluorine.

$R^3$ and $R^4$ are preferably each independently
(1) hydrogen, or
(2) methyl, or
$R^3$ and $R^4$ are taken together to form cyclopropane with the carbon atom to which they are bonded.

$R^5$ is preferably hydrogen.

$R^6$ is preferably monofluoromethyl, difluoromethyl or trifluoromethyl.

$R^6$ is more preferably trifluoromethyl.

$R^7$ is preferably hydrogen.

L is preferably ethylene or trimethylene.

L is more preferably ethylene.

m is preferably 0, 1 or 2.

n is preferably 0, 1 or 2.

One of preferable embodiments of Compound [I] is Compound [I] wherein
$Cy^1$ is
(1) $C_{3-7}$ cycloalkyl,
(2) 4 to 7-membered heterocycloalkyl containing one or two heteroatoms independently selected from the group consisting of oxygen and sulfur atoms (the sulfur atom may be oxidized), as a ring constituting atom besides carbon atom(s), (3) $C_{7-11}$ spirocycloalkyl, or (4) 7 to 11-membered spiroheterocycloalkyl containing one to three oxygen atoms as a ring constituting atom besides carbon atom(s);

$R^1$ in the number of m are each independently (1) halogen, (2) hydroxy, (3) $C_{1-6}$ alkyl wherein the alkyl is optionally substituted by
  (a) hydroxy,
  (b) $C_{1-4}$ alkoxy,
  (c) cyano, or
  (d) $SO_2R^{12}$ wherein $R^{12}$ is $C_{1-4}$ alkyl, (4) $C_{1-4}$ haloalkyl wherein the haloalkyl is optionally substituted by hydroxy, (5) $C_{1-4}$ alkoxy wherein the alkoxy is optionally substituted by 1 to 3 halogen, (6) $COR^{13}$ wherein $R^{13}$ is
  (a) hydroxy, or
  (b) $NR^{14}R^{15}$ wherein $R^{14}$ and $R^{15}$ are each independently hydrogen or $C_{1-4}$ alkyl, (7) cyano, (8) $SO_2R^{16}$ wherein $R^{16}$ is $C_{1-4}$ alkyl, or (9) $C_{3-4}$ cycloalkyl wherein the cycloalkyl is optionally substituted by hydroxy, or two $R^1$ bonded to the same carbon atom are taken together to form oxo;

$R^2$ in the number of n are each independently halogen, or two $R^2$ bonded to the same carbon atom are taken together to form $C_{3-4}$ cycloalkane with the carbon atom to which they are bonded;

$R^3$ and $R^4$ are each independently
(1) hydrogen, or
(2) $C_{1-4}$ alkyl, or
$R^3$ and $R^4$ are taken together to form $C_{3-4}$ cycloalkane with the carbon atom to which they are bonded;

$R^5$ is hydrogen;

$R^6$ is $C_{1-4}$ haloalkyl;

$R^7$ is hydrogen;

L is ethylene or trimethylene;

m is 0, 1, 2, 3 or 4; and n is 0, 1, 2 or 3.

One of the other preferable embodiments of Compound [I] is a compound represented by Formula [II]:

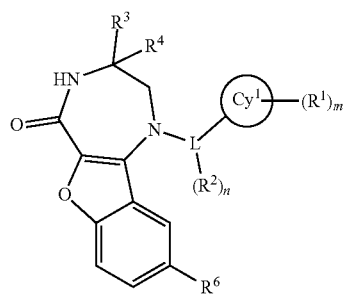

wherein $Cy^1$, $R^1$, $R^2$, $R^3$, $R^4$, $R^6$, L, m and n are as defined above.

One of the other preferable embodiments of Compound [I] is a compound represented by Formula [III]:

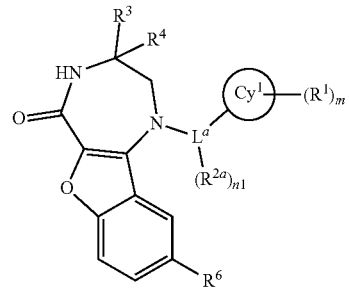

wherein $R^{2a}$ in the number of n1 are each independently halogen;

$L^a$ is ethylene or trimethylene;

n1 is 0, 1 or 2; and $Cy^1$, $R^1$, $R^3$, $R^4$, $R^6$ and m are as defined above.

One of the other preferable embodiments of Compound [I] is a compound represented by Formula [IV]:

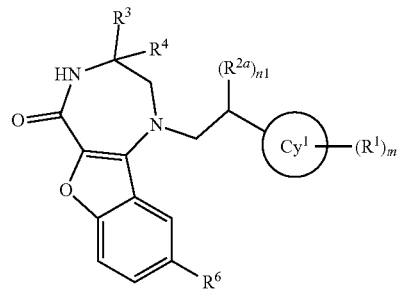

wherein $Cy^1$, $R^1$, $R^{2a}$, $R^3$, $R^4$, $R^6$, m and n1 are as defined above.

One of the other preferable embodiments of Compound [I] is a compound represented by Formula [V]:

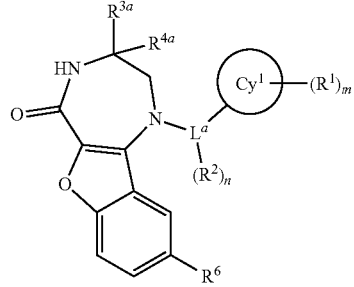

wherein $R^{3a}$ and $R^{4a}$ are each independently hydrogen or methyl, or $R^{3a}$ and $R^{4a}$ are taken together to form cyclopropane with the carbon atom to which they are bonded; and $Cy^1$, $R^1$, $R^2$, $R^6$, $L^a$, m and n are as defined above.

One of the other preferable embodiments of Compound [I] is a compound represented by Formula [VI]:

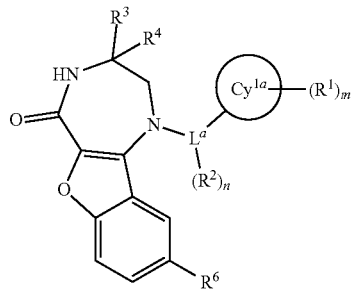
[VI]

wherein
Cy$^{1a}$ is
(1) C$_{3-7}$ cycloalkyl, or
(2) 4 to 7-membered heterocycloalkyl containing one or two heteroatoms independently selected from the group consisting of oxygen and sulfur atoms (the sulfur atom may be oxidized), as a ring constituting atom besides carbon atom(s); and
R$^1$, R$^2$, R$^3$, R$^4$, R$^6$, L$^a$, m and n are as defined above.

One of the other preferable embodiments of Compound [I] is a compound represented by Formula [VII], [VIII], [IX], [X], [XI], [XII], [XIII], [XIV], [XV] or [XVI]:

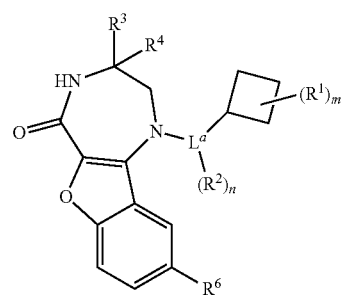
[VII]

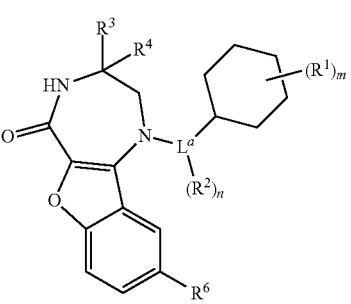
[VIII]

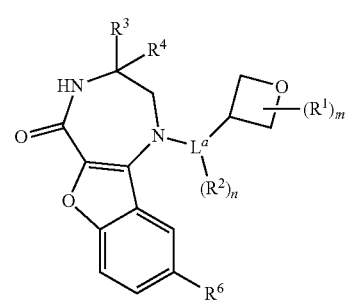
[IX]

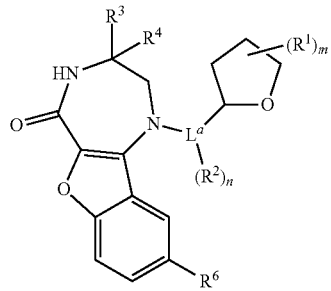
[X]

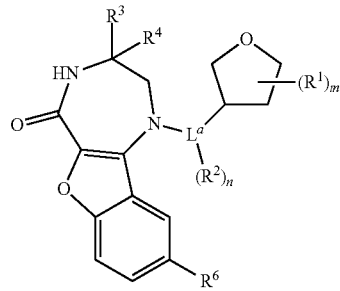
[XI]

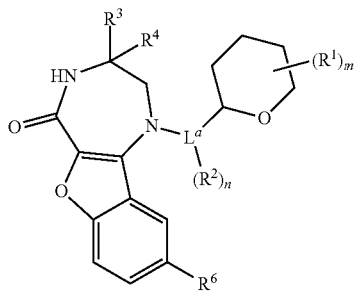
[XII]

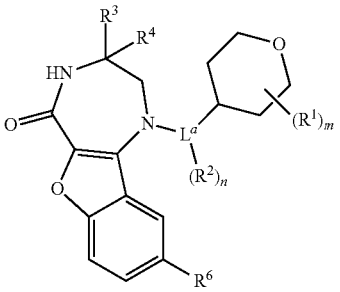
[XIII]

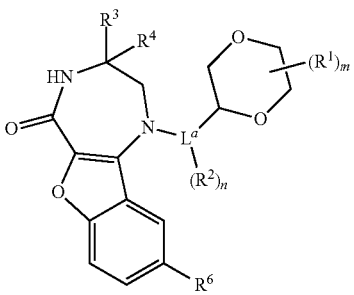
[XIV]

[Formula XV shown]

[Formula XVI shown]

wherein R¹, R², R³, R⁴, R⁶, $L^a$, m and n are as defined above.

One of the other preferable embodiments of Compound [I] is a compound represented by Formula [XVII], [XVIII] or [XIX]:

[Formula XVII shown]

[Formula XVIII shown]

[Formula XIX shown]

wherein
m1 is 0 or 1; and
R¹, R², R³, R⁴, R⁶, $L^a$ and n are as defined above.

One of the other preferable embodiments of Compound [I] is a compound represented by Formula [XX]:

[Formula XX shown]

wherein Cy¹, R¹, $R^{2a}$, $R^{3a}$, $R^{4a}$, R⁶, $L^a$, m and n1 are as defined above.

One of the other preferable embodiments of Compound [I] is a compound represented by Formula [XXI]:

[Formula XXI shown]

wherein Cy¹, R¹, $R^{2a}$, $R^{3a}$, $R^{4a}$, $L^a$, m and n1 are as defined above.

One of the other preferable embodiments of Compound [I] is a compound represented by Formula [XXII]:

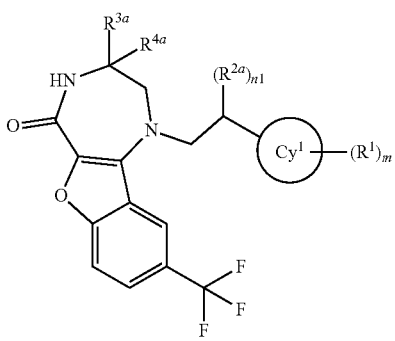

[XXII]

wherein Cy¹, R¹, R²ᵃ, R³ᵃ, R⁴ᵃ, m and n1 are as defined above.

One of the other preferable embodiments of Compound [I] is a compound represented by Formula [XXIII]:

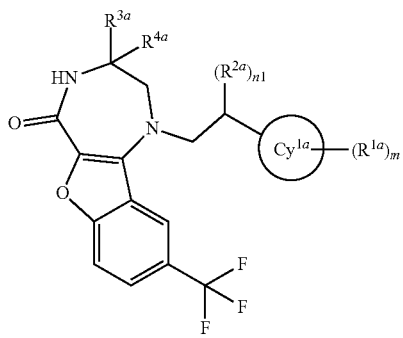

[XXIII]

wherein
R¹ᵃ in the number of m are each independently
(1) fluorine,
(2) hydroxy,
(3) $C_{1-4}$ alkyl wherein the alkyl is optionally substituted by
   (a) hydroxy, or
   (b) $SO_2R^{12}$ wherein $R^{12}$ is methyl,
(4) $C_{1-4}$ haloalkyl wherein the haloalkyl is optionally substituted by hydroxy,
(5) methoxy wherein the methoxy optionally substituted by 1 to 3 fluorine,
(6) cyano, or
(7) cyclopropyl wherein the cyclopropyl is optionally substituted by hydroxy, or
two R¹ bonded to the same carbon atom are taken together to form oxo; and
Cy¹ᵃ, R²ᵃ, R³ᵃ, R⁴ᵃ, m and n1 are as defined above.

One of the other preferable embodiments of Compound [I] is a compound represented by Formula [XXIV], [XXV] or [XXVI]:

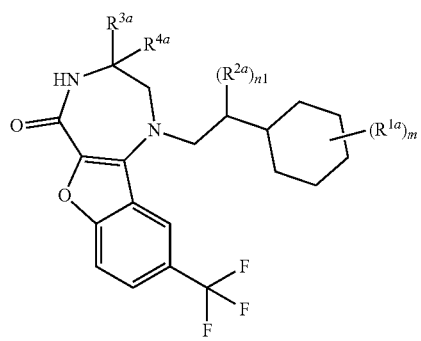

[XXIV]

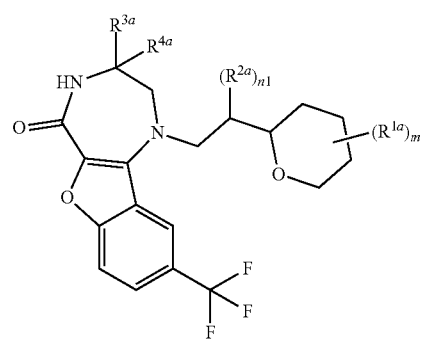

[XXV]

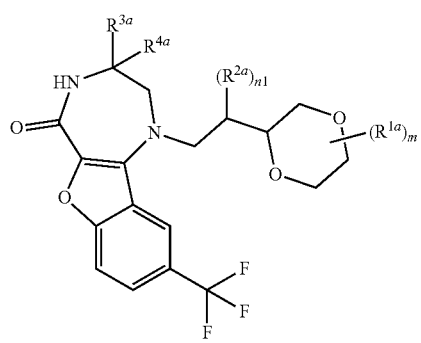

[XXVI]

wherein R¹ᵃ, R²ᵃ, R³ᵃ, R⁴ᵃ, m and n1 are as defined above.

One of the other preferable embodiments of Compound [I] is a compound represented by Formula [XXVII], [XXVIII] or [XXIX]:

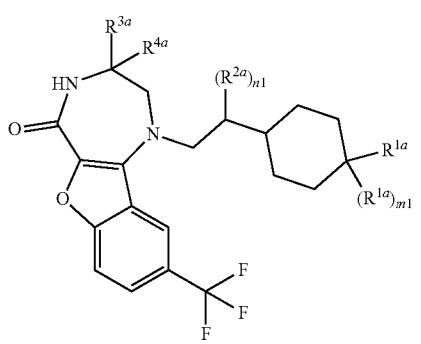

[XXVII]

-continued

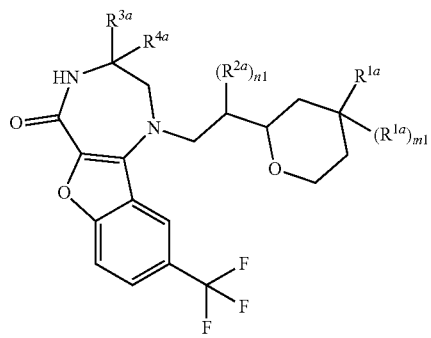

[XXVIII]

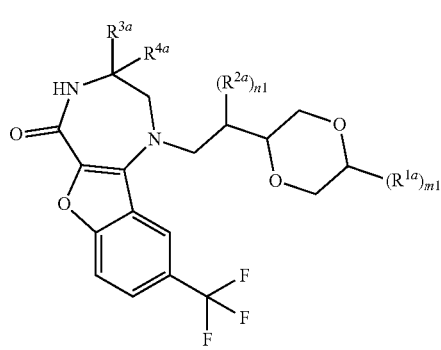

[XXIX]

wherein $R^{1a}$, $R^{2a}$, $R^{3a}$, $R^{4a}$, m1 and n1 are as defined above.

The "pharmaceutically acceptable salt" may be any salt known in the art as long as it is not associated with undue toxicity. Specific examples thereof include salts with inorganic acid, salts with organic acid, salts with inorganic base, and salts with organic base. Various forms of pharmaceutically acceptable salts are well known in the art, and they are described in the following documents.

(a) Berge et al., J. Pharm. Sci., 66, p 1-19 (1977),
(b) Stahl et al., "Handbook of Pharmaceutical Salt: Properties, Selection, and Use" (Wiley-VCH, Weinheim, Germany, 2002),
(c) Paulekuhn et al., J. Med. Chem., 50, p 6665-6672 (2007)

The pharmaceutically acceptable salt of Compound [I] can be obtained by reacting the compound of the formula [I] with an inorganic base, an organic base, an inorganic acid or an organic acid, according to a known method.

Examples of the salt with inorganic acid include salts with hydrofluoric acid, hydrochloric acid, hydrobromic acid, hydriodic acid, nitric acid, phosphoric acid and sulfuric acid. Preferable examples of the salt with inorganic acid include salts with hydrochloric acid, nitric acid, sulfuric acid, phosphoric acid and hydrobromic acid.

Examples of the salt with organic acid include salts with acetic acid, adipic acid, alginic acid, 4-aminosalicylic acid, anhydromethylenecitric acid, benzoic acid, benzenesulfonic acid, calcium edetate, camphoric acid, camphor-10-sulfonic acid, carbonic acid, citric acid, edetic acid, ethane-1,2-disulfonic acid, dodecylsulfuric acid, ethanesulfonic acid, fumaric acid, glucoheptonic acid, gluconic acid, glucuronic acid, glycollylarsanilic acid, hexylresorcinoic acid, hydroxynaphthoic acid, 2-hydroxy-1-ethanesulfonic acid, lactic acid, lactobionic acid, malic acid, maleic acid, mandelic acid, methanesulfonic acid, methylsulfuric acid, methylnitric acid, methylenebis(salicylic acid), galactaric acid, naphthalene-2-sulfonic acid, 2-naphthoic acid, 1,5-naphthalenedisulfonic acid, oleic acid, oxalic acid, pamoic acid, pantothenic acid, pectic acid, picric acid, propionic acid, polygalacturonic acid, salicylic acid, stearic acid, succinic acid, tannic acid, tartaric acid, teoclic acid, thiocyanic acid, trifluoroacetic so acid, p-toluenesulfonic acid, undecanoic acid, aspartic acid and glutamic acid. Preferable examples of the salt with organic acid include salts with oxalic acid, maleic acid, citric acid, fumaric acid, lactic acid, malic acid, succinic acid, tartaric acid, acetic acid, trifluoroacetic acid, benzoic acid, glucuronic acid, oleic acid, pamoic acid, methanesulfonic acid, benzenesulfonic acid, p-toluenesulfonic acid and 2-hydroxy-1-ethanesulfonic acid.

Examples of the salt with inorganic base include salts with ammonium, aluminium, barium, bismass, calcium, lithium, magnesium, potassium, sodium and zinc. Preferable examples of the salt with inorganic base include salts with sodium, potassium, calcium, magnesium and zinc.

Examples of the salt with organic base include salts with arecoline, ammonium, betaine, choline, clemizole, ethylene diamine, N-methylglucamine, N-benzyl phenethylamine, tris(hydroxymethyl)methylamine, arginine and lysine. Preferable examples of the salt with organic base include salts with tris(hydroxymethyl)methylamine, N-methylglucamine and lysine.

Compound [I] or a pharmaceutically acceptable salt thereof may be present as a solvate.

The "solvate" is a solvate in which a solvent molecule is coordinated with Compound [I] or a pharmaceutically acceptable salt thereof, and also encompasses hydrates. The solvate is preferably a pharmaceutically acceptable solvate, and examples thereof include a hydrate, an ethanolate, a dimethyl sulfoxidate or the like of Compound [I] or a pharmaceutically acceptable salt thereof.

Specific examples include semihydrate, monohydrate, dihydrate and monoethanolate of Compound [I], monohydrate of sodium salt of Compound [I], and ⅔ ethanolate of dihydrochloride of Compound [I]. These solvates can be obtained according to a known method.

Compound [I] or a pharmaceutically acceptable salt thereof may be present as a tautomer. In this case, Compound [I] or a pharmaceutically acceptable salt thereof can be a single tautomer or a mixture thereof.

Compound [I] or a pharmaceutically acceptable salt thereof may have a carbon-carbon double bond. In this case, Compound [I] or a pharmaceutically acceptable salt thereof can be present as an E form, a Z form, or a mixture thereof.

Compound [I] or a pharmaceutically acceptable salt thereof may contain a stereoisomer that should be recognized as a cis/trans isomer. In this case, Compound [I] or a pharmaceutically acceptable salt thereof can be present as a cis form, a trans form, or a mixture thereof.

Compound [I] or a pharmaceutically acceptable salt thereof may contain one or more asymmetric carbons. In this case, Compound [I] or a pharmaceutically acceptable salt thereof may be present as a single enantiomer, a single diastereomer, a mixture of enantiomers or a mixture of diastereomers.

Compound [I] or a pharmaceutically acceptable salt thereof may be present as an atropisomer. In this case, Compound [I] or a pharmaceutically acceptable salt thereof may be present as a single atropisomer or a mixture thereof.

Compound [I] or a pharmaceutically acceptable salt thereof may simultaneously contain a plurality of structural features that give rise to the above-mentioned isomers. Moreover, Compound [I] or a pharmaceutically acceptable salt thereof may contain the above-mentioned isomers at any ratio.

The formulas, chemical structures and compound names indicated herein without specifying the stereochemistry thereof encompass all the above-mentioned isomers that may be present, unless otherwise noted. For example, the structure represented so by the formula:

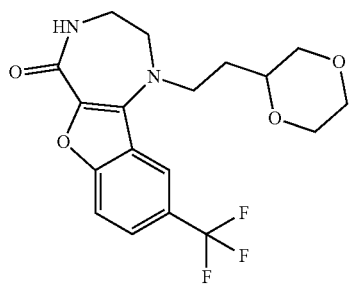 [SMILES: O=C1NCCN(CCC2COCCO2)c2c1oc1ccc(C(F)(F)F)cc21]

encompass all of
(1) a racemate of two enantiomers (S-form and R-form) represented by the formulas:

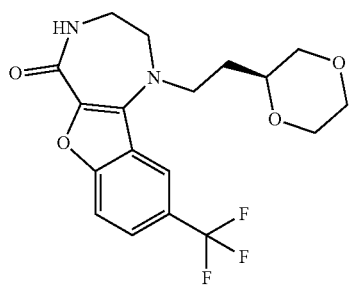

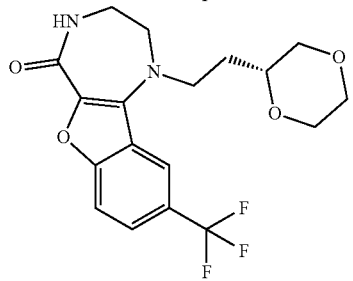

(2) S-form enantiomer, and
(3) R-form enantiomer,
unless otherwise noted.

A diastereomeric mixture can be separated into each diastereomer by conventional methods such as chromatography and crystallization. Alternatively, each diastereomer can also be produced by using a stereochemically single starting material, or by a synthesis method employing a stereoselective reaction.

An enantiomeric mixture can be separated into each single enantiomer by a method well known in the art. For example, first, a diastereomeric mixture can be prepared by reacting an enantiomeric mixture with a substantially pure enantiomer compound known as a chiral auxiliary. Next, the obtained diastereomeric mixture can be separated into a single diastereomer having high isomer ratio or a substantially pure single diastereomer by a conventional method such as fractional crystallization and chromatography. Finally, the separated diastereomer can be converted to a desired enantiomer by removing the added chiral auxiliary by cleavage. Moreover, an enantiomeric mixture can also be directly separated by a chromatography method using a chiral solid phase well known in the art. Alternatively, one of enantiomers can also be obtained by using a substantially pure optically active starting material or by employing stereoselective synthesis (asymmetric induction) of a prochiral intermediate using a chiral auxiliary and an asymmetric catalyst.

The absolute steric configuration can be determined by the X-ray crystal analysis of the crystalline product or intermediate. In this case, a crystalline product or intermediate derivatized with a reagent having an asymmetric center with a known steric configuration may be used if necessary.

Compound [I] or a pharmaceutically acceptable salt thereof may be labeled with isotope (e.g., $^2H$, $^3H$, $^{14}C$, and $^{35}S$).

Compound [I] or a pharmaceutically acceptable salt thereof is preferably substantially pure, more preferably has a purity of 80% or more.

As used herein, the pharmaceutical composition may be produced by appropriately mixing Compound [I] or a pharmaceutically acceptable salt thereof with an appropriate amount of at least one of pharmaceutically acceptable carrier and the like, according to a method known per se in the field of pharmaceutical preparations. The content of Compound [I] or a pharmaceutically acceptable salt thereof in the pharmaceutical composition varies depending on the dosage form, dose and the like, and is, for example, 0.1 to 100 wt % of the whole composition.

Examples of the dosage form of Compound [I] or a pharmaceutically acceptable salt thereof include oral preparations such as tablet, capsule, granule, powder, troche, syrup, emulsion and suspension, and parenteral preparations such as external preparation, suppository, injection, eye drop, nasal preparations and pulmonary preparation.

Examples of the "pharmaceutically acceptable carrier" include various organic or inorganic carrier substances conventionally used as preparation materials, and specifically include excipient, disintegrant, binder, glidant, lubricant and the like for solid preparations; solvent, solubilizing agent, suspending agent, isotonicity agent, buffering agent, soothing agent and the like for liquid preparations; and base, emulsifier, moistening agent, stabilizer, stabilizing agent, dispersant, plasticizer, pH adjuster, absorption enhancer, gelling agent, preservative, filler, solvent, solubilizing agent, suspending agent and the like for semi-solid preparations. Where necessary, additives such as preservative, antioxidant, colorant, sweetening agent and the like may be used.

Examples of the "excipient" include lactose, sucrose, D-mannitol, D-sorbitol, corn starch, dextrin, microcrystalline cellulose, crystalline cellulose, carmellose, carmellose calcium, sodium carboxymethyl starch, low-substituted hydroxypropylcellulose, gum arabic and the like.

Examples of the "disintegrant" include carmellose, carmellose calcium, carmellose sodium, sodium carboxymethyl starch, croscarmellose sodium, crospovidone, low-substituted hydroxypropylcellulose, hydroxypropylmethylcellulose, crystalline cellulose and the like.

Examples of the "binder" include hydroxypropylcellulose, hydroxypropylmethylcellulose, povidone, crystalline cellulose, sucrose, dextrin, starch, gelatin, carmellose sodium, gum arabic and the like.

Examples of the "glidant" include light anhydrous silicic acid, magnesium stearate and the like.

Examples of the "lubricant" include magnesium stearate, calcium stearate, talc and the like.

Examples of the "solvent" include purified water, ethanol, propylene glycol, macrogol, sesame oil, corn oil, olive oil and the like.

Examples of the "solubilizing agent" include propylene glycol, D-mannitol, benzyl benzoate, ethanol, triethanolamine, sodium carbonate, sodium citrate and the like.

Examples of the "suspending agent" include benzalkonium chloride, carmellose, hydroxypropylcellulose, propylene glycol, povidone, methylcellulose, glycerol monostearate and the like.

Examples of the "isotonic agent" include glucose, D-sorbitol, sodium chloride, D-mannitol and the like.

Examples of the "buffering agent" include sodium hydrogenphosphate, sodium acetate, sodium carbonate, sodium citrate and the like.

Examples of the "soothing agent" include benzyl alcohol and the like.

Examples of the "base" include water, animal and vegetable oils (olive oil, corn oil, arachis oil, sesame oil, castor oil etc.), lower alcohols (ethanol, propanol, propylene glycol, 1,3-butylene glycol, phenol etc.), higher fatty acids and esters thereof, wax, higher alcohols, polyalcohols, hydrocarbons (white vaseline, liquid paraffin, paraffin etc.), hydrophilic vaseline, purified lanolin, absorptive ointment, hydrous lanolin, so hydrophilic ointment, starch, pullulan, gum arabic, tragacanth gum, gelatin, dextran, cellulose derivatives (methyl cellulose, carboxymethyl cellulose, hydroxyethyl cellulose, hydroxypropyl cellulose etc.), synthetic polymers (carboxyvinyl polymer, sodium polyacrylate, polyvinyl alcohol, polyvinyl pyrrolidone etc.), propylene glycol, Macrogol (Macrogol 200 to 600), and combinations of two or more types thereof.

Examples of the "preservative" include ethyl parahydroxybenzoate, chlorobutanol, benzyl alcohol, sodium dehydroacetate, sorbic acid and the like.

Examples of the "antioxidant" include sodium sulfite, ascorbic acid and the like.

Examples of the "colorant" include food colors (Food Color Red No. 2 or 3, and Food Color Yellow No. 4 or 5 etc.), $-carotene and the like.

Examples of the "sweetening agent" include saccharin sodium, dipotassium glycyrrhizinate, aspartame and the like.

As used herein, the pharmaceutical composition can be administered orally or parenterally (topically, rectally, intravenously, intramuscularly, and subcutaneously etc.) to human as well as mammals other than human (mouse, rat, hamster, guinea pig, rabbit, cat, dog, swine, bovine, horse, sheep, monkey etc.). The dose (hereinafter, also to be referred to as "therapeutically effective amount") varies depending on administration subject, disease, symptom, dosage form, administration route and the like. For example, the daily dose for oral administration to an adult patient is generally within the range of about 0.01 mg to 1 g based on the active ingredient (i.e., Compound [I]). This amount can be administered in one to several portions.

Since Compound [I] or a pharmaceutically acceptable salt thereof has a Pim-1 inhibitory activity, it is useful as a Pim-1 inhibitor.

The expression "have a Pim-1 inhibitory activity" or "inhibit Pim-1" means elimination or attenuation of Pim-1 activity by inhibiting a Pim-1 function, for example, it means inhibition of Pim-1 function under the below-mentioned condition of Experimental Example 1.

The "Pim-1" is preferably "human Pim-1".

Since Compound [I] or a pharmaceutically acceptable salt thereof has a Pim-1 inhibitory activity, it can be used as an active ingredient for the treatment or prophylaxis of the following diseases and the like:

(a) pulmonary arterial hypertension;
(b) cancer such as hematologic cancers (acute lymphocytic leukemia, acute myelogenous leukemia, multiple myeloma, chronic myelogenous leukemia, diffuse large B-cell lymphoma, myeloproliferative neoplasms, etc.), colorectal cancer, pancreatic cancer, prostate cancer, bladder cancer, osteosarcoma, breast cancer and the like;
(c) psoriasis; and
(d) systemic lupus erythematosus.

As used herein, the "treatment" encompasses improving symptoms, preventing the aggravation of symptoms, maintaining the remission of symptoms, preventing the exacerbation of symptoms, and preventing the relapse of symptoms.

As used herein, the "prophylaxis" means suppressing the onset of symptoms.

As used herein, the therapeutically effective amount can be appropriately selected depending on an administration subject, administration route, target disease, symptom, disease severity, combination thereof and the like. When Compound [I] or a pharmaceutically acceptable salt thereof is orally administered to human (body weight 60 kg), the lower limit of the therapeutically effective amount is, for example, about 0.01 mg, about 0.1 mg, about 0.5 mg, about 1 mg, about 10 mg, about 20 mg or about 50 mg, per day, and the upper limit of the therapeutically effective amount is, for example, about 1 mg, about 5 mg, about 10 mg, about 20 mg, about 50 mg, about 100 mg, about 200 mg, about 500 mg or about 1000 mg, per day.

As used herein, the frequency of administration of Compound [I] or a pharmaceutically acceptable salt thereof is once, twice, three times or more, per day.

In some embodiments, the Pim-1 inhibitor or pharmaceutical composition may be provided in the form of a kit (administration, treatment and/or prevention kits, etc.), a package (packaging good, etc.) and a medicine set (and/or a container), associated therewith a written matter stating that it can or should be used for the prophylaxis or treatment of the above-mentioned diseases. Such kit, package and medicine set may contain one or more containers filled with Pim-1 inhibitor and/or other medicines or drugs (or components). Examples of such kit, package and medicine set include commercial kits, commercial packages and commercial medicines, which are appropriately directed to the treatment and/or prevention of target diseases. Examples of the written matter contained therein include precautions or package inserts in the form directed by the government organization which regulates manufacture, use or sale of pharmaceutical or biological products, which show the approval of the government organization about manufacture, use or sale of the products related to human administration. In the above-mentioned kit, package and medicine set, packed products may also be included, and structures constructed for suitable administration step may also be included, and structures constructed to achieve more preferred medical treatment and/or prevention, including treatment and/or prevention of the target diseases, may also be included.

As used herein, the presentation of preferred embodiments and options of the compounds, methods, uses and compositions of the present invention also includes the presentation of combinations of such preferred embodiments and options, as long as they are combinable and consistent.

The production methods of Compound [I] or a pharmaceutically acceptable salt thereof are explained in the following, which should not be construed as limitative. Unless otherwise referred, the salt of each compound in general production methods can be selected appropriately from the above-mentioned "pharmaceutically acceptable salt".

The compound obtained in each step can be, if necessary, isolated or purified according to a method known per se such as distillation, recrystallization and column chromatography, or directly used in the next step without isolation or purification.

As used herein, the room temperature means a temperature in a state where the temperature is not controlled, and one embodiment includes 1° C. to 40° C.

Production Method A1: Production Method of Compound [I] or a Salt Thereof

Compound [I] or a salt thereof can be produced, for example, according to the following Production Method A1.

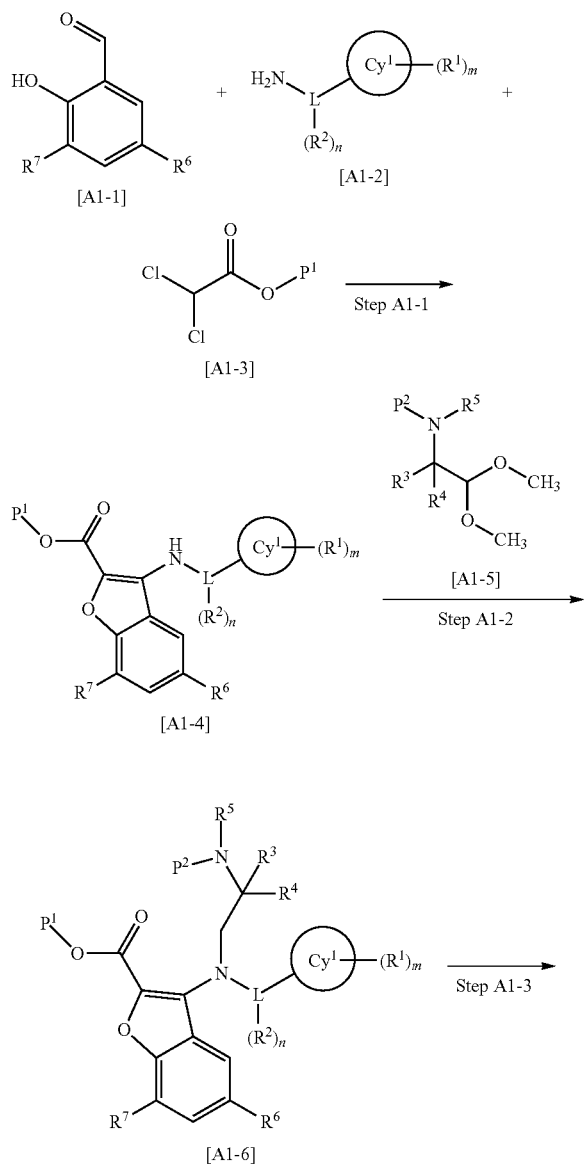

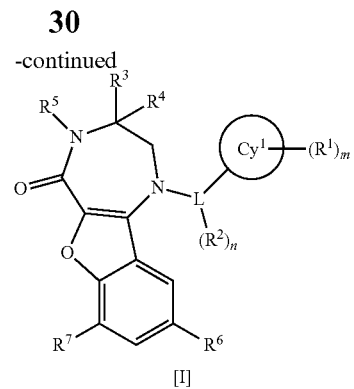

wherein
$Cy^1$, $R^1$, $R^2$, $R^3$, $R^4$, $R^5$, $R^6$, $R^7$, L, m, and n are as defined above, $P^1$ is a carboxy-protecting group (e.g., methyl and ethyl), and P2 is an amino-protecting group (e.g., 9-fluorenylmethyloxycarbonyl and benzyloxycarbonyl).

(Step A1-1)

Compound [A1-4] or a salt thereof can be produced by subjecting Compound [A1-1] or a salt thereof to a dehydration condensation reaction with Compound [A1-2] or a salt thereof in a solvent, and reacting the obtained product with Compound [A1-3] or a salt thereof in the presence of a base.

Examples of the solvent include N,N-dimethylformamide and N,N-dimethylacetamide. The preferred solvent is N,N-dimethylformamide.

Examples of the base include potassium carbonate and tripotassium phosphate. The preferred base is potassium carbonate.

The reaction temperature is, for example, 0° C. to 30° C., preferably 10° C. to 20° C.

Compound [A1-1] or a salt thereof may be a commercially available product, or can be produced from a commercially available product by a known method.

Compound [A1-2] or a salt thereof may be a commercially available product, or can be produced from a commercially available product by a known method. Compound [A1-2] or a salt thereof can also be produced, for example, according to the below-mentioned Production Method M1 or M2.

Compound [A1-3] or a salt thereof may be a commercially available product, or can be produced from a commercially available product by a known method.

(Step A1-2)

Compound [A1-6] or a salt thereof can be produced by reacting Compound [A1-4] or a salt thereof with Compound [A1-5] or a salt thereof, in a solvent, in the presence of an acid and a reducing agent.

Examples of the acid include trifluoroacetic acid. The preferred acid is trifluoroacetic acid.

Examples of the reducing agent include triethylsilane. The preferred reducing agent is triethylsilane.

Examples of the solvent include toluene and dichloromethane. The preferred solvent is toluene.

The reaction temperature is, for example, 0° C. to 30° C., preferably 10° C. to 20° C.

Compound [A1-5] or a salt thereof may be a commercially available product, or can be produced from a commercially available product by a known method.

(Step A1-3)

Compound [I] or a salt thereof can be produced by subjecting Compound [A1-6] or a salt thereof to a deprotection reaction of $P^2$, followed by a cyclization reaction.

The deprotection reaction can be carried out under conditions suitable for the kind of $P^2$.

For example, when $P^2$ is 9-fluorenylmethyloxycarbonyl, Compound [I] or a salt thereof can be produced by reacting Compound [A1-6] or a salt thereof in the presence of a base, in a solvent reaction, and then subjecting the resulting compound to a cyclization reaction.

Examples of the base include 1,8-diazabicyclo [5.4.0] undec-7-ene. The preferred base is 1,8-diazabicyclo [5.4.0] undec-7-ene.

Examples of the solvent include methanol and tetrahydrofuran. The preferred solvent is methanol.

The reaction temperature for the deprotection reaction is, for example, 0° C. to 60° C., preferably 20° C. to 60° C.

The reaction temperature for the cyclization reaction is, for example, 20° C. to 60° C., preferably 50° C. to 60° C.

Alternatively, Compound [I] or a salt thereof can also be produced by carrying out this production method using a compound or salt thereof having, on Ring $Cy^1$, a functional group or a protected functional group that can be converted to $R^1$ by a known reaction, instead of Compound [A1-2] or a salt thereof, and then so by converting the functional group of the obtained compound corresponding to Compound [I] or a salt thereof to $R^1$.

Production Method A2: Production Method of Compound [I-A] or a Salt Thereof

Compound [I-A], which is Compound [I] wherein $R^5$ is hydrogen, or a salt thereof can also be produced, for example, according to the following Production Method A2.

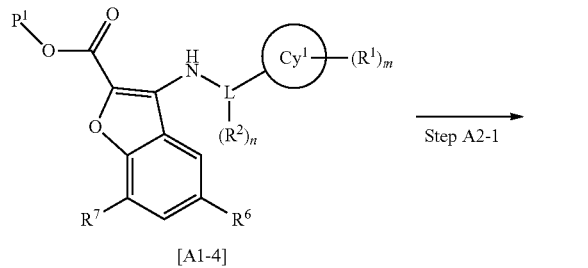

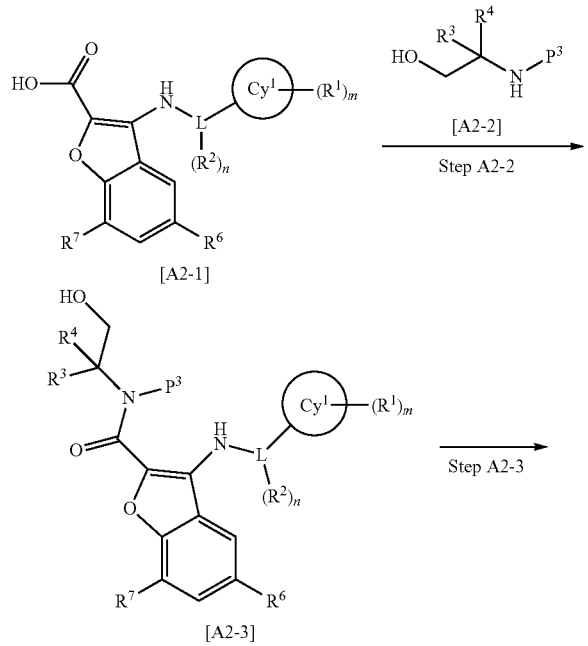

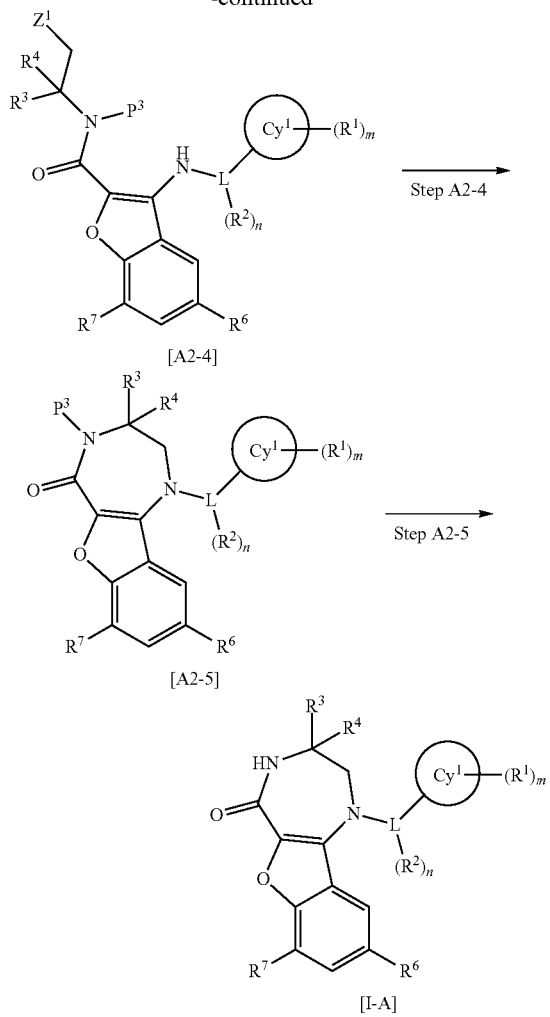

wherein $Cy^1$, $R^1$, $R^2$, $R^3$, $R^4$, $R^6$, $R^7$, L, m, n, and $P^1$ are as defined above, $P^3$ is an amino-protecting group (e.g., p-methoxybenzyl and benzyl), and $Z^1$ is a leaving group (e.g., methanesulfonyloxy, bromine and p-toluenesulfonyloxy).

(Step A2-1)

Compound [A2-1] or a salt thereof can be produced by removing $P^1$ of Compound [A1-4] or a salt thereof by a deprotection reaction. The deprotection reaction can be carried out under conditions suitable for the kind of $P^1$.

For example, when $P^1$ is $C_{1-4}$ alkyl, Compound [A2-1] or a salt thereof can be produced by subjecting Compound [A1-4] or a salt thereof to alkali hydrolysis in a solvent.

Examples of the alkali include lithium hydroxide monohydrate, sodium hydroxide and potassium hydroxide. The preferred alkali is lithium hydroxide monohydrate.

Examples of the solvent include methanol, tetrahydrofuran, water, and mixed solvent thereof. The preferred solvent is a mixed solvent of methanol, tetrahydrofuran and water.

The reaction temperature is, for example, 20° C. to 50° C., preferably 40° C. to 50° C.

(Step A2-2)

Compound [A2-3] or a salt thereof can be produced by reacting Compound [A2-1] or a salt thereof with Compound [A2-2] or a salt thereof in the presence of a condensing agent and a base, in a solvent.

Examples of the condensing agent include 1-[bis(dimethylamino)methylene]-1H-1,2,3-triazolo[4,5-b]pyridinium 3-oxide hexafluorophosphate. The preferred condensing agent is 1-[bis(dimethylamino)methylene]-1H-1,2,3-triazolo[4,5-b]pyridinium 3-oxide hexafluorophosphate.

Examples of the base include N,N-diisopropylethylamine and triethylamine. The preferred base is N,N-diisopropylethylamine.

Examples of the solvent include N,N-dimethylformamide and N,N-dimethylacetamide. The preferred solvent is N,N-dimethylformamide.

The reaction temperature is, for example, 0° C. to 20° C., preferably 10° C. to 20° C.

Compound [A2-2] or a salt thereof may be a commercially available product, or can be produced from a commercially available product by a known method.

(Step A2-3)

Compound [A2-4] or a salt thereof can be produced by converting the hydroxy of Compound [A2-3] or a salt thereof to $Z^1$. The conversion can be carried out under conditions suitable for the kind of $Z^1$.

For example, when $Z^1$ is methanesulfonyloxy, Compound [A2-4] or a salt thereof can be produced by subjecting Compound [A2-3] or a salt thereof to methanesulfonylation in the presence of a base, in a solvent.

Examples of the methanesulfonylating agent include methanesulfonic anhydride and methanesulfonyl chloride. The preferred methanesulfonylating agent is methanesulfonic anhydride.

Examples of the base include triethylamine and pyridine. The preferred base is triethylamine.

Examples of the solvent include dichloromethane and tetrahydrofuran. The preferred solvent is dichloromethane.

The reaction temperature is, for example, 0° C. to 20° C., preferably 0° C. to 10° C.

(Step A2-4)

Compound [A2-5] or a salt thereof can be produced by subjecting Compound [A2-4] or a salt thereof to a cyclization reaction in the presence of a base, in a solvent.

Examples of the base include cesium carbonate and potassium carbonate. The preferred base is cesium carbonate.

Examples of the solvent include N,N-dimethylformamide and N,N-dimethylacetamide. The preferred solvent is N,N-dimethylformamide.

The reaction temperature is, for example, 0° C. to 30° C., preferably 10° C. to 30° C.

(Step A2-5)

Compound [I-A] or a salt thereof can be produced by subjecting Compound [A2-5] or a salt thereof to a deprotection reaction of $P^3$. The deprotection reaction can be carried out under conditions suitable for the kind of $P^3$.

For example, when $P^3$ is p-methoxybenzyl, Compound [I-A] or a salt thereof can be produced by reacting Compound [A2-5] or a salt thereof in the presence of an acid, in a solvent.

Examples of the acid include trifluoroacetic acid and hydrochloric acid. The preferred acid is trifluoroacetic acid.

Examples of the solvent include anisole. The preferred solvent is anisole.

The reaction temperature is, for example, 50° C. to 90° C., preferably 70° C. to 90° C.

Alternatively, Compound [I-A] or a salt thereof can also be produced by carrying out this production method using a compound or salt thereof having, on Ring $Cy^1$, a functional group or a protected functional group that can be converted to $R^1$ by a known reaction, instead of Compound [A1-4] or a salt thereof, and then by converting the functional group of the obtained compound corresponding to Compound [I-A] or a salt thereof to $R^1$.

Production Method A3: Another Production Method of Compound [I-A] or a Salt Thereof Compound [I-A], which is Compound [I] wherein $R^5$ is hydrogen, or a salt thereof can also be produced, for example, according to the following Production Method A3.

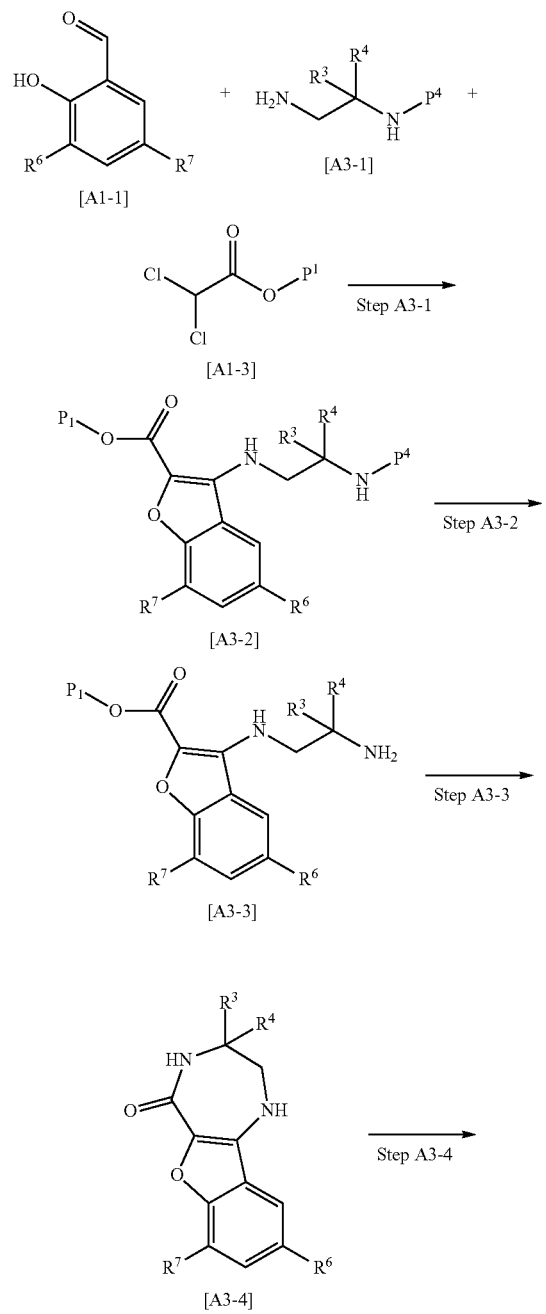

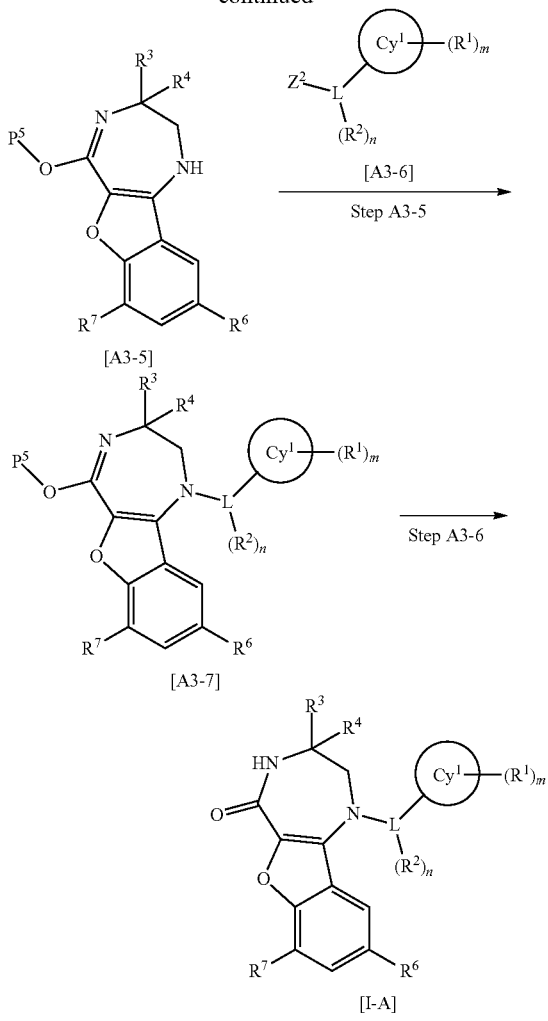

wherein
Cy$^1$, R$^1$, R$^2$, R$^3$, R$^4$, R$^6$, R$^7$, L, m, n, and P$^1$ are as defined above, P$^4$ is an amino-protecting group (e.g., tert-butoxycarbonyl), P$^5$ is a hydroxy-protecting group (e.g., C$_{1-4}$ alkyl such as methyl, ethyl etc.), and
Z$^2$ is a leaving group (e.g., p-toluenesulfonyloxy, bromine and methanesulfonyloxy).

(Step A3-1)

Compound [A3-2] or a salt thereof can be produced by reacting Compound [A1-1] or a salt thereof and Compound [A3-1] or a salt thereof and Compound [A1-3] or a salt thereof according to Step A1-1.

Compound [A3-1] or a salt thereof may be a commercially available product, or can be produced from a commercially available product by a known method.

(Step A3-2)

Compound [A3-3] or a salt thereof can be produced by removing P$^4$ of Compound [A3-2] or a salt thereof by a deprotection reaction. The deprotection reaction can be carried out under conditions suitable for the kind of P$^4$.

For example, when P$^4$ is tert-butoxycarbonyl, Compound [A3-3] or a salt thereof can be produced by reacting Compound [A3-2] or a salt thereof in the presence of an acid, in a solvent. The acid and solvent may be the same.

Examples of the acid include trifluoroacetic acid and hydrochloric acid. The preferred acid is trifluoroacetic acid.

Examples of the solvent include trifluoroacetic acid and chloroform. The preferred solvent is trifluoroacetic acid.

The reaction temperature is, for example, 0° C. to 20° C., preferably 10° C. to 20° C.

(Step A3-3)

Compound [A3-4] or a salt thereof can be produced by reacting Compound [A3-3] or a salt thereof in the presence of a base, in a solvent.

Examples of the base include sodium methoxide and sodium ethoxide. The preferred base is sodium methoxide.

Examples of the solvent include methanol and ethanol. The preferred solvent is methanol.

The reaction temperature is, for example, 0° C. to 60° C., preferably 20° C. to 60° C.

(Step A3-4)

Compound [A3-5] or a salt thereof can be produced by introducing P$^5$ to the lactam of Compound [A3-4] or a salt thereof. The introduction of P$^5$ can be carried out under conditions suitable for the kind.

For example, when P$^5$ is C$_{1-4}$ alkyl, Compound [A3-5] or a salt thereof can be produced by subjecting Compound [A3-4] or a salt thereof to alkylation in the presence of a base, in a solvent.

Examples of the alkylating agent include trimethyloxonium tetrafluoroborate and triethyloxonium tetrafluoroborate. The preferred alkylating agent is trimethyloxonium tetrafluoroborate.

Examples of the base include cesium carbonate and potassium carbonate. The preferred base is cesium carbonate.

Examples of the solvent include ethyl acetate and 1,2-dimethoxyethane. The preferred solvent is ethyl acetate.

The reaction temperature is, for example, 0° C. to 30° C., preferably 20° C. to 30° C.

(Step A3-5)

Compound [A3-7] or a salt thereof can be produced by reacting Compound [A3-5] or a salt thereof with Compound [A3-6] or a salt thereof in the presence of a base, in a solvent.

Examples of the base include sodium bistrimethylsilylamide and potassium tert-butoxide. The preferred base is sodium bistrimethylsilylamide.

Examples of the solvent include tetrahydrofuran and N,N-dimethylformamide. The preferred solvent is tetrahydrofuran.

The reaction temperature is, for example, 0° C. to 30° C., preferably 20° C. to 30° C.

Compound [A3-6] or a salt thereof may be a commercially available product, or can be produced from a commercially available product by a known method. Compound [A3-6] or a salt thereof can also be produced, for example, according to the below-mentioned Production Method M1 or M2.

(Step A3-6)

Compound [I-A] or a salt thereof can be produced by removing P$^5$ of Compound [A3-7] or a salt thereof by a deprotection reaction. The deprotection reaction can be carried out under conditions suitable for the kind of P$^5$.

For example, when P$^5$ is C$_{1-4}$ alkyl, Compound [I-A] or a salt thereof can be produced by subjecting Compound [A3-7] or a salt thereof to de-alkylation in a solvent.

Examples of the de-alkylating agent include hydrochloric acid and acetic acid. The preferred de-alkylating agent is hydrochloric acid.

Examples of the solvent include 1,2-dimethoxyethane and acetic acid. The preferred solvent is 1,2-dimethoxyethane.

The reaction temperature is, for example, 60° C. to 90° C., preferably 80° C. to 90° C.

Alternatively, Compound [I-A] or a salt thereof can also be produced by carrying out this production method using a compound or salt thereof having, on Ring Cy¹, a functional group or a protected functional group that can be converted to R¹ by a known reaction, instead of Compound [A3-6] or a salt thereof, and then by converting the functional group of the obtained compound corresponding to Compound [I-A] or a salt thereof to R¹.

Production Method A4: Production Method of Compound [I-B] or a Salt Thereof

Compound [I-B], which is Compound [I] wherein R³, R⁴ and R⁵ are hydrogen, or a salt thereof can also be produced, for example, according to the following Production Method A4.

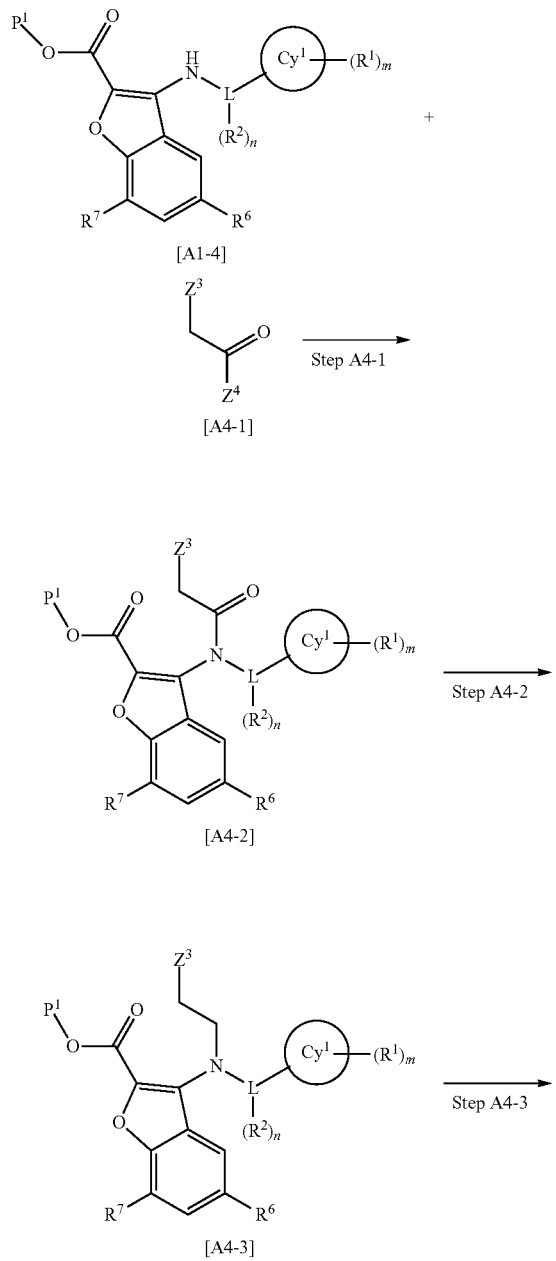

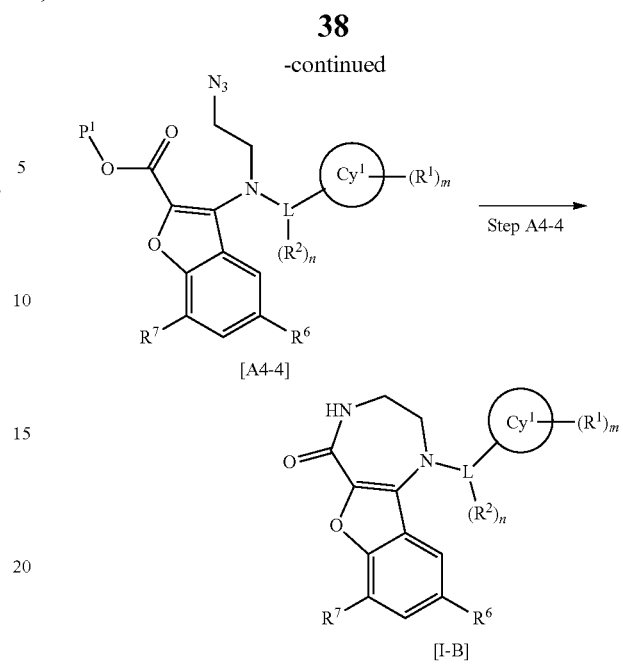

wherein Cy¹, R¹, R², R⁶, R⁷, L, m, n, and P¹ are as defined above,

Z³ is a leaving group (e.g., chlorine), and

Z⁴ is a leaving group (e.g., chlorine).

(Step A4-1)

Compound [A4-2] or a salt thereof can be produced by reacting Compound [A1-4] or a salt thereof with Compound [A4-1] or a salt thereof in the presence of a base, in a solvent.

Examples of the base include N,N-dimethylaniline. The preferred base is N,N-dimethylaniline.

Examples of the solvent include dichloromethane and chloroform. The preferred solvent is dichloromethane.

The reaction temperature is, for example, 0° C. to 20° C., preferably 10° C. to 20° C.

Compound [A4-1] or a salt thereof may be a commercially available product, or can be produced from a commercially available product by a known method.

(Step A4-2)

Compound [A4-3] or a salt thereof can be produced by subjecting Compound [A4-2] or a salt thereof to reduction in a solvent.

Examples of the reducing agent include borane-tetrahydrofuran complex. The preferred reducing agent is borane-tetrahydrofuran complex.

Examples of the solvent include tetrahydrofuran. The preferred solvent is tetrahydrofuran.

The reaction temperature is, for example, 0° C. to 30° C., preferably 10° C. to 20° C.

(Step A4-3)

Compound [A4-4] or a salt thereof can be produced by subjecting Compound [A4-3] or a salt thereof to azidation in a solvent, in the presence of a catalyst.

Examples of the azidating agent include potassium azide. The preferred azidating agent is potassium azide.

Examples of the catalyst include sodium iodide and potassium iodide. The preferred catalyst is sodium iodide.

Examples of the solvent include N,N-dimethylformamide and N,N-dimethylacetamide. The preferred solvent is N,N-dimethylformamide.

The reaction temperature is, for example, 20° C. to 80° C., preferably 60° C. to 80° C.

(Step A4-4)

Compound [I-B] or a salt thereof can be produced by so subjecting Compound [A4-4] or a salt thereof to a reduction and cyclization reaction in a solvent.

Examples of the reducing agent include triphenylphosphine. The preferred reducing agent is triphenylphosphine.

Examples of the solvent include 1,2-dimethoxyethane, tetrahydrofuran, and solvents thereof mixed with water. The preferred solvent is a mixed solvent of 1,2-dimethoxyethane and water.

The reaction temperature is, for example, 20° C. to 90° C., preferably 80° C. to 90° C.

Alternatively, Compound [I-B] or a salt thereof can also be produced by carrying out this production method using a compound or salt thereof having, on Ring $Cy^1$, a functional group or a protected functional group that can be converted to $R^1$ by a known reaction, instead of Compound [A1-4] or a salt thereof, and then by converting the functional group of the obtained compound corresponding to Compound [I-B] or a salt thereof to $R^1$.

Production Method M1: Production Methods of Compound [M1-8] and Compound [M1-6] or Salts Thereof The following compounds:

(1) regarding Compound [A1-2] or a salt thereof used in Production Method A1, Compound [M1-8] which is Compound [A1-2] wherein $R^2$ is halogen, L is ethylene and n is 2, or a salt thereof, and (2) regarding Compound [A3-6] or a salt thereof used in Production Method A3, Compound [M1-6] which is Compound [A3-6] wherein $R^2$ is halogen, L is ethylene and n is 2, or a salt thereof, can be produced, for example, according to the following Production Method M1.

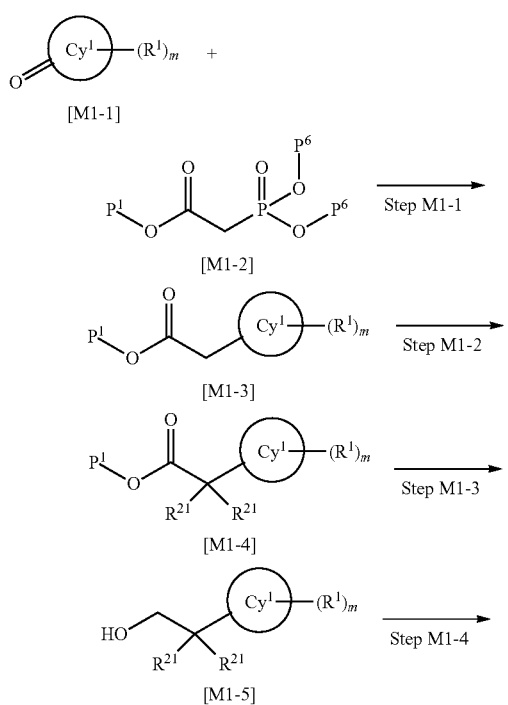

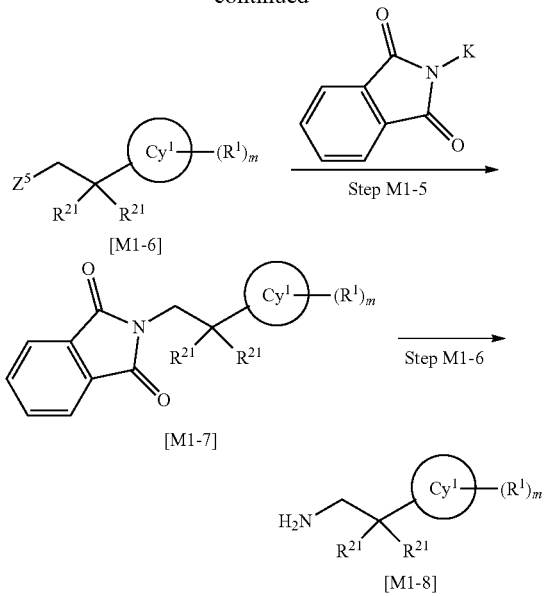

wherein
$Cy^1$, $R^1$, m, and $P^1$ are as defined above,
$R^{21}$ is halogen,
$P^6$ is a hydroxy-protecting group (e.g., methyl and ethyl), and
$Z^5$ is a leaving group (e.g., trifluoromethanesulfonyloxy).

(Step M1-1)

Compound [M1-3] or a salt thereof can be produced by subjecting Compound [M1-1] or a salt thereof to Horner-Wadsworth-Emmons reaction with Compound [M1-2] or a salt thereof in the presence of a base, in a solvent, and then subjecting the obtained product to catalytic hydrogenation in the presence of a palladium catalyst, in a solvent.

Examples of the base used in the Horner-Wadsworth-Emmons reaction include potassium carbonate and sodium hydride. The preferred base is potassium carbonate.

Examples of the solvent used in the Horner-Wadsworth-Emmons reaction include N,N-dimethylformamide and tetrahydrofuran. The preferred solvent is N,N-dimethylformamide.

The reaction temperature for the Horner-Wadsworth-Emmons reaction is, for example, 0° C. to 80° C., preferably 30° C. to 80° C.

Examples of the palladium catalyst used in the catalytic hydrogenation include palladium on carbon, and palladium hydroxide carbon. The preferred palladium catalyst is palladium on carbon.

Examples of the solvent used in the catalytic hydrogenation include tetrahydrofuran and ethyl acetate. The preferred solvent is tetrahydrofuran.

The reaction temperature for the catalytic hydrogenation is, for example, 0° C. to 20° C., preferably 10° C. to 20° C.

Compound [M1-1] or a salt thereof may be a commercially available product, or can be produced from a commercially available product by a known method.

Compound [M1-2] or a salt thereof may be a commercially available product, or can be produced from a commercially available product by a known method.

(Step M1-2)

Compound [M1-4] or a salt thereof can be produced by subjecting Compound [M1-3] or a salt thereof to halogenation. The halogenation can be carried out under conditions suitable for the kind of halogen.

For example, when $R^{21}$ is fluorine, Compound [M1-4] or a salt thereof can be produced by subjecting Compound [M1-3] or a salt thereof to fluorination in the presence of a base, in a solvent.

Examples of the fluorinating agent include N-fluorobenzenesulfonimide. The preferred fluorination is N-fluorobenzenesulfonimide.

Examples of the base include sodium bistrimethylsilylamide and lithiumbistrimethylsilylamide. The preferred base is sodium bistrimethylsilylamide.

Examples of the solvent include tetrahydrofuran, toluene, and mixed solvents thereof. The preferred solvent is a mixed solvent of tetrahydrofuran and toluene.

The reaction temperature is, for example, −78° C. to 20° C., preferably −78° C. to −20° C.

(Step M1-3)

Compound [M1-5] or a salt thereof can be produced by subjecting Compound [M1-4] or a salt thereof to reduction in a solvent.

Examples of the reducing agent include lithium aluminium hydride and sodium borohydride. The preferred reducing agent is lithium aluminium hydride.

Examples of the solvent include tetrahydrofuran. The preferred solvent is tetrahydrofuran.

The reaction temperature is, for example, 0° C. to 20° C., preferably 0° C. to 10° C.

(Step M1-4)

Compound [M1-6] or a salt thereof can be produced by converting the hydroxy of Compound [M1-5] or a salt thereof to $Z^5$. The conversion can be carried out under conditions suitable for the kind of $Z^5$.

For example, when $Z^5$ is trifluoromethanesulfonyloxy, Compound [M1-6] or a salt thereof can be produced by subjecting Compound [M1-5] or a salt thereof to trifluoromethanesulfonylation in the presence of a base, in a solvent. The base and solvent may be the same.

Examples of the trifluoromethanesulfonylating agent include trifluoromethanesulfonic anhydride and trifluoromethanesulfonyl chloride. The preferred trifluoromethanesulfonylating agent is trifluoromethanesulfonic anhydride.

Examples of the base include pyridine and triethylamine. The preferred base is pyridine.

Examples of the solvent include pyridine and dichloromethane. The preferred solvent is pyridine.

The reaction temperature is, for example, 0° C. to 30° C., preferably 0° C. to 10° C.

(Step M1-5)

Compound [M1-7] or a salt thereof can be produced by reacting Compound [M1-6] or a salt thereof with potassium phthalimide in a solvent.

Examples of the solvent include N,N-dimethylformamide and N,N-dimethylacetamide. The preferred solvent is N,N-dimethylformamide.

The reaction temperature is, for example, 0° C. to 30° C., preferably 20° C. to 30° C.

(Step M1-6)

Compound [M1-8] or a salt thereof can be produced by removing the phthaloyl of Compound [M1-7] or a salt thereof. Known methods can be employed as a method of removing the phthaloyl. For example, Compound [M1-8] or a salt thereof can be produced by reacting Compound [M1-7] or a salt thereof with hydrazine monohydrate in a solvent.

Examples of the solvent include tetrahydrofuran, ethanol, methanol, and mixed solvent thereof. The preferred solvent is a mixed solvent of tetrahydrofuran and ethanol.

The reaction temperature is, for example, 20° C. to 60° C., preferably 50° C. to 60° C.

Production Method M2: Production Methods of Compound [M2-4] and Compound [M2-2] or Salts Thereof The following compounds:

(1) regarding Compound [A1-2] or a salt thereof used in Production Method A1, Compound [M2-4] which is Compound [A1-2] wherein L is ethylene and n is 0, or a salt thereof, and (2) regarding Compound [A3-6] or a salt thereof used in Production Method A3, Compound [M2-2] which is Compound [A3-6] wherein L is ethylene and n is 0, or a salt thereof, can also be produced, for example, according to the following Production Method M2.

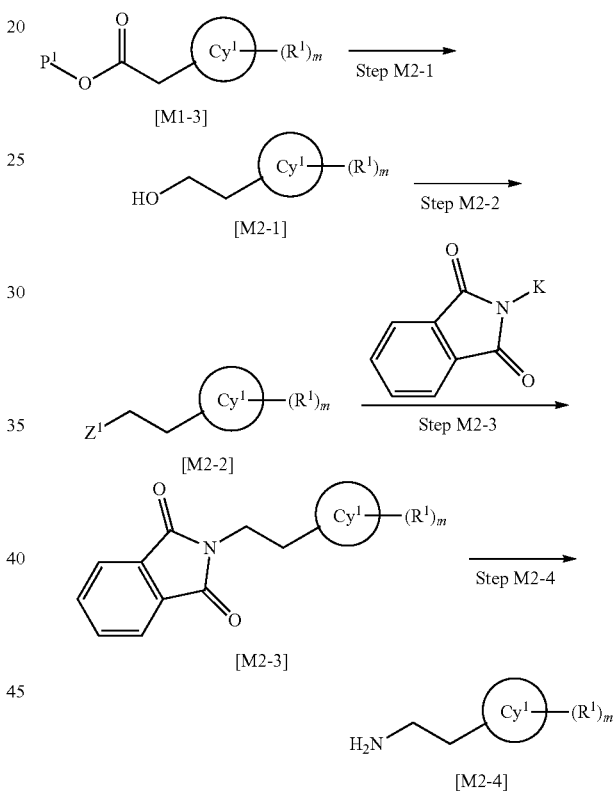

wherein $Cy^1$, $R^1$, m, $P^1$, and $Z^1$ are as defined above.

(Step M2-1)

Compound [M2-1] or a salt thereof can be produced by reacting Compound [M1-3] or a salt thereof according to Step M1-3.

(Step M2-2)

Compound [M2-2] or a salt thereof can be produced by reacting Compound [M2-1] or a salt thereof according to Step A2-3.

(Step M2-3)

Compound [M2-3] or a salt thereof can be produced by reacting Compound [M2-2] or a salt thereof according to Step M1-5.

(Step M2-4)

Compound [M2-4] or a salt thereof can be produced by reacting Compound [M2-3] or a salt thereof according to Step M1-6.

EXAMPLES

Next, the production method of Compound [I] or a pharmaceutically acceptable salt thereof is concretely explained by referring to Production Examples, which should not be construed as limitative.

[Production Example 1]: Synthesis of Cis Isomer (Example 12 Racemate), Trans Isomer (Example 11 Racemate) and Each Optical Active Form (Examples 58, 59, 66 and 67) of 1-(2,2-difluoro-2-(4-hydroxy-4-methyltetrahydro-2H-pyran-2-yl)ethyl)-9-(trifluoromethyl)-1,2,3,4-tetrahydro-5H-benzofuro[3,2-e][1,4]diazepin-5-one

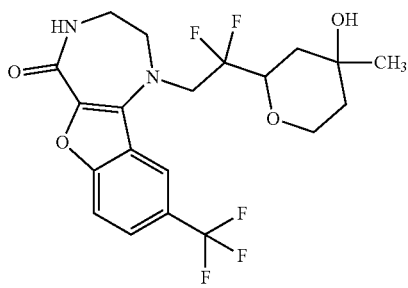 [SMILES: CC1(O)CCOC(C(F)(F)CN2CCNC(=O)c3oc4ccc(C(F)(F)F)cc4c32)C1]

(1) ethyl (E)-3-(but-3-en-1-yloxy)acrylate

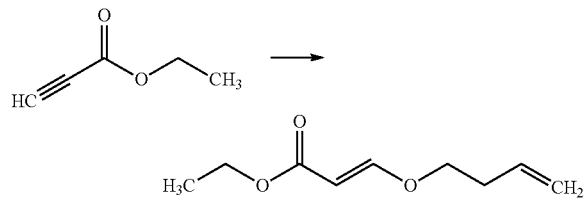

Under ice-cooling, to a solution of 3-buten-1-ol (68.4 mL, 806 mmol) and 4-methylmorpholine (89 mL, 806 mmol) in cyclopentyl methyl ether (540 mL) was added dropwise ethyl propiolate (82 mL, 806 mmol). The used dropping funnel was washed with cyclopentyl methyl ether (41 mL), and the mixture was stirred at room temperature for 17 hr. Under ice-cooling, to the reaction solution was added dropwise a mixture of acetic acid (55.4 mL, 967 mmol)-water (1162 mL), and separated. The aqueous layer was re-extracted with hexane/ethyl acetate=3/1 (400 mL). The organic layers were combined, and washed twice with water (300 mL) and once with saturated brine (200 mL). The organic layer was dried over sodium sulfate, and concentrated under reduced pressure to give the title compound (151.4 g, purity 911, yield 100%).

$^1$H-NMR (DMSO-D$_6$) δ: 1.18 (3H, t, J=7.1 Hz), 2.36-2.42 (2H, m), 3.98 (2H, t, J=6.6 Hz), 4.07 (2H, q, J=7.1 Hz), 5.05-5.09 (1H, m), 5.13 (1H, dq, J=17.2, 1.7 Hz), 5.26 (1H, d, J=12.6 Hz), 5.74-5.85 (1H, m), 7.58 (1H, d, J=12.6 Hz).

(2) ethyl 2-(4-hydroxytetrahydro-2H-pyran-2-yl)acetate

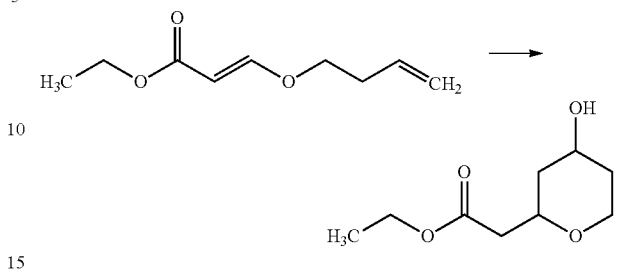

2.5 Under ice-cooling, to a solution of ethyl (E)-3-(but-3-en-1-yloxy)acrylate (151.4 g, purity 91%, 806 mmol) obtained in (1) in chloroform (686 mL) was added dropwise trifluoroacetic acid (186 mL, 2418 mmol), and the mixture was stirred at room temperature for 7 hr. Under ice-cooling, an aqueous solution (1235 mL) of tripotassium phosphate (257 g, 1209 mmol) was added dropwise thereto, and the mixture was extracted with chloroform. The aqueous layer was re-extracted with chloroform. The organic layers were combined, and washed with water and saturated brine. The organic layer was dried over sodium sulfate, and concentrated under azeotrope with ethanol and under reduced pressure. To the obtained residue were added ethanol (1616 mL) and potassium carbonate (9.82 g, 71.1 mmol), and the mixture was stirred at room temperature for 2 hr. The insoluble substance was removed by filtration through Celite, and the filtrate was concentrated under reduced pressure. The residue was purified by silica gel column chromatography (eluent: hexane/ethyl acetate=9/1 to 0/100) to give the title compound (106 g, purity 93%, yield 74).

$^1$H-NMR (DMSO-D$_6$) δ: 1.00-1.09 (0.78H, m), 1.17 (2.34H, t, J=7.2 Hz), 1.18 (0.66H, t, J=7.2 Hz), 1.20-1.30 (0.78H, m), 1.34-1.44 (0.44H, m), 1.52-1.65 (0.44H, m), 1.65-1.73 (0.78H, m), 1.79-1.87 (0.78H, m), 2.27-2.48 (2H, m), 3.23-3.31 (0.78H, m), 3.51-3.74 (2H, m), 3.81 (0.78H, ddd, J=11.6, 4.8, 1.7 Hz), 3.95-4.00 (0.22H, m), 4.00-4.09 (2.22H, m), 4.62 (0.22H, d, J=2.9 Hz), 4.75 (0.78H, d, J=4.6 Hz).

(3) ethyl 2-(4-oxotetrahydro-2H-pyran-2-yl)acetate

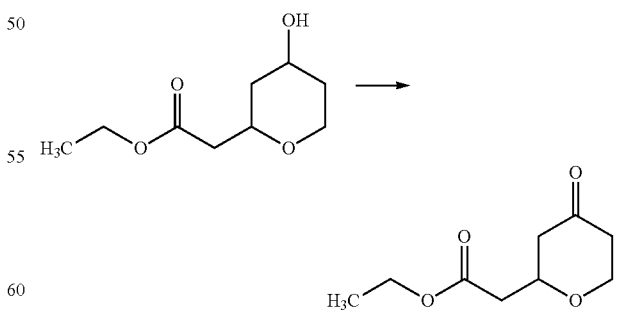

Under water-cooling, to a solution of 1,1,1-triacetoxy-1,1-dihydro-1,2-benziodoxol-3-(1H)-one (126 g, 296 mmol) in chloroform (400 mL) was added dropwise a solution of ethyl 2-(4-hydroxytetrahydro-2H-pyran-2-yl)acetate (50 g, purity 93%, 247 mmol) obtained in (2) in chloroform (65 mL), and the mixture was stirred at room temperature for 3 hr. 1,1,1-Triacetoxy-1,1-dihydro-1,2-benziodoxol-3-(1H)-one (31.4 g, 74.0 mmol) was added thereto, and the mixture was stirred for additional 30 min. To the reaction solution was added hexane (465 mL), and the mixture was stirred at room temperature for 30 min. The insoluble substance was removed by filtration, to the filtrate were added saturated aqueous sodium hydrogencarbonate solution (1000 mL) and 10% aqueous sodium thiosulfate solution (100 mL) at room temperature, and the mixture was stirred for 1 hr. The insoluble substance was removed by filtration, and the filtrate was separated. The organic layer was washed with saturated brine, dried over sodium sulfate, and concentrated under reduced pressure to give the title compound (62.5 g, purity 77%, yield 105%).

$^1$H-NMR (DMSO-d$_6$) δ: 1.18 (3H, t, J=7.1 Hz), 2.12-2.20 (1H, m), 2.28-2.34 (1H, m), 2.39 (1H, ddd, J=14.6, 10.8, 0.9 Hz), 2.48-2.63 (3H, m), 3.58-3.65 (1H, m), 3.94-4.01 (1H, m), 4.07 (2H, q, J=7.1 Hz), 4.14 (1H, ddd, J=11.4, 7.5, 1.4 Hz).

(4) ethyl 2-(1,4,8-trioxaspiro[4,5]decan-7-yl)acetate

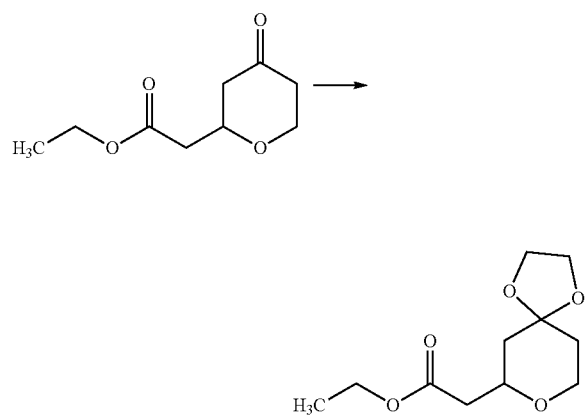

Under argon atmosphere, to a solution of ethyl 2-(4-oxotetrahydro-2H-pyran-2-yl)acetate (60 g, 322 mmol) obtained by the same reaction as (3) in toluene (600 mL) were added ethylene glycol (25.2 mL, 451 mmol) and pyridinium p-toluenesulfonate (4.86 g, 19.33 mmol), and the mixture was subjected to a dehydration reaction using Dean-Stark apparatus at 140° C. for 3 hr. The reaction solution was cooled to room temperature, saturated aqueous sodium hydrogencarbonate solution (200 mL) and water (200 mL) were added thereto, and the mixture was separated. The aqueous layer was extracted three times with hexane/ethyl acetate=1/1. The organic layers were combined, and washed with water and saturated brine, dried over sodium sulfate, and concentrated under reduced pressure. The residue was purified by silica gel column chromatography (eluent: hexane/ethyl acetate=90/10 to 0/100) to give the title compound (67.8 g, purity 90%, yield 82).

$^1$H-NMR (DMSO-Dc) δ: 1.17 (3H, t, J=7.2 Hz), 1.41 (1H, dd, J=12.9, 11.7 Hz), 1.53-1.64 (2H, m), 1.70 (1H, dt, J=12.9, 2.1 Hz), 2.39 (1H, dd, J=15.5, 8.3 Hz), 2.44-2.50 (1H, m), 3.39-3.47 (1H, m), 3.76-3.93 (6H, m), 4.05 (2H, q, J=7.2 Hz).

(5) ethyl 2,2-difluoro-2-(1,4,8-trioxaspiro[4,5]decan-7-yl)acetate

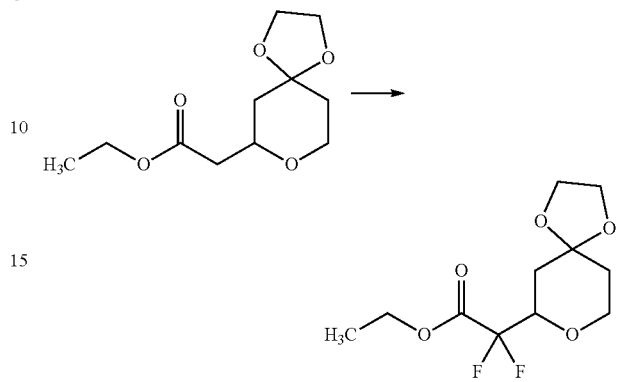

To a mixed solution of ethyl 2-(1,4,8-trioxaspiro[4,5] decan-7-yl)acetate (17.0 g, 66.4 mmol) obtained in (4) in toluene (230 mL)-tetrahydrofuran (765 mL) was added N-fluorobenzenesulfonimide (84.0 g, 266 mmol), and the mixture was cooled to −78° C. 1M Sodium bistrimethylsilylamide-tetrahydrofuran solution (233 mL, 233 mmol) was added dropwise thereto, and the mixture was warmed to 0° C. over 1 hr, and stirred under ice-cooling for additional 2 hr. To the reaction solution was added dropwise triethylamine (74.1 mL, 532 mmol). To the reaction solution were added water (1000 mL), followed by hexane (330 mL), and the mixture was separated. The aqueous layer was extracted twice with hexane/ethyl acetate=1/1 (600 mL). The organic layers were combined, washed three times with water (400 mL), with 5% aqueous sodium sulfite solution (580 mL) and saturated brine (340 mL). To the organic layer were added sodium sulfate and silica gel, and the mixture was stirred. The insoluble substance was removed by filtration through Celite, and the filtrate was concentrated under reduced pressure. The residue was purified by silica gel column chromatography (eluent: hexane/ethyl acetate=94/6 to 50/50) to give the title compound (15.1 g, yield 85%).

$^1$H-NMR (DMSO-D6) δ: 1.26 (3H, t, J=7.2 Hz), 1.58-1.82 (4H, m), 3.48-3.56 (1H, m), 3.89-4.03 (6H, m), 4.32 (2H, q, J=7.1 Hz).

(6) 2,2-difluoro-2-(1,4,8-trioxaspiro[4,5]decan-7-yl) ethan-1-ol

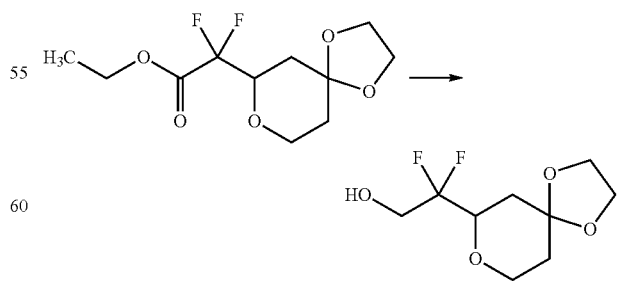

Under argon atmosphere and ice-cooling, to a suspension of lithium aluminium hydride (2.82 g, 74.4 mmol) in tetrahydrofuran (90 mL) was added dropwise a solution of ethyl 2,2-difluoro-2-(1,4,8-trioxaspiro[4,5]decan-7-yl)acetate (18.0 g, 67.6 mmol) obtained by the same reaction as (5) in tetrahydrofuran (36 mL), and the mixture was stirred for 1 hr. To the reaction solution was successively added dropwise water (2.8 mL), 4N aqueous sodium hydroxide solution (2.8 mL) and water (8.4 mL), and the mixture was stirred at room temperature for 2 hr. The insoluble substance was removed by filtration through Celite, and the filtrate was concentrated under reduced pressure. The residue was purified by silica gel column chromatography (eluent: hexane/ethyl acetate=88/12 to 0/100) to give the title compound (14.5 g, yield 94%).

¹H-NMR (DMSO-D$_6$) δ: 1.54-1.79 (4H, m), 3.46-4.01 (9H, m), 5.45 (1H, t, J=6.4 Hz).

(7) 2,2-difluoro-2-(1,4,8-trioxaspiro[4,5]decan-7-yl) ethyl trifluoromethanesulfonate

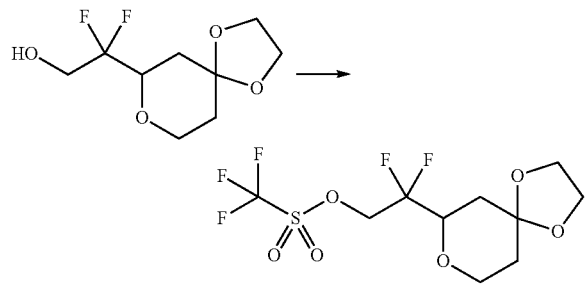

Under ice-cooling, to a solution of 2,2-difluoro-2-(1,4,8-trioxaspiro[4,5]decan-7-yl)ethan-1-ol (14.0 g, 62.4 mmol) obtained in (6) and triethylamine (11.3 mL, 81 mmol) in dichloromethane (140 mL) was added dropwise trifluoromethanesulfonyl chloride (8 mL, 71.2 mmol), and the mixture was stirred for 2.5 hr. Triethylamine (1.7 mL, 12.5 mmol) and trifluoromethanesulfonyl chloride (1.4 mL, 12.5 mmol) were added again thereto, and the mixture was stirred for additional 2 hr. Triethylamine (0.85 mL, 6.2 mmol) and trifluoromethanesulfonyl chloride (0.7 mL, 6.2 mmol) were added again thereto, and the mixture was stirred for additional 30 min. To the reaction solution was added water, and the mixture was separated. The organic layer was washed with water and saturated brine, dried over sodium sulfate, and concentrated under reduced pressure. To the residue were added ethyl acetate and water, and the mixture was separated. The organic layer was washed with water and saturated brine, dried over sodium sulfate, and concentrated under reduced pressure to give the title compound (23.4 g, yield 100%).

¹H-NMR (CDCl$_3$) δ: 1.61-1.67 (1H, m), 1.75-1.92 (3H, m), 3.64-3.73 (1H, m), 3.84-4.09 (6H, m), 4.60-4.78 (2H, m).

(8) 2-(2,2-difluoro-2-(1,4,8-trioxaspiro[4,5]decan-7-yl)ethyl)isoindoline-1,3-dione

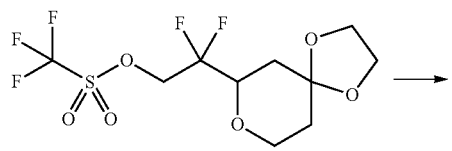

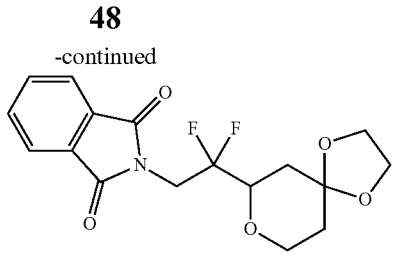

To a solution of 2,2-difluoro-2-(1,4,8-trioxaspiro[4,5]decan-7-yl)ethyl trifluoromethanesulfonate (22.2 g, 62.4 mmol) obtained in (7) in N,N-dimethylformamide (133 mL) was added potassium phthalimide (15.0 g, 81 mmol), and the mixture was stirred at room temperature for 15 hr. To the reaction solution was added water (150 mL), the mixture was stirred for 30 min, and the precipitated solid was collected by filtration. To the obtained solid were added hexane/ethyl acetate=3/1 (80 mL), and the mixture was stirred for additional 1 hr. The precipitated solid was collected by filtration, and dried under reduced pressure to give the title compound (16.4 g, yield 74%).

¹H-NMR (CDCl$_3$) δ: 1.60-1.66 (1H, m), 1.76-1.95 (3H, m), 3.65-3.73 (1H, m), 3.79-3.89 (1H, m), 3.93-4.03 (4H, m), 4.08 (1H, dd, J=11.6, 5.5 Hz), 4.13-4.32 (2H, m), 7.72-7.77 (2H, m), 7.87-7.92 (2H, m).

(9) 2,2-difluoro-2-(1,4,8-trioxaspiro[4,5]decan-7-yl) ethan-1-amine

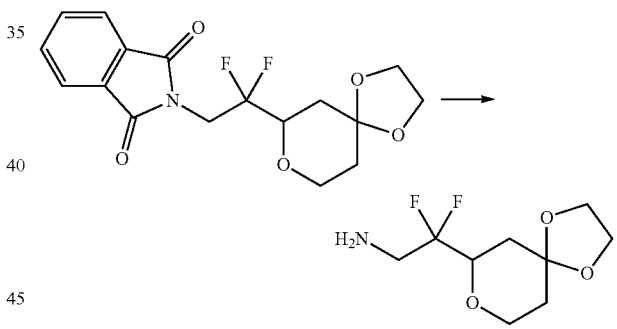

To a mixed solution of 2-(2,2-difluoro-2-(1,4,8-trioxaspiro[4,5]decan-7-yl)ethyl)isoindoline-1,3-dione (16.4 g, 46.4 mmol) obtained in (8) in ethanol (115 mL) and tetrahydrofuran (115 mL) was added hydrazine monohydrate (4.51 mL, 93 mmol), and the mixture was stirred at 60° C. for 2 hr. Hydrazine monohydrate (2.5 mL, 51.7 mmol) was added again thereto, and the mixture was stirred at 60° C. for additional 1 hr. The reaction solution was cooled under ice bath, and the insoluble substance was removed by filtration, and washed twice with ethanol (115 mL). The filtrate was concentrated, to the precipitated solid was added ethanol (60 mL), and the solid was removed by filtration. The filtrate was concentrated under reduced pressure to give the title compound (10.6 g, yield 92%).

¹H-NMR (DMSO-D$_6$) δ: 1.53-1.77 (4H, m), 1.91 (2H, br s), 2.81-3.02 (2H, m), 3.54 (1H, td, J=11.8, 3.1 Hz), 3.82-3.99 (6H, m).

(10) methyl 3-((2,2-difluoro-2-(1,4,8-trioxaspiro[4,5]decan-7-yl)ethyl)amino)-5-(trifluoromethyl)benzofuran-2-carboxylate

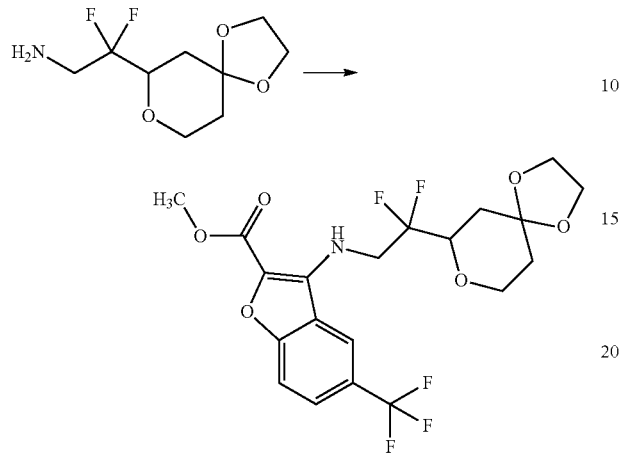

To a solution of 2,2-difluoro-2-(1,4,8-trioxaspiro[4,5]decan-7-yl)ethan-1-amine (10.4 g, 46.4 mmol) obtained in (9) in N,N-dimethylformamide (88 mL) was added 2-hydroxy-5-(trifluoromethyl)benzaldehyde (8.82 g, 46.4 mmol), and the mixture was stirred at room temperature for 30 min. Potassium carbonate (19.24 g, 139 mmol) and methyl 2,2-dichloroacetate (5.77 mL, 55.7 mmol) were added thereto, and the mixture was stirred at room temperature for 15 hr. Under ice-cooling, to the reaction solution was added water (180 mL), and the precipitated solid was collected by filtration, and washed with water (90 mL). To the obtained solid were added hexane/ethyl acetate=2/1 (120 mL), and the mixture was stirred for 30 min. The solid was collected by filtration, washed with hexane/ethyl acetate=2/1 (60 mL), and dried under reduced pressure at room temperature to give the title compound (13.7 g, yield 63%).

$^1$H-NMR (CDCl$_3$) δ: 1.58-1.65 (1H, m), 1.78-1.94 (3H, m), 3.52-3.61 (1H, m), 3.85-4.23 (11H, m), 6.39 (1H, t, J=7.4 Hz), 7.54 (1H, d, J=8.8 Hz), 7.68 (1H, dd, J=8.8, 1.6 Hz), 8.26 (1H, br s).

(11) methyl 3-(2-chloro-N-(2,2-difluoro-2-(1,4,8-trioxaspiro[4,5]decan-7-yl)ethyl)acetamido)-5-(trifluoromethyl)benzofuran-2-carboxylate

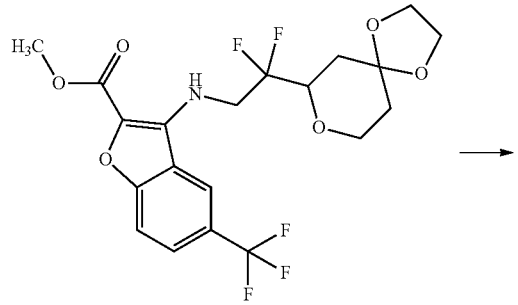

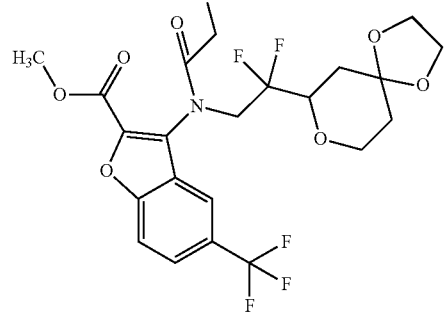

Under ice-cooling, to a solution of methyl 3-((2,2-difluoro-2-(1,4,8-trioxaspiro[4,5]decan-7-yl)ethyl)amino)-5-(trifluoromethyl)benzofuran-2-carboxylate (13.6 g, 29.2 mmol) obtained in (10), and N,N-dimethylaniline (14.8 mL, 117 mmol) in dichloromethane (340 mL) was added dropwise chloroacetyl chloride (7.02 mL, 88 mmol), and the mixture was stirred at room temperature for 16 hr. N,N-Dimethylaniline (3.7 mL, 29.2 mmol) and chloroacetyl chloride (2.3 mL, 28.8 mmol) were added again thereto, and the mixture was stirred for additional 6 hr. 10% Aqueous citric acid was added thereto, and the mixture was separated. The organic layer was washed with 10% aqueous citric acid, saturated aqueous sodium hydrogencarbonate solution and saturated brine, dried over sodium sulfate, and concentrated under reduced pressure. The residue was purified by silica gel column chromatography (eluent: hexane/ethyl acetate=6/1 to 3/2), and dissolved in ethyl acetate (20 mL). Hexane (40 mL) was added thereto, and the mixture was stirred for 1 hr, and the precipitated solid was collected by filtration, and dried under reduced pressure to give the title compound (14.3 g, yield 90%).

$^1$H-NMR (DMSO-Dc) δ: 1.47-1.77 (4H, m), 3.33-3.44 (1H, m), 3.67-3.80 (1H, m), 3.82-3.98 (8H, m), 4.03-4.28 (2H, m), 4.32 (1H, dd, J=14.4, 0.8 Hz), 4.44-4.80 (1H, m), 7.89-7.97 (1H, m), 8.01-8.08 (1H, m), 8.20 (1H, d, J=8.6 Hz).

(12) methyl 3-((2-chloroethyl) (2,2-difluoro-2-(1,4,8-trioxaspiro[4,5]decan-7-yl)ethyl)amino)-5-(trifluoromethyl)benzofuran-2-carboxylate

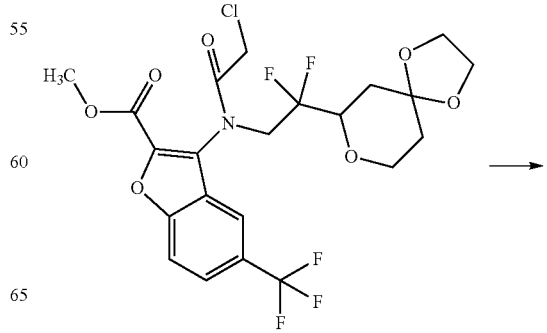

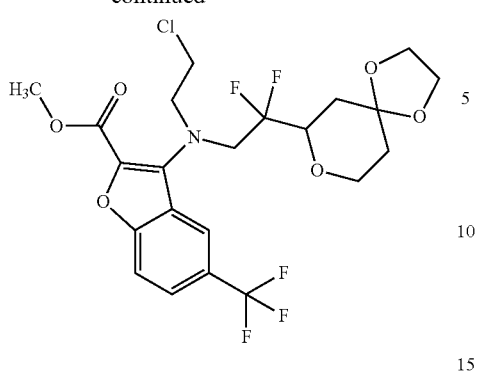

Under ice-cooling, to a solution of methyl 3-(2-chloro-N-(2,2-difluoro-2-(1,4,8-trioxaspiro[4,5]decan-7-yl)ethyl)acetamido)-5-(trifluoromethyl)benzofuran-2-carboxylate (12.3 g, 22.7 mmol) obtained in (11) in tetrahydrofuran (148 mL) was added dropwise 0.91M borane-tetrahydrofuran complex (54.9 mL, 49.9 mmol), and the mixture was stirred at room temperature for 7 hr. Under ice-cooling, to the reaction solution was added 20% aqueous citric acid, and the mixture was stirred for 10 min, and extracted with ethyl acetate. The aqueous layer was re-extracted with ethyl acetate, and the organic layers were combined, washed with saturated brine, dried over sodium sulfate, and concentrated under reduced pressure. The residue was purified by silica gel column chromatography (eluent: hexane/ethyl acetate=6/1 to 3/2) to give the title compound (7.2 g, yield 54).

$^1$H-NMR (DMSO-D6) δ: 1.45-1.68 (4H, m), 3.10 (1H, td, J=11.8, 2.5 Hz), 3.62-4.10 (15H, m), 7.87 (1H, dd, J=9.0, 1.6 Hz), 7.91 (1H, d, J=9.0 Hz), 8.20 (1H, br s).

(13) methyl 3-((2-azidoethyl) (2,2-difluoro-2-(1,4,8-trioxaspiro[4,5]decan-7-yl)ethyl)amino)-5-(trifluoromethyl)benzofuran-2-carboxylate

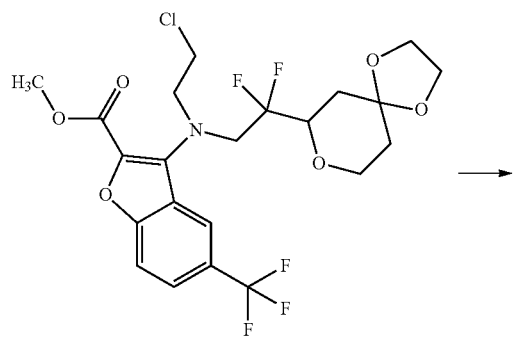

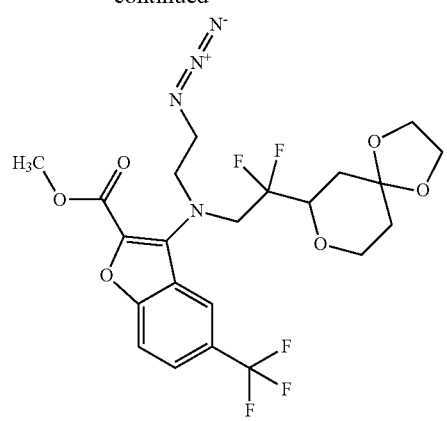

To a solution of methyl 3-((2-chloroethyl) (2,2-difluoro-2-(1,4,8-trioxaspiro[4,5]decan-7-yl)ethyl)amino)-5-0.5 (trifluoromethyl)benzofuran-2-carboxylate (8.5 g, 16.10 mmol) obtained by the same reaction as (12) in N,N-dimethylformamide (85 mL) were added potassium azide (2.61 g, 32.2 mmol) and sodium iodide (0.483 g, 3.22 mmol), and the mixture was stirred at 80° C. for 4 hr. The reaction solution was cooled to room temperature, water was added thereto, and the mixture was extracted with ethyl acetate. The organic layer was washed with water and saturated brine, dried over sodium sulfate, and concentrated under reduced pressure to give the title compound (8.6 g, yield 100%).

$^1$H-NMR (DMSO-D$_6$) δ: 1.45-1.67 (4H, m), 3.09 (1H, td, J=11.8, 2.6 Hz), 3.40-3.52 (2H, m), 3.57-3.70 (3H, m), 3.78-4.09 (10H, m), 7.87 (1H, dd, J=8.9, 1.7 Hz), 7.91 (1H, d, J=8.9 Hz), 8.19 (1H, br s).

(14) 1-(2,2-difluoro-2-(1,4,8-trioxaspiro[4,5]decan-7-yl)ethyl)-9-(trifluoromethyl)-1,2,3,4-tetrahydro-5H-benzofuro[3,2-e] [1,4]diazepin-5-one

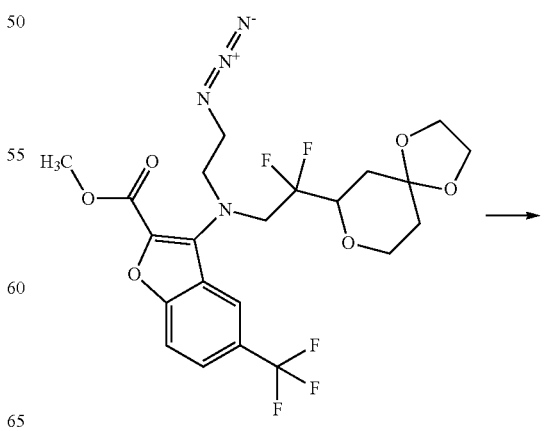

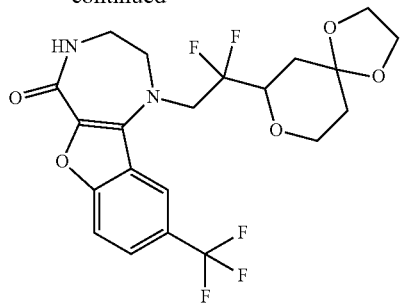

To a solution of methyl 3-((2-azidoethyl) (2,2-difluoro-2-(1,4,8-trioxaspiro[4,5]decan-7-yl)ethyl)amino)-5-(trifluoromethyl)benzofuran-2-carboxylate (8.60 g, 16.1 mmol) obtained in (13) in water (8.6 mL) and 1,2-dimethoxyethane (86 mL) was added triphenylphosphine (5.07 g, 19.32 mmol), and the mixture was stirred at 80° C. for 8 hr. The reaction solution was concentrated under reduced pressure, and to the obtained residue were added hexane/ethyl acetate=1/1 (34 mL). The mixture was stirred for 1 hr, and the resulting solid was collected by filtration. To the obtained solid was added ethyl acetate (34 mL), and the mixture was stirred for 1 hr. The precipitated solid was collected by filtration, and dried under reduced pressure to give the title compound (4.5 g, yield 53%).

$^1$H-NMR (DMSO-D$_6$) δ: 1.61-1.85 (4H, m), 3.29-3.41 (2H, m), 3.47-3.61 (3H, m), 3.81-4.33 (8H, m), 7.76-7.79 (2H, m), 8.08 (1H, t, J=5.0 Hz), 8.32 (1H, br s).

(15) 1-(2,2-difluoro-2-(4-oxotetrahydro-2H-pyran-2-yl)ethyl)-9-(trifluoromethyl)-1,2,3,4-tetrahydro-5H-benzofuro[3,2-e][1,4]diazepin-5-one

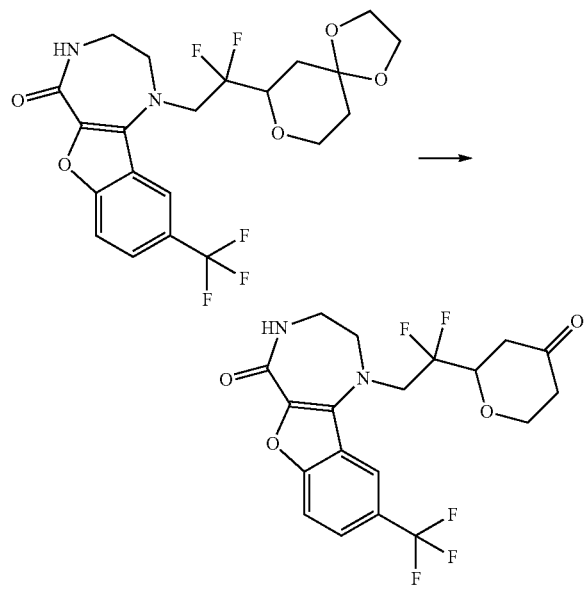

To a solution of 1-(2,2-difluoro-2-(1,4,8-trioxaspiro[4,5]decan-7-yl)ethyl)-9-(trifluoromethyl)-1,2,3,4-tetrahydro-5H-benzofuro[3,2-e][1,4]diazepin-5-one (0.452 g, 0.949 mmol) obtained in (14) in acetic acid (3.6 mL) was added 2N hydrochloric acid (0.904 mL, 1.808 mmol), and the mixture was stirred at 80° C. for 3 hr. The mixture was cooled to room temperature, and slowly diluted with ethyl acetate and water, and 10l aqueous sodium carbonate solution was slowly added dropwise thereto. The mixture was separated, and the aqueous layer was re-extracted with ethyl acetate. The organic layer was washed with water and saturated brine, dried over sodium sulfate, and concentrated under reduced pressure. To the residue was added ethanol (4 mL), and the mixture was stirred for 1 hr. The precipitated solid was collected by filtration, and dried under reduced pressure to give the title compound (0.304 g, yield 74%).

$^1$H-NMR (DMSO-D$_6$) δ: 2.27 (1H, d, J=15.3 Hz), 2.38 (1H, d, J=14.3 Hz), 2.60-2.73 (2H, m), 3.28-3.62 (4H, m), 3.78 (1H, td, J=11.7, 2.8 Hz), 4.07-4.39 (4H, m), 7.75-7.84 (2H, m), 8.11 (1H, t, J=5.0 Hz), 8.34 (1H, br s).

(16) 1-(2,2-difluoro-2-(4-hydroxy-4-methyltetrahydro-2H-pyran-2-yl)ethyl)-9-(trifluoromethyl)-1,2,3,4-tetrahydro-5H-benzofuro[3,2-e][1,4]diazepin-5-one

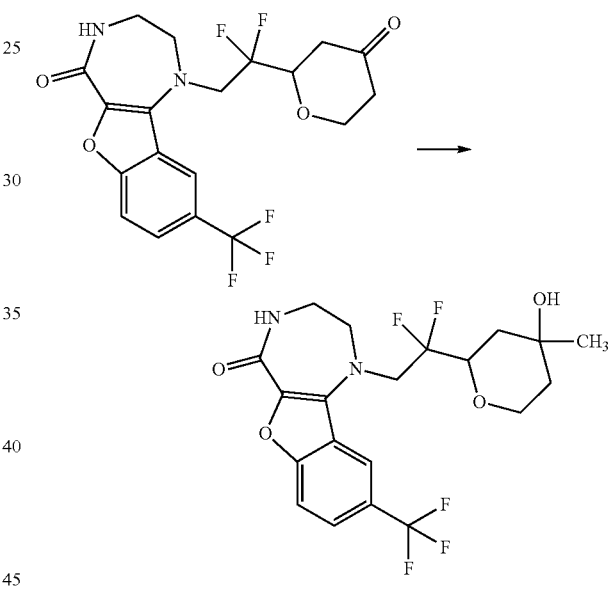

Under argon atmosphere and ice-cooling, to a suspension of 1-(2,2-difluoro-2-(4-oxotetrahydro-2H-pyran-2-yl)ethyl)-9-(trifluoromethyl)-1,2,3,4-tetrahydro-5H-benzofuro[3,2-e][1,4]diazepin-5-one (0.925 g, 1.879 mmol) obtained by the same reaction as (15) in tetrahydrofuran (37 mL) was added dropwise 3.0M methylmagnesium chloride-tetrahydrofuran solution (2.25 mL, 6.76 mmol), and the mixture was stirred for 2 hr. Under ice-cooling, to the reaction solution was added dropwise 10% aqueous ammonium chloride solution (50 mL), and the mixture was extracted three times with ethyl acetate. The organic layers were combined, washed with saturated aqueous sodium hydrogencarbonate solution and saturated brine, dried over sodium sulfate, and concentrated under reduced pressure. The residue was purified by silica gel column chromatography (eluent: chloroform/methanol=9/1), followed by preparative thin layer chromatography (eluent: chloroform/methanol=9/1). The fraction was concentrated under reduced pressure, and the obtained residue was purified by reverse-phase liquid chromatography (column: XTERRA PrepMS C18 OBD™ 5 μm, 30×50 mm Column, mobile phase: water (0.15 trifluoroacetic acid)/acetonitrile (0.1% trifluoroacetic acid)) to give a racemate (0.205 g, yield 24%, the compound of Example 12) wherein the relative configuration of the substituents on the tetrahydropyran ring is cis configuration, and a racemate (0.272 g, yield 32%, the compound of Example 11) wherein the relative configuration of the substituents on the tetrahydropyran ring is trans configuration. The racemate (0.205 g) wherein the relative configuration of the substituents on the tetrahydropyran ring is cis configuration was subjected to an optical resolution with supercritical fluid chromatography (apparatus: Waters SFC Prep15 System, column: Daicel CHIRALPAK IG/SFC, 10 mm (I.D.)×250 mm (L), 5 μm, column temperature: 40° C., column backpressure: 120 bar, mobile phase flow rate: 15 mL/min, mobile phase mixed ratio: isocratic, carbon dioxide/methanol=85/15, fraction trigger: IV 214 nm) to give the compound of Example 58 (0.086 g) as the first peak fraction (10.0-11.9 min), and the compound of Example 59 (0.085 g) as the second peak fraction (12.3-14.8 min). The racemate (0.136 g) wherein the relative configuration of the substituents on the tetrahydropyran ring is trans configuration was subjected to an optical resolution with supercritical fluid chromatography (apparatus: Waters SFC Prep15 System, column: Daicel CHIRALPAK IF/SFC, 10 mm (I.D.)× 250 mm (L), 5 μm, column temperature: 40° C., column backpressure: 120 bar, mobile phase flow rate: 15 mL/min, mobile phase mixed ratio: gradient, carbon dioxide/(methanol/acetonitrile=10/90)=60/40 (0 min)-60/40 (10 min)-50/50 (10.5 min)-50/50 (15 min), fraction trigger: UV 254 nm) to give the compound of Example 66 (0.043 g) as the first peak fraction (7.9-10.4 min), and the compound of Example 67 (0.043 g) as the second peak fraction (11.0-13.7 min).

Example 12, Example 58, and Example 59

$^1$H-NMR (DMSO-D$_6$) δ: 1.23 (3H, s), 1.47-1.68 (4H, m), 3.30-3.43 (2H, m), 3.45-3.60 (3H, m), 3.73-3.85 (1H, m), 3.91 (1H, dd, J=11.6, 4.3 Hz), 3.97-4.13 (1H, m), 4.16-4.32 (1H, m), 4.78 (1H, br s), 7.76-7.79 (2H, m), 8.08 (1H, t, J=5.0 Hz), 8.34 (1H, br s).

Example 11, Example 66, and Example 67

$^1$H-NMR (DMSO-D$_6$) δ: 1.19 (3H, s), 1.38-1.66 (4H, m), 3.27-3.41 (2H, m), 3.45-3.61 (2H, m), 3.66-3.80 (2H, m), 3.93-4.31 (3H, m), 4.53 (1H, s), 7.78 (2H, br s), 8.07 (1H, t, J=5.0 Hz), 8.34 (1H, br s).

[Production Example 2]: Synthesis of 1-(2,2-difluoro-2-((2R,5R)-5-(hydroxymethyl)-1,4-dioxan-2-yl)ethyl)-9-(trifluoromethyl)-1,2,3,4-tetrahydro-5H-benzofuro[3,2-e][1,4]diazepin-5-one (Example 95), and 1-(2,2-difluoro-2-((2S,5S)-5-(hydroxymethyl)-1,4-dioxan-2-yl)ethyl)-9-(trifluoromethyl)-1,2,3,4-tetrahydro-5H-benzofuro[3,2-e] [1,4]diazepin-5-one (Example 77)

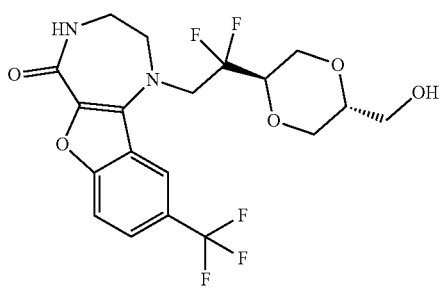

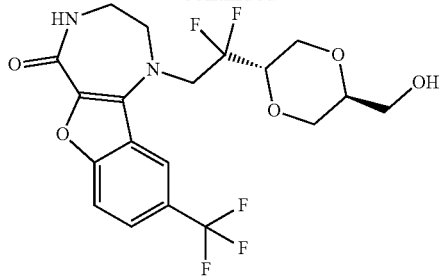

(1) methyl (S)-3,4-dihydroxybutanoate

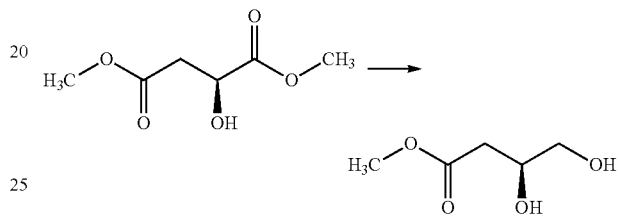

Under ice-cooling, to a solution of dimethyl (S)-2-hydroxysuccinate (35 g, 216 mmol) in tetrahydrofuran (350 mL) was added dropwise borane-dimethyl sulfide complex (26.6 mL, 281 mol), and the mixture was stirred for 1 hr. Sodium borohydride (0.204 g, 5.40 mmol) was added thereto, and the mixture was stirred for 2 hr. Sodium borohydride (0.204 g, 5.40 mmol) was added thereto, and the mixture was stirred for additional 30 min. To the reaction solution was added dropwise methanol (140 mL), and the mixture was stirred for 15 min, and concentrated under azeotrope with toluene and methanol and under reduced pressure to give the title compound (29.9 g, yield 103%).

$^1$H-NMR (DMSO-D$_6$) δ: 2.22 (1H, dd, J=15.0, 8.8 Hz), 2.52 (1H, dd, J=14.9, 4.0 Hz), 3.18-3.23 (1H, m), 3.31-3.37 (1H, m), 3.58 (3H, s), 3.83 (1H, ddd, J=9.7, 5.1, 3.3 Hz), 4.63 (1H, t, J=5.8 Hz), 4.78 (1H, d, J=5.3 Hz).

(2) methyl (S)-4-((tert-butyldiphenylsilyl)oxy)-3-hydroxybutanoate

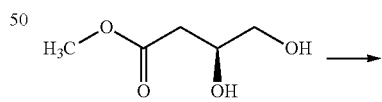

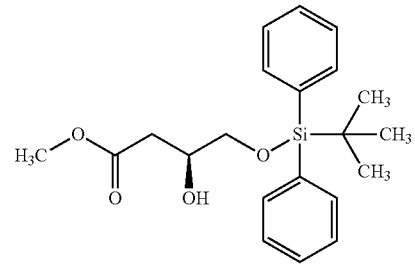

Under ice-cooling, to a solution of methyl (S)-3,4-dihydroxybutanoate (29.6 g, 207 mmol) obtained in (1), and imidazole (31.1 g, 456 mmol) in N,N-dimethylformamide (223 mL) was added dropwise tert-butyldiphenylchlorosilane (58.6 mL, 228 mmol), and the mixture was stirred at room temperature for 5 hr. To the reaction solution was added water, and the mixture was extracted with hexane/ethyl acetate=1/3. The organic layer was washed with water and saturated brine, dried over sodium sulfate, and concentrated under reduced pressure. The residue was purified by silica gel column chromatography (eluent: hexane/ethyl acetate=96/4 to 60/40) to give the title compound (65.6 g, yield 85%).

$^1$H-NMR (DMSO-D$_6$) δ: 0.99 (9H, s), 2.35 (1H, dd, J=15.0, 8.3 Hz), 2.64 (1H, dd, J=15.0, 4.6 Hz), 3.48 (1H, dd, J=9.9, 6.5 Hz), 3.59 (3H, s), 3.60-3.61 (1H, m), 3.99-4.02 (1H, m), 4.99 (1H, d, J=5.5 Hz), 7.44-7.47 (6H, m), 7.62-7.63 (4H, m).

(3) methyl (S)-3-(allyloxy)-4-((tert-butyldiphenylsilyl)oxy)butanoate

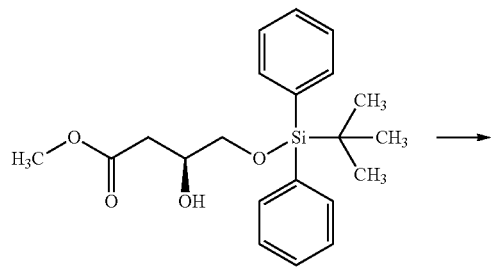

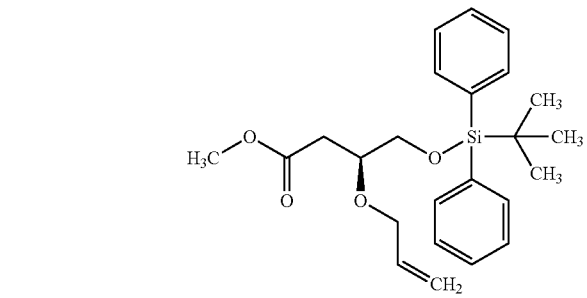

To a solution of methyl (S)-4-((tert-butyldiphenylsilyl)oxy)-3-hydroxybutanoate (65.6 g, 176 mmol) obtained in (2), and allyl 2,2,2-trichloroacetimidate (37.2 mL, 247 mmol) in cyclohexane (328 mL) was added trifluoromethanesulfonic acid (1.24 mL, 14.1 mmol), and the mixture was stirred at room temperature for 3 days. To the reaction solution was added hexane, the insoluble substance was removed by filtration, and the filtrate was concentrated under reduced pressure. The residue was purified by silica gel column chromatography (eluent: hexane/ethyl acetate=97/3 to 70/30) to give the title compound (61.1 g, yield 84%).

$^1$H-NMR (DMSO-D$_6$) δ: 0.99 (9H, s), 2.53 (1H, dd, J=15.5, 7.6 Hz), 2.64 (1H, dd, J=15.5, 5.3 Hz), 3.59 (3H, s), 3.66-3.67 (2H, m), 3.84-3.86 (1H, m), 3.92-4.06 (2H, m), 5.09 (1H, dq, J=10.4, 1.6 Hz), 5.19 (1H, dq, J=17.2, 1.8 Hz), 5.76-5.86 (1H, m), 7.41-7.50 (6H, m), 7.60-7.65 (4H, m).

(4) methyl (S)-3-(allyloxy)-4-hydroxybutanoate

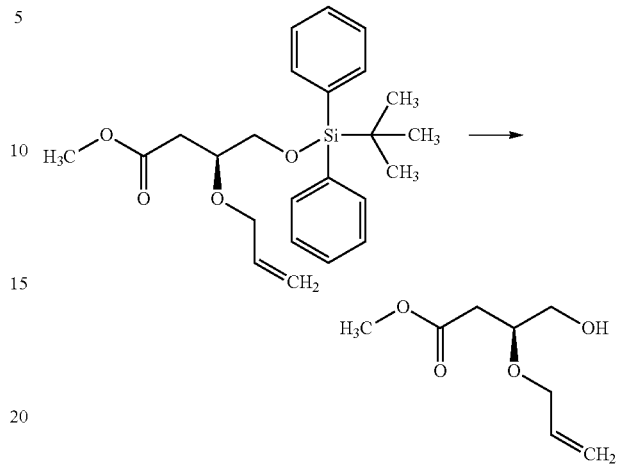

Under ice-cooling, to a mixed solution of methyl (S)-3-(allyloxy)-4-((tert-butyldiphenylsilyl)oxy)butanoate (6.9 g, 16.7 mmol) obtained by the same reaction as (3) in acetic acid (0.956 mL, 16.7 mmol) and tetrahydrofuran (35 mL) was added 1M tetrabutylammonium fluoride-tetrahydrofuran solution (20.1 mL, 20.1 mmol), and the mixture was stirred for 4 hr. The same operation was performed using methyl (S)-3-(allyloxy)-4-((tert-butyldiphenylsilyl)oxy)butanoate (61.1 g, 148 mmol) obtained in (3), and these reaction solutions were combined. To the reaction solution was added water (400 mL), and the mixture was extracted with ethyl acetate (400 mL). The aqueous layer was re-extracted with ethyl acetate (200 mL). The organic layers were combined, washed with saturated brine, dried over sodium sulfate, and concentrated under reduced pressure. The residue was purified by silica gel column chromatography (eluent: hexane/ethyl acetate=82/18 to 20/80) to give the title compound (24.6 g, yield 86%).

$^1$H-NMR (DMSO-D$_6$) δ: 2.40 (1H, dd, J=15.5, 8.1 Hz), 2.56 (1H, dd, J=15.5, 4.6 Hz), 3.36-3.38 (1H, m), 3.44-3.47 (1H, m), 3.59 (3H, s), 3.69-3.72 (1H, m), 3.96 (1H, ddt, J=13.2, 5.3, 1.8 Hz), 4.02-4.08 (1H, m), 4.71-4.74 (1H, br m), 5.09 (1H, dq, J=10.4, 1.6 Hz), 5.21 (1H, dq, J=17.2, 1.8 Hz), 5.78-5.88 (1H, m).

(5) methyl 2-((2S)-5-(iodomethyl)-1,4-dioxan-2-yl)acetate

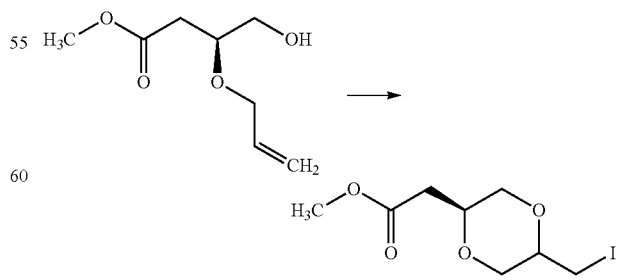

Under ice-cooling, to a solution of methyl (S)-3-(allyloxy)-4-hydroxybutanoate (24.6 g, 141 mmol) obtained in (4) in acetonitrile (738 mL) was added N-iodosuccinimide (47.7 g, 212 mmol), and the mixture was stirred at room temperature for 2 days. To the reaction solution was added an aqueous solution (400 mL) of sodium hydrogen sulfite (14.7 g, 141 mmol), and the mixture was stirred for 30 min. To the reaction solution was added water (400 mL), and the mixture was extracted with ethyl acetate (800 mL). The organic layer was washed with saturated brine, dried over sodium sulfate, and concentrated under reduced pressure. The residue was purified by silica gel column chromatography (eluent: hexane/ethyl acetate=95/5 to hexane/ethyl acetate/methanol=60/40/2) to give the title compound (16.0 g, yield 42%).

$^1$H-NMR (DMSO-D$_6$) δ: 2.34 (0.33H, td, J=14.1, 7.5 Hz), 2.46-2.49 (0.33H, m), 2.58-2.65 (1.34H, m), 3.10 (0.33H, dd, J=10.6, 6.9 Hz), 3.23-3.26 (0.66H, m), 3.40-3.43 (1.67H, m), 3.56-3.61 (5.01H, m), 3.65-3.84 (2H, m), 3.86-3.95 (1H, m), 4.00-4.06 (0.33H, m).

(6) ((5S)-5-(2-methoxy-2-oxoethyl)-1,4-dioxan-2-yl)methyl 4-nitrobenzoate

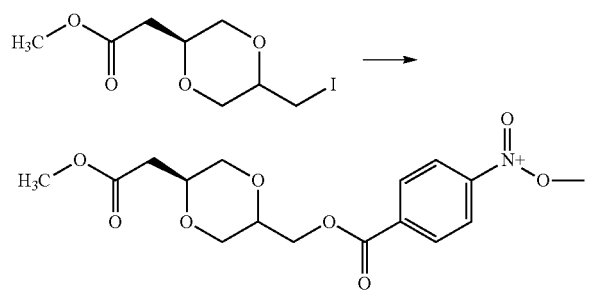

To a solution of methyl 2-((2S)-5-(iodomethyl)-1,4-dioxan-2-yl)acetate (16.0 g, 53.3 mmol) obtained in (5) in dimethyl sulfoxide (112 mL) were added potassium 4-nitrobenzoate (32.8 g, 160 mmol) and 18-crown-6 (1.41 g, 5.33 mmol), and the mixture was stirred at 90° C. for 3 hr. At room temperature, to the reaction solution was added water, and the mixture was extracted with ethyl acetate. The aqueous layer was re-extracted with ethyl acetate. The organic layers were combined, washed with water, saturated aqueous sodium hydrogencarbonate solution and saturated brine, dried over sodium sulfate, and concentrated under reduced pressure to give the title compound (18.9 g, yield 104%).

$^1$H-NMR (DMSO-D$_6$) δ: 2.35 (0.5H, dd, J=15.8, 8.0 Hz), 2.52-2.54 (0.5H, m), 2.62 (1H, dd, J=6.8, 2.7 Hz), 3.34-3.36 (0.5H, m), 3.49 (0.5H, dd, J=11.2, 10.5 Hz), 3.60-3.61 (3.5H, m), 3.65-3.88 (2.5H, m), 3.92-3.95 (1.5H, m), 3.99-4.25 (0.5H, m), 4.27-4.42 (1.5H, m), 4.66 (0.5H, dd, J=11.7, 7.5 Hz), 8.19-8.22 (2H, m), 8.35-8.37 (2H, m).

(7) methyl 2-((2S)-5-(hydroxymethyl)-1,4-dioxan-2-yl)acetate

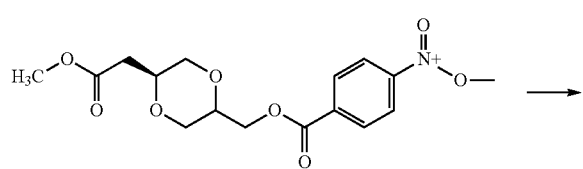

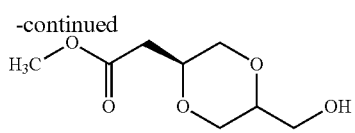

To a solution of ((5S)-5-(2-methoxy-2-oxoethyl)-1,4-dioxan-2-yl)methyl 4-nitrobenzoate (18.9 g, 55.7 mmol) obtained in (6) in methanol (189 mL) was added potassium carbonate (30.8 g, 223 mmol), and the mixture was stirred at room temperature for 17 hr. To the reaction solution was added water, and the mixture was extracted with ethyl acetate. The aqueous layer was re-extracted with ethyl acetate. The organic layers were combined, dried over sodium sulfate, and concentrated under reduced pressure. The residue was extracted twice with ethyl acetate, and the organic layer were combined, dried over sodium sulfate, and concentrated under reduced pressure to give the title compound (5.4 g, yield 51%).

$^1$H-NMR (DMSO-D$_6$) δ: 2.32 (0.5H, dd, J=15.7, 7.9 Hz), 2.45-2.48 (0.5H, m), 2.60-2.64 (1H, m), 3.22-3.30 (2H, m), 3.37-3.55 (2H, m), 3.58-3.60 (4H, m), 3.75-3.79 (2.5H, m), 3.90-3.91 (0.5H, m), 4.69-4.71 (1H, m).

(8) methyl 2-((2S)-5-(((tert-butyldiphenylsilyl)oxy)methyl)-1,4-dioxan-2-yl)acetate

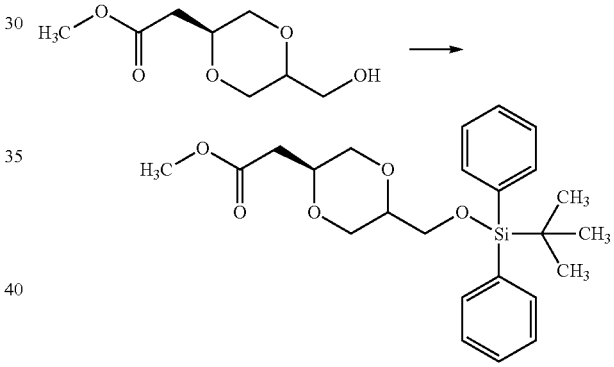

Under ice-cooling, to a solution of methyl 2-((2S)-5-(hydroxymethyl)-1,4-dioxan-2-yl)acetate (5.38 g, 28.3 mmol) obtained in (7), and imidazole (4.24 g, 62.2 mmol) in N,N-dimethylformamide (43 mL) was added dropwise tert-butyldiphenylchlorosilane (8.0 mL, 31.1 mmol), and the mixture was stirred at room temperature for 18 hr. Imidazole (0.4 g, 5.9 mmol) and tert-butyldiphenylchlorosilane (0.73 mL, 2.8 mmol) were added again thereto, and the mixture was stirred for additional 2 hr. To the reaction solution was added water, and the mixture was extracted with ethyl acetate. The aqueous layer was re-extracted with ethyl acetate. The organic layers were combined, washed with water and saturated brine, dried over sodium sulfate, and concentrated under reduced pressure. The residue was purified by silica gel column chromatography (eluent: hexane/ethyl acetate=97/3 to 75/25) to give the title compound (5.8 g, yield 48%).

$^1$H-NMR (DMSO-D$_6$) δ: 0.99-1.00 (9H, m), 2.33 (0.6H, dd, J=15.8, 8.0 Hz), 2.45-2.47 (0.6H, m), 2.58-2.62 (0.8H, m), 3.27 (0.6H, t, J=11.6 Hz), 3.39 (0.6H, t, J=11.3 Hz), 3.47 (0.4H, dd, J=11.8, 5.3 Hz), 3.54-3.66 (5.8H, m), 3.74-3.84 (3.2H, m), 3.90-3.93 (0.4H, m), 7.39-7.51 (6H, m), 7.58-7.66 (4H, m).

(9) methyl 2-(5-(((tert-butyldiphenylsilyl)oxy)methyl)-1,4-dioxan-2-yl)-2,2-difluoroacetate (Trans Isomer and Cis Isomer)

(10) 2-(5-(((tert-butyldiphenylsilyl)oxy)methyl)-1,4-dioxan-2-yl)-2,2-difluoroethan-1-ol (Trans Isomer)

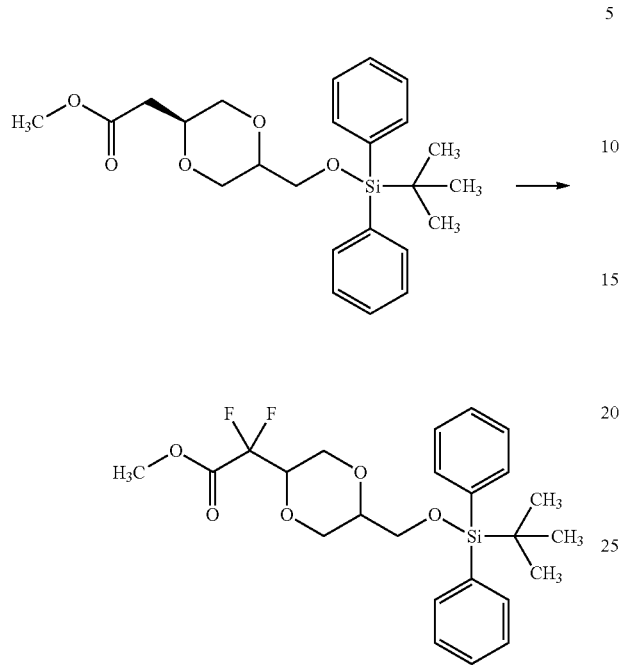

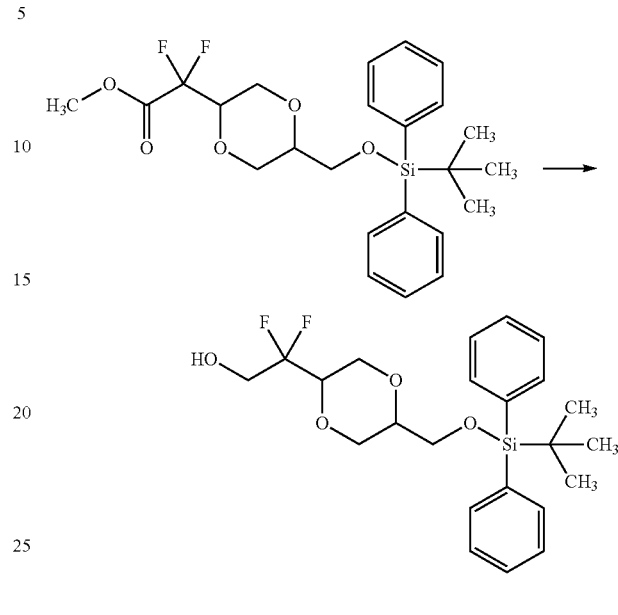

To methyl 2-((2S)-5-(((tert-butyldiphenylsilyl)oxy)methyl)-1,4-dioxan-2-yl)acetate (5.82 g, 13.6 mmol) obtained in (8) was added toluene, and the mixture was concentrated under reduced pressure. To the residue was added a mixed solvent of toluene (29 mL)-tetrahydrofuran (116 mL), and N-fluorobenzenesulfonimide (17.1 g, 54.3 mmol) was added thereto under ice-cooling, and the mixture was cooled to −78° C. 1M Sodium bistrimethylsilylamide-tetrahydrofuran solution (47.5 mL, 47.5 mmol) was added dropwise thereto, and the mixture was gradually warmed over 30 min. To the reaction solution was added dropwise triethylamine (15.1 mL, 109 mmol) at −10° C. To the reaction solution was added water, and the mixture was extracted with ethyl acetate. The aqueous layer was re-extracted with ethyl acetate. The organic layers were combined, and washed with saturated aqueous sodium hydrogencarbonate solution and saturated brine. To the organic layer were added sodium sulfate and silica gel, and the mixture was stirred. The insoluble substance was removed by filtration through Celite, and the filtrate was concentrated under reduced pressure. The residue was purified by silica gel column chromatography (eluent: hexane/ethyl acetate=97/3 to 80/20) to give the title compound (3.2 g, yield 51%) as a trans isomer, and the title compound (1.8 g, yield 29%) as a cis isomer.

trans isomer:

$^1$H-NMR (DMSO-D$_6$) δ: 0.98 (9H, s), 3.49 (1H, dd, J=11.1, 9.9 Hz), 3.56-3.66 (4H, m), 3.86 (3H, s), 3.93-4.01 (2H, m), 4.02-4.09 (1H, m), 7.40-7.48 (6H, m), 7.60-7.61 (4H, m).

cis isomer:

$^1$H-NMR (DMSO-D) δ: 1.00 (9H, s), 3.72-3.77 (5H, m), 3.80-3.92 (5H, m), 4.06-4.15 (1H, m), 7.42-7.50 (6H, m), 7.62-7.63 (4H, m).

Under ice-cooling, to a suspension of lithium aluminium hydride (0.288 g, 7.58 mmol) in tetrahydrofuran (16 mL) was added dropwise a solution of the trans isomer of methyl 2-(5-(((tert-butyldiphenylsilyl)oxy)methyl)-1,4-dioxan-2-yl)-2,2-difluoroacetate (3.2 g, 6.89 mmol) obtained in (9) in tetrahydrofuran (4.8 mL), and the mixture was stirred for 30 min. To the reaction solution was successively added dropwise water (0.288 mL), 4N aqueous sodium hydroxide solution (0.288 mL) and water (0.864 mL), and the mixture was stirred for 2.5 hr. The insoluble substance was removed by filtration through Celite, and the filtrate was concentrated under reduced pressure to give the title compound (3.1 g, yield 103%). The relative configuration of the compound was determined by NOESY measurement of the compound synthesized by the same method.

$^1$H-NMR (DMSO-D$_6$) δ: 1.00 (9H, s), 3.48 (1H, t, J=10.6 Hz), 3.55-3.70 (6H, m), 3.84-3.88 (1H, m), 3.93 (2H, t, J=11.3 Hz), 5.55 (1H, t, J=6.4 Hz), 7.42-7.50 (6H, m), 7.62-7.63 (4H, m).

(11) 2-(5-(((tert-butyldiphenylsilyl)oxy)methyl)-1,4-dioxan-2-yl)-2,2-difluoroethyl trifluoromethanesulfonate (Trans Isomer)

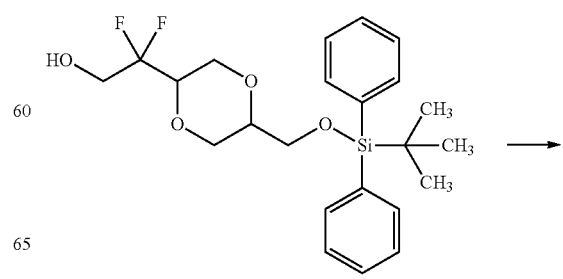

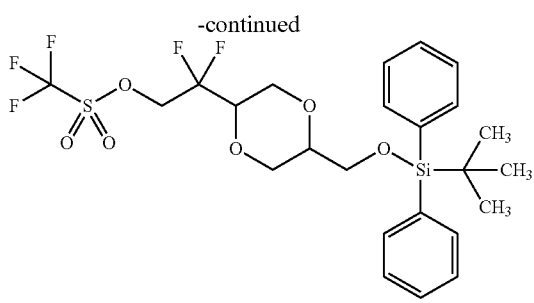

Under ice-cooling, to a solution of 2-(5-(((tert-butyldiphenylsilyl)oxy)methyl)-1,4-dioxan-2-yl)-2,2-difluoroethan-1-ol (3.1 g, 7.03 mmol) obtained in (10), and triethylamine (1.47 mL, 10.55 mmol) in dichloromethane (31 mL) was added dropwise trifluoromethanesulfonyl chloride (1.12 mL, 10.55 mmol), and the mixture was stirred at room temperature for 2 hr. To the reaction solution was added water, and the mixture was extracted with chloroform. The organic layer was washed with saturated brine, dried over sodium sulfate, and concentrated under reduced pressure to give the title compound (4.14 g, yield 104%).

$^1$H-NMR (DMSO-d$_6$) δ: 1.00 (9H, s), 3.52 (1H, t, J=10.5 Hz), 3.63-3.66 (4H, m), 3.97-4.03 (3H, m), 5.13-5.18 (2H, m), 7.43-7.48 (6H, m), 7.61-7.62 (4H, m).

(12) ((5-(2-azido-1,1-difluoroethyl)-1,4-dioxan-2-yl)methoxy) (tert-butyl)diphenylsilane (Trans Isomer)

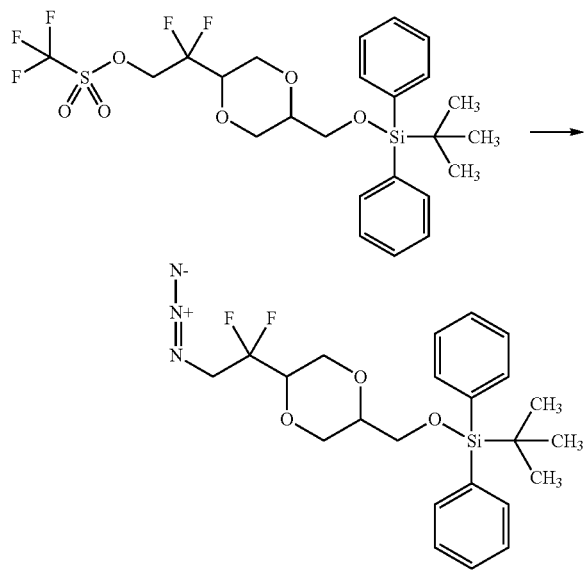

To a solution of 2-(5-(((tert-butyldiphenylsilyl)oxy)methyl)-1,4-dioxan-2-yl)-2,2-difluoroethyl trifluoromethanesulfonate (4.14 g, 7.28 mmol) obtained in (11) in N,N-dimethylformamide (33 mL) was added potassium azide (0.886 g, 10.92 mmol), and the mixture was stirred at room temperature for 1 hr. To the reaction solution was added water, and the mixture was extracted with ethyl acetate. The organic layer was washed with water and saturated brine, dried over sodium sulfate, and concentrated under reduced pressure to give the title compound (3.27 g, yield 97%).

$^1$H-NMR (DMSO-D$_6$) δ: 0.99 (9H, s), 3.49-3.54 (1H, m), 3.58-3.68 (4H, m), 3.80-3.97 (5H, m), 7.44-7.47 (6H, m), 7.61-7.63 (4H, m).

(13) 2-(5-(((tert-butyldiphenylsilyl)oxy)methyl)-1,4-dioxan-2-yl)-2,2-difluoroethan-1-amine (Trans Isomer)

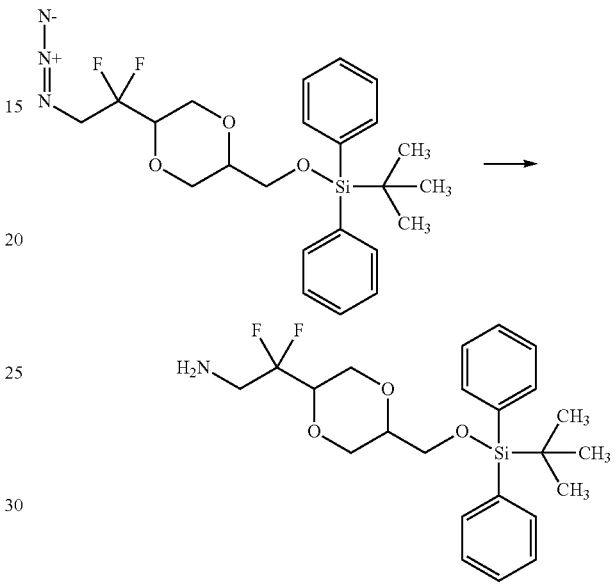

To a mixed solution of ((5-(2-azido-1,1-difluoroethyl)-1,4-dioxan-2-yl)methoxy) (tert-butyl)diphenylsilane (3.27 g, 7.08 mmol) obtained in (12) in tetrahydrofuran (16.4 mL) and methanol (16.4 mL) was added 10% palladium on carbon (0.654 g), and the mixture was stirred under normal pressure of hydrogen at room temperature for 3 hr. The insoluble substance was removed by filtration through Celite, and the filtrate was concentrated under reduced pressure to give the title compound (2.9 g, yield 95%).

$^1$H-NMR (DMSO-D$_6$) δ: 1.00 (9H, s), 2.18 (2H, br s), 2.90-2.96 (2H, m), 3.47-3.67 (5H, m), 3.91-3.96 (3H, m), 7.42-7.50 (6H, m), 7.61-7.63 (4H, m).

(14) methyl 3-((2-(5-(((tert-butyldiphenylsilyl)oxy)methyl)-1,4-dioxan-2-yl)-2,2-difluoroethyl)amino)-5-(trifluoromethyl)benzofuran-2-carboxylate (trans isomer)

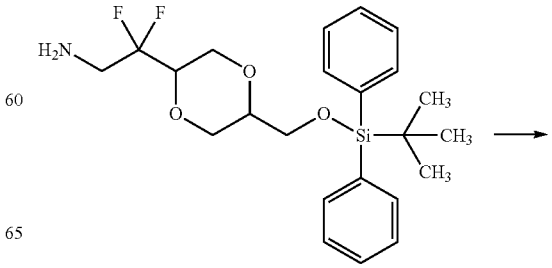

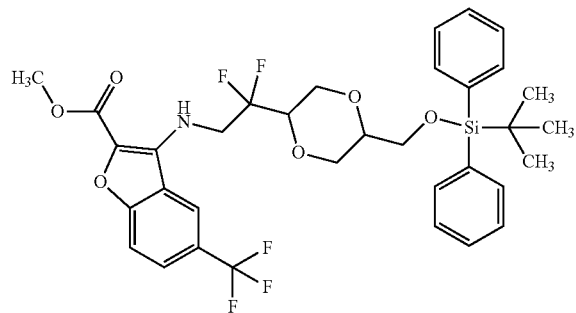

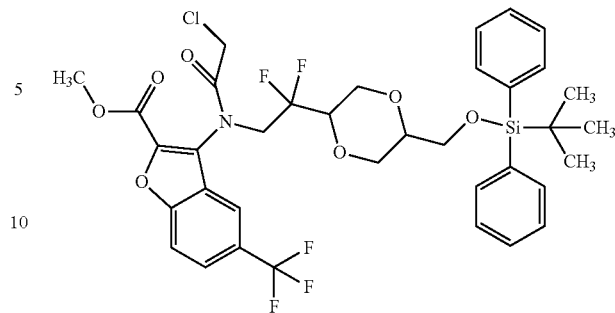

To a solution of 2-(5-(((tert-butyldiphenylsilyl)oxy)methyl)-1,4-dioxan-2-yl)-2,2-difluoroethan-1-amine (2.92 g, 6.70 mmol) obtained in (13) in N,N-dimethylformamide (29 mL) was added 2-hydroxy-5-(trifluoromethyl)benzaldehyde (1.21 g, 6.38 mmol), and the mixture was stirred at room temperature for 1.5 hr. Potassium carbonate (2.65 g, 19.15 mmol) and methyl 2,2-dichloroacetate (0.794 mL, 7.66 mmol) were added thereto, and the mixture was stirred at room temperature for 17 hr. To the reaction solution was added water, and the mixture was extracted with ethyl acetate. The organic layer was washed with water and saturated brine, dried over sodium sulfate, and concentrated under reduced pressure. To the residue were added hexane/ethyl acetate=5/1, and the mixture was stirred for 1 hr. The precipitated solid was collected by filtration, and dried under reduced pressure to give the title compound (1.35 g, yield 313). Moreover, the filtrate was concentrated under reduced pressure, and the residue was purified by silica gel column chromatography (eluent: hexane/ethyl acetate=95/5 to 75/25) to give the title compound (1.0 g, yield 23%).

$^1$H-NMR (DMSO-D$_6$) δ: 0.98 (9H, s), 3.42 (1H, t, J=10.8 Hz), 3.57-3.68 (4H, m), 3.86 (3H, s), 3.91-3.94 (3H, m), 4.22-4.24 (2H, m), 6.73 (1H, t, J=7.3 Hz), 7.41-7.50 (6H, m), 7.59-7.61 (4H, m), 7.78 (1H, d, J=8.8 Hz), 7.86 (1H, dd, J=9.0, 1.6 Hz), 8.48 (1H, s).

(15) methyl 3-(N-(2-(-5-(((tert-butyldiphenylsilyl)oxy)methyl)-1,4-dioxan-2-yl)-2,2-difluoroethyl)-2-chloroacetamido)-5-(trifluoromethyl)benzofuran-2-carboxylate (trans isomer)

To a solution of methyl 3-((2-(5-(((tert-butyldiphenylsilyl)oxy)methyl)-1,4-dioxan-2-yl)-2,2-difluoroethyl)amino)-5-(trifluoromethyl)benzofuran-2-carboxylate (2.35 g, 3.47 mmol) obtained in (14), and N,N-dimethylaniline (1.76 mL, 13.87 mmol) in dichloromethane (24 mL) was added dropwise chloroacetyl chloride (0.833 mL, 10.4 mmol), and the mixture was stirred at room temperature for 16 hr. To the reaction solution were again added N,N-dimethylaniline (0.85 mL, 6.94 mmol) and chloroacetyl chloride (0.4 mL, 5.2 mmol), and the mixture was stirred at room temperature for additional 4 hr. Chloroacetyl chloride (0.2 mL, 2.6 mmol) was added again thereto, and the mixture was stirred at room temperature for additional 1 hr. To the reaction solution was added 10% aqueous citric acid, and the mixture was extracted with chloroform. The organic layer was washed with 10% citric acid water and saturated brine, dried over sodium sulfate, and concentrated under reduced pressure. The residue was purified by silica gel column chromatography (eluent: hexane/ethyl acetate=95/5 to 65/35) to give the title compound (2.22 g, yield 85%).

$^1$H-NMR (DMSO-D$_6$) δ: 0.98 (9H, s), 3.40 (1H, dd, J=20.7, 10.5 Hz), 3.49-3.67 (4H, m), 3.87-3.96 (6H, m), 4.06-4.12 (1H, m), 4.22 (1H, dd, J=14.3, 1.4 Hz), 4.33 (1H, dd, J=14.3, 0.9 Hz), 4.50-4.67 (1H, m), 7.41-7.49 (6H, m), 7.60 (4H, dt, J=7.8, 1.5 Hz), 7.94 (1H, dd, J=9.0, 1.8 Hz), 8.05 (1H, d, J=8.8 Hz), 8.23 (1H, s).

(16) methyl 3-((2-(5-(((tert-butyldiphenylsilyl)oxy)methyl)-1,4-dioxan-2-yl)-2,2-difluoroethyl) (2-chloroethyl)amino)-5-(trifluoromethyl)benzofuran-2-carboxylate (trans isomer)

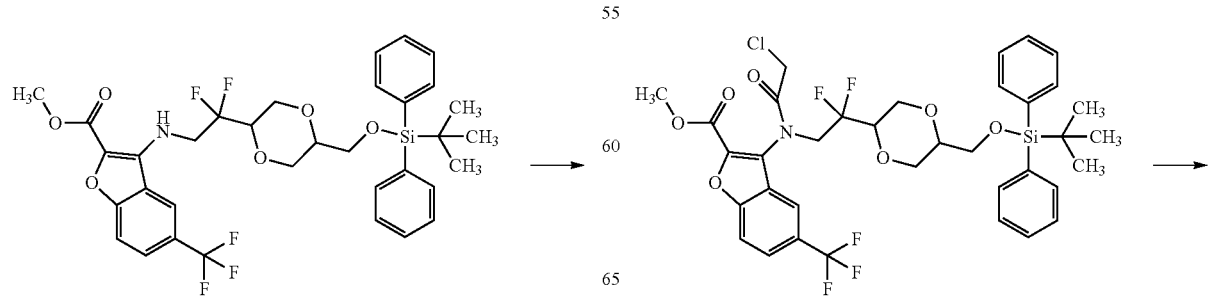

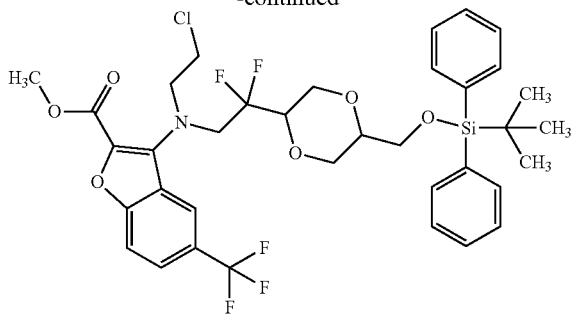

Under ice-cooling, to a solution of methyl 3-(N-(2-(~5-(((tert-butyldiphenylsilyl)oxy)methyl)-1,4-dioxan-2-yl)-2,2-difluoroethyl)-2-chloroacetamido)-5-(trifluoromethyl)benzofuran-2-carboxylate (2.22 g, 2.94 mmol) obtained in (15) in tetrahydrofuran (27 mL) was added dropwise 0.91M borane-tetrahydrofuran complex (9.7 mL, 8.83 mmol), and the mixture was stirred at room temperature for 18 hr. Under ice-cooling, to the reaction solution was added 10% aqueous citric acid, and the mixture was stirred for 5 min, and extracted with ethyl acetate. The aqueous layer was re-extracted with ethyl acetate, and the organic layers were combined, washed with saturated brine, dried over sodium sulfate, and concentrated under reduced pressure. The residue was purified by silica gel column chromatography (eluent: hexane/ethyl acetate=95/5 to 60/40) to give the title compound (1.09 g, yield 50%).

$^1$H-NMR (DMSO-D$_6$) δ: 0.96 (9H, s), 3.20 (1H, t, J=10.2 Hz), 3.49-3.61 (4H, m), 3.69-3.76 (5H, m), 3.92-3.98 (7H, m), 7.41-7.49 (6H, m), 7.57-7.59 (4H, m), 7.89-7.89 (2H, m), 8.24 (1H, s).

(17) methyl 3-((2-azidoethyl) (2-(5-(((tert-butyldiphenylsilyl)oxy)methyl)-1,4-dioxan-2-yl)-2,2-difluoroethyl)amino)-5-(trifluoromethyl)benzofuran-2-carboxylate (Trans Isomer)

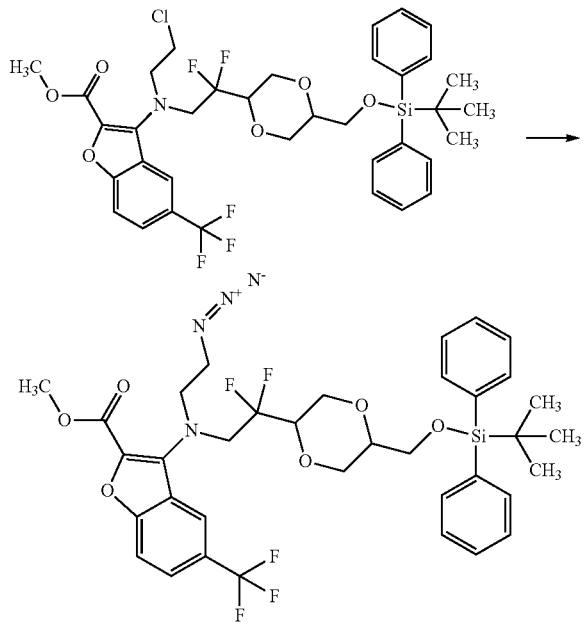

To a solution of methyl 3-((2-(5-(((tert-butyldiphenylsilyl)oxy)methyl)-1,4-dioxan-2-yl)-2,2-difluoroethyl)(2-chloroethyl)amino)-5-(trifluoromethyl)benzofuran-2-carboxylate (1.09 g, 1.473 mmol) obtained in (16) in N,N-dimethylformamide (10.9 mL) were added potassium azide (0.239 g, 2.95 mmol) and sodium iodide (0.044 g, 0.295 mmol), and the mixture was stirred at 80° C. for 1 hr. To the reaction solution was added water at room temperature, and the mixture was extracted with ethyl acetate. The organic layer was washed with water and saturated brine, dried over sodium sulfate, and concentrated under reduced pressure to give the title compound (1.24 g, yield 113%).

$^1$H-NMR (DMSO-d$_6$) δ: 0.96 (9H, s), 3.18 (1H, t, J=10.5 Hz), 3.44-3.73 (10H, m), 3.86-3.89 (5H, m), 3.96-3.98 (1H, m), 7.41-7.49 (6H, m), 7.57-7.59 (4H, m), 7.89-7.89 (2H, m), 8.24 (1H, s).

(18) 1-(2-(5-(((tert-butyldiphenylsilyl)oxy)methyl)-1,4-dioxan-2-yl)-2,2-difluoroethyl)-9-(trifluoromethyl)-1,2,3,4-tetrahydro-5H-benzofuro[3,2-e][1,4]diazepin-5-one (Trans Isomer)

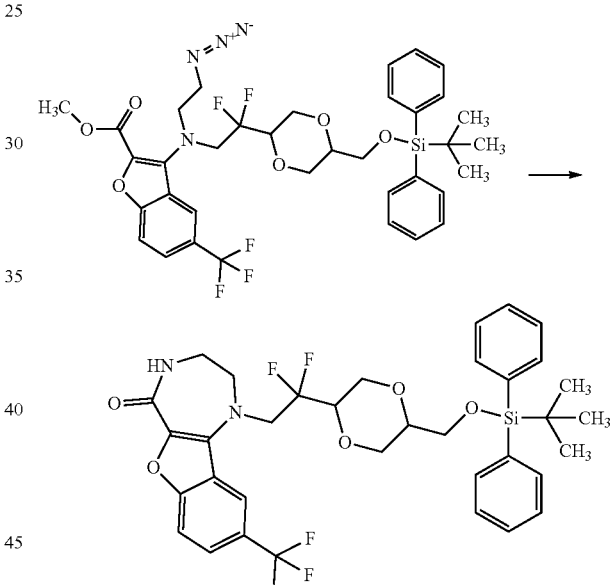

To a mixed solution of methyl 3-((2-azidoethyl) (2-(5-(((tert-butyldiphenylsilyl)oxy)methyl)-1,4-dioxan-2-yl)-2,2-difluoroethyl)amino)-5-(trifluoromethyl)benzofuran-2-carboxylate (1.12 g, 1.500 mmol) obtained in (17) in water (1.12 mL) and 1,2-dimethoxyethane (11.2 mL) was added triphenylphosphine (0.472 g, 1.800 mmol), and the mixture was stirred at 80° C. for 1 hr, and then at 100° C. for additional 1 hr. The reaction solution was concentrated under reduced pressure, to the obtained residue was added ethyl acetate, and the mixture was stirred for 1 hr. The precipitated solid was collected by filtration, and dried under reduced pressure to give the title compound (0.458 g, yield 44%).

$^1$H-NMR (DMSO-D$_6$) δ: 0.98 (9H, s), 3.33-3.35 (2H, m), 3.45-3.53 (3H, m), 3.56-3.61 (1H, m), 3.64-3.70 (3H, m), 3.96-3.99 (3H, m), 4.14-4.21 (2H, m), 7.43-7.46 (6H, m), 7.59-7.61 (4H, m), 7.77-7.78 (2H, m), 8.09 (1H, t, J=4.9 Hz), 8.35 (1H, s).

(19) 1-(2,2-difluoro-2-(5-(hydroxymethyl)-1,4-di-oxan-2-yl)ethyl)-9-(trifluoromethyl)-1,2,3,4-tetrahydro-5H-benzofuro[3,2-e][1,4]diazepin-5-one (Trans Isomer)

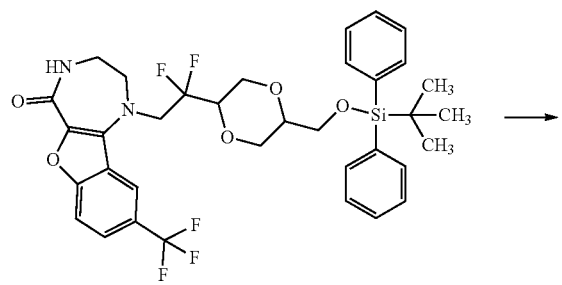

(20) 1-(2,2-difluoro-2-((2R,5R)-5-(hydroxymethyl)-1,4-dioxan-2-yl)ethyl)-9-(trifluoromethyl)-1,2,3,4-tetrahydro-5H-benzofuro[3,2-e] [1,4]diazepin-5-one (Example 95), and 1-(2,2-difluoro-2-((2S,5S)-5-(hydroxymethyl)-1,4-dioxan-2-yl)ethyl)-9-(trifluoromethyl)-1,2,3,4-tetrahydro-5H-benzofuro[3,2-e][1,4]diazepin-5-one (Example 77)

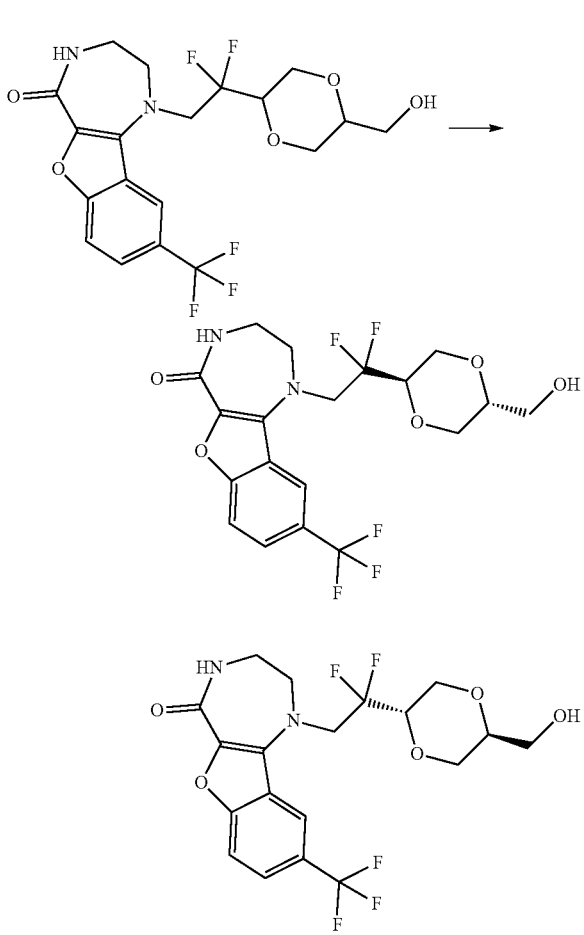

To a solution of 1-(2-(5-((((tert-butyldiphenylsilyl)oxy)methyl)-1,4-dioxan-2-yl)-2,2-difluoroethyl)-9-(trifluoromethyl)-1,2,3,4-tetrahydro-5H-benzofuro[3,2-e] [1,4]diazepin-5-one (0.380 g, 0.552 mmol) obtained in (18) in tetrahydrofuran (3.8 mL) was added 1M tetrabutylammonium fluoride-tetrahydrofuran solution (1.10 mL, 1.10 mmol), and the mixture was stirred at room temperature for 1 hr. To the reaction solution was added water, and the mixture was extracted with ethyl acetate. The organic layer was washed with saturated brine, dried over sodium sulfate, and concentrated under reduced pressure. To the obtained residue was added ethyl acetate, and the mixture was stirred for 1 hr. The precipitated solid was collected by filtration, and dried under reduced pressure to give the title compound (0.193 g, yield 78%). Moreover, the filtrate was concentrated, and the obtained residue was purified by reverse-phase column chromatography (column: ODS, eluent: water/acetonitrile=85/15 to 0/100) to give the title compound (0.02 g, yield 8%).

$^1$H-NMR (DMSO-D$_6$) δ: 3.34-3.35 (3H, m), 3.39-3.45 (2H, m), 3.50-3.55 (3H, m), 3.64 (1H, t, J=11.1 Hz), 3.90-3.95 (3H, m), 4.11-4.23 (2H, m), 4.79 (1H, t, J=5.4 Hz), 7.79-7.79 (2H, m), 8.10 (1H, t, J=4.8 Hz), 8.32 (1H, s).

1-(2,2-Difluoro-2-(5-(hydroxymethyl)-1,4-dioxan-2-yl)ethyl)-9-(trifluoromethyl)-1,2,3,4-tetrahydro-5H-benzofuro[3,2-e][1,4]diazepin-5-one (0.210 g, 0.466 mmol) obtained by the same reaction as (19) was subjected to an optical resolution with supercritical fluid chromatography (apparatus: Waters SFC Prep15 System, column: Daicel CHIRALPAK IA/SFC, 10 mm (I.D.)×250 mm (L), 5 μm, column temperature: 40° C., column backpressure: 120 bar, mobile phase flow rate: 15 mL/min, mobile phase mixed ratio: isocratic, carbon dioxide/(methanol/acetonitrile=20/80)=70/30, fraction trigger: UI 214 nm) to give the compound of Example 95 (0.149 g, yield 71%) as the first peak fraction (10.7-13.7 min), and the compound of Example 77 (0.030 g, yield 14%) as the second peak fraction (14.4-17.0 min). The absolute configuration on the dioxane ring of the compound of Example 95 was determined by X-ray crystallography.

Compound of Example 95

$^1$H-NMR (DMSO-D$_b$) δ: 3.34-3.35 (3H, m), 3.39-3.45 (2H, m), 3.50-3.55 (3H, m), 3.64 (1H, t, J=11.1 Hz), 3.90-3.95 (3H, m), 4.11-4.23 (2H, m), 4.79 (1H, t, J=5.4 Hz), 7.79-7.79 (2H, m), 8.10 (1H, t, J=4.8 Hz), 8.32 (1H, s).

Compound of Example 77

4H-NMR (DMSO-D$_6$) δ: 3.34-3.35 (3H, m), 3.39-3.45 (2H, m), 3.50-3.55 (3H, m), 3.64 (1H, t, J=11.1 Hz), 3.90-3.95 (3H, m), as 4.11-4.23 (2H, m), 4.79 (1H, t, J=5.4 Hz), 7.79-7.79 (2H, m), 8.10 (1H, t, J=4.8 Hz), 8.32 (1H, s).

[Production Example 3]: Synthesis of 1-(2-((1s,4s)-4-hydroxy-4-(hydroxymethyl)cyclohexyl)ethyl)-9-(trifluoromethyl)-1,2,3,4-tetrahydro-5H-benzofuro[3,2-e][1,4]diazepin-5-one (Example 90)

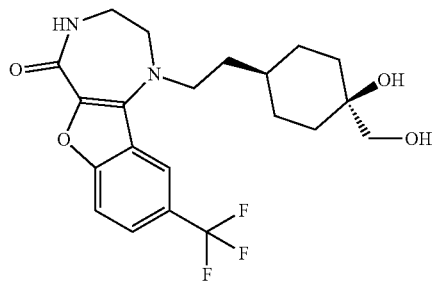 [SMILES: O=C1NCCN(CC[C@H]2CC[C@](O)(CO)CC2)c2c1oc1ccc(C(F)(F)F)cc21]

(1) ethyl 2-(1,4-dioxaspiro[4,5]decan-8-ylidene)acetate

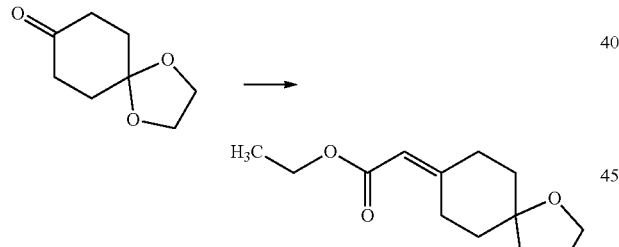

Under argon atmosphere, a solution of 1,4-dioxaspiro[4,5]decan-8-one (15.0 g, 96 mmol), triethyl phosphonoacetate (32.7 mL, 163 mmol) and potassium carbonate (13.3 g, 96 mmol) in N,N-dimethylformamide (120 mL) was stirred at 80° C. for 21 hr. Triethyl phosphonoacetate (9 mL, 45 mmol) was added again thereto, and the mixture was stirred at 80° C. for additional 21 hr. To the reaction solution was added water, and the mixture was extracted with ethyl acetate. The organic layer was washed with saturated brine, dried over sodium sulfate, and concentrated under reduced pressure. The residue was purified by silica gel column chromatography (eluent: hexane/ethyl acetate=10/1 to 3/1) to give the title compound (18.7 g, yield 86%).

$^1$H-NMR (CDCl$_3$) δ: 1.28 (3H, t, J=7.2 Hz), 1.77 (4H, dt, J=12.5, 4.5 Hz), 2.38 (2H, t, J=6.6 Hz), 3.00 (2H, t, J=6.6 Hz), 3.98 (4H, s), 4.15 (2H, q, J=7.2 Hz), 5.67 (1H, s).

(2) ethyl 2-(1,4-dioxaspiro[4,5]decan-8-yl)acetate

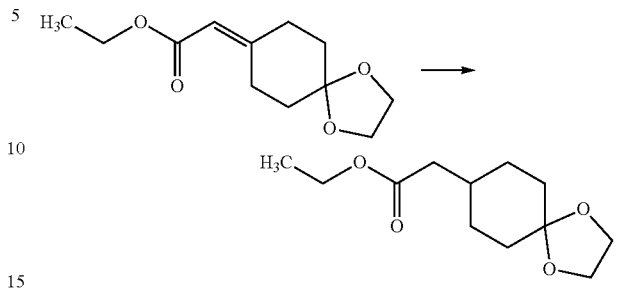

To a solution of ethyl 2-(1,4-dioxaspiro[4,5]decan-8-ylidene)acetate (18.7 g, 83 mmol) obtained in (1) in tetrahydrofuran (187 mL) was added 10% palladium on carbon (3.8 g), and the mixture was stirred under normal pressure of hydrogen at room temperature for 24 hr. The insoluble substance was removed by filtration through Celite, and the filtrate was concentrated under azeotrope with toluene and under reduced pressure to give the title compound (18.6 g, yield 99).

$^1$H-NMR (CDCl$_3$) δ: 1.26 (3H, t, J=7.2 Hz), 1.27-1.36 (2H, m), 1.53-1.64 (2H, m), 1.70-1.78 (4H, m), 1.79-1.88 (1H, m), 2.22 (2H, d, J=7.2 Hz), 3.94 (4H, s), 4.13 (2H, q, J=7.2 Hz).

(3) 2-(1,4-dioxaspiro[4,5]decan-8-yl)ethan-1-ol

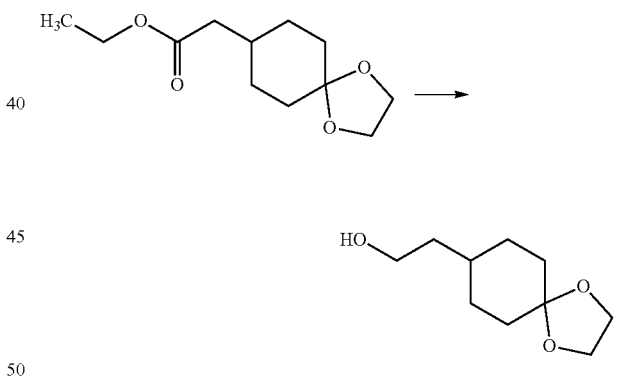

Under argon atmosphere and ice-cooling, to a suspension of lithium aluminium hydride (6.2 g, 163 mmol) in tetrahydrofuran (93 mL) was added dropwise a solution of ethyl 2-(1,4-dioxaspiro[4,5]decan-8-yl)acetate (18.6 g, 82 mmol) obtained in (2) in tetrahydrofuran (93 mL), and the mixture was stirred for 1 hr. To the reaction solution was successively added dropwise water (6.2 mL), 4N aqueous sodium hydroxide solution (6.2 mL) and water (18.6 mL), and the mixture was stirred at room temperature for 15 min. The insoluble substance was removed by filtration through Celite, and the filtrate was concentrated under azeotrope with toluene and under reduced pressure to give the title compound (13.3 g, yield 88%).

$^1$H-NMR (CDCl$_3$) δ: 1.19-1.32 (3H, m), 1.45-1.57 (5H, m), 1.72-1.77 (4H, m), 3.67-3.72 (2H, m), 3.94 (4H, s).

(4) 2-(1,4-dioxaspiro[4,5]decan-8-yl)ethyl 4-methyl-benzenesulfonate

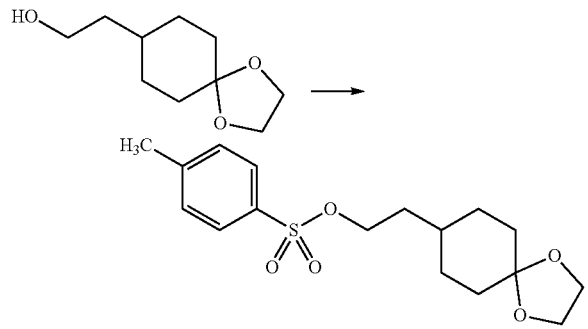

Under ice-cooling, to a solution of 2-(1,4-dioxaspiro[4,5]decan-8-yl)ethan-1-ol (13.3 g, 71.4 mmol) obtained in (3), triethylamine (14.9 mL, 107 mmol) and 1-methyl-1H-imidazole (8.5 mL, 107 mmol) in tetrahydrofuran (67 mL) was added dropwise a solution of 4-methylbenzenesulfonyl chloride (20.4 g, 107 mmol) in tetrahydrofuran (67 mL), and the mixture was stirred at room temperature for 4 hr. To the reaction solution was added saturated aqueous sodium hydrogencarbonate solution, and the mixture was extracted with ethyl acetate. The organic layer was washed with saturated brine, dried over sodium sulfate, and concentrated under reduced pressure. The residue was purified by silica gel column chromatography (eluent: hexane/ethyl acetate=6/1 to 2/3) to give the title compound (21.4 g, yield 88%).

$^1$H-NMR (CDCl$_3$) δ: 1.12-1.22 (2H, m), 1.35-1.50 (3H, m), 1.54-1.61 (4H, m), 1.64-1.70 (2H, m), 2.45 (3H, s), 3.88-3.95 (4H, m), 4.06 (2H, t, J=6.5 Hz), 7.35 (2H, d, J=8.1 Hz), 7.79 (2H, d, J=8.1 Hz).

(5) methyl 3-((2-((tert-butoxycarbonyl)amino)ethyl)amino)-5-(trifluoromethyl)benzofuran-2-carboxylate

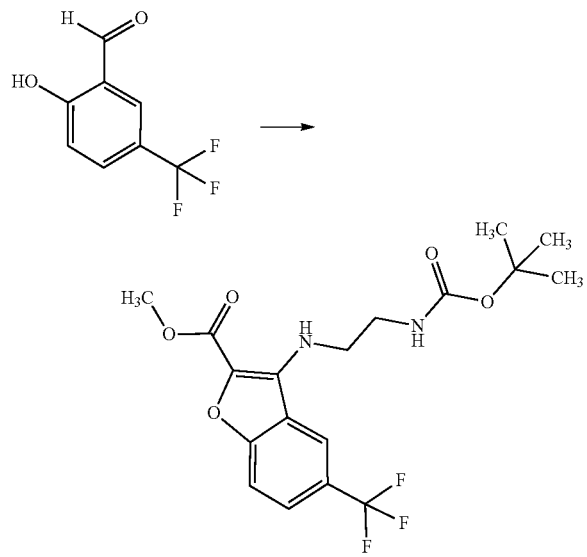

To a solution of 2-hydroxy-5-(trifluoromethyl)benzaldehyde (3.0 g, 15.8 mmol) in methanol (15 mL) was added dropwise a solution of tert-butyl (2-aminoethyl)carbamate (2.5 g, 15.8 mmol) in methanol (15 mL), and the mixture was stirred at room temperature for 16 hr, and concentrated under azeotrope with toluene and under reduced pressure. The obtained residue was dissolved in N,N-dimethylformamide (52 mL), methyl 2,2-dichloroacetate (2.0 mL, 18.9 mmol) and potassium carbonate (6.5 g, 47.3 mmol) were added thereto, and the mixture was stirred at room temperature for 16 hr. To the reaction solution was added water, and the mixture was extracted with ethyl acetate. The organic layer was washed with water and saturated brine, dried over sodium sulfate, and concentrated under reduced pressure to give the title compound (5.6 g, yield 88%).

$^1$H-NMR (DMSO-D$_6$) δ: 1.34 (9H, s), 3.16-3.21 (2H, m), 3.65-3.70 (2H, m), 3.83 (3H, s), 6.55 (1H, t, J=6.6 Hz), 7.03 (1H, t, J=5.4 Hz), 7.76 (1H, d, J=8.8 Hz), 7.84 (1H, dd, J=8.8, 1.4 Hz), 8.47 (1H, s).

(6) 9-(trifluoromethyl)-1,2,3,4-tetrahydro-5H-benzofuro[3,2-e][1,4]diazepin-5-one

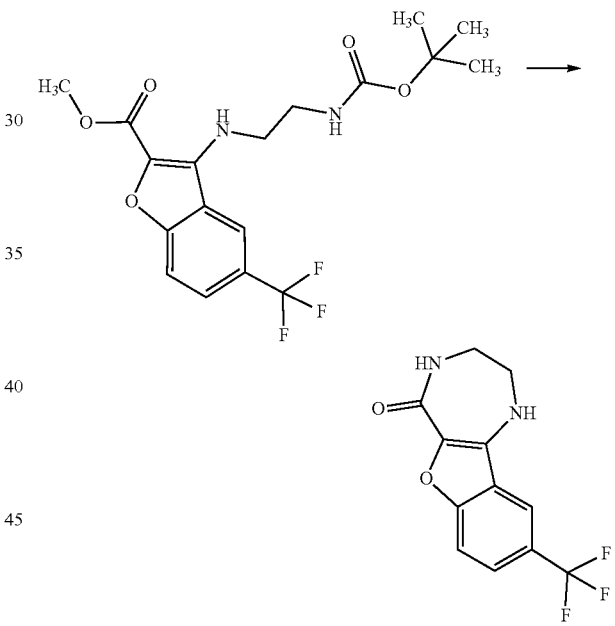

To methyl 3-((2-((tert-butoxycarbonyl)amino)ethyl)amino)-5-(trifluoromethyl)benzofuran-2-carboxylate (5.6 g, 13.9 mmol) obtained in (5) was added 2M hydrochloric acid-methanol solution (62.6 mL, 125 mmol), and the mixture was stirred at room temperature for 16 hr, and concentrated under azeotrope with toluene and under reduced pressure. To the obtained residue was added methanol (112 mL), and 5M sodium methoxide-methanol solution (9.7 mL, 48.7 mmol) was added dropwise thereto under water-cooling, and the mixture was stirred at room temperature for 16 hr. Under ice-cooling, to the reaction solution was added water, and the mixture was extracted with ethyl acetate. The aqueous layer was re-extracted with ethyl acetate. The organic layer was washed with saturated brine, dried over sodium sulfate, and concentrated under reduced pressure. To the obtained residue was added ethyl acetate (28 mL), and the mixture was stirred at room temperature for 2 hr. The precipitated solid was collected by filtration, and dried under reduced pressure to give the title compound (2.9 g, yield 77%).

¹H-NMR (DMSO-D₆) δ: 3.29-3.36 (2H, m), 3.42-3.45 (2H, m), 7.26 (1H, t, J=3.6 Hz), 7.70-7.72 (2H, m), 7.76 (1H, dd, J=8.8, 1.8 Hz), 8.32 (1H, s).

(7) 5-methoxy-9-(trifluoromethyl)-2,3-dihydro-1H-benzofuro[3,2-e] [1,4]diazepine

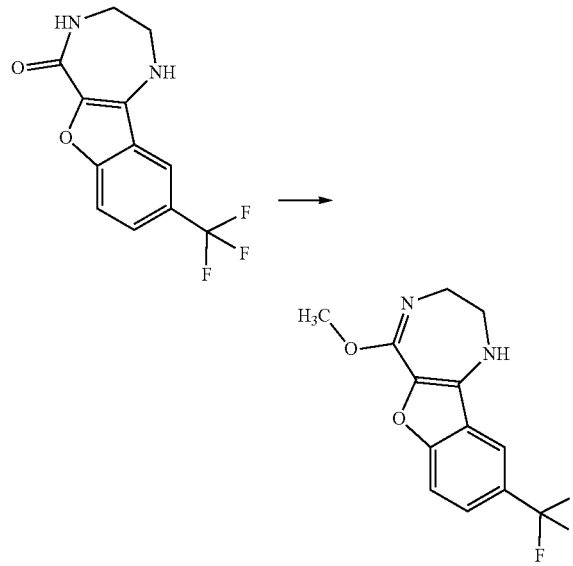

To a solution of 9-(trifluoromethyl)-1,2,3,4-tetrahydro-5H-benzofuro[3,2-e][1,4]diazepin-5-one (2.9 g, 10.8 mmol) obtained in (6) in ethyl acetate (44 mL) was added trimethyloxonium tetrafluoroborate (1.9 g, 12.9 mmol), and the mixture was stirred at room temperature for 16 hr. To the reaction solution was added dropwise an aqueous solution (44 mL) of sodium carbonate (3.4 g, 32.3 mmol), and the mixture was stirred for 10 min, and extracted with ethyl acetate. The organic layer was washed with saturated brine, dried over sodium sulfate, and concentrated under reduced pressure. The obtained residue was purified by silica gel column chromatography (eluent: hexane/ethyl acetate=2/1 to 1/2) to give the title compound (2.7 g, yield 87%).

¹H-NMR (DMSO-D₆) δ: 3.34 (2H, br, s), 3.72 (3H, s), 3.75 (2H, br, s), 7.17 (1H, t, J=4.3 Hz), 7.70 (1H, d, J=8.8 Hz), 7.77 (1H, dd, J=8.8, 1.8 Hz), 8.26 (1H, s).

(8) 1-(2-(1,4-dioxaspiro[4,5]decan-8-yl)ethyl)-5-methoxy-9-(trifluoromethyl)-2,3-dihydro-1H-benzofuro[3,2-e] [1,4]diazepine

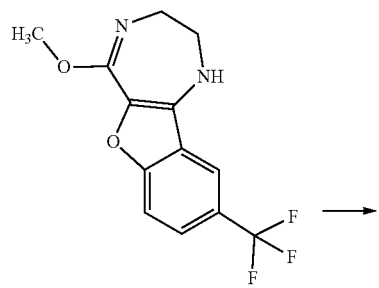

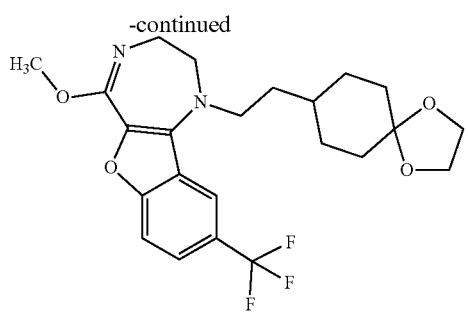

To a solution of 5-methoxy-9-(trifluoromethyl)-2,3-dihydro-1H-benzofuro[3,2-e][1,4]diazepine (1.5 g, 5.28 mmol) obtained by the same reaction as (7), and 2-(1,4-dioxaspiro[4,5]decan-8-yl)ethyl 4-methylbenzenesulfonate (4.5 g, 13.2 mmol) obtained in (4) in tetrahydrofuran (23 mL) was added dropwise 1M sodium bistrimethylsilylamide-tetrahydrofuran solution (13.2 mL, 13.2 mmol), and the mixture was stirred at room temperature for 19 hr. To the reaction solution was added water, and the mixture was extracted with ethyl acetate. To the aqueous layer were added 10% aqueous citric acid solution and saturated brine, and the mixture was re-extracted with ethyl acetate. The organic layers were combined, washed with saturated brine, dried over sodium sulfate, and concentrated under reduced pressure. To the obtained residue was added a mixed solvent of hexane/ethyl acetate=1/1, and the mixture was stirred at room temperature. The precipitated solid was collected by filtration, and dried under reduced pressure to give the title compound (1.2 g, yield 51%). Moreover, the filtrate was concentrated, and obtained residue was purified by silica gel column chromatography (eluent: hexane/ethyl acetate=3/1 to 1/4) to give the title compound (0.94 g, yield 39%).

¹H-NMR (DMSO-D₆) δ: 1.21-1.31 (2H, m), 1.36-1.48 (3H, m), 1.65-1.67 (4H, m), 1.72-1.76 (2H, m), 3.17 (2H, br, s), 3.42-3.46 (2H, m), 3.68 (2H, br, s), 3.74 (3H, s), 3.84 (4H, s), 7.80-7.81 (2H, m), 7.99 (1H, s).

(9) 1-(2-(4-oxocyclohexyl)ethyl)-9-(trifluoromethyl)-1,2,3,4-tetrahydro-5H-benzofuro[3,2-e][1,4]diazepin-5-one

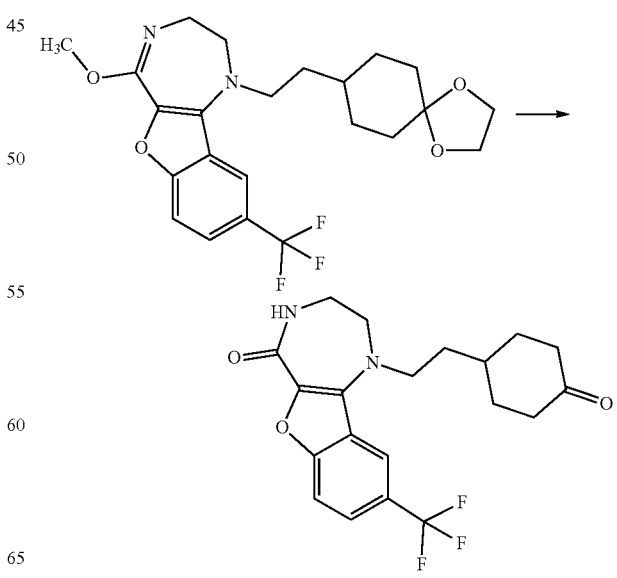

To a solution of 1-(2-(1,4-dioxaspiro[4,5]decan-8-yl)ethyl)-5-methoxy-9-(trifluoromethyl)-2,3-dihydro-1H-benzofuro[3,2-e] [1,4]diazepine (2.2 g, 4.80 mmol) obtained in (8) in 1,2-dimethoxyethane (22 mL) was added 6N hydrochloric acid (8.0 mL, 48.0 mmol), and the mixture was stirred at 90° C. for 3 hr. Under ice-cooling, to the reaction solution were added ethyl acetate and aqueous tripotassium phosphate solution. The precipitated solid was collected by filtration, and dried under reduced pressure to give the title compound (1.1 g, yield 58%). Moreover, the organic layer of the filtrate was washed with saturated brine, dried over sodium sulfate, and concentrated under reduced pressure. To the obtained residue was added ethyl acetate, and the mixture was stirred at room temperature for 1 hr. The precipitated solid was collected by filtration, and dried under reduced pressure to give the title compound (0.459 g, yield 25%).

$^1$H-NMR (DMSO-D$_6$) δ: 1.39-1.49 (2H, m), 1.69-1.75 (2H, m), 1.80-1.87 (1H, m), 2.02-2.06 (2H, m), 2.18-2.22 (2H, m), 2.39 (2H, td, J=13.6, 5.8 Hz), 3.30-3.34 (2H, m), 3.42-3.44 (2H, m), 3.57-3.61 (2H, m), 7.79-7.80 (2H, m), 8.02 (1H, t, J=4.8 Hz), 8.07 (1H, s).

(10) methyl 1-((tert-butyldimethylsilyl)oxy)-4-(2-(5-oxo-9-(trifluoromethyl)-2,3,4,5-tetrahydro-1H-benzofuro[3,2-e][1,4]diazepin-1-yl)ethyl)cyclohexane-1-carboxylate

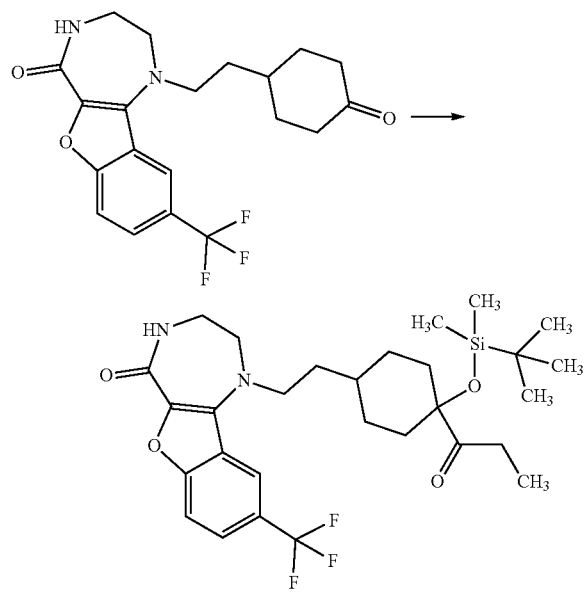

Under ice-cooling, to a solution of 1-(2-(4-oxocyclohexyl)ethyl)-9-(trifluoromethyl)-1,2,3,4-tetrahydro-5H-benzofuro[3,2-e] [1,4]diazepin-5-one (600 mg, 1.52 mmol) obtained in (9), and 2-((tert-butyldimethylsilyl)oxy)malononitrile (448 mg, 2.28 mmol) in tetrahydrofuran (9 mL) were added methanol (0.308 mL, 7.61 mmol) and 4-dimethylaminopyridine (0.372 g, 3.04 mmol), and the mixture was stirred for 2 hr. The mixture was warmed to room temperature, and stirred for additional 2 hr. To the reaction solution was added water, and the mixture was extracted with ethyl acetate. The aqueous layer was re-extracted with ethyl acetate. The organic layers were combined, washed with saturated brine, dried over sodium sulfate, and concentrated under reduced pressure. The obtained residue was purified by silica gel column chromatography (eluent: hexane/ethyl acetate=1/4 to ethyl acetate/methanol=3/1) to give the title compound (0.373 g, yield 43%).

$^1$H-NMR (DMSO-D$_6$) δ: 0.03 (6H, s), 0.85 (9H, s), 1.38-1.44 (3H, m), 1.63-1.68 (6H, m), 1.76-1.80 (2H, m), 3.28-3.32 (2H, m), 3.39-3.41 (2H, m), 3.52-3.57 (2H, m), 3.66 (3H, s), 7.79-7.80 (2H, m), 8.01 (1H, t, J=4.8 Hz), 8.03 (1H, s).

(11) 1-(2-(4-((tert-butyldimethylsilyl)oxy)-4-(hydroxymethyl)cyclohexyl)ethyl)-9-(trifluoromethyl)-1,2,3,4-tetrahydro-5H-benzofuro[3,2-e][1,4]diazepin-5-one

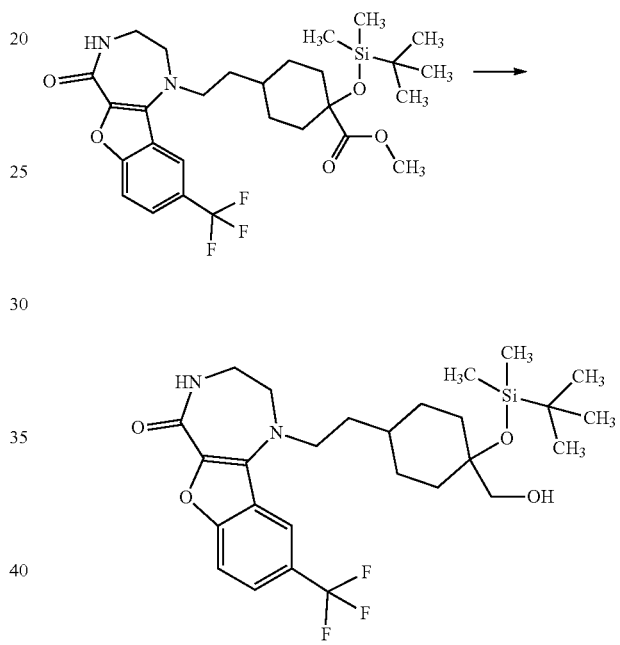

Under ice-cooling, to a solution of methyl 1-((tert-butyldimethylsilyl)oxy)-4-(2-(5-oxo-9-(trifluoromethyl)-2,3,4,5-tetrahydro-1H-benzofuro[3,2-e][1,4]diazepin-1-yl)ethyl)cyclohexane-1-carboxylate (0.373 g, 0.656 mmol) obtained in (10) in tetrahydrofuran (3.7 mL) was added dropwise 1M lithium borohydride-tetrahydrofuran solution (1.31 mL, 1.31 mmol), and the mixture was stirred at room temperature for 24 hr. To the reaction solution was added saturated aqueous sodium hydrogencarbonate solution, and the mixture was extracted with ethyl acetate. The organic layer was washed with water and saturated brine, dried over sodium sulfate, and concentrated under reduced pressure. To the obtained residue were added ethyl acetate and methanol, and the mixture was stirred at room temperature for 1 hr. The precipitated solid was collected by filtration, and dried under reduced pressure to give the title compound (0.232 g, yield 65%).

$^1$H-NMR (DMSO-Dc) δ: 0.07 (6H, s), 0.83 (9H, s), 1.24-1.45 (5H, m), 1.50-1.63 (6H, m), 3.25 (2H, d, J=5.3 Hz), 3.30-3.32 (2H, m), 3.39-3.41 (2H, m), 3.53-3.57 (2H, m), 4.75 (1H, t, J=5.3 Hz), 7.79-7.80 (2H, m), 8.00 (1H, t, J=4.7 Hz), 8.04 (1H, s).

(12) 1-(2-((1s,4s)-4-hydroxy-4-(hydroxymethyl)cyclohexyl)ethyl)-9-(trifluoromethyl)-1,2,3,4-tetrahydro-5H-benzofuro[3,2-e][1,4]diazepin-5-one

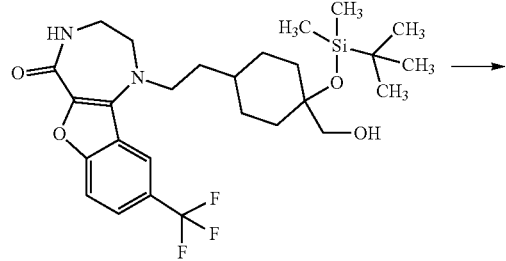

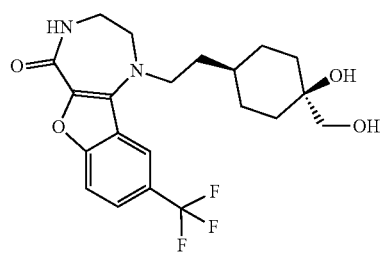

To a solution of 1-(2-(4-((tert-butyldimethylsilyl)oxy)-4-(hydroxymethyl)cyclohexyl)ethyl)-9-(trifluoromethyl)-1,2,3,4-tetrahydro-5H-benzofuro[3,2-e][1,4]diazepin-5-one (90 mg, 0.166 mmol) obtained in (11) in tetrahydrofuran (0.9 mL) was added 1M tetrabutylammonium fluoride-tetrahydrofuran solution (0.333 mL, 0.333 mmol), and the mixture was stirred at room temperature for 1 hr. To the reaction solution was added water, and the mixture was extracted with ethyl acetate. The organic layer was washed with saturated brine, dried over sodium sulfate, and concentrated under reduced pressure. The residue was purified by reverse-phase liquid chromatography (apparatus: Waters Prep System, column: XTERRA PrepMS C18 OBD™ 5 µm, 30×50 mm Column, column temperature: room temperature, mobile phase flow rate: 40 mL/min, mobile phase mixed ratio: gradient, water (0.1, trifluoroacetic acid)/acetonitrile (0.1% trifluoroacetic acid)=90/10 (0 min)-50/50 (8 min)-0/100 (8.05 min)) to give the title compound (0.021 g, yield 30%). The relative configuration on the cyclohexane ring was determined by X-ray crystallography.

$^1$H-NMR (DMSO-D$_6$) δ: 1.18-1.45 (7H, m), 1.49-1.56 (2H, m), 1.57-1.65 (2H, m), 3.12 (2H, d, J=5.9 Hz), 3.28-3.34 (2H, m), 3.38-3.42 (2H, m), 3.51-3.57 (2H, m), 3.80 (1H, s), 4.44 (1H, t, J=5.9 Hz), 7.77-7.82 (2H, m), 8.00 (1H, t, J=4.9 Hz), 8.06 (1H, br s).

To 1-(2-((1s,4s)-4-hydroxy-4-(hydroxymethyl)cyclohexyl)ethyl)-9-(trifluoromethyl)-1,2,3,4-tetrahydro-5H-benzofuro[3,2-e] [1,4]diazepin-5-one (50 mg) obtained by the same reaction as above was added a mixed solvent (500 µL) of toluene/N,N-dimethylformamide=2/1, and the mixture was stirred at room temperature for one week. A part of the suspension was filtered, and the obtained solid was dried to give a crystal of 1-(2-((1s,4s)-4-hydroxy-4-(hydroxymethyl)cyclohexyl)ethyl)-9-(trifluoromethyl)-1,2,3,4-tetrahydro-5H-benzofuro[3,2-e][1,4]diazepin-5-one.

[Production Example 4]: Synthesis of 1-(2,2-difluoro-2-((1r,4r)-4-hydroxycyclohexyl)ethyl)-9-(trifluoromethyl)-1,2,3,4-tetrahydro-5H-benzofuro[3,2-e][1,4]diazepin-5-one (Example 106), and 1-(2,2-difluoro-2-(4-hydroxycyclohexyl)ethyl)-9-(trifluoromethyl)-1,2,3,4-tetrahydro-5H-benzofuro[3,2-e] [1,4]diazepin-5-one (Example 107)

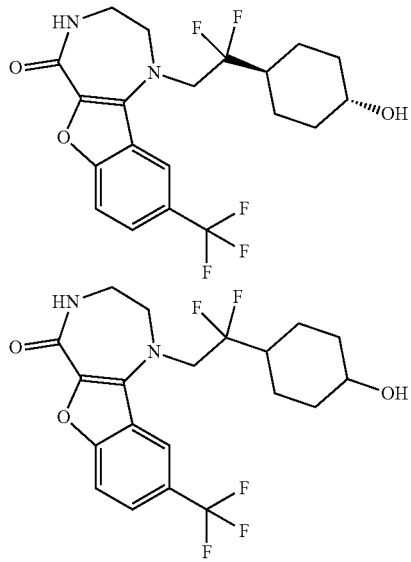

(1) ethyl 2-fluoro-2-(1,4-dioxaspiro[4,5]decan-8-ylidene)acetate

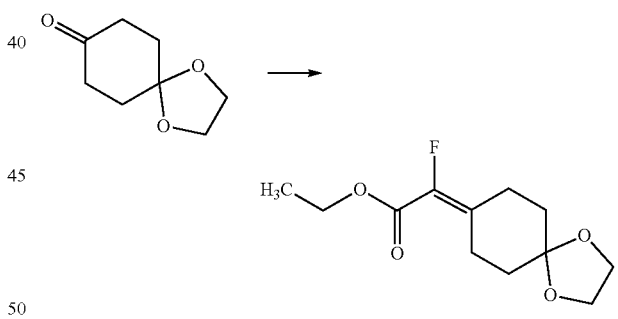

Under argon atmosphere and ice-cooling, to a solution of sodium hydride (60%) (0.141 g, 3.52 mmol) in N,N-dimethylformamide (2.5 mL) was added dropwise triethyl 2-fluoro-2-phosphonoacetate (0.651 mL, 3.20 mmol), and the mixture was stirred for 15 min. A solution of 1,4-dioxaspiro[4,5]decan-8-one (0.5 g, 3.20 mmol) in N,N-dimethylformamide (2.5 mL) was added dropwise thereto, and the mixture was stirred for 1 hr. To the reaction solution was added water, and the mixture was extracted with ethyl acetate. The aqueous layer was re-extracted with ethyl acetate, and the organic layers were combined, washed with water and saturated brine, dried over sodium sulfate, and concentrated under reduced pressure. The residue was purified by silica gel column chromatography (eluent: hexane/ethyl acetate=7/1 to 4/1) to give the title compound (0.569 g, yield 73%).

¹H-NMR (DMSO-D₆) δ: 1.24 (3H, t, J=7.1 Hz), 1.66-1.69 (4H, m), 2.43 (2H, td, J=6.6, 2.4 Hz), 2.82 (2H, td, J=6.5, 1.3 Hz), 3.90 (4H, s), 4.21 (2H, q, J=7.1 Hz).

(2) ethyl 2-fluoro-2-(1,4-dioxaspiro[4,5]decan-8-yl)acetate

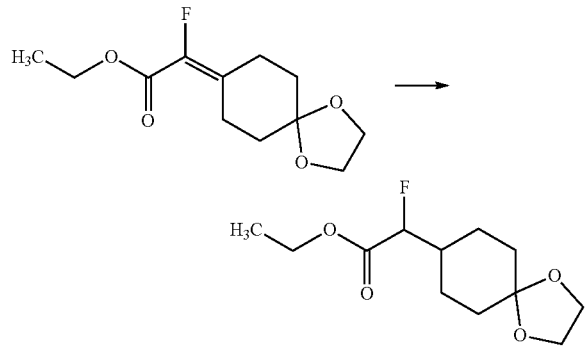

To a solution of ethyl 2-fluoro-2-(1,4-dioxaspiro[4,5]decan-8-ylidene)acetate (0.569 g, 2.33 mmol) obtained in (1) in ethyl acetate (5.7 mL) was added 10% palladium on carbon (0.057 g), and the mixture was stirred under normal pressure of hydrogen at room temperature for 6 hr. The insoluble substance was removed by filtration through Celite, and the filtrate was concentrated under azeotrope with toluene and under reduced pressure to give the title compound (0.583 g, yield 102%).

¹H-NMR (DMSO-d₆) δ: 1.22 (3H, t, J=7.2 Hz), 1.38-1.53 (5H, m), 1.65-1.72 (3H, m), 1.81-1.95 (1H, m), 3.84 (4H, s), 4.19 (2H, q, J=7.1 Hz), 4.96 (1H, dd, J=48.3, 4.2 Hz).

(3) ethyl 2,2-difluoro-2-(1,4-dioxaspiro[4,5]decan-8-yl)acetate

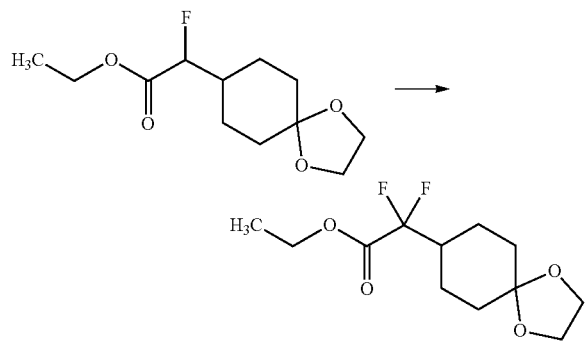

Under argon stream, to a mixed solution of ethyl 2-fluoro-2-(1,4-dioxaspiro[4,5]decan-8-yl)acetate (0.574 g, 2.33 mmol) obtained in (2) in tetrahydrofuran (5.7 mL)-toluene (1.7 mL) was added dropwise 1M sodium bistrimethylsilylamide-tetrahydrofuran solution (3.0 mL, 3.03 mmol) at −78° C., and the mixture was stirred for 15 min. N-Fluorobenzenesulfonimide (0.882 g, 2.80 mmol) was added thereto, and the mixture was stirred for 2 hr. To the reaction solution was added dropwise triethylamine (0.65 mL, 4.66 mmol) under ice-cooling, water and a mixed solvent of hexane/ethyl acetate=3/1 were added thereto, and the mixture was subjected to extraction. The aqueous layer was re-extracted with a mixed solvent of hexane/ethyl acetate=3/1, and the organic layers were combined, washed with saturated aqueous sodium hydrogencarbonate solution and saturated brine, dried over sodium sulfate, and concentrated under reduced pressure. The residue was purified by silica gel column chromatography (eluent: hexane/ethyl acetate=7/1 to 3/1) to give the title compound (0.403 g, yield 65%).

¹H-NMR (DMSO-D₆) δ: 1.26 (3H, t, J=7.1 Hz), 1.33-1.44 (2H, m), 1.47-1.55 (2H, m), 1.67-1.72 (4H, m), 2.10-2.25 (1H, m), 3.85 (4H, s), 4.31 (2H, q, J=7.1 Hz).

(4) 2,2-difluoro-2-(1,4-dioxaspiro[4,5]decan-8-yl)ethan-1-ol

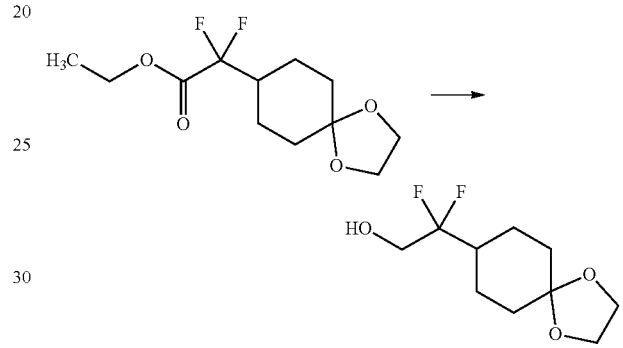

Under argon stream and under ice-cooling, to a suspension of lithium aluminium hydride (0.087 g, 2.29 mmol) in tetrahydrofuran (2.0 mL) was added dropwise a solution of ethyl 2,2-difluoro-2-(1,4-dioxaspiro[4,5]decan-8-yl)acetate (0.403 g, 1.53 mmol) obtained in (3) in tetrahydrofuran (2.0 mL), and the mixture was stirred for 30 min. To the reaction solution was successively added dropwise water (0.087 mL), 4N aqueous sodium hydroxide solution (0.087 mL) and water (0.261 mL), and the mixture was stirred at room temperature for 30 min. The insoluble substance was removed by filtration through Celite, and the filtrate was concentrated under reduced pressure. The residue was purified by silica gel column chromatography (eluent: hexane/ethyl acetate=3/1 to 2/3) to give the title compound (0.236 g, yield 70%).

¹H-NMR (DMSO-D₆) δ: 1.35-1.50 (4H, m), 1.69-1.77 (4H, m), 1.91-2.02 (1H, m), 3.59 (2H, td, J=14.1, 6.0 Hz), 3.85 (4H, s), 5.42 (1H, t, J=6.1 Hz).

(5) 2,2-difluoro-2-(1,4-dioxaspiro[4,5]decan-8-yl)ethyl trifluoromethanesulfonate

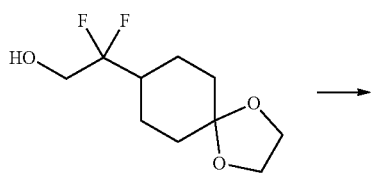

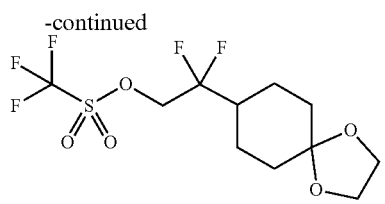

Under ice-cooling, to a solution of 2,2-difluoro-2-(1,4-dioxaspiro[4,5]decan-8-yl)ethan-1-ol (0.236 g, 1.06 mmol) obtained in (4) in pyridine (1.9 mL) was added dropwise trifluoromethanesulfonic anhydride (0.359 mL, 2.12 mmol), and the mixture was stirred for 30 min. To the reaction solution was added water, and the mixture was extracted with ethyl acetate. The organic layer was washed with water and saturated brine, dried over sodium sulfate, and concentrated under reduced pressure to give the title compound (0.338 g, yield 90%). 4H-NMR (DMSO-D$_6$) δ: 1.36-1.51 (4H, m), 1.70-1.79 (4H, m), 2.03-2.11 (1H, m), 3.85 (4H, s), 5.12 (2H, t, J=14.2 Hz).

(6) 2-(2,2-difluoro-2-(1,4-dioxaspiro[4,5]decan-8-yl)ethyl)isoindoline-1,3-dione

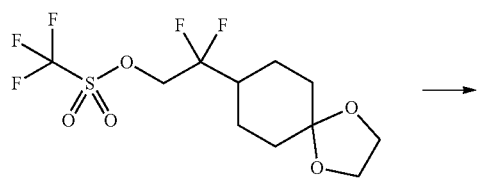

To a solution of 2,2-difluoro-2-(1,4-dioxaspiro[4,5]decan-8-yl)ethyl trifluoromethanesulfonate (0.338 g, 0.954 mmol) obtained in (5) in N,N-dimethylformamide (3.4 mL) was added potassium phthalimide (0.212 g, 1.15 mmol), and the mixture was stirred at room temperature for 16 hr. To the reaction solution was added water, and the mixture was extracted with ethyl acetate. The organic layer was washed with water and saturated brine, dried over sodium sulfate, and concentrated under reduced pressure. The residue was purified by silica gel column chromatography (eluent: hexane/ethyl acetate=4/1 to 1/1) to give the title compound (0.270 g, yield 81%).

$^1$H-NMR (DMSO-D$_6$) δ: 1.42-1.52 (4H, m), 1.72-1.75 (2H, m), 1.89-1.91 (2H, m), 1.94-2.10 (1H, m), 3.86 (4H, s), 4.04 (2H, t, J=15.5 Hz), 7.87-7.94 (4H, m).

(7) 2,2-difluoro-2-(1,4-dioxaspiro[4,5]decan-8-yl)ethan-1-amine

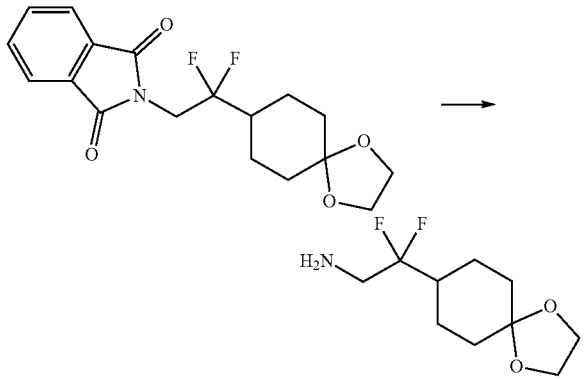

To a mixed solution of 2-(2,2-difluoro-2-(1,4-dioxaspiro[4,5]decan-8-yl)ethyl)isoindoline-1,3-dione (0.270 g, 0.768 mmol) obtained in (6) in ethanol (1.9 mL) and tetrahydrofuran (1.9 mL) was added hydrazine monohydrate (0.112 mL, 2.31 mmol), and the mixture was stirred at 60° C. for 2 hr. Toluene (3.8 mL) was added thereto, and the mixture was stirred at 60° C. for additional 2 hr. The insoluble substance was removed by filtration, and the filtrate was concentrated under reduced pressure to give the title compound (0.180 g, yield 106%).

$^1$H-NMR (DMSO-D$_6$) δ: 1.32-1.50 (4H, m), 1.59 (2H, br, s), 1.68-1.76 (4H, m), 1.95-2.10 (1H, m), 2.84 (2H, t, J=15.3 Hz), 3.85 (4H, s).

(8) methyl 3-((2,2-difluoro-2-(1,4-dioxaspiro[4,5]decan-8-yl)ethyl)amino)-5-(trifluoromethyl)benzofuran-2-carboxylate

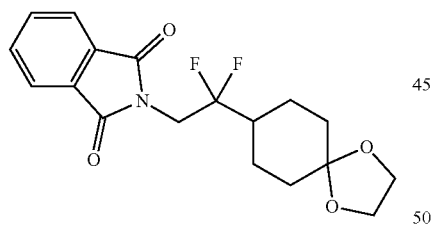

To a solution of 2,2-difluoro-2-(1,4-dioxaspiro[4,5]decan-8-yl)ethan-1-amine (0.170 g, 0.768 mmol) obtained in (7) in N,N-dimethylformamide (1.5 mL) was added 2-hydroxy-5-(trifluoromethyl)benzaldehyde (0.146 g, 0.768 mmol), and the mixture was stirred at room temperature for 2 hr. Potassium carbonate (0.318 g, 2.30 mmol) and methyl 2,2-dichloroacetate (0.095 mL, 0.922 mmol) were added thereto, and the mixture was stirred at room temperature for 16 hr. To the reaction solution was added water, and the mixture was extracted with ethyl acetate. The aqueous layer was re-extracted with ethyl acetate, and the organic layers were combined, washed with water and saturated brine, dried over sodium sulfate, and concentrated under reduced pressure. The residue was purified by silica gel column chromatography (eluent: hexane/ethyl acetate=4/1 to 1/1) to give the title compound (0.272 g, yield 76%).

$^1$H-NMR (DMSO-D$_6$) δ: 1.44-1.53 (4H, m), 1.69-1.76 (2H, m), 1.84-1.86 (2H, m), 1.94-2.08 (1H, m), 3.85 (3H, s), 3.86 (4H, s), 4.20 (2H, td, J=15.8, 7.1 Hz), 6.70 (1H, t, J=6.9 Hz), 7.77 (1H, d, J=8.8 Hz), 7.85 (1H, dd, J=8.8, 1.6 Hz), 8.40 (1H, s).

(9) methyl 3-(2-chloro-N-(2,2-difluoro-2-(1,4-dioxaspiro[4,5]decan-8-yl)ethyl)acetamido)-5-(trifluoromethyl)benzofuran-2-carboxylate

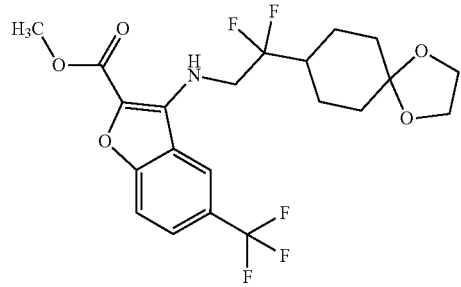

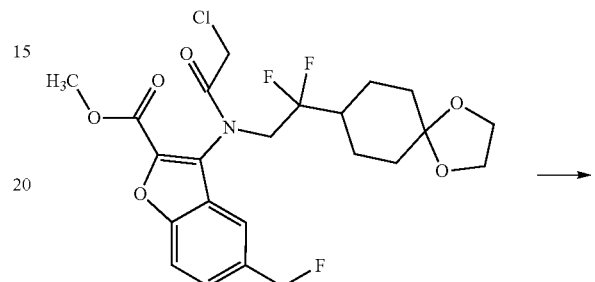

Under ice-cooling, to a solution of methyl 3-(((2,2-difluoro-2-(1,4-dioxaspiro[4,5] decan-8-yl)ethyl) amino)-5-(trifluoromethyl)benzofuran-2-carboxylate (0.272 g, 0.587 mmol) obtained in (8), and N,N-dimethylaniline (0.297 mL, 2.35 mmol) in dichloromethane (2.7 mL) was added dropwise chloroacetyl chloride (0.141 mL, 1.77 mmol), and the mixture was stirred at room temperature for 16 hr. 10% Aqueous citric acid and hexane/ethyl acetate=1/1 were added thereto, and the mixture was subjected to extraction. The aqueous layer was re-extracted with hexane/ethyl acetate=1/1, and the organic layers were combined, washed with 10% aqueous citric acid, water and saturated brine, dried over sodium sulfate, and concentrated under reduced pressure. The residue was purified by silica gel column chromatography (eluent: hexane/ethyl acetate=7/1 to 1/1) to give the title compound (0.296 g, yield 93%).

$^1$H-NMR (DMSO-Dc) δ: 1.33-1.47 (4H, m), 1.68-1.81 (4H, m), 1.99-2.08 (1H, m), 3.84 (4H, s), 3.90 (3H, s), 4.00-4.06 (1H, m), 4.22 (1H, d, J=14.4 Hz), 4.33 (1H, d, J=14.4 Hz), 4.45-4.57 (1H, m), 7.94 (1H, dd, J=8.9, 1.7 Hz), 8.04 (1H, d, J=8.8 Hz), 8.24 (1H, s).

(10) methyl 3-((2-chloroethyl) (2,2-difluoro-2-(1,4-dioxaspiro[4,5]decan-8-yl)ethyl)amino)-5-(trifluoromethyl)benzofuran-2-carboxylate

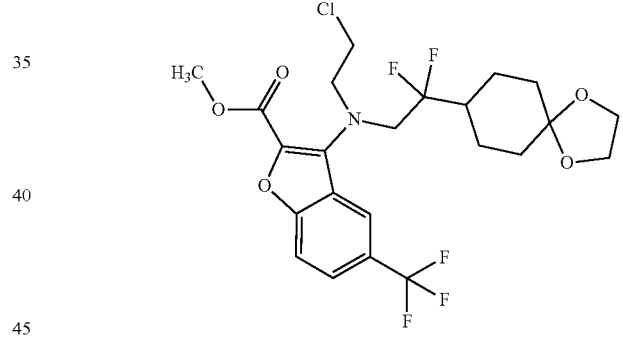

Under argon stream and ice-cooling, to a solution of methyl 3-(2-chloro-N-(2,2-difluoro-2-(1,4-dioxaspiro[4,5] decan-8-yl)ethyl)acetamido)-5-(trifluoromethyl)benzofuran-2-carboxylate (0.296 g, 0.548 mmol) obtained in (9) in tetrahydrofuran (3.0 mL) was added dropwise 0.91M borane-tetrahydrofuran complex (1.5 mL, 1.37 mmol), and the mixture was stirred for 16 hr. Under ice-cooling, 10% aqueous citric acid was added thereto, and the mixture was stirred for 5 min, and extracted with ethyl acetate. The aqueous layer was re-extracted with ethyl acetate, and the organic layers were combined, washed with 10% aqueous sodium carbonate solution, water and saturated brine, dried over sodium sulfate, and concentrated under reduced pressure. The residue was purified by silica gel column chromatography (eluent: hexane/ethyl acetate=4/1 to 3/2) to give the title compound (0.148 g, yield 51%).

$^1$H-NMR (DMSO-D$_6$) δ: 1.25-1.37 (4H, m), 1.60-1.64 (4H, m), 2.04-2.15 (1H, m), 3.68-3.77 (4H, m), 3.81 (4H, s), 3.91 (3H, s), 3.93 (2H, t, J=14.4 Hz), 7.86-7.92 (2H, m), 8.23 (1H, s).

(11) methyl 3-((2-azidoethyl) (2,2-difluoro-2-(1,4-dioxaspiro[4,5]decan-8-yl)ethyl)amino)-5-(trifluoromethyl)benzofuran-2-carboxylate

(12) 1-(2,2-difluoro-2-(1,4-dioxaspiro[4,5]decan-8-yl)ethyl)-9-(trifluoromethyl)-1,2,3,4-tetrahydro-5H-benzofuro[3,2-e][1,4]diazepin-5-one

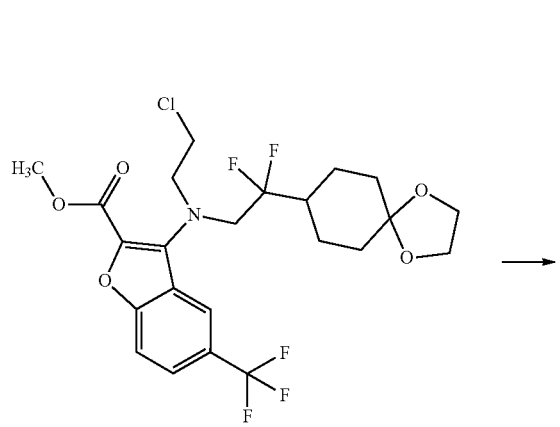

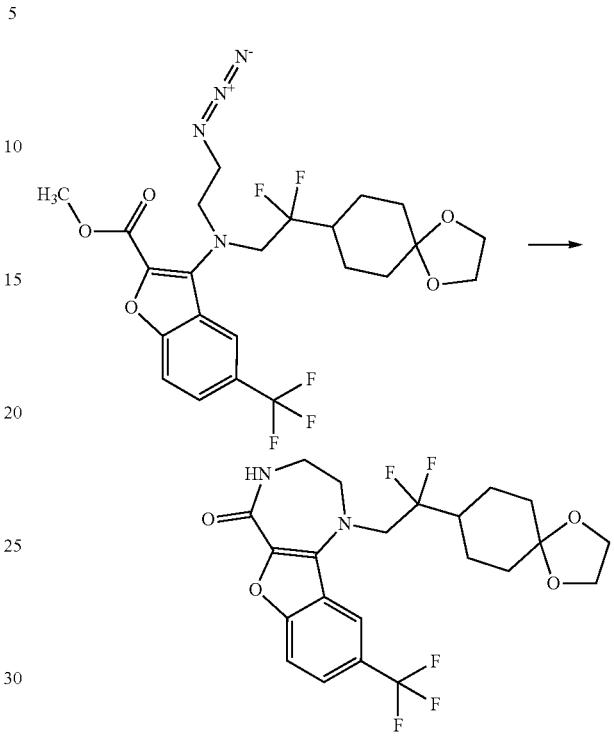

To a solution of methyl 3-((2-chloroethyl) (2,2-difluoro-2-(1,4-dioxaspiro[4,5]decan-8-yl)ethyl)amino)-5-(trifluoromethyl)benzofuran-2-carboxylate (0.148 g, 0.281 mmol) obtained in (10) in N,N-dimethylformamide (1.5 mL) were added potassium azide (0.041 g, 0.507 mmol) and sodium iodide (0.008 g, 0.056 mmol), and the mixture was stirred at 80° C. for 16 hr. The reaction solution was cooled to room temperature, water was added thereto, and the mixture was extracted with ethyl acetate. The organic layer was washed with water and saturated brine, dried over sodium sulfate, and concentrated under reduced pressure to give the title compound (0.128 g, yield 85%).

$^1$H-NMR (CDCl$_3$) δ: 1.36-1.46 (2H, m), 1.46-1.55 (2H, m), 1.68-1.75 (4H, m), 1.86-2.00 (1H, m), 3.39 (2H, t, J=5.8 Hz), 3.72 (2H, t, J=5.8 Hz), 3.82-3.93 (6H, m), 4.00 (3H, s), 7.62 (1H, d, J=8.8 Hz), 7.72 (1H, dd, J=8.8, 1.6 Hz), 8.03 (1H, s).

To a mixed solution of methyl 3-((2-azidoethyl) (2,2-difluoro-2-(1,4-dioxaspiro[4,5] decan-8-yl)ethyl) amino)-5-(trifluoromethyl)benzofuran-2-carboxylate (0.128 g, 0.240 mmol) obtained in (11) in 1,2-dimethoxyethane (2.6 mL) and water (0.26 mL) was added triphenylphosphine (0.076 g, 0.288 mmol), and the mixture was stirred at 100° C. for 5 hr. The mixture was cooled to room temperature, and concentrated under azeotrope with toluene and under reduced pressure. To the residue was added ethanol, and the mixture was stirred for 1 hr. The precipitated solid was collected by filtration, and dried under reduced pressure to give the title compound (0.070 g, yield 61%).

$^1$H-NMR (DMSO-D$_6$) δ: 1.44-1.55 (4H, m), 1.70-1.75 (2H, m), 1.87-1.88 (2H, m), 1.96-2.10 (1H, m), 3.32-3.35 (2H, m), 3.51-3.53 (2H, m), 3.87 (4H, s), 4.10 (2H, t, J=16.8 Hz), 7.79-7.80 (2H, m), 8.09 (1H, t, J=5.0 Hz), 8.14 (1H, s).

(13) 1-(2,2-difluoro-2-(4-oxocyclohexyl)ethyl)-9-(trifluoromethyl)-1,2,3,4-tetrahydro-5H-benzofuro[3,2-e] [1,4]diazepin-5-one

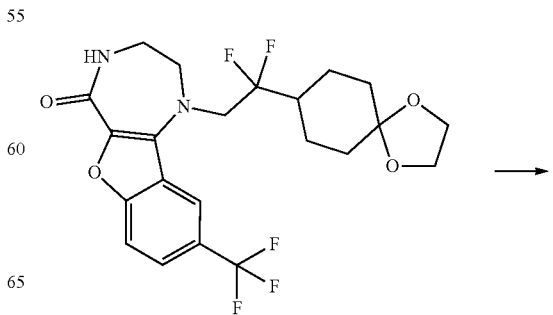

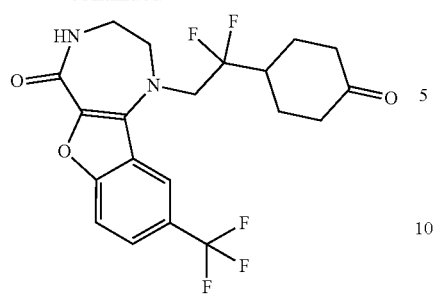

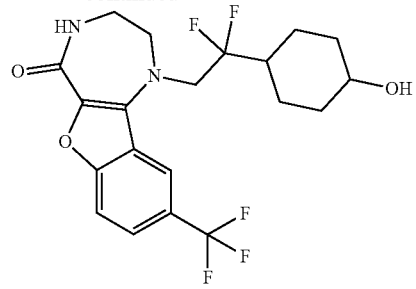

To a solution of 1-(2,2-difluoro-2-(1,4-dioxaspiro[4,5]decan-8-yl)ethyl)-9-(trifluoromethyl)-1,2,3,4-tetrahydro-5H-benzofuro[3,2-e][1,4]diazepin-5-one (0.07 g, 0.148 mol) obtained in (12) in acetic acid (0.56 mL) was added 2N hydrochloric acid (0.14 mL), and the mixture was stirred at 80° C. for 4 hr. 10% Aqueous dipotassium hydrogenphosphate solution was added thereto at room temperature, and the mixture was extracted with ethyl acetate. The aqueous layer was re-extracted twice with ethyl acetate, and the organic layers were combined, washed with saturated brine, dried over sodium sulfate, and concentrated under reduced pressure to give the title compound (0.056 g, yield 88%).

$^1$H-NMR (DMSO-D$_6$) δ: 1.67-1.76 (2H, m), 2.16-2.18 (2H, m), 2.24-2.28 (2H, m), 2.45-2.55 (3H, m), 3.32-3.37 (2H, m), 3.54-3.56 (2H, m), 4.17 (2H, t, J=16.8 Hz), 7.79-7.80 (2H, m), 8.10 (1H, t, J=4.9 Hz), 8.16 (1H, s).

(14) 1-(2,2-difluoro-2-((1r,4r)-4-hydroxycyclohexyl)ethyl)-9-(trifluoromethyl)-1,2,3,4-tetrahydro-5H-benzofuro[3,2-e][1,4]diazepin-5-one (Example 106), and 1-(2,2-difluoro-2-(4-hydroxycyclohexyl)ethyl)-9-(trifluoromethyl)-1,2,3,4-tetrahydro-5H-benzofuro[3,2-e][1,4]diazepin-5-one (Example 107)

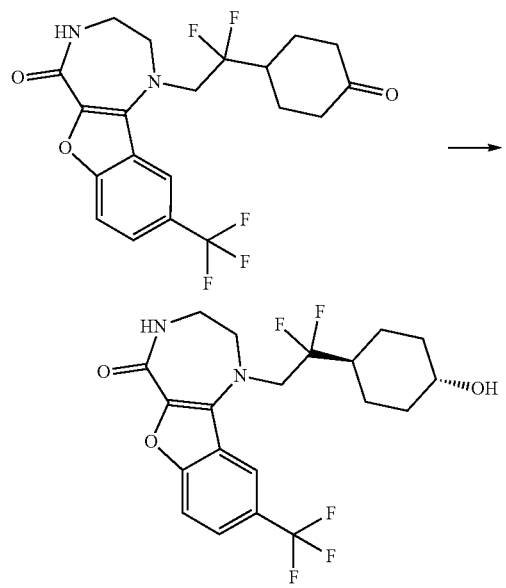

Under ice-cooling, to a mixed solution of 1-(2,2-difluoro-2-(4-oxocyclohexyl)ethyl)-9-(trifluoromethyl)-1,2,3,4-tetrahydro-5H-benzofuro[3,2-e][1,4]diazepin-5-one (0.056 g, 0.130 mmol) obtained in (13) in methanol (0.45 mL) and tetrahydrofuran (0.45 mL) was added sodium borohydride (0.009 g, 0.260 mmol), and the mixture was stirred for 3 hr. 5% Aqueous potassium hydrogensulfate solution was added thereto under ice-cooling, and the mixture was extracted with ethyl acetate. The organic layer was washed with saturated aqueous sodium hydrogencarbonate solution and saturated brine, dried over sodium sulfate, and concentrated under reduced pressure. The residue was purified by reverse-phase liquid chromatography (apparatus: Waters Prep System, column: XTERRA PrepMS C18 OBD™ 5 µm, 30×50 mm Column, column temperature: room temperature, mobile phase flow rate: 40 mL/min, mobile phase mixed ratio: gradient, water (0.1% trifluoroacetic acid)/acetonitrile (0.1% trifluoroacetic acid)=90/10(0 min)-50/50(8 min)-0/100(8.05 min)) to give the compound of Example 106 (0.028 g, yield 50%), and the compound of Example 107 (0.003 g, yield 6%). The relative configuration on the cyclohexane ring of the compound of Example 106 was determined by two-dimensional NMR. The compound of Example 107 was obtained as a mixture of cis/trans=4/1.

Compound of Example 106

$^1$H-NMR (DMSO-D$_6$) δ: 1.08-1.37 (4H, m), 1.82-1.94 (5H, m), 3.27-3.41 (3H, m), 3.49-3.55 (2H, m), 4.09 (2H, t, J=16.6 Hz), 4.61 (1H, d, J=4.4 Hz), 7.77-7.80 (2H, m), 8.08 (1H, t, J=4.3 Hz), 8.14 (1H, br s).

Compound of Example 107

$^1$H-NMR (DMSO-D$_6$) δ: 1.08-1.37 (0.8H, m), 1.40-1.46 (1.6H, m), 1.57-1.78 (4.8H, m), 1.82-1.97 (1.8H, m), 3.27-3.41 (2.2H, m), as 3.49-3.55 (2H, m), 3.83-3.87 (0.8H, m), 4.09 (2H, t, J=16.6 Hz), 4.38 (0.8H, d, J=2.8 Hz), 4.61 (0.2H, d, J=4.4 Hz), 7.77-7.80 (2H, m), 8.09 (1H, t, J=4.7 Hz), 8.14-8.16 (1H, m).

The compounds of the other Examples were obtained by the same method as the above-mentioned Production Methods or Production Examples, employing the known method if necessary. The structures and physical property data of the compounds of Examples 1 to 167 and 2-01 to 2-07 are shown in Table 1-1 to Table 1-25.

Experimental Example 1: Evaluation of Human Pim-1 Inhibitory Activity

The human Pim-1 inhibitory activity of the test compounds was evaluated as follows.
(1) Purification of Human Pim-1
DNA fragment in which a His-Tag sequence and a translation termination sequence are added to the 3'-end of human Pim-1 translation sequence was amplified by PCR (Polymerase Chain Reaction), using human Pim-1 gene-inserted plasmid DNA (Kazusa DNA Laboratory, model number FXC11400) as a template. The amplified DNA fragment was fused with pGEx-6P-1 (GE Healthcare Japan, model number 27-4597-1) digested with BamHI and EcoRI using In-Fusion HD Cloning Kit (Takara Bio, model number 639649). The human Pim-1-expressed plasmid DNA was isolated from *Escherichia coli* DH5α (TOYOBO, model number DNA-903) transformed with the obtained In-Fusion reaction product. The base sequence of Pim-1 cloned into vector was determined by Dye Terminator method using BigDye Terminator v3.1 Cycle Sequencing Kit (Applied Biosystems, model number 4337456). The determined sequence was a sequence in which the His-Tag sequence and translation termination sequence were introduced on the 3'-end of the sequence of human Pim-1 (Accession number NM_002648.3) translation region registered in NCBI Reference Database. *Escherichia coli* BL21 (DE3) (Merck KGaA, model number 69449-4) transformed with human Pim-1-expressed plasmid DNA was cultured in 2×YT medium (Becton Dickinson, model number 2404020) at 30° C., until the optical concentration at 620 nm (OD620) reached 0.6, and then cultured overnight at 20° C. in the presence of 0.5 mmol/L isopropyl b-D-1-thiogalactopyranoside. After the completion of so the culture, the cells were collected and suspended in Homogenate Buffer (50 mmol/L Tris-HCl (pH 7.5), 500 mmol/L NaCl, 1% Tween20, complete, EDTA-free (Roche, model number 1873580)), and the suspended cells were lysed by passing through a microfluidizer M-110H (Mizuho Kogyo Co., Ltd.). The lysate was centrifuged at 10,100×g for 10 minutes, 4° C., and the supernatant was filtered through MILLEX-HV Filter (0.45 μm) (Millipore, SLHV033RS) to remove the cell residues. The filtrate was loaded onto complete His-Tag Purification Resin (Roche Diagnostics, model number 05 893 682 0.01). The column was washed with Equilibration Buffer-1 (50 mmol/L Tris-HCl (pH 7.5), 500 mmol/L NaCl, 1% Tween 20) containing 5 mmol/L Imidazole, followed by Equilibration Buffer-1 containing 50 mmol/L Imidazole, the human Pim-1 to which GST-Tag derived from pGEx-6P-1 was eluted with Equilibration Buffer-1 containing 150 mmol/L imidazole. Glutathione Sepharose 4B (GE Healthcare Japan, model number 17-0756-05) was added to the eluate, and the column was washed with Equilibration Buffer-2 (50 mmol/L Tris-HCl (pH 7.5), 500 mmol/L NaCl, 0.05, Tween20, 0.5 mmol/L EDTA, 2 mmol/L DTT), and then suspended in Equilibration Buffer-2 containing 20 units/mL PreScission Protease (GE Healthcare, model number 27-0843-01). The protease reaction was carried out by stirring overnight at 4° C., and the human Pim-1 in which the GST-Tag sequence was cleaved was eluted. The eluate was loaded onto a gel filtration column (Superdex-200 30/100 GL (GE Healthcare, model number 17-5175-01)) equilibrated with Equilibration Buffer-3 (50 mmol/L Tris-HCl (pH 7.5), 500 mmol/L NaCl, 0.05% Tween20, 0.5 mmol/L EDTA, 2 mmol/L DTT, 10% Glycerol), and eluted. The eluate was used as a human Pim-1 purified fraction.
The protein concentration of the human Pim-1 purified fraction was measured with Pierce 660 nm Protein Assay Reagent (Thermo Fisher Scientific, model number 22660). The purified fraction was rapidly frozen in liquid nitrogen, and then stored at −80° C. The His-Tag-added human Pim-1 was detected by Western blotting using a mouse anti-His monoclonal antibody (WAKO, model number 011-23091).
(2) Evaluation of Human Pim-1 Inhibitory Activity
The calculation of the Pim-1 inhibitory activity of the compound was performed using the following solution according to the protocol attached to ADP-Glo Kinase Assay (cat. V9102, Promega). The purified enzyme of human Pim-1 described above was used.
(i) Preparation of Solution
The kinase buffer solution (50 mmol/L HEPES (pH 7.5), 5 mmol/L $MgCl_2$, 1 mmol/L DTT, 0.05% BSA) was prepared by dissolving HEPES (Jena Bioscience), $MgCl_2$ (Sigma-Aldrich), DTT (Sigma-Aldrich) and BSA (Sigma-Aldrich) in purified water.
The ATP solution (288 μmol/L) was prepared by dissolving 100 mmol/L ATP (Promega) in the kinase buffer solution.
The enzyme/substrate solution (0.2 mmol/L Pim-1, 30 μmol/L Pim2tide) was prepared by dissolving Pim-1 (described above) and Pim2tide (custom synthetic product by GenScript USA, the same product as PIM2tide cat. 12-542 by Millipore) in the kinase buffer solution.
The test compound solution (containing 12.5% DMSO) was prepared by dissolving the DMSO solution of the test compound in the kinase buffer solution.
The vehicle solution (containing 12.5% DMSO) was prepared by dissolving DMSO in the kinase buffer solution.
(ii) Method
To a 384-well assay plate (Corning, 4513), the test compound solution or vehicle solution (control) was added by 1 μL/well, the enzyme/substrate solution or kinase buffer solution (blank) was added by 2 μL/well, and the ATP solution was added by 2 μL/well, and they were mixed. After enzymatically reacting at room temperature for 45 minutes, ADP-Glo Reagent (Promega) was added by 5 μL/well, and they were mixed. After reacting at room temperature for 60 minutes, Kinase Detection Reagent (Promega) was added by 10 μL/well, and they were mixed. After reacting at room temperature for 30 minutes, the luminescence amount of each well was measured for 10 msec with a multi-label plate reader EnVision (PerkinElmer).
(iii) Aggregate Calculation
The value obtained by subtracting the luminescence amount of each well by the luminescence amount of the blank well was used as the data. The Pim-1 inhibition rate at each concentration of the test compounds was calculated using [Equation 1]. The $IC_{50}$ (50% inhibitory concentration) of the test compounds was calculated by applying the inhibition rate of each concentration of the test compounds to the logistic curve. In addition, it was converted into the Ki value using [Equation 2].

$$\frac{A-B}{A} \times 100 \qquad \text{Equation 1}$$

A: measured value of vehicle solution (control)
B: measured value of test compound $$Ki = \frac{IC50 - \frac{1}{2}E}{1 + \frac{S}{Km}} \qquad \text{Equation 2}$$

E: enzyme concentration
S: ATP concentration
Km: Michaelis-Menten constant
The results are shown in Table 1-1 to Table 1-25.

TABLE 1-1

| Ex. No. | Structure | Notes | 1H-NMR (400 MHz) | MS (M + H) | MS (M − H) | hPim1 Ki (nM) |
|---|---|---|---|---|---|---|
| 1 | 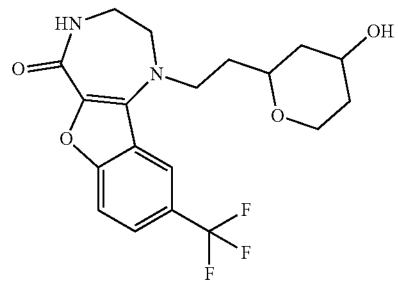 [SMILES: O=C1NCCN(CCC2CC(O)CCO2)c2c1oc1ccc(C(F)(F)F)cc21] | mixture of four isomers | 1H-NMR (DMSO-D6) δ: 1.07-1.16 (1H, m), 1.26-1.36 (1H, m), 1.67-1.85 (3H, m), 1.92-1.99 (1H, m), 3.23-3.35 (3H, m), 3.38-3.74 (6H, m), 3.89-3.92 (0.85H, m), 4.00-4.02 (0.15H, m), 4.59 (0.15H, d, J = 2.4 Hz), 4.74 (0.85H, d, J = 4.9 Hz), 7.75-7.80 (2H, m), 8.02 (1H, t, J = 4.4 Hz), 8.41 (1H, s). | 399 | 397 | 0.6973 |
| 2 | 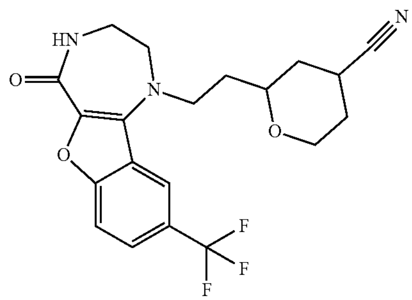 [SMILES: N#CC1CCOC(CCN2CCNC(=O)c3oc4ccc(C(F)(F)F)cc4c32)C1] | mixture of four isomers | 1H-NMR (DMSO-D6) δ: 1.46-1.55 (0.6H, m), 1.57-1.84 (4.6H, m), 1.88-2.03 (1.8H, m), 3.02-3.08 (0.4H, m), 3.34-3.54 (5.2H, m), 3.56-3.70 (2.4H, m), 3.88-3.96 (1H, m), 7.76-7.81 (2H, m), 8.03 (1H, br s), 8.36 (0.4H, s), 8.38 (0.6H, s). | 408 | 406 | 1.1154 |
| 3 | 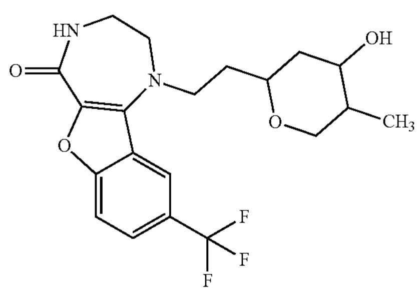 [SMILES: CC1COC(CCN2CCNC(=O)c3oc4ccc(C(F)(F)F)cc4c32)CC1O] | mixture of eight isomers | 1H-NMR (DMSO-D6) δ: 0.82 (2.6H, d, J = 6.6 Hz), 0.93 (0.4H, d, J = 6.9 Hz), 1.15-1.25 (1H, m), 1.37-1.40 (1H, m), 1.68-1.75 (1H, m), 1.80-1.83 (1H, m), 1.94-1.97 (1H, m), 2.93 (1H, t, J = 11.4 Hz), 3.07-3.14 (1H, m), 3.27-3.29 (3H, m), 3.42-3.69 (4H, m), 3.77 (1H, dd, J = 11.4, 4.5 Hz), 4.68 (1H, d, J = 5.4 Hz), 7.77 (2H, s), 8.02 (1H, t, J = 4.5 Hz), 8.40 (1H, s). | 413 | 411 | 0.6062 |
| 4 | 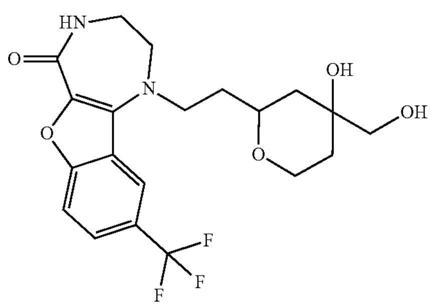 [SMILES: O=C1NCCN(CCC2CC(O)(CO)CCO2)c2c1oc1ccc(C(F)(F)F)cc21] | mixture of four isomers | 1H-NMR (DMSO-D6) δ: 1.20-1.39 (3H, m), 1.53-1.72 (2H, m), 1.83-1.97 (1H, m), 3.12-3.19 (2H, m), 3.23-3.36 (2H, m), 3.40-3.57 (3H, m), 3.59-3.70 (2H, m), 3.72-3.82 (2H, m), 4.18 (0.9H, s), 4.37 (0.1H, s), 4.47 (0.1H, br, s), 4.58 (0.9H, t, J = 5.6 Hz), 7.73-7.83 (2H, m), 7.97-8.08 (1H, m), 8.44 (1H, s). | 429 | 427 | 0.4418 |
| 5 | 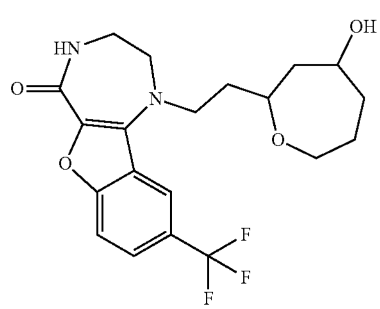 [SMILES: O=C1NCCN(CCC2CC(O)CCCO2)c2c1oc1ccc(C(F)(F)F)cc21] | racemate The relative configuration of the substituents on the oxepane ring is cis or trans. diastereomer of Example 6 | 1H-NMR (CDCl3) δ: 1.55-2.08 (8H, m), 3.45-3.97 (10H, m), 6.46 (1H, s), 7.55-7.70 (2H, m), 8.32 (1H, s). | 413 | N.D. | 1.1126 |

TABLE 1-1-continued

| Ex. No. | Structure | Notes | 1H-NMR (400 MHz) | MS (M + H) | MS (M − H) | hPim1 Ki (nM) |
|---|---|---|---|---|---|---|
| 6 | 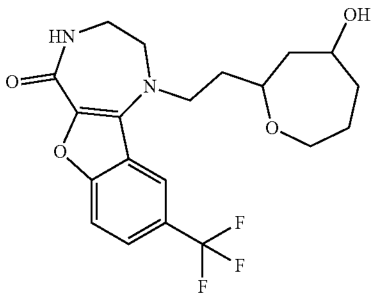 [SMILES: O=C1NCCN(CCC2CC(O)CCCO2)c2c1oc1ccc(C(F)(F)F)cc21] | racemate The relative configuration of the substituents on the oxepane ring is cis or trans. diastereomer of Example 5 | 1H-NMR (CDCl3) δ: 1.57-2.07 (8H, m), 3.43-4.18 (10H, m), 6.62 (1H, s), 7.56-7.69 (2H, m), 8.34 (1H, t, J = 3.0 Hz). | 413 | N.D. | 0.9275 |
| 7 | 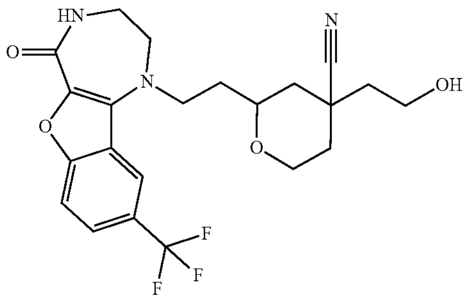 [SMILES: N#CC1(CCO)CCOC(CCN2CCNC(=O)c3oc4ccc(C(F)(F)F)cc4c32)C1] | racemate The relative configuration of the substituents on the tetrahydropyran ring is presumed to be trans. | 1H-NMR (DMSO-D6) δ: 1.36-1.46 (1H, m), 1.54-1.64 (1H, m), 1.64-1.79 (3H, m), 1.84-2.06 (3H, m), 3.23-3.37 (2H, m), 3.39-3.72 (8H, m), 3.91-4.04 (1H, m), 4.67 (1H, t, J = 5.6 Hz), 7.78 (2H, s), 8.02-8.05 (1H, m), 8.38 (1H, s). | 452 | 450 | 0.4683 |

TABLE 1-2

| 8 | | racemate The relative configuration of the substituents on the tetrahydropyran ring is cis. | 1H-NMR (DMSO-D6) δ: 1.35 (1H, d, J = 9.3 Hz), 1.59-1.72 (4H, m), 1.88-1.96 (1H, m), 3.21-3.28 (3H, m), 3.39-3.52 (4H, m), 3.57 (1H, br s), 3.66-3.75 (2H, m), 4.53 (1H, d, J = 4.2 Hz), 7.78 (2H, s), 8.04 (1H, t, J = 5.1 Hz), 8.38 (1H, s). | 399 | 397 | 6.2202 |
| 9 | | mixture of four isomers | 1H-NMR (CDCl3) δ: 1.25-2.08 (9H, m), 3.37-4.05 (11H, m), 6.39 (1H, s), 7.58-7.67 (2H, m), 8.34 (1H, s). | 427 | N.D. | 0.4815 |
| 10 | | racemate The relative configuration of the substituents on the tetrahydropyran ring is cis or trans. diastereomer of Example 51 | 1H-NMR (DMSO-D6) δ: 1.25-1.42 (2H, m), 1.79 (1H, d, J = 10.5 Hz), 1.94 (1H, d, J = 12.3 Hz), 3.33-3.38 (2H, m), 3.33-3.48 (1H, m), 3.50-3.56 (2H, m), 3.62-3.82 (2H, m), 3.94 (1H, dd, J = 11.1, 5.5 Hz), 3.99-4.27 (2H, m), 4.97 (1H, d, J = 4.8 Hz), 7.78 (2H, s), 8.09 (1H, t, J = 4.9 Hz), 8.34 (1H, s). | 435 | 433 | 0.0412 |

TABLE 1-2-continued

| # | Structure | Config | 1H-NMR | MS1 | MS2 | Value |
|---|---|---|---|---|---|---|
| 11 | 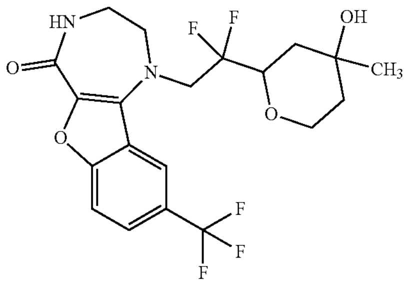 [SMILES: CC1(O)CCOC(C(F)(F)CN2CCNC(=O)c3oc4ccc(C(F)(F)F)cc4c32)C1] | racemate. The relative configuration of the substituents on the tetrahydropyran ring is trans. diastereomer of Example 12 | 1H-NMR (DMSO-D6) δ: 1.19 (3H, s), 1.38-1.66 (4H, m), 3.27-3.41 (2H, m), 3.45-3.61 (2H, m), 3.66-3.80 (2H, m), 3.93-4.31 (3H, m), 4.53 (1H, s), 7.78 (2H, br s), 8.07 (1H, t, J = 5.0 Hz), 8.34 (1H, br s). | 449 | 447 | 0.0596 |
| 12 | 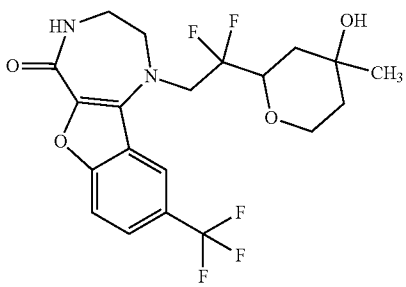 [SMILES: CC1(O)CCOC(C(F)(F)CN2CCNC(=O)c3oc4ccc(C(F)(F)F)cc4c32)C1] | racemate. The relative configuration of the substituents on the tetrahydropyran ring is cis. diastereomer of Example 11 | 1H-NMR (DMSO-D6) δ: 1.23 (3H, s), 1.47-1.68 (4H, m), 3.30-3.43 (2H, m), 3.45-3.60 (3H, m), 3.73-3.85 (1H, m), 3.91 (1H, dd, J = 11.6, 4.3 Hz), 3.97-4.13 (1H, m), 4.16-4.32 (1H, m), 4.78 (1H, br s), 7.76-7.79 (2H, m), 8.08 (1H, t, J = 5.0 Hz), 8.34 (1H, br s). | 449 | 447 | 0.0388 |
| 13 | 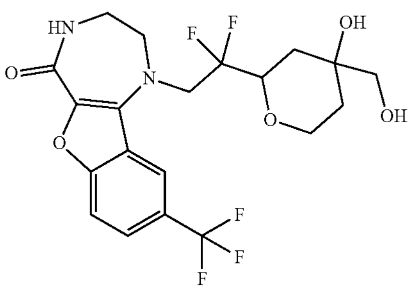 [SMILES: O=C1NCCN(CC(F)(F)C2CC(O)(CO)CCO2)c2c1oc1ccc(C(F)(F)F)cc21] | racemate. The relative configuration of the substituents on the tetrahydropyran ring is cis or trans or mixture of cis/trans isomers. | 1H-NMR (DMSO-D6) δ: 1.30 (1H, d, J = 12.9 Hz), 1.50 (1H, d, J = 12.9 Hz), 1.61-1.65 (2H, m), 3.22 (2H, d, J = 5.7 Hz), 3.33-3.36 (2H, br m), 3.53 (2H, qd, J = 16.0, 4.8 Hz), 3.70-3.82 (2H, m), 3.96-4.25 (3H, m), 4.48 (1H, s), 4.73 (1H, t, J = 5.7 Hz), 7.78 (2H, s), 8.09 (1H, t, J = 4.9 Hz), 8.36 (1H, s). | 465 | 463 | 0.0210 |
| 14 | 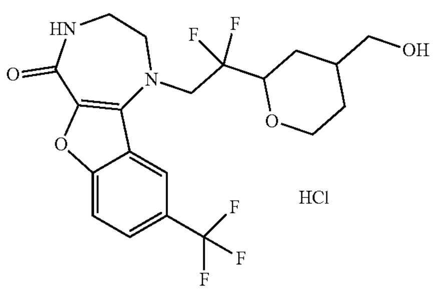 [SMILES: O=C1NCCN(CC(F)(F)C2CC(CO)CCO2)c2c1oc1ccc(C(F)(F)F)cc21 ; Cl] | racemate. The relative configuration of the substituents on the tetrahydropyran ring is cis or trans. diastereomer of Example 15 | 1H-NMR (DMSO-D6) δ: 1.13-1.19 (2H, m), 1.58-1.82 (3H, m), 3.26-3.76 (10H, m), 4.05-4.25 (2H, m), 7.78 (2H, d, J = 1.0 Hz), 8.10 (1H, d, J = 4.4 Hz), 8.35 (1H, s). | 449 | N.D. | 0.0334 |

TABLE 1-3

| # | Structure | Config | 1H-NMR | MS1 | MS2 | Value |
|---|---|---|---|---|---|---|
| 15 | 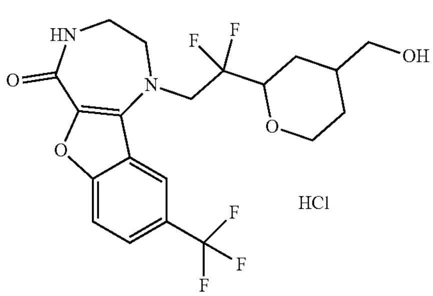 [SMILES: O=C1NCCN(CC(F)(F)C2CC(CO)CCO2)c2c1oc1ccc(C(F)(F)F)cc21 ; Cl] | racemate. The relative configuration of the substituents on the tetrahydropyran ring is cis or trans. diastereomer of Example 14 | 1H-NMR (DMSO-D6) δ: 1.16-1.99 (5H, m), 3.24-4.29 (12H, m), 7.79 (2H, s), 8.06-8.11 (1H, m), 8.35 (1H, s). | 449 | N.D. | 0.0289 |

TABLE 1-3-continued

| | | | | | | |
|---|---|---|---|---|---|---|
| 16 | 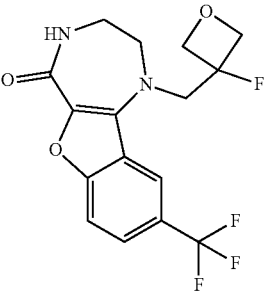 [SMILES: O=C1NCCN(CC2(F)COC2)c2c1oc1ccc(C(F)(F)F)cc21] | | 1H-NMR (DMSO-D6) δ: 3.31 (2H, m), 3.44 (2H, t, J = 3.5 Hz), 4.17 (2H, d, J = 22.7 Hz), 4.74 (4H, td, J = 20.40, 8.6 Hz), 7.80 (2H, d, J = 1.2 Hz), 8.10 (1H, t, J = 4.7 Hz), 8.26 (1H, s). | 359 | 357 | 10.8761 |
| 17 | 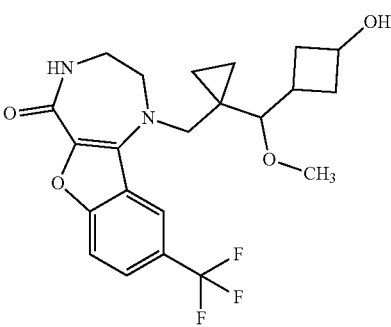 [SMILES: COC(C1CC(O)C1)C1(CN2CCNC(=O)c3oc4ccc(C(F)(F)F)cc4c32)CC1] | mixture of four isomers | 1H-NMR (DMSO-D6) δ: 0.40-0.46 (1H, m), 0.49-0.54 (1H, m), 0.57-0.64 (2H, m), 1.63-1.70 (2H, m), 2.12-2.33 (3H, m), 2.65 (1H, d, J = 7.9 Hz), 3.21-3.29 (3H, m), 3.45 (2.4H, s), 3.49 (0.6H, s), 3.51-3.54 (2H, m), 3.76-3.86 (2H, m), 4.82 (0.2H, d, J = 5.8 Hz), 4.90 (0.8H, d, J = 6.5 Hz), 7.73-7.80 (2H, m), 8.04 (1H, t, J = 4.1 Hz), 8.65 (1H, s). | 439 | 437 | 0.2341 |
| 18 | 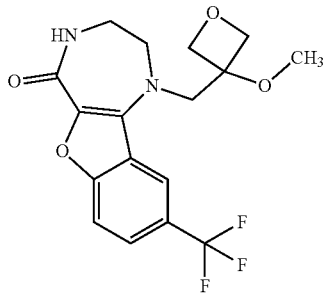 [SMILES: COC1(CN2CCNC(=O)c3oc4ccc(C(F)(F)F)cc4c32)COC1] | | 1H-NMR (DMSO-D6) δ: 3.29-3.32 (2H, m), 3.34 (3H, s), 3.43 (2H, t, J = 3.6 Hz), 3.99 (2H, s), 4.50 (2H, d, J = 7.6 Hz), 4.71 (2H, d, J = 7.4 Hz), 7.80 (2H, d, J = 1.2 Hz), 8.07 (1H, t, J = 4.7 Hz), 8.37 (1H, d, J = 0.7 Hz). | 371 | 369 | 13.9035 |
| 19 | 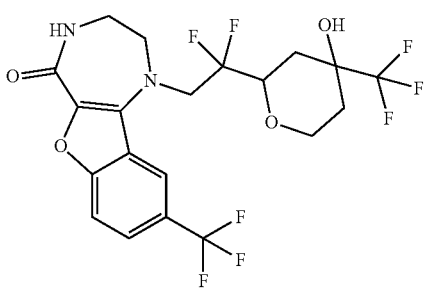 [SMILES: O=C1NCCN(CC(F)(F)C2CC(O)(C(F)(F)F)CCO2)c2c1oc1ccc(C(F)(F)F)cc21] | racemate The relative configuration of the substituents on the tetrahydropyran ring is cis or trans or mixture of cis/trans isomers. | 1H-NMR (DMSO-D6) δ: 1.71-1.76 (2H, m), 2.09-2.19 (2H, m), 3.35-3.39 (2H, m), 3.49-3.58 (3H, m), 3.87-4.37 (4H, m), 6.38 (1H, s), 7.78 (2H, d, J = 1.2 Hz), 8.08 (1H, t, J = 5.0 Hz), 8.31 (1H, s). | 503 | 501 | 0.1009 |
| 20 | 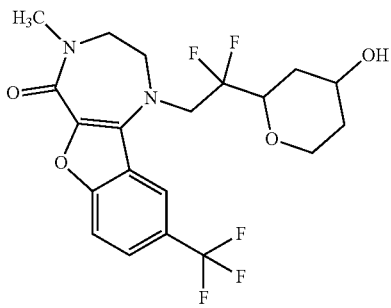 [SMILES: CN1CCN(CC(F)(F)C2CC(O)CCO2)c2c(oc3ccc(C(F)(F)F)cc23)C1=O] | mixture of four isomers | 1H-NMR (DMSO-D6) δ: 1.23-1.40 (2H, m), 1.82-1.94 (2H, m), 3.04 (3H, s), 3.39-4.30 (10H, m), 4.95 (0.8H, d, J = 4.9 Hz), 5.48 (0.2H, d, J = 3.5 Hz), 7.78 (2H, dd, J = 10.6, 9.2 Hz), 8.33 (1H, s). | 449 | N.D. | 0.3800 |

TABLE 1-3-continued

| | | | | | | |
|---|---|---|---|---|---|---|
| 21 | 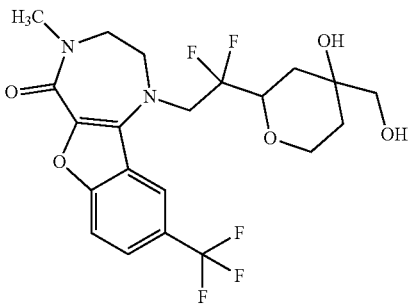 [SMILES: CN1CCN(CC(F)(F)C2CC(O)(CO)CCO2)c2c(oc3ccc(C(F)(F)F)cc23)C1=O] | | mixture of four isomers | 1H-NMR (DMSO-D6) δ: 1.28-1.92 (4H, m), 3.04 (3H, s), 3.17-3.22 (2H, m), 3.47-4.46 (9H, m), 4.60-4.70 (1H, m), 7.75-7.80 (2H, m), 8.35 (1H, s). | 479 | 477 | 0.3300 |

TABLE 1-4

| 22 | ![structure] | racemate The relative configuration of the substituents on the cyclobutane ring is presumed to be cis. | 1H-NMR (DMSO-D6) δ: 0.38-0.43 (1H, m), 0.48-0.54 (1H, m), 0.56-0.63 (2H, m), 1.23-1.30 (2H, m), 1.72-1.78 (2H, m), 2.05-2.25 (3H, m), 2.70 (1H, d, J = 7.9 Hz), 3.18-3.23 (4H, m), 3.45 (3H, s), 3.48-3.54 (1H, m), 3.75 (1H, d, J = 15.0 Hz), 4.41 (1H, t, J = 6.0 Hz), 4.65 (1H, s), 7.73-7.79 (2H, m), 8.03 (1H, t, J = 4.4 Hz), 8.65 (1H, s). | 469 | 467 | 0.8483 |
| 23 | ![structure] | racemate The relative configuration of the substituents on the cyclobutane ring is presumed to be trans. | 1H-NMR (DMSO-D6) δ: 0.38-0.43 (1H, m), 0.49-0.54 (1H, m), 0.61-0.66 (2H, m), 1.24-1.28 (2H, m), 1.76-1.88 (2H, m), 1.96-2.07 (2H, m), 2.70 (1H, d, J = 9.0 Hz), 2.82-2.90 (1H, m), 3.12 (2H, d, J = 5.5 Hz), 3.17-3.27 (2H, m), 3.55 (3H, s), 3.53-3.56 (1H, m), 3.83 (1H, d, J = 14.8 Hz), 4.51 (1H, t, J = 5.7 Hz), 4.61 (1H, s), 7.75-7.80 (2H, m), 8.05-8.07 (1H, m), 8.73 (1H, s). | 469 | 467 | 0.8049 |
| 24 | 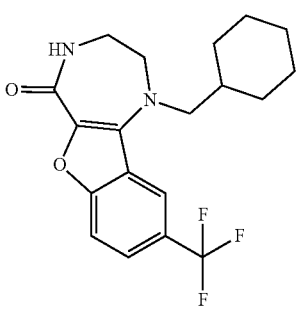 [SMILES: O=C1NCCN(CC2CCCCC2)c2c1oc1ccc(C(F)(F)F)cc21] | | 1H-NMR (DMSO-D6) δ: 0.93-1.11 (2H, m), 1.11-1.31 (3H, m), 1.59-1.87 (6H, m), 3.27-3.34 (2H, m), 3.38 (2H, d, J = 6.9 Hz), 3.42-3.47 (2H, m), 7.76-7.82 (2H, m), 7.99 (1H, t, J = 5.0 Hz), 8.06 (1H, s). | 367 | 365 | 17.0021 |

TABLE 1-4-continued

| 25 | 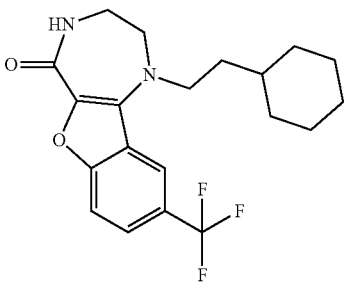 [SMILES: O=C1NCCN(CCC2CCCCC2)c2c1oc1ccc(C(F)(F)F)cc21] | | 1H-NMR (DMSO-D6) δ: 1H-NMR (DMSO-D6) δ: 0.99-1.02 (2H, m), 1.18-1.29 (4H, m), 1.57-1.77 (7H, m), 3.30-3.31 (2H, m), 3.39-3.40 (2H, m), 3.52-3.54 (2H, m), 7.78-7.81 (2H, m), 7.99 (1H, t, J = 6.4 Hz), 8.05 (1H, s). | 381 | 379 | 11.0093 |
|---|---|---|---|---|---|---|
| 26 | 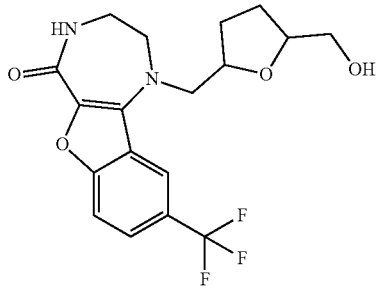 [SMILES: O=C1NCCN(CC2CCC(CO)O2)c2c1oc1ccc(C(F)(F)F)cc21] | racemate The relative configuration of the substituents on the tetrahydrofuran ring is cis. | 1H-NMR (DMSO-D6) δ: 1.54-1.62 (1H, m), 1.68-1.77 (1H, m), 1.91-1.96 (2H, m), 3.23-3.29 (2H, m), 3.44-3.60 (4H, m), 3.56-3.64 (2H, m), 3.87-3.93 (1H, m), 4.14-4.20 (1H, m), 4.62 (1H, d, J = 5.6 Hz), 7.75-7.80 (2H, m), 8.04 (1H, br, s), 8.40 (1H, s). | 385 | 383 | 27.3532 |
| 27 | 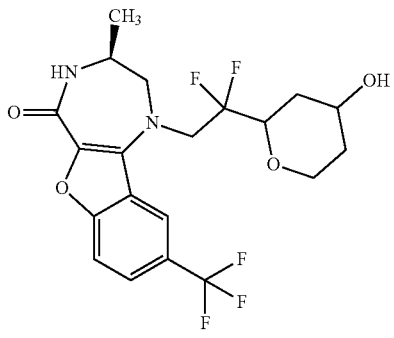 [SMILES: C[C@H]1CN(CC(F)(F)C2CC(O)CCO2)c2c(oc3ccc(C(F)(F)F)cc23)C(=O)N1] | The relative configuration of the substituents on the tetrahydropyran ring is cis or trans or mixture of cis/trans isomers. | 1H-NMR (DMSO-D6) δ: 1.16-1.24 (3H, m), 1.30-1.38 (2H, m), 1.76-1.84 (1H, m), 1.92-2.00 (1H, m), 3.35-3.39 (4H, m), 3.69-3.82 (2H, m), 3.92-4.00 (1H, m), 4.08-4.43 (2H, m), 4.96 (1H, t, J = 4.5 Hz), 7.74-7.79 (2H, m), 7.97 (1H, t, J = 4.3 Hz), 8.38 (1H, d, J = 5.5 Hz). | 449 | 447 | 0.1868 |
| 28 | 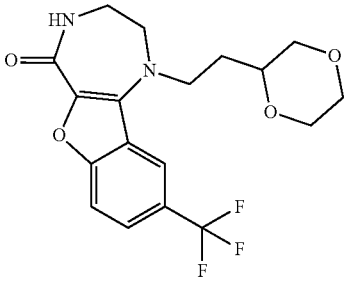 [SMILES: O=C1NCCN(CCC2COCCO2)c2c1oc1ccc(C(F)(F)F)cc21] | racemate | 1H-NMR (DMSO-D6) δ: 1.54-1.65 (1H, m), 1.82-1.93 (1H, m), 3.21-3.35 (5H, m), 3.40-3.77 (8H, m), 7.75-7.81 (2H, m), 8.04 (1H, t, J = 4.5 Hz), 8.41 (1H, s). | 385 | 383 | 0.4408 |

TABLE 1-5

| 29 | 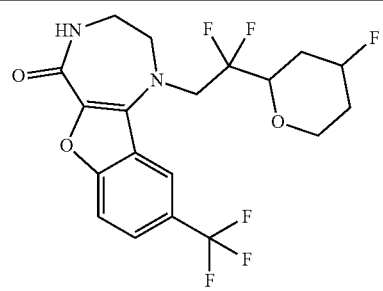 | racemate The relative configuration of the substituents on the tetrahydropyran ring is presumed to be trans. diastereomer of Example 39 | 1H-NMR (DMSO-D6) δ: 1.74-2.05 (4H, m), 3.26-3.42 (2H, m), 3.50 (1H, dd, J = 13.6, 4.8 Hz), 3.57 (1H, dd, J = 13.6, 4.5 Hz), 3.68-3.89 (2H, m), 3.98-4.35 (3H, m), 5.16 (1H, d, J = 48.4 Hz), 7.77-7.80 (2H, m), 8.09 (1H, t, J = 4.5 Hz), 8.33 (1H, s). | 437 | 435 | 0.1248 |

TABLE 1-5-continued

| # | Structure | Stereochem | 1H-NMR | | | |
|---|---|---|---|---|---|---|
| 30 | (structure) | racemate. The relative configuration of the substituents on the tetrahydropyran ring is cis or trans or mixture of cis/trans isomers. | 1H-NMR (DMSO-D6) δ: 1.08 (3H, s), 1.08 (3H, s), 1.38 (1H, m), 1.59 (1H, m), 1.66-1.78 (2H, m), 3.34-.3.37 (2H, m), 3.48-3.59 (2H, m), 3.67-3.72 (1H, m), 3.79-3.83 (1H, m), 3.95-4.24 (3H, m), 4.25 (1H, s), 4.28 (1H, s), 7.78 (1H, d, J = 0.8 Hz), 7.78 (1H, d, J = 0.8 Hz), 8.07 (1H, t, J = 4.8 Hz), 8.36 (1H, s) | 493 | 491 | 0.0577 |
| 31 | (structure) | racemate. The relative configuration of the substituents on the tetrahydropyran ring is cis or trans or mixture of cis/trans isomers. | 1H-NMR (DMSO-D6) δ: 0.45-0.47 (2H, m), 0.53-0.61 (2H, m), 1.22-1.33 (2H, m), 1.69-1.73 (2H, m), 3.18 (1H, d, J = 10.9 Hz), 3.27-3.39 (6H, m), 3.51-3.52 (1H, m), 3.67 (1H, d, J = 14.6 Hz), 3.93 (1H, dd, J = 11.3, 3.7 Hz), 4.71 (1H, d, J = 4.9 Hz), 7.75-7.78 (2H, m), 8.06 (1H, t, J = 4.9 Hz), 8.71 (1H, s). | 425 | 423 | 0.1795 |
| 32 | (structure) | racemate | 1H-NMR (DMSO-D6) δ: 2.27 (1H, d, J = 15.3 Hz), 2.38 (1H, d, J = 14.3 Hz), 2.60-2.73 (2H, m), 3.28-3.62 (4H, m), 3.78 (1H, td, J = 11.7, 2.8 Hz), 4.07-4.39 (4H, m), 7.75-7.84 (2H, m), 8.11 (1H, t, J = 5.0 Hz), 8.34 (1H, br s). | 433 | 431 | 0.0922 |
| 33 | (structure) | racemate. The relative configuration of the substituents on the tetrahydropyran ring is cis or trans or mixture of cis/trans isomers. | 1H-NMR (DMSO-D6) δ: 1.67 (2H, t, J = 12.7 Hz), 1.83 (2H, t, J = 7.1 Hz), 1.95 (1H, d, J = 14.6 Hz), 2.12 (1H, d, J = 13.6 Hz), 3.35-3.39 (2H, m), 3.50-3.58 (2H, m), 3.63-3.67 (3H, m), 4.02-4.23 (4H, m), 4.72 (1H, t, J = 5.0 Hz), 7.78 (2H, d, J = 0.9 Hz), 8.08 (1H, t, J = 5.1 Hz), 8.31 (1H, s). | 488 | 486 | 0.0793 |
| 34 | (structure) | mixture of four isomers | 1H-NMR (CDCl3) δ: 1.51-1.54 (1H, m), 1.66-1.89 (2H, m), 1.98-2.09 (1H, m), 3.26 (2.4H, s), 3.28 (0.6H, s), 3.44-3.64 (4H, m), 3.67-3.74 (3H, m), 3.87-4.15 (3H, m), 4.21-4.34 (1H, m), 6.69-6.70 (1H, m), 7.61-7.67 (1H, m), 7.61-7.67 (1H, m), 8.32-8.34 (1H, s) | 479 | 477 | 0.0206 |

TABLE 1-5-continued

| 35 | (structure) | racemate. The relative configuration of the substituents on the tetrahydropyran ring is cis or trans. diastereomer of Example 36 | 1H-NMR (DMSO-D6) δ: 0.37-0.61 (4H, m), 1.08 (3H, s), 1.31-1.41 (4H, m), 3.2-3.35 (4H, m), 3.44-3.48 (1H, m), 3.56-3.64 (2H, m), 3.71 (1H, dd, J = 10.5, 4.0 Hz), 3.82 (1H, d, J = 14.8 Hz), 4.22 (1H, s), 7.75-7.80 (2H, m), 8.04 (1H, t, J = 4.7 Hz), 8.69 (1H, s). | 439 | 437 | 0.3978 |

TABLE 1-6

| 36 | (structure) | racemate. The relative configuration of the subsituents on the tetrahydropyran ring is cis or trans. diastereomer of Example 35 | 1H-NMR (DMSO-D6) δ: 0.43-0.48 (2H, m), 0.54-0.57 (2H, m), 1.10 (3H, s), 1.40 (2H, d, J = 12.5 Hz), 1.45-1.56 (2H, m), 3.18 (1H, d, J = 10.9 Hz), 3.28-3.30 (3H, m), 3.38-3.47 (3H, m), 3.63 (1H, d, J = 14.6 Hz), 3.86 (1H, dd, J = 11.8, 4.4 Hz), 4.49 (1H, s), 7.77-7.78 (2H, m), 8.05 (1H, t, J = 4.7 Hz), 8.70 (1H, s). | 439 | 437 | 0.2219 |
| 37 | (structure) | racemate | 1H-NMR (DMSO-D6) δ: 1.70-1.73 (1H, m), 2.06-2.10 (1H, m), 2.29-2.43 (4H, m), 2.52-2.59 (3H, m), 3.35-3.36 (3H, m), 3.44-3.54 (2H, m), 3.63-3.68 (1H, m), 7.80 (2H, s), 8.02 (1H, t, J = 4.7 Hz), 8.07 (1H, s). | 431 | 429 | 0.4593 |
| 38 | (structure) | racemate. The relative configuration of the substituents on the cyclohexane ring is cis or trans or mixture of cis/trans isomers. | 1H-NMR (DMSO-D6) δ: 1.24 (1H, q, J = 10.6 Hz), 1.36 (1H, q, J = 13.9 Hz), 1.66-1.67 (1H, m), 1.84 (2H, d, J = 12.9 Hz), 2.03 (4H, t, J = 16.4 Hz), 3.31-3.39 (3H, m), 3.45-3.51 (2H, m), 3.60-3.65 (2H, m), 4.79 (1H, br s), 7.79 (2H, s), 8.01 (1H, t, J = 4.7 Hz), 8.05 (1H, s). | 433 | 431 | 0.1885 |
| 39 | (structure) | racemate. The relative configuration of the substituents on the tetrahydropyran ring is presumed to be cis. diastereomer of Example 29 | 1H-NMR (DMSO-D6) δ: 1.52-1.69 (2H, m), 2.02-2.27 (2H, m), 3.30-3.60 (5H, m), 3.81-3.91 (1H, m), 3.96-4.32 (3H, m), 4.77-5.00 (1H, m), 7.76-7.80 (2H, m), 8.09 (1H, t, J = 4.9 Hz), 8.31 (1H, s). | 437 | 435 | 0.1500 |

TABLE 1-6-continued

| | Structure | 1H-NMR | MS | | |
|---|---|---|---|---|---|
| 40 | (structure) | 1H-NMR (DMSO-D6) δ: 1.24-1.29 (2H, m), 1.56-1.65 (5H, m), 3.26-3.30 (4H, m), 3.39-3.42 (2H, m), 3.54-3.58 (2H, m), 3.82-3.85 (2H, m), 7.79-7.80 (2H, m), 8.00 (1H, br, s), 8.05 (1H, s). | 383 | N.D. | 0.9688 |
| 41 | (structure) | 1H-NMR (DMSO-D6) δ: 1.53-1.64 (1H, m), 1.84-1.95 (1H, m), 3.24-3.34 (6H, m), 3.36-3.50 (3H, m), 3.51-3.68 (3H, m), 3.75 (1H, dd, J = 11.4, 2.6 Hz), 3.85 (1H, dd, J = 11.4, 2.3 Hz), 4.71 (1H, t, J = 5.4 Hz), 7.76-7.81 (2H, m), 8.04 (1H, t, J = 4.8 Hz), 8.41 (1H, s). | 415 | N.D. | 0.9335 |
| 42 | (structure) | 1H-NMR (DMSO-D6) δ: 1.84-1.91 (2H, m), 3.24-3.31 (3H, m), 3.35-3.64 (9H, m), 3.66-3.75 (2H, m), 4.66 (1H, t, J = 5.4 Hz), 7.76-7.81 (2H, m), 8.05 (1H, t, J = 4.6 Hz), 8.39 (1H, s). | 415 | N.D. | 0.5674 |

TABLE 1-7

| | Structure | 1H-NMR | MS | | |
|---|---|---|---|---|---|
| 43 | (structure) | 1H-NMR (DMSO-D6) δ: 1.14 (3H, d, J = 6.6 Hz), 1.81-1.92 (1H, m), 1.96-2.07 (1H, m), 3.25-3.34 (3H, m), 3.41-3.64 (7H, m), 3.65-3.75 (2H, m), 7.76-7.81 (2H, m), 8.06 (1H, t, J = 4.4 Hz), 8.40 (1H, s). | 399 | 397 | 0.7413 |
| 44 | (structure) | 1H-NMR (DMSO-D6) δ: 0.99 (3H, d, J = 6.4 Hz), 1.52-1.63 (1H, m), 1.84-1.95 (1H, m), 3.11-3.18 (1H, m), 3.24-3.35 (4H, m), 3.39-3.48 (1H, m), 3.50-3.67 (4H, m), 3.68-3.76 (2H, m), 7.75-7.81 (2H, m), 8.04 (1H, t, J = 4.4 Hz), 8.39 (1H, s). | 399 | 397 | 1.0396 |

TABLE 1-7-continued

| | | | | |
|---|---|---|---|---|
| 45 | 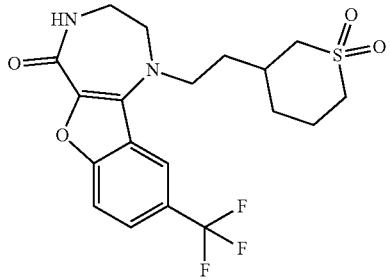 [SMILES: O=C1NCCN(CCC2CCCS(=O)(=O)C2)c2c1oc1ccc(C(F)(F)F)cc21] | racemate | 1H-NMR (DMSO-D6) δ: 1.29 (1H, q, J = 12.9 Hz), 1.70-1.84 (4H, m), 2.01-2.05 (2H, m), 2.91-3.03 (3H, m), 3.15 (1H, d, J = 14.3 Hz), 3.29-3.32 (2H, m), 3.40 (2H, d, J = 4.4 Hz), 3.59 (2H, dd, J = 10.1, 6.6 Hz), 7.80-7.80 (2H, m), 8.01 (1H, t, J = 4.9 Hz), 8.07 (1H, s). | 431 429 4.8039 |
| 46 | 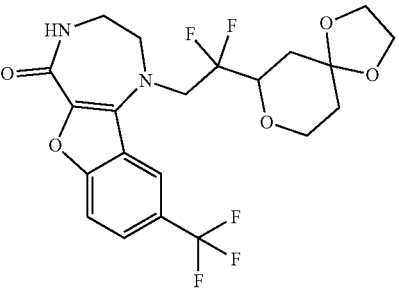 [SMILES: O=C1NCCN(CC(F)(F)C2CC3(CCO2)OCCO3)c2c1oc1ccc(C(F)(F)F)cc21] | racemate | 1H-NMR (DMSO-D6) δ: 1.61-1.85 (4H, m), 3.29-3.41 (2H, m), 3.47-3.61 (3H, m), 3.81-4.33 (8H, m), 7.76-7.79 (2H, m), 8.08 (1H, t, J = 5.0 Hz), 8.32 (1H, br s). | 477 475 0.0715 |
| 47 | 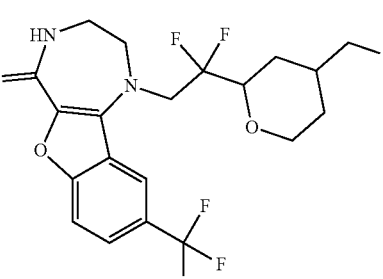 | mixture of four isomers | 1H-NMR (DMSO-D6) δ: 1.11 (2H, m), 1.53-1.81 (3H, m), 3.25-3.31 (2H, m), 3.34-3.39 (2H, m), 3.43-3.49 (1H, m), 3.51-3.58 (2H, m), 3.73-3.78 (1H, m), 3.97-4.38 (3H, m), 4.55 (0.84H, t, J = 5.2 Hz), 4.62 (0.16H, t, J = 5.2 Hz), 7.78-7.79 (1H, m), 7.78-7.79 (1H, m), 8.08 (1H, t, J = 4.8 Hz), 8.35 (1H, s) | 449 N.D. 0.0246 |
| 48 | 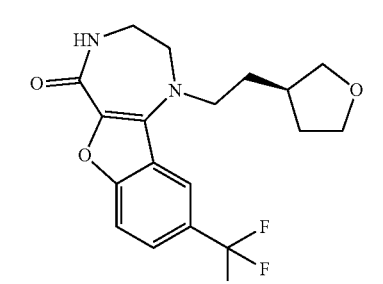 | | 1H-NMR (DMSO-D6) δ: 1.50-1.57 (1H, m), 1.74-1.80 (2H, m), 2.01-2.08 (1H, m), 2.17 (1H, dd, J = 14.7, 7.3 Hz), 3.27-3.34 (3H, m), 3.40-3.42 (2H, m), 3.49-3.57 (2H, m), 3.59-3.66 (1H, m), 3.73 (1H, td, J = 8.3, 4.8 Hz), 3.82 (1H, t, J = 7.6 Hz), 7.78-7.82 (2H, m), 8.02 (1H, t, J = 4.7 Hz), 8.06 (1H, s). | 369 N.D. 2.2396 |
| 49 | 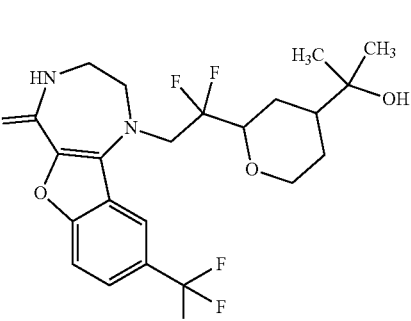 | mixture of four isomers | 1H-NMR (DMSO-D6) δ: 1.05-1.07 (6H, m), 1.21-1.28 (2H, m), 1.54-1.61 (2H, m), 1.82 (1H, d, J = 12.3 Hz), 3.37-3.43 (3H, m), 3.51-3.54 (2H, m), 3.69-3.72 (1H, m), 4.00-4.27 (4H, m), 7.78-7.79 (2H, m), 8.07 (1H, t, J = 5.0 Hz), 8.31 (0.1H, s), 8.35 (0.9H, s). | 477 475 0.0389 |

TABLE 1-8

| 50 | (structure) | | 1H-NMR (DMSO-D6) δ: 1.50-1.57 (1H, m), 1.74-1.80 (2H, m), 2.01-2.08 (1H, m), 2.17 (1H, dd, J = 14.7, 7.3 Hz), 3.27-3.34 (3H, m), 3.40-3.42 (2H, m), 3.49-3.57 (2H, m), 3.59-3.66 (1H, m), 3.73 (1H, td, J = 8.3, 4.8 Hz), 3.82 (1H, t, J = 7.6 Hz), 7.78-7.82 (2H, m), 8.02 (1H, t, J = 4.7 Hz), 8.06 (1H, s). | 369 | N.D. | 3.7571 |
|---|---|---|---|---|---|---|
| 51 | (structure) | racemate The relative configuration of the substituents on the tetrahydropyran ring is cis or trans. diastereomer of Example 10 | 1H-NMR (DMSO-D6) δ: 1.48-1.52 (1H, m), 1.69-1.76 (3H, m), 3.34-3.41 (2H, m), 3.47-3.60 (2H, m), 3.72 (1H, dd, J = 11.1, 5.1 Hz), 3.77-3.83 (1H, m), 4.02-4.28 (4H, m), 4.85 (1H, d, J = 2.1 Hz), 7.77-7.78 (2H, m), 8.07 (1H, t, J = 4.9 Hz), 8.35 (1H, s). | 435 | 433 | 0.0331 |
| 52 | (structure) | racemate The relative configuration of the substituents on the tetrahydropyran ring is cis or trans. diastereomer of Example 53 | 1H-NMR (CDCl3) δ: 1.81-1.92 (2H, m), 2.06-2.10 (1H, m), 2.25-2.28 (1H, m), 3.49-3.58 (2H, m), 3.60-3.72 (3H, m), 3.84-3.96 (2H, m), 4.05-4.10 (1H, m), 4.27-4.39 (1H, m), 5.79 (1H, t, J = 56 Hz), 7.09-7.10 (1H, m), 7.61-7.67 (1H, m), 7.61-7.67 (1H, m), 8.32 (1H, s) | 485 | 483 | 0.1041 |
| 53 | (structure) | racemate The relative configuration of the substituents on the tetrahydropyran ring is cis or trans. diastereomer of Example 52 | 1H-NMR (CDCl3) δ: 1.53-1.58 (1H, m), 1.80-1.91 (3H, m), 3.46-3.56 (2H, m), 3.62-3.68 (2H, m), 3.78-4.09 (4H, m), 4.23-4.34 (1H, m), 5.54 (1H, t, 56 Hz), 6.66 (1H, m), 7.59-7.65 (1H, m), 7.59-7.65 (1H, m), 8.30 (1H, s) | 485 | 483 | 0.0921 |
| 54 | (structure) | racemate The relative configuration of the substituents on the tetrahydropyran ring is cis or trans or mixture of cis/trans isomers. | 1H-NMR (DMSO-D6) δ: 1.51-1.62 (2H, m), 1.94-1.99 (1H, m), 2.10-2.14 (1H, m), 3.27-3.39 (2H, m), 3.47-3.53 (3H, m), 3.86-3.99 (2H, m), 4.05-4.28 (2H, m), 4.39-4.45 (1H, m), 6.78 (1H, t, J = 75.9 Hz), 7.78-7.78 (2H, m), 8.08 (1H, t, J = 4.8 Hz), 8.31 (1H, s). | 485 | 483 | 0.1325 |

TABLE 1-8-continued

| | Structure | Form | 1H-NMR | | | |
|---|---|---|---|---|---|---|
| 55 | 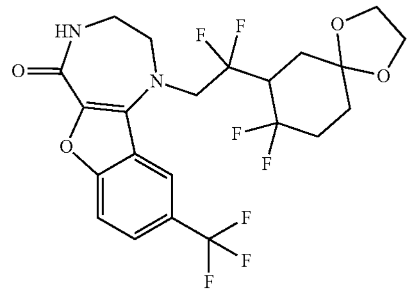 [SMILES: O=C1NCCN(CC(F)(F)C2CC3(CCC2(F)F)OCCO3)c2c1oc1ccc(C(F)(F)F)cc21] | racemate | 1H-NMR (DMSO-D6) δ: 1.75-1.92 (3H, m), 1.99-2.19 (3H, m), 2.92-2.97 (1H, br m), 3.35-3.38 (2H, m), 3.51-3.56 (2H, m), 3.90-3.99 (4H, m), 4.15-4.30 (2H, m), 7.79 (2H, d, J = 0.7 Hz), 8.09 (1H, t, J = 4.9 Hz), 8.18 (1H, s). | 511 | 509 | 0.1153 |
| 56 | 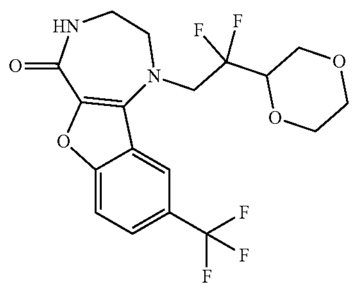 [SMILES: O=C1NCCN(CC(F)(F)C2COCCO2)c2c1oc1ccc(C(F)(F)F)cc21] | racemate | 1H-NMR (DMSO-D6) δ: 3.33-3.38 (2H, m), 3.46-3.62 (4H, m), 3.65-3.75 (2H, m), 3.78-3.84 (1H, m), 3.86-3.92 (1H, m), 3.98-4.29 (3H, m), 7.77-7.80 (2H, m), 8.10 (1H, t, J = 4.8 Hz), 8.32 (1H, s). | 421 | 419 | 0.0723 |

TABLE 1-9

| | Structure | Form | 1H-NMR | | | |
|---|---|---|---|---|---|---|
| 57 | 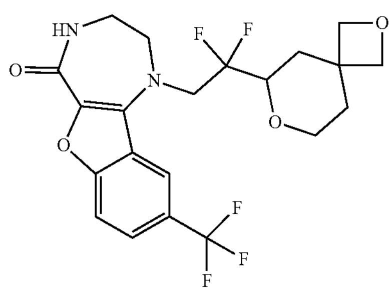 [SMILES: O=C1NCCN(CC(F)(F)C2CC3(CCO2)COC3)c2c1oc1ccc(C(F)(F)F)cc21] | racemate | 1H-NMR (CDCl3) δ: 1.70-1.82 (2H, m), 2.06-2.09 (1H, m), 2.30-2.33 (1H, m), 3.31-3.37 (1H, m), 3.45-3.61 (3H, m), 3.67-3.70 (2H, m), 3.88-4.00 (1H, m), 4.05-4.09 (1H, m), 4.19-4.30 (1H, m), 4.44 (2H, s), 4.52-4.56 (2H, m), 6.66 (1H, m), 7.61-7.67 (1H, m), 7.61-7.67 (1H, m), 8.30 (1H, s) | 461 | 459 | 0.0448 |
| 58 | 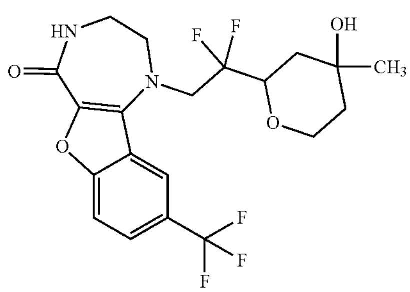 [SMILES: CC1(O)CCOC(C(F)(F)CN2CCNC(=O)c3oc4ccc(C(F)(F)F)cc4c32)C1] | optical active form derived from Example 12 enantiomer of Example 59 | 1H-NMR (DMSO-D6) δ: 1.23 (3H, s), 1.47-1.68 (4H, m), 3.30-3.43 (2H, m), 3.45-3.60 (3H, m), 3.73-3.85 (1H, m), 3.91 (1H, dd, J = 11.6, 4.3 Hz), 3.97-4.13 (1H, m), 4.16-4.32 (1H, m), 4.78 (1H, br s), 7.76-7.79 (2H, m), 8.08 (1H, t, J = 5.0 Hz), 8.34 (1H, br s). | 449 | 447 | 0.0167 |
| 59 | 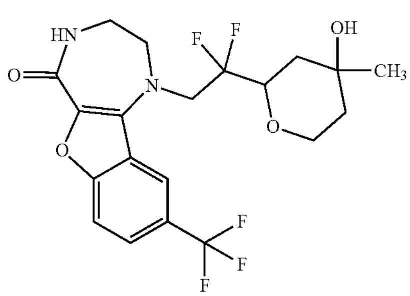 [SMILES: CC1(O)CCOC(C(F)(F)CN2CCNC(=O)c3oc4ccc(C(F)(F)F)cc4c32)C1] | optical active form derived from Example 12 enantiomer of Example 58 | 1H-NMR (DMSO-D6) δ: 1.23 (3H, s), 1.47-1.68 (4H, m), 3.30-3.43 (2H, m), 3.45-3.60 (3H, m), 3.73-3.85 (1H, m), 3.91 (1H, dd, J = 11.6, 4.3 Hz), 3.97-4.13 (1H, m), 4.16-4.32 (1H, m), 4.78 (1H, br s), 7.76-7.79 (2H, m), 8.08 (1H, t, J = 5.0 Hz), 8.34 (1H, br s). | 449 | 447 | 0.1071 |

TABLE 1-9-continued

| # | Structure | Config | 1H-NMR | M1 | M2 | Val |
|---|---|---|---|---|---|---|
| 60 | 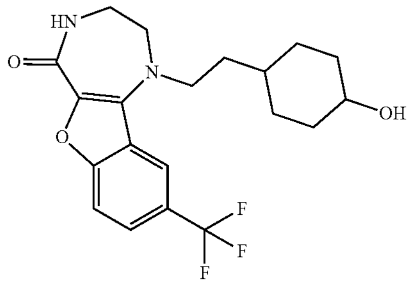 [SMILES: O=C1NCCN(CCC2CCC(O)CC2)c2c1oc1ccc(C(F)(F)F)cc21] | The relative configuration of the substituents on the cyclohexane ring is trans. | 1H-NMR (DMSO-D6) δ: 0.95-1.05 (2H, m), 1.08-1.17 (2H, m), 1.20-1.29 (1H, m), 1.55-1.61 (2H, m), 1.74-1.82 (4H, m), 3.30-3.32 (3H, m), 3.38-3.40 (2H, m), 3.50-3.54 (2H, m), 4.48 (1H, s), 7.79-7.80 (2H, m), 8.00 (1H, t, J = 5.2 Hz), 8.04 (1H, s). | 397 | N.D. | 0.2733 |
| 61 | 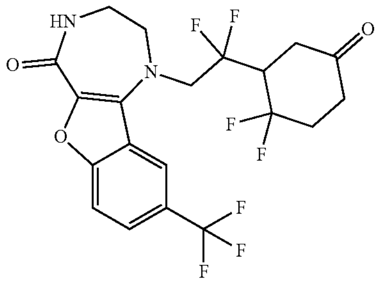 [SMILES: O=C1CCC(F)(F)C(C(F)(F)CN2CCNC(=O)c3oc4ccc(C(F)(F)F)cc4c32)C1] | racemate | 1H-NMR (DMSO-D6) δ: 2.36-2.43 (3H, m), 2.54-2.67 (2H, m), 2.81 (1H, dd, J = 15.5, 12.7 Hz), 3.35-3.37 (2H, m), 3.52-3.56 (3H, m), 4.02-4.19 (1H, m), 4.29-4.36 (1H, m), 7.80-7.80 (2H, m), 8.11 (1H, t, J = 4.9 Hz), 8.18 (1H, s). | 467 | 465 | 0.0391 |
| 62 | 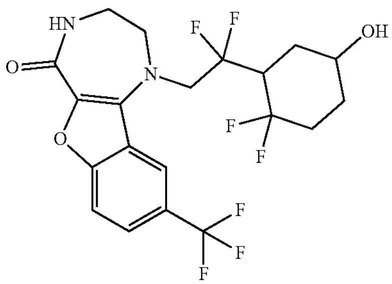 [SMILES: O=C1NCCN(CC(F)(F)C2CC(O)CCC2(F)F)c2c1oc1ccc(C(F)(F)F)cc21] | racemate The relative configuration of the substituents on the cyclohexane ring is cis or trans or mixture of cis/trans isomers. | 1H-NMR (DMSO-D6) δ: 1.39-1.43 (1H, m), 1.52 (1H, q, J = 12.3 Hz), 1.87-2.12 (4H, m), 2.94-2.97 (1H, br m), 3.34-3.37 (2H, m), 3.51-3.58 (2H, m), 3.69-3.70 (1H, m), 4.10-4.21 (2H, m), 4.99 (1H, d, J = 4.9 Hz), 7.79 (2H, d, J = 0.9 Hz), 8.10 (1H, t, J = 5.0 Hz), 8.18 (1H, s). | 469 | 467 | 0.0461 |
| 63 | 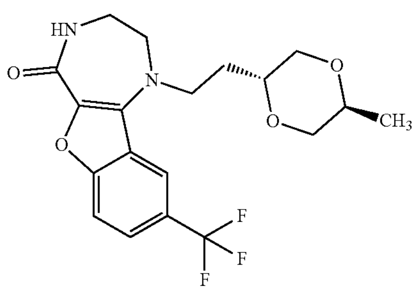 [SMILES: C[C@H]1CO[C@H](CCN2CCNC(=O)c3oc4ccc(C(F)(F)F)cc4c32)CO1] | | 1H-NMR (DMSO-D6) δ: 0.99 (3H, d, J = 6.4 Hz), 1.52-1.63 (1H, m), 1.84-1.95 (1H, m), 3.11-3.18 (1H, m), 3.24-3.35 (4H, m), 3.39-3.48 (1H, m), 3.50-3.67 (4H, m), 3.68-3.76 (2H, m), 7.75-7.81 (2H, m), 8.04 (1H, t, J = 4.4 Hz), 8.39 (1H, s). | 399 | 397 | 0.4524 |

TABLE 1-10

| # | Structure | 1H-NMR | M1 | M2 | Val |
|---|---|---|---|---|---|
| 64 | | 1H-NMR (DMSO-D6) δ: 1.14 (3H, d, J = 6.6 Hz), 1.81-1.92 (1H, m), 1.96-2.07 (1H, m), 3.25-3.34 (3H, m), 3.41-3.64 (7H, m), 3.65-3.75 (2H, m), 7.76-7.81 (2H, m), 8.06 (1H, t, J = 4.4 Hz), 8.40 (1H, s). | 399 | N.D. | 0.2630 |

TABLE 1-10-continued

| 65 | | | 1H-NMR (DMSO-D6) δ: 1.47-1.56 (2H, m), 1.71-1.75 (2H, m), 2.23-2.30 (1H, m), 3.28-3.36 (4H, m), 3.53-3.54 (2H, m), 3.91-3.95 (2H, m), 4.11 (2H, t, J = 16.8 Hz), 7.79-7.80 (2H, m), 8.09 (1H, t, J = 5.1 Hz), 8.15 (1H, s). | 419 | 417 | 0.1199 |
|---|---|---|---|---|---|---|
| 66 | | optical active form derived from Example 11 enantiomer of Example 67 | 1H-NMR (DMSO-D6) δ: 1.19 (3H, s), 1.38-1.66 (4H, m), 3.27-3.41 (2H, m), 3.45-3.61 (2H, m), 3.66-3.80 (2H, m), 3.93-4.31 (3H, m), 4.53 (1H, s), 7.78 (2H, br s), 8.07 (1H, t, J = 5.0 Hz), 8.34 (1H, br s). | 449 | 447 | 0.0283 |
| 67 | | optical active form derived from Example 11 enantiomer of Example 66 | 1H-NMR (DMSO-D6) δ: 1.19 (3H, s), 1.38-1.66 (4H, m), 3.27-3.41 (2H, m), 3.45-3.61 (2H, m), 3.66-3.80 (2H, m), 3.93-4.31 (3H, m), 4.53 (1H, s), 7.78 (2H, br s), 8.07 (1H, t, J = 5.0 Hz), 8.34 (1H, br s). | 449 | 447 | 0.2421 |
| 68 | | single optical active form enantiomer of Example 70 | 1H-NMR (DMSO-D6) δ: 3.33-3.38 (2H, m), 3.46-3.62 (4H, m), 3.65-3.75 (2H, m), 3.78-3.84 (1H, m), 3.86-3.92 (1H, m), 3.98-4.29 (3H, m), 7.77-7.80 (2H, m), 8.10 (1H, t, J = 4.8 Hz), 8.32 (1H, s). | 421 | 419 | 0.0461 |
| 69 | | | 1H-NMR (CDCl3) δ: 1.81-1.91 (1H, m), 1.94-2.04 (1H, m), 3.40-3.57 (4H, m), 3.63-3.84 (5H, m), 3.86 (1H, dd, J = 12.2, 3.4 Hz), 3.94 (1H, dd, J = 12.2, 2.6 Hz), 4.00-4.06 (1H, m), 4.43 (1H, dd, J = 11.6, 5.5 Hz), 4.84 (1H, dd, J = 11.6, 7.7 Hz), 6.63 (1H, t, J = 4.8 Hz), 7.41-7.47 (2H, m), 7.55-7.60 (1H, m), 7.62 (1H, d, J = 8.8 Hz), 7.66 (1H, dd, J = 8.8, 1.7 Hz), 8.03-8.08 (2H, m), 8.36 (1H, d, J = 1.7 Hz). | 519 | N.D. | 18.5323 |

TABLE 1-10-continued
| 70 | 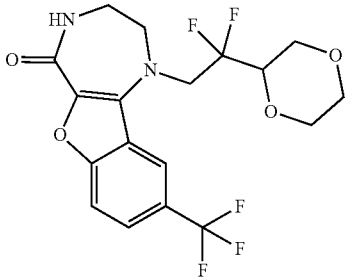 [SMILES: O=C1NCCN(CC(F)(F)C2COCCO2)c2c1oc1ccc(C(F)(F)F)cc21] | single optical form enantiomer of Example 68 | 1H-NMR (DMSO-D6) δ: 3.33-3.38 (2H, m), 3.46-3.62 (4H, m), 3.65-3.75 (2H, m), 3.78-3.84 (1H, m), 3.86-3.92 (1H, m), 3.98-4.29 (3H, m), 7.77-7.80 (2H, m), 8.10 (1H, t, J = 4.8 Hz), 8.32 (1H, s). | 421 | N.D. | 0.0734 |
TABLE 1-11
| 71 | 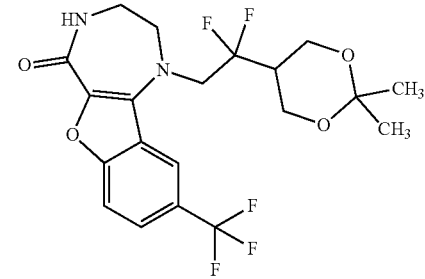 [SMILES: CC1(C)OCC(C(F)(F)CN2CCNC(=O)c3oc4ccc(C(F)(F)F)cc4c32)CO1] | 1H-NMR (DMSO-D6) δ: 1.33 (3H, s), 1.42 (3H, s), 2.21-2.36 (1H, m), 3.33-3.41 (2H, m), 3.55-3.64 (2H, m), 3,88 (2H, dd, J = 12.7, 4.3 Hz), 4.16 (2H, dd, J = 12.7, 3.9 Hz), 4.31 (2H, t, J = 17.5 Hz), 7.80-7.80 (2H, m), 8.06 (1H, t, J = 5.0 Hz), 8.20 (1H, br s). | 449 | 447 | 1.2987 |
| 72 | 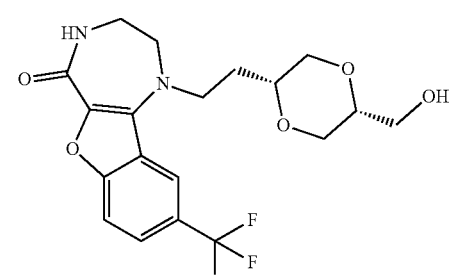 | 1H-NMR (DMSO-D6) δ: 1.84-1.91 (2H, m), 3.24-3.31 (3H, m), 3.35-3.61 (9H, m), 3.66-3.75 (2H, m), 4.66 (1H, t, J = 5.4 Hz), 7.76-7.81 (2H, m), 8.05 (1H, t, J = 4.6 Hz), 8.39 (1H,s). | 415 | 413 | 2.2949 |
| 73 | 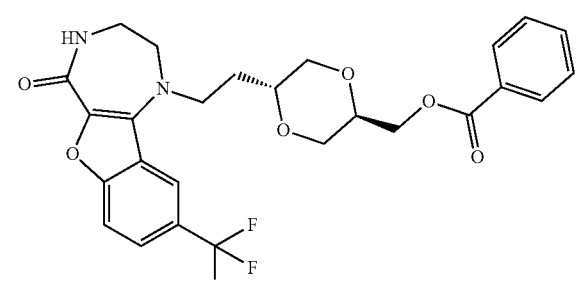 | 1H-NMR (DMSO-D6) δ: 1.55-1.66 (1H, m), 1.86-1.96 (1H, m), 3.27-3.30 (2H, m), 3.35-3.51 (4H, m), 3.51-3.69 (3H, m), 3.82 (1H, dd, J = 11.6, 2.3 Hz), 3.82-3.89 (1H, m), 3.92 (1H, dd, J = 11.6, 2.4 Hz), 4.25-4.33 (2H, m), 7.51-7.56 (2H, m), 7.65-7.70 (1H, m), 7.75-7.81 (2H, m), 7.93-7.98 (2H, m), 8.04 (1H, t, J = 4.5 Hz), 8.40 (1H, s). | 519 | N.D. | 4.7419 |
| 74 | 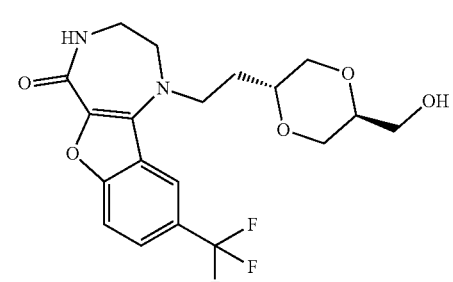 | 1H-NMR (DMSO-D6) δ: 1.53-1.64 (1H, m), 1.84-1.95 (1H, m), 3.24-3.31 (6H, m), 3.36-3.50 (3H, m), 3.51-3.68 (3H, m), 3.75 (1H, dd, J = 11.4, 2.6 Hz), 3.85 (1H, dd, J = 11.4, 2.3 Hz), 4.71 (1H, t, J = 5.4 Hz), 7.76-7.81 (2H, m), 3.04 (1H, t, J = 4.8 Hz), 3.41 (1H, s). | 415 | N.D. | 0.7383 |

TABLE 1-11-continued

| # | Structure | | NMR | | | |
|---|---|---|---|---|---|---|
| 75 | 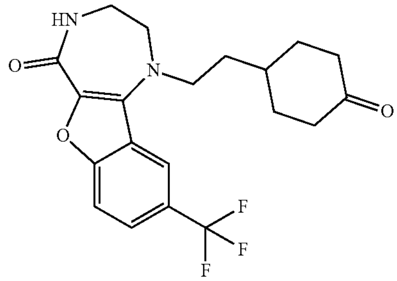 [SMILES: O=C1CCC(CCN2CCNC(=O)c3oc4ccc(C(F)(F)F)cc4c32)CC1] | | 1H-NMR (DMSO-D6) δ: 1.39-1.49 (2H, m), 1.69-1.75 (2H, m), 1.80-1.87 (1H, m), 2.02-2.06 (2H, m), 2.18-2.22 (2H, m), 2.39 (2H, td, J = 13.6, 5.8 Hz), 3.30-3.34 (2H, m), 3.42-3.44 (2H, m), 3.57-3.61 (2H, m), 7.79-7.80 (2H, m), 8.02 (1H, t, J = 4.8 Hz), 8.07 (1H, s). | 395 | 393 | 1.6199 |
| 76 | 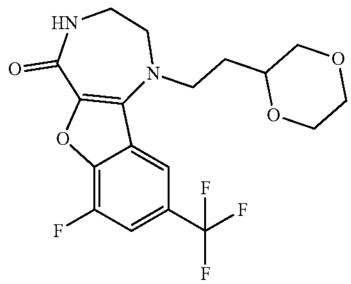 [SMILES: O=C1NCCN(CCC2COCCO2)c2c1oc1c(F)cc(C(F)(F)F)cc21] | race-mate | 1H-NMR (CDCl3) δ: 1.70-1.88 (2H, m), 3.35-3.53 (5H, m), 3.61-3.77 (7H, m), 3.84-3.87 (1H, m), 6.64 (1H, m), 7.41 (1H, d, J = 8.8 Hz), 8.22 (1H, s) | 403 | N.D. | 0.3986 |
| 77 | 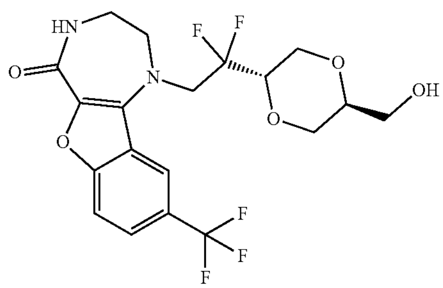 [SMILES: O=C1NCCN(CC(F)(F)[C@@H]2CO[C@@H](CO)CO2)c2c1oc1ccc(C(F)(F)F)cc21] | | 1H-NMR (DMSO-D6) δ: 3.34-3.35 (3H, m), 3.39-3.45 (2H, m), 3.50-3.55 (3H, m), 3.64 (1H, t, J = 11.1 Hz), 3.90-3.95 (3H, m), 4.11-4.23 (2H, m), 4.79 (1H, t, J = 5.4 Hz), 7.79-7.79 (2H, m), 8.10 (1H, t, J = 4.8 Hz), 8.32 (1H, s). | 451 | 449 | 0.0438 |

TABLE 1-12

| # | Structure | NMR | | | |
|---|---|---|---|---|---|
| 78 | 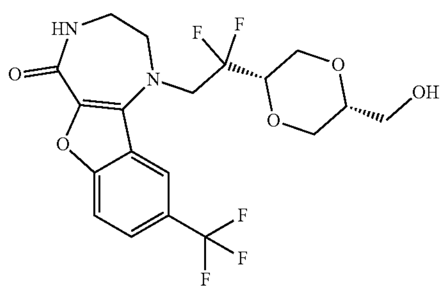 [SMILES: O=C1NCCN(CC(F)(F)[C@@H]2CO[C@H](CO)CO2)c2c1oc1ccc(C(F)(F)F)cc21] | 1H-NMR (DMSO-D6) δ: 3.36-3.40 (2H, m), 3.47-3.60 (4H, m), 3.67-3.76 (4H, m), 3.91 (1H, dd, J = 11.9, 8.0 Hz), 3.98-1.29 (3H, m), 4.74 (1H, t, J = 5.3 Hz), 7.79 (2H, d, J = 0.9 Hz), 8.11 (1H, t, J = 4.9 Hz), 8.28 (1H, s). | 451 | 449 | 0.2274 |
| 79 | 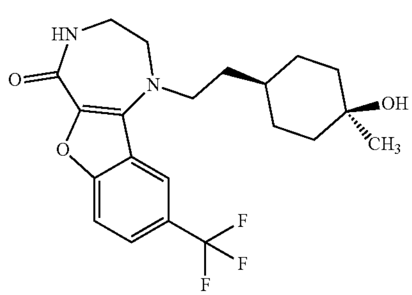 [SMILES: C[C@]1(O)CC[C@@H](CCN2CCNC(=O)c3oc4ccc(C(F)(F)F)cc4c32)CC1] | 1H-NMR (DMSO-D6) δ: 1.08 (3H, s), 1.19-1.26 (3H, m), 1.33-1.40 (2H, m), 1.46-1.54 (4H, m), 1.58-1.61 (2H, m), 3.27-3.32 (2H, m), 3.39-3.41 (2H, m), 3.52-3.55 (2H, m), 3.91 (1H, s), 7.79-7.80 (2H, m), 8.00 (1H, t, J = 5.1 Hz), 8.06 (1H, s). | 411 | 409 | 0.7045 |

TABLE 1-12-continued

| | Structure | Notes | NMR | MS1 | MS2 | Value |
|---|---|---|---|---|---|---|
| 80 | 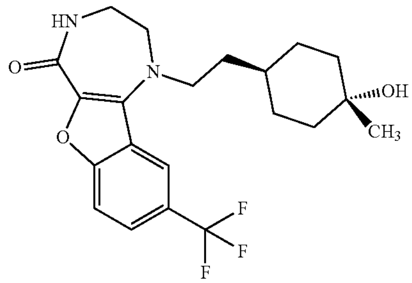 [SMILES: C[C@]1(O)CC[C@H](CCN2CCNC(=O)c3oc4ccc(C(F)(F)F)cc4c32)CC1] | | 1H-NMR (DMSO-D6) δ: 1.08-1.15 (5H, m), 1.30-1.37 (3H, m), 1.48-1.55 (2H, m), 1.60-1.73 (4H, m), 3.27-3.31 (2H, m), 3.39-3.41 (2H, m), 3.51-3.55 (2H, m), 4.20 (1H, s), 7.79-7.80 (2H, m), 8.00 (1H, t, J = 4.7 Hz), 8.05 (1H, s). | 411 | 409 | 0.2048 |
| 81 | 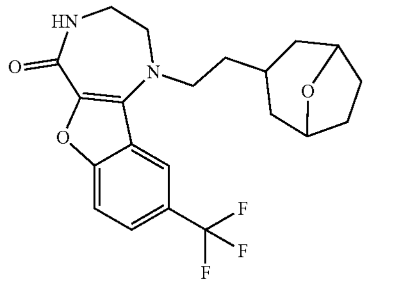 [SMILES: O=C1NCCN(CCC2CC3CCC(C2)O3)c2c1oc1ccc(C(F)(F)F)cc21] | mixture of two isomers | 1H-NMR (DMSO-D6) δ: 1.23-1.36 (2H, m), 1.52-1.87 (8H, m), 2.04-2.11 (1H, m), 3.31-3.35 (2H, m), 3.39-3.41 (2H, m), 3.49-3.51 (2H, m), 4.25-4.26 (2H, m), 7.80-7.82 (2H, m), 8.00-8.03 (1H, m), 8.05 (1H, s). | 409 | 407 | 1.1113 |
| 82 | 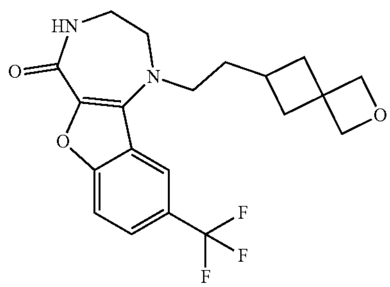 [SMILES: O=C1NCCN(CCC2CC3(COC3)C2)c2c1oc1ccc(C(F)(F)F)cc21] | | 1H-NMR (DMSO-D6) δ: 1.70-1.76 (2H, m), 1.82-1.89 (2H, m), 2.06-2.14 (1H, m), 2.32-2.37 (2H, m), 3.29-3.39 (6H, m), 4.13 (2H, s), 4.56 (2H, s), 7.78-7.82 (2H, m), 8.00-8.03 (2H, m), | 395 | N.D. | 2.0597 |
| 83 | 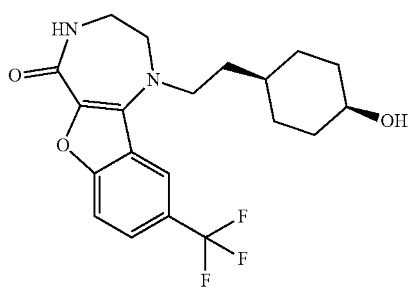 [SMILES: O=C1NCCN(CC[C@H]2CC[C@@H](O)CC2)c2c1oc1ccc(C(F)(F)F)cc21] | | 1H-NMR (DMSO-D6) δ: 1.31-1.51 (7H, m), 1.56-1.65 (4H, m), 3.20-3.46 (4H, m), 3.48-3.59 (2H, m), 3.68-3.77 (1H, m), 4.28 (1H, br s), 7.76-7.85 (2H, m), 8.01 (1H, t, J = 4.3 Hz), 8.05 (1H, s). | 397 | 395 | 0.7617 |
| 84 | 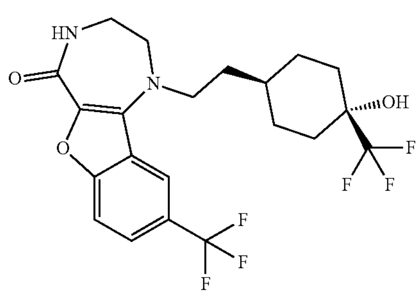 [SMILES: O=C1NCCN(CC[C@H]2CC[C@@](O)(C(F)(F)F)CC2)c2c1oc1ccc(C(F)(F)F)cc21] | | 1H-NMR (DMSO-D6) δ: 1.40-1.44 (2H, m), 1.49-1.52 (2H, m), 1.65-1.72 (5H, m), 1.78-1.84 (2H, m), 3.29-3.36 (2H, m), 3.40-3.42 (2H, m), 3.50-3.54 (2H, m), 5.66 (1H, s), 7.80-7.82 (2H, m), 8.01-8.02 (2H, m). | 465 | 463 | 0.2364 |

TABLE 1-13

| 85 | 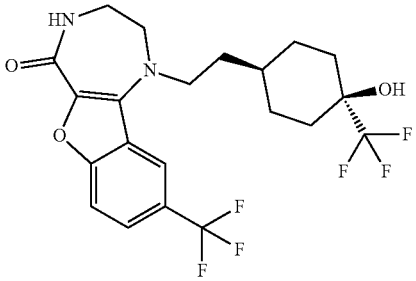 [SMILES: O=C1NCCN(CC[C@H]2CC[C@](O)(C(F)(F)F)CC2)c2c1oc1ccc(C(F)(F)F)cc21] | | 1H-NMR (DMSO-D6) δ: 1.32-1.10 (3H, m), 1.13-1.40 (2H, m), 1.60-1.67 (4H, m), 1.72 (2H, dd, J = 11.9, 1.0 Hz), 3.27-3.35 (2H, m), 3.39-3.41 (2H, m), 3.53-3.56 (2H, m), 5.64 (1H, s), 7.79-7.80 (2H, m), 8.01 (1H, t, J = 5.3 Hz), 8.05 (1H, s), | 465 | 463 | 4.0770 |
| 86 | 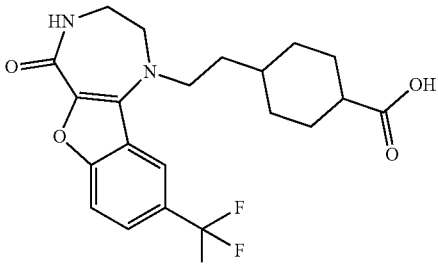 | mixture of cis/trans isomers | 1H-NMR (DMSO-D6) δ: 0.98-1.03 (2H, m), 1.26-1.29 (3H, m), 1.56-1.60 (2H, m), 1.79-1.88 (4H, m), 2.09-2.12 (1H, m), 3.22-3.30 (2H, m), 3.37-3.39 (2H, m), 3.52 (2H, t, J = 8.3 Hz), 7.78 (2H, t, J = 9.6 Hz), 7.98 (1H, t, J = 4.9 Hz), 8.03 (1H, s), 12.07 (1H, br s). | 425 | 423 | 4.0634 |
| 87 | 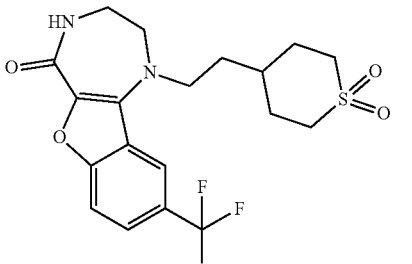 | | 1H-NMR (CDCl3) δ: 1.69 (1H, m), 1.81-1.87 (2H, m), 1.97-2.07 (2H, m), 2.15-2.17 (2H, m), 2.96-3.04 (2H, m), 3.08-3.11 (2H, m), 3.49-3.50 (4H, m), 3.56-3.60 (2H, m), 6.38 (1H, m), 7.65-7.71 (1H, m), 7.65-7.71 (1H, m), 7.88 (1H, m) | 431 | N.D. | 1.9700 |
| 88 | 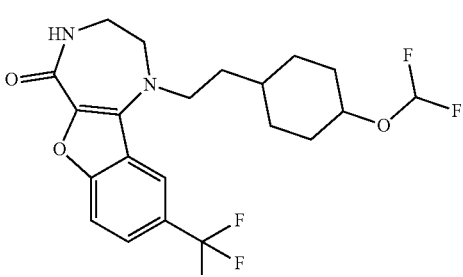 | mixture of cis/trans isomers | 1H-NMR (DMSO-D6) δ: 1.03-1.13 (2H, m), 1.30-1.36 (3H, m), 1.60 (2H, dt, J = 11.2, 5.5 Hz), 1.76-1.87 (2H, m), 1.92-1.99 (2H, m), 3.28-3.32 (2H, m), 3.39-3.40 (2H, m), 3.51-3.55 (2H, m), 3.99 (1H, tt, J = 10.8, 4.7 Hz), 6.69 (0.15H, t, J = 76.8 hz), 6.70 (0.85H, t, J = 76.8 Hz), 7.78-7.82 (2H, m), 8.01 (1H, t, J = 4.7 Hz), 8.04 (1H, s). | 447 | 445 | 6.9505 |
| 89 | 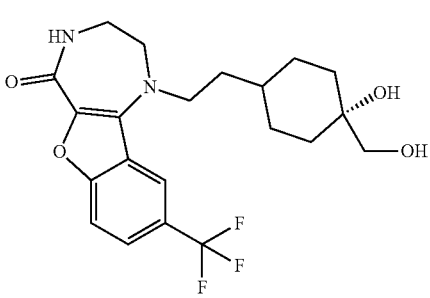 | mixture of cis/trans isomers | 1H-NMR (DMSO-D6) δ: 1.05-1.46 (6H, m), 1.49-1.56 (1H, m), 1.57-1.72 (4H, m), 3.12 (1H, d, J = 5.9 Hz), 3.28-3.34 (3H, m), 3.38-3.42 (2H, m), 3.50-3.57 (2H, m), 3.80 (0.5H, s), 3.98 (0.5H, s), 4.30 (0.5H, t, J = 5.6 Hz), 4.44 (0.5H, t, J = 6.0 Hz), 7.77-7.82 (2H, m), 8.00 (1H, t, J = 4.9 Hz), 8.04 (0.5H, br s), 8.06 (0.5H, br s). | 427 | 425 | 0.0329 |

TABLE 1-13-continued

| | | | | | | |
|---|---|---|---|---|---|---|
| 90 | 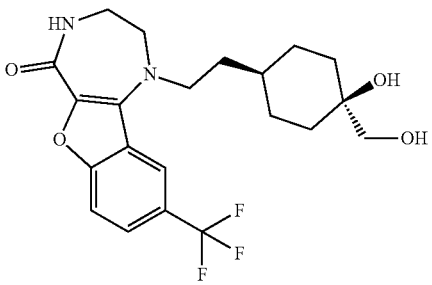 [SMILES: O=C1NCCN(CC[C@H]2CC[C@](O)(CO)CC2)c2c1oc1ccc(C(F)(F)F)cc21] | | 1H-NMR (DMSO-D6) δ: 1.18-1.45 (7H, m), 1.49-1.56 (2H, m), 1.57-1.65 (2H, m), 3.12 (2H, d, J = 5.9 Hz), 3.28-3.34 (2H, m), 3.33-3.42 (2H, m), 3.51-3.57 (2H, m), 3.80 (1H, s), 4.44 (1H, t, J = 5.9 Hz), 7.77-7.82 (2H, m), 8.00 (1H, t, J = 4.9 Hz), 8.06 (1H, br s). | 427 | 425 | 0.0091 |
| 91 | 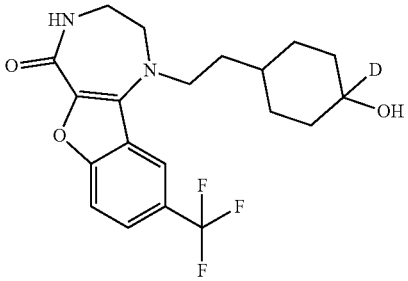 [SMILES: [2H]C1(O)CCC(CCN2CCNC(=O)c3oc4ccc(C(F)(F)F)cc4c32)CC1] | The relative configuration of the substituents on the cyclohexane ring is cis or trans. | 1H-NMR (DMSO-D6) δ: 0.96-1.25 (5H, m), 1.55-1.61 (2H, m), 1.74-1.82 (4H, m), 3.28-3.31 (2H, m), 3.38-3.41 (2H, m), 3.50-3.54 (2H, m), 4.45 (1H, s), 7.79-7.80 (1H, m), 7.79-7.80 (1H, m), 7.99-8.02 (1H, m), 8.04 (1H, s) | 398 | N.D. | 0.1984 |

TABLE 1-14

| | | | | | | |
|---|---|---|---|---|---|---|
| 92 | 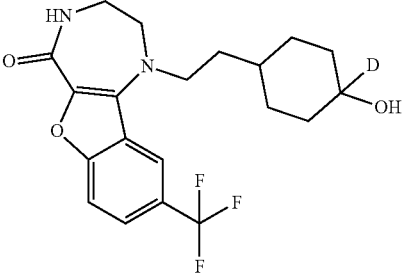 [SMILES: [2H]C1(O)CCC(CCN2CCNC(=O)c3oc4ccc(C(F)(F)F)cc4c32)CC1] | mixture of cis/trans isomers | 1H-NMR (DMSO-D6) δ: 0.96-1.25 (0.9H, m), 1.36-1.47 (5.74H, m), 1.53-1.61 (3.64H, m), 1.74-1.82 (0.72H, m), 3.28-3.31 (2H, m), 3.36-3.41 (2H, m), 3.50-3.54 (2H, m), 4.25 (0.82H, s), 4.45 (0,18H, s), 7.77-7.82 (2H, m), 8.01 (1H, m), 8.05 (1H, s) | 398 | N.D. | 0.7073 |
| 93 | 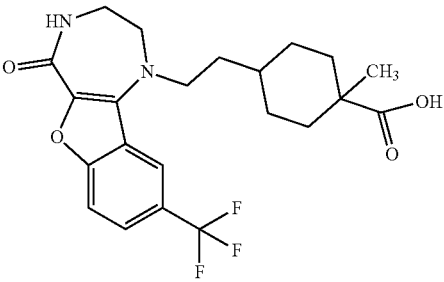 [SMILES: CC1(C(=O)O)CCC(CCN2CCNC(=O)c3oc4ccc(C(F)(F)F)cc4c32)CC1] | mixture of cis/trans isomers | 1H-NMR (DMSO-D6) δ: 0.88-0.93 (4H, m), 1.18 (3H, s), 1.35-1.36 (1H, m), 1.56-1.60 (5H, m), 2.01-2.11 (1H, m), 3.28-3.31 (2H, m), 3.37-3.39 (2H, m), 3.49-3.51 (2H, m), 7.79 (2H, s), 8.00-8.04 (2H, m). | 439 | 437 | 5.1494 |
| 94 | 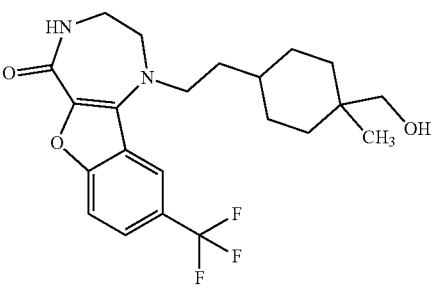 [SMILES: CC1(CO)CCC(CCN2CCNC(=O)c3oc4ccc(C(F)(F)F)cc4c32)CC1] | mixture of cis/trans isomers | 1H-NMR (DMSO-D6) δ: 0.81 (3H, s), 0.98-1.31 (5H, m), 1.56-1.63 (6H, m), 3.05 (0.4H, d, J = 5.5 Hz), 3.24 (1.6H, d, J = 5.3 Hz), 3.29-3.31 (2H, m), 3.39-3.40 (2H, m), 3.51-3.56 (2H, m), 4.31 (0.8H, t, J = 5.3 Hz), 4.41 (0.2H , t, J = 5.4 Hz), 7.79 (2H, s), 8.01-8.06 (2H, m). | 425 | 423 | 0.1291 |

TABLE 1-14-continued

| 95 | 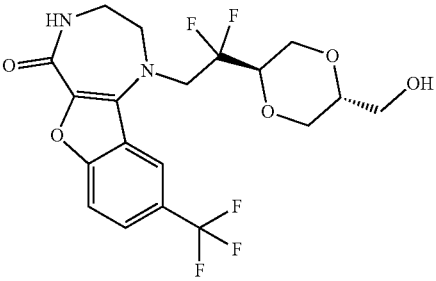 [SMILES: O=C1NCCN(CC(F)(F)[C@H]2CO[C@H](CO)CO2)c2c1oc1ccc(C(F)(F)F)cc21] | | 1H-NMR (DMSO-D6) δ: 3.34-3.35 (3H, m), 3.39-3.45 (2H, m), 3.50-3.55 (3H, m), 3.64 (1H, t, J = 11.1 Hz), 3.90-3.95 (3H, m), 4.11-4.23 (2H, m), 4.79 (1H, t, J = 5.4 Hz), 7.79-7.79 (2H, m), 8.10 (1H, t, J = 4.8 Hz), 8.32 (1H, s). | 451 | 449 | 0.0443 |
|---|---|---|---|---|---|---|
| 96 | 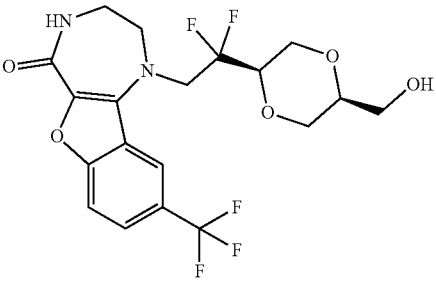 [SMILES: O=C1NCCN(CC(F)(F)[C@H]2CO[C@@H](CO)CO2)c2c1oc1ccc(C(F)(F)F)cc21] | | 1H-NMR (DMSO-D6) δ: 3.36-3.40 (2H, m), 3.47-3.60 (4H, m), 3.67-3.76 (4H, m), 3.91 (1H, dd, J = 11.9, 8.0 Hz), 3.98-4.29 (3H, m), 4.74 (1H, t, J = 5.3 Hz), 7.79 (2H, d, J = 0.9 Hz), 8.11 (1H, t, J = 4.9 Hz), 8.28 (1H, s). | 451 | 449 | 0.0283 |
| 97 | 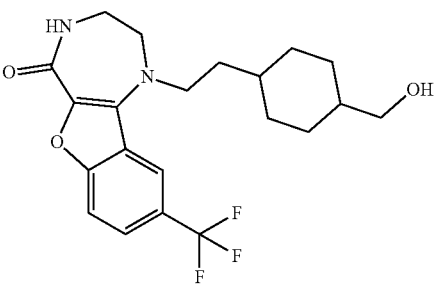 [SMILES: O=C1NCCN(CCC2CCC(CO)CC2)c2c1oc1ccc(C(F)(F)F)cc21] | mixture of cis/trans isomers | 1H-NMR (DMSO-D6) δ: 0.90-1.01 (2H, m), 1.30-1.81 (10H, m), 3.20 (1H, t, J = 5.8 Hz), 3.27-3.29 (3H, m), 3.40-3.40 (2H, m), 3.48-3.56 (2H, m), 4.32-4.34 (1H, m), 7.79 (2H, s), 8.01-8.05 (2H, m). | 411 | 409 | 0.1075 |
| 98 | 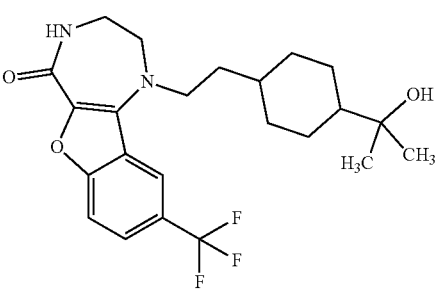 [SMILES: CC(C)(O)C1CCC(CCN2CCNC(=O)c3oc4ccc(C(F)(F)F)cc4c32)CC1] | mixture of cis/trans isomers | 1H-NMR (DMSO-D6) δ: 0.95-1.00 (10H, m), 1.13-1.21 (2H, m), 1.59-1.65 (2H, m), 1.77-1.83 (4H, m), 3.29-3.31 (2H, m), 3.37-3.40 (2H, m), 3.54 (2H, t, J = 8.2 Hz), 3.94 (0.1H, s), 3.98 (0.9H, s), 7.79-7.80 (2H, m), 8.00-8.04 (2H, m). | 439 | 437 | 1.0728 |

TABLE 1-15

| 99 | 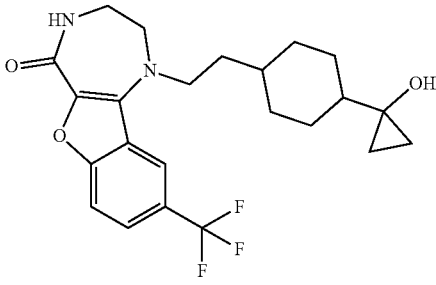 [SMILES: O=C1NCCN(CCC2CCC(C3(O)CC3)CC2)c2c1oc1ccc(C(F)(F)F)cc21] | The relative configuration of the substituents on the cyclohexane ring is presumed to be trans. | 1H-NMR (DMSO-D6) δ: 0.31 (2H, dd, J = 6.5, 4.6 Hz), 0.46 (2H, dd, J = 6.5, 4.6 Hz), 0.83-1.00 (3H, m), 1.20-1.26 (3H, m), 1.59 (2H, dd, J = 16.1, 6.8 Hz), 1.68 (2H, d, J = 9.9 Hz), 1.82 (2H, d, J = 10.9 Hz), 3.17 (1H, d, J = 5.1 Hz), 3.29-3.31 (1H, m), 3.37-3.39 (2H, m), 3.54 (2H, t, J = 7.9 Hz), 4.81 (1H, s), 7.79-7.80 (2H, m), 8.01-8.04 (2H, m). | 437 | 435 | 0.0764 |

TABLE 1-15-continued

| | Structure | Isomer | 1H-NMR | MS1 | MS2 | Value |
|---|---|---|---|---|---|---|
| 100 | 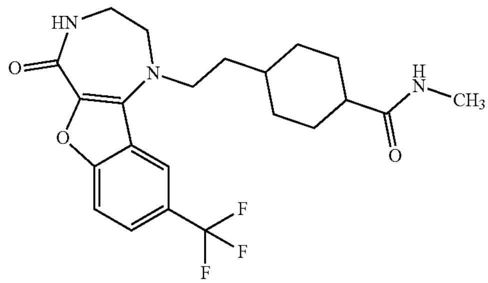 [SMILES: CNC(=O)C1CCC(CCN2CCNC(=O)c3oc4ccc(C(F)(F)F)cc4c32)CC1] | mixture of cis/trans isomers | 1H-NMR (DMSO-D6) δ: 0.95-1.01 (2H, m), 1.30-1.39 (3H, m), 1.58-1.62 (2H, m), 1.71 (2H, d, J = 10.6 Hz), 1.82 (2H, d, J = 10.9 Hz), 2.00-2.06 (1H, m), 2.54 (3H, d, J = 4.6 Hz), 3.29-3.31 (2H, m), 3.40-3.40 (2H, m), 3.54 (2H, t, J = 8.2 Hz), 7.63 (1H, d, J = 4.6 Hz), 7.78-7.81 (2H, m), 8.00-8.04 (2H, m). | 438 | 436 | 0.9998 |
| 101 | 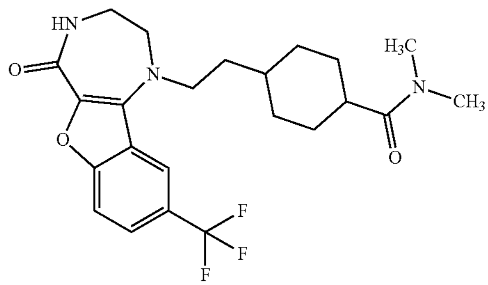 [SMILES: CN(C)C(=O)C1CCC(CCN2CCNC(=O)c3oc4ccc(C(F)(F)F)cc4c32)CC1] | mixture of cis/trans isomers | 1H-NMR (DMSO-D6) δ: 1.03-1.13 (2H, m), 1.31-1.37 (3H, m), 1.60-1.66 (4H, m), 1.81 (2H, d, J = 10.6 Hz), 2.53-2.58 (1H, m), 2.79 (3H, s), 2.99 (3H, s), 3.29-3.32 (2H, m), 3.37-3.40 (2H, m), 3.55 (2H, t, J = 8.1 Hz), 7.80 (2H, s), 8.01-8.04 (2H, m). | 452 | N.D. | 0.7750 |
| 102 | 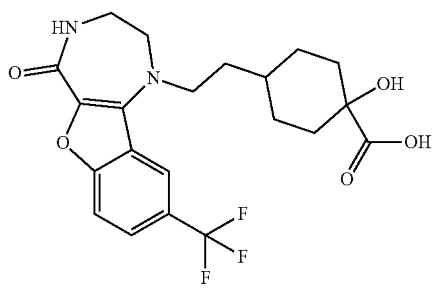 [SMILES: O=C1NCCN(CCC2CCC(O)(C(=O)O)CC2)c2c1oc1ccc(C(F)(F)F)cc21] | mixture of cis/trans isomers | 1H-NMR (DMSO-D6) δ: 1.32-1.38 (3H, m), 1.56-1.74 (8H, m), 3.30-3.32 (2H, m), 3.39-3.41 (2H, m), 3.52-3.56 (2H, m), 7.79-7.80 (2H, m), 8.01 (1H, t, J = 4.9 Hz), 8.05 (1H, s). | 441 | 439 | 5.4689 |
| 103 | 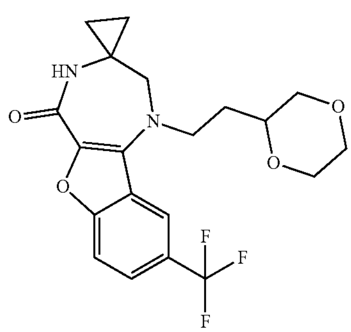 [SMILES: O=C1NC2(CC2)CN(CCC2COCCO2)c2c1oc1ccc(C(F)(F)F)cc21] | racemate | 1H-NMR (DMSO-D6) δ: 0.86-0.92 (4H, s), 1.54-1.62 (1H, m), 1.76-1.83 (1H, m), 3.19-3.24 (1H, m), 3.37-3.49 (3H, m), 3.51-3.68 (5H, m), 3.71-3.74 (1H, m), 3.77-3.85 (1H, m), 7.74-7.80 (1H, m), 7.74-7.80 (1H, m), 8.16 (1H, s), 8.49 (1H, s) | 411 | N.D. | 0.0577 |
| 104 | 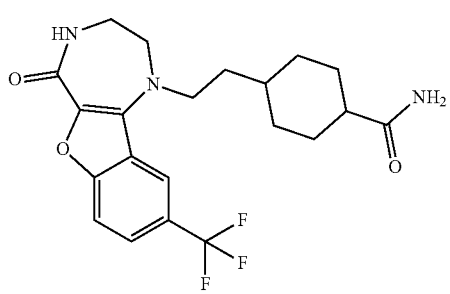 [SMILES: NC(=O)C1CCC(CCN2CCNC(=O)c3oc4ccc(C(F)(F)F)cc4c32)CC1] | mixture of cis/trans isomers | 1H-NMR (DMSO-D6) δ: 0.99-1.02 (2H, m), 1.29-1.31 (3H, m), 1.57-1.59 (2H, m), 1.74-1.82 (4H, m), 2.00-2.03 (1H, m), 3.29-3.31 (2H, m), 3.40-3.41 (2H, m), 3.55 (2H, t, J = 8.1, Hz), 6.63 (1H, s), 7.17 (1H, s), 7.80 (2H, s), 8.00-8.04 (2H, m). | 424 | 422 | 0.8185 |

TABLE 1-15-continued

| 105 | (structure) | mixture of cis/trans isomers | 1H-NMR (DMSO-D6) δ: 1.15 (2H, dd, J = 24.4, 12.2 Hz), 1.39-1.52 (3H, m), 1.65 (2H, dd, J = 16.1, 8.0 Hz), 1.89 (2H, d, J = 9.7 Hz), 1.98 (2H, d, J = 10.6 Hz), 2.70-2.72 (1H, br m), 3.31-3.33 (2H, m), 3.41-3.43 (2H, m), 3.58 (2H, t, J = 8.2 Hz), 7.79-7.80 (2H, m), 8.01, (1H, t, J = 4.5 Hz), 8.08 (1H, s), 13.56 (1H, s). | 448 | 446 | 0.6066 |

TABLE 1-16

| 106 | (structure) | | 1H-NMR (DMSO-D6) δ: 1.08-1.37 (4H, m), 1.82-1.94 (5H, m), 3.27-3.41 (3H, m), 3.49-3.55 (2H, m), 4.09 (2H, t, J = 16.6 Hz), 4.61 (1H, d, J = 4.4 Hz), 7.77-7.80 (2H, m), 8.08 (1H, t, J = 4.3 Hz), 8.14 (1H, br s). | 433 | 431 | 0.0409 |
| 107 | (structure) | mixture of cis/trans isomers | 1H-NMR (DMSO-D6) δ: 1.08-1.37 (0.8H, m), 1.40-1.46 (1.6H, m), 1.57-1.78 (4.8H, m), 1.82-1.97 (1.8H, m), 3.27-3.41 (2.2H, m), 3.49-3.55 (2H, m), 3.83-3.87 (0.8H, m), 4.09 (2H, t, J = 16.6 Hz), 4.38 (0.8H, d, J = 2.8 Hz), 4.61 (0.2H, d, J = 4.4 Hz), 7.77-7.80 (2H, m), 8.09 (1H, t, J = 4.7 Hz), 8.14-8.16 (1H, m). | 433 | 431 | 0.0862 |
| 108 | (structure) | | 1H-NMR (DMSO-D6) δ: 1.23-1.26 (3H, m), 1.31-1.42 (2H, m), 1.47-1.60 (8H, m), 3.30-3.35 (2H, m), 3.39-3.40 (2H, m), 3.51-3.57 (4H, m), 3.95 (1H, s), 4.32 (1H, t, J = 4.9 Hz), 7.79-7.80 (2H, m), 8.00 (1H, t, J = 5.3 Hz), 8.05 (1H, s). | 441 | 439 | 0.2977 |
| 109 | (structure) | | 1H-NMR (DMSO-D6) δ: 1.05-1.17 (2H, m), 1.28 (2H, td, J = 12.3, 3.3 Hz), 1.34-1.41 (1H, m), 1.59-1.71 (8H, m), 3.28-3.32 (2H, m), 3.39-3.40 (2H, m), 3.50-3.56 (4H, m), 4.22 (1H, s), 4.32 (1H, t, J = 4.9 Hz), 7.79-7.80 (2H, m), 8.00 (1H, t, J = 4.7 Hz), 8.04 (1H, s). | 441 | 439 | 0.1931 |

TABLE 1-16-continued

| | | | | | | |
|---|---|---|---|---|---|---|
| 110 | 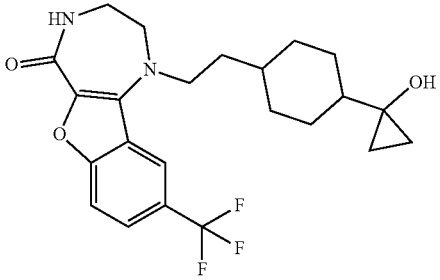 [SMILES: O=C1NCCN(CCC2CCC(C3(O)CC3)CC2)c2c1oc1ccc(C(F)(F)F)cc21] | mixture of cis/trans isomers | 1H-NMR (DMSO-D6) δ: 0.30 (2H, dt, J = 8.3, 3.2 Hz), 0.44-0.48 (2H, m), 0.85-0.98 (2H, m), 1.16-1.25 (2H, m), 1.39-1.45 (3H, m), 1.65-1.78 (5H, m), 3.30-3.32 (2H, m), 3.41 (2H, t, J = 7.1 Hz), 3.48-3.57 (2H, m), 4.75 (0.5H, s), 4.81 (0.5H, s), 7.79-7.80 (2H, m), 8.00-8.06 (2H, m). | 437 | 435 | 0.1331 |
| 111 | 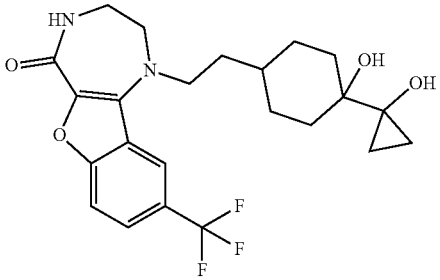 [SMILES: O=C1NCCN(CCC2CCC(O)(C3(O)CC3)CC2)c2c1oc1ccc(C(F)(F)F)cc21] | mixture of cis/trans isomers | 1H-NMR (DMSO-D6) δ: 0.32 (2H, dd, J = 6.4, 4.3 Hz), 0.62-0.65 (2H, m), 1.20-1.37 (5H, m), 1.62-1.74 (6H, m), 3.31-3.32 (2H, m), 3.40-3.41 (2H, m), 3.55 (2H, t, J = 8.3 Hz), 3.63 (0.9H, s), 3.67 (0.1H, s), 4.84 (0.1H, s), 4.92 (0.9H, s), 7.79-7.81 (2H, m), 7.99-8.07 (2H, m). | 453 | 451 | 0.0110 |
| 112 | 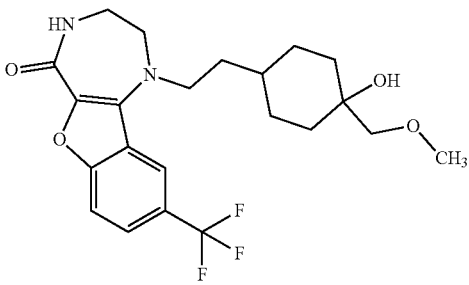 [SMILES: COCC1(O)CCC(CCN2CCNC(=O)c3oc4ccc(C(F)(F)F)cc4c32)CC1] | mixture of cis/trans isomers | 1H-NMR (DMSO-D6) δ: 1.22-1.25 (1H, m), 1.30-1.53 (8H, m), 1.59-1.63 (2H, m), 3.08 (2H, s), 3.23-3.25 (3H, m), 3.28-3.30 (2H, m), 3.40-3.42 (2H, m), 3.53 (2H, t, J = 8.2 Hz), 4.05 (0.9H, s), 4.18 (0.1H, s), 7.78-7.81 (2H, m), 8.00 (1H, t, J = 4.7 Hz), 8.05 (1H, s). | 441 | N.D. | 1.0328 |

TABLE 1-17

| | | | | | | |
|---|---|---|---|---|---|---|
| 113 | 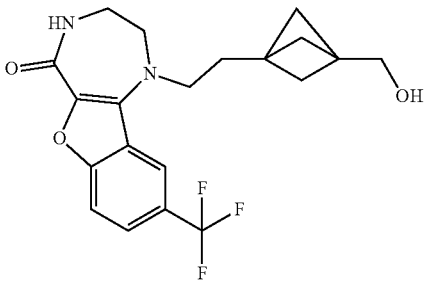 [SMILES: O=C1NCCN(CCC23CC(CO)(C2)C3)c2c1oc1ccc(C(F)(F)F)cc21] | | 1H-NMR (CDCl3) δ: 1.70 (6H, s), 1.97-2.01 (2H, m), 3.50-3.51 (2H, m), 3.50-3.51 (2H, m), 3.53-3.57 (2H, m), 3.62-3.63 (2H, m), 6.48 (1H, m), 7.62-7.68 (1H, m), 7.62-7.68 (1H, m), 7.94 (1H, s) | 395 | N.D. | 0.7262 |
| 114 | 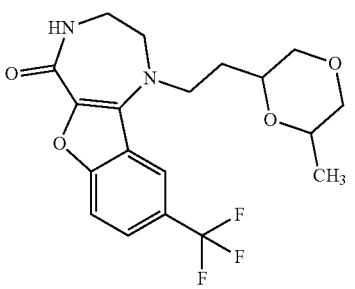 [SMILES: CC1COCC(CCN2CCNC(=O)c3oc4ccc(C(F)(F)F)cc4c32)O1] | racemate The relative configuration of the substituents on the dioxane ring is cis. diastereomer of Example 115 | 1H-NMR (DMSO-D6) δ: 0.98 (3H, d, J = 6.3 Hz), 1.56- 1.67 (1H, m), 1.81-1.92 (1H, m), 3.01 (1H, dd, J = 11.3, 10.3 Hz), 3.12 (1H, dd, J = 11.0, 10.3 Hz), 3.23-3.46 (4H, m), 3.49-3.77 (6H, m), 7.76-7.82 (2H, m), 8.03 (1H, t, J = 5.0 Hz), 8.18 (1H, s). | 399 | 397 | 0.7077 |

TABLE 1-17-continued

| | | | | | | |
|---|---|---|---|---|---|---|
| 115 | (structure) | racemate. The relative configuration of the substituents on the dioxane ring is trans. diastereomer of Example 114 | 1H-NMR (DMSO-D6) δ: 1.09 (3H, d, J = 6.5 Hz), 1.80-1.90 (1H, m), 1.90-2.01 (1H, m), 3.25-3.34 (4H, m), 3.35-3.41 (1H, m), 3.42-3.55 (2H, m), 3.55-3.70 (3H, m), 3.85-3.96 (2H, m), 7.76-7.82 (2H, m), 8.07 (1H, t, J = 4.4 Hz), 8.39 (1H, s). | 399 | 397 | 0.6723 |
| 116 | (structure) | The relative configuration of the substituents on the cyclohexane ring is cis or trans. | 1H-NMR (DMSO-D6) δ: 0.88 (4H, s), 1.23 (1H, m), 1.29-1.46 (6H, m), 1.49-1.52 (4H, m), 3.12 (2H, d, J = 6.0 Hz), 3.43 (2H, s), 3.64-3.68 (2H, m), 3.79 (1H, s), 4.44 (1H, t, J = 6.0 H), 7.75-7.81 (1H, m), 7.75-7.81 (1H, m), 8.12-8.13 (1H, m), 8.12-8.13 (1H, m) | 453 | 451 | 0.0092 |
| 117 | (structure) | mixture of cis/trans isomers | 1H-NMR (DMSO-D6) δ: 1.36-1.43 (1H, m), 1.68-1.78 (2H, m), 1.86-1.89 (2H, m), 2.04-2.10 (1H, m), 2.15-2.29 (2H, m), 3.30-3.32 (3H, m), 3.36-3.42 (5H, m), 4.37 (0.5H, t, J = 5.2 Hz), 4.46 (0.5H, t, J = 5.3 Hz), 7.79-7.80 (2H, m), 8.01-8.05 (2H, m). | 383 | 381 | 0.8012 |
| 118 | (structure) | The relative configuration of the substituents on the cyclohexane ring is cis or trans. stereoisomer of Example 119 | 1H-NMR (DMSO-D6) δ: 1.38-1.45 (4H, m), 1.62-1.83 (7H, m), 3.28-3.32 (2H, m), 3.40-3.42 (2H, m), 3.49-3.54 (2H, m), 3.72 (2H, td, J = 16.0, 6.3 Hz), 4.95 (1H, s), 5.13 (1H, t, J = 6.3 Hz), 7.79-7.80 (2H, m), 8.02-8.05 (2H, m). | 477 | 475 | 0.1273 |
| 119 | (structure) | The relative configuration of the substituents on the cyclohexane ring is cis or trans. stereoisomer of Example 118 | 1H-NMR (DMSO-D6) δ: 1.30-1.45 (5H, m), 1.59-1.78 (6H, m), 3.30-3.32 (2H, m), 3.39-3.41 (2H, m), 3.52-3.56 (2H, m), 3.74 (2H, t, J = 16.1, 6.5 Hz), 4.93 (1H, s), 5.14 (1H, t, J = 6.5 Hz), 7.79-7.80 (2H, m), 8.01 (1H, t, J = 4.4 Hz), 8.05 (1H, s). | 477 | 475 | 0.1444 |

TABLE 1-18

| | | | | | | |
|---|---|---|---|---|---|---|
| 120 | (structure) | The relative configuration of the substituents on the cyclohexane ring is cis or trans. | 1H-NMR (DMSO-D6) δ: 1.35-1.41 (2H, m), 1.49-1.52 (2H, m), 1.61-1.67 (4H, m), 1.78-1.90 (1H, m), 3.15 (2H, d, J = 5.8 Hz), 3.32-3.36 (2H, m), 3.52-3.54 (2H, m), 3.98 (1H, s), 4.09 (2H, t, J = 16.6 Hz), 4.54 (1H, t, J = 5.8 Hz), 7.79-7.80 (2H, m), 8.09 (1H, t, J = 5.1 Hz), 8.16 (1H, s). | 463 | 461 | 0.0060 |
| 121 | (structure) | The relative configuration of the substituents on the cyclohexane ring is presumed to be cis. | 1H-NMR (DMSO-D6) δ: 1.31-1.35 (5H, m), 1.56-1.65 (6H, m), 2.55 (2H, s), 3.29-3.31 (2H, m), 3.40-3.41 (2H, m), 3.54 (2H, t, J = 7.9 Hz), 4.77 (1H, s), 7.78-7.81 (2H, m), 8.01 (1H, t, J = 5.0 Hz), 8.06 (1H, s). | 436 | N.D. | 0.7049 |
| 122 | (structure) | The relative configuration of the substituents on the cyclohexane ring is presumed to be cis. | 1H-NMR (DMSO-D6) δ: 1.32-1.42 (5H, m), 1.50-1.53 (2H, m), 1.60-1.63 (2H, m), 1.85 (2H, d, J = 11.8 Hz), 2.99 (3H, s), 3.20 (2H, s), 3.30-3.32 (2H, m), 3.39-3.41 (2H, m), 3.54 (2H, t, J = 8.0 Hz), 4.71 (1H, s), 7.80 (2H, s), 8.00 (1H, t, J = 4.7 Hz), 8.06 (1H, s). | 489 | 487 | 0.5317 |
| 123 | (structure) | The relative configuration of the substituents on the cyclohexane ring is presumed to be trans. | 1H-NMR (DMSO-D6) δ: 1.05-1.15 (2H, m), 1.28-1.46 (3H, m), 1.56-1.66 (2H, m), 1.88-1.97 (2H, m), 2.05-2.13 (2H, m), 2.90 (3H, s), 2.98-3.08 (1H, m), 3.27-3.35 (2H, m), 3.37-3.44 (2H, m), 3.52-3.59 (2H, m), 7.77-7.83 (2H, m), 8.02 (1H, t, J = 5.0 Hz), 8.05 (1H, s). | 459 | 457 | 0.7845 |
| 124 | (structure) | racemate The relative configuration of the substituents on the dioxane ring is trans. | 1H-NMR (DMSO-D6) δ: 1.53-1.65 (1H, m), 1.86-1.96 (1H, m), 3.25-3.49 (6H, m), 3.50-3.87 (6H, m), 4.36 (1H, ddd, J = 15.6, 10.4, 4.0 Hz), 4.48 (1H, ddd, J = 15.4, 10.4, 3.9 Hz), 7.76-7.82 (2H, m), 8.05 (1H, t, J = 4.4 Hz), 8.38 (1H, s). | 417 | 415 | 1.1610 |

TABLE 1-18-continued

| 125 | 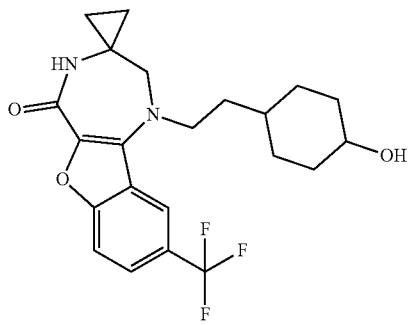 [SMILES: O=C1NC2(CC2)CN(CCC2CCC(O)CC2)c2c1oc1ccc(C(F)(F)F)cc21] | The relative configuration of the substituents on the cyclohexane ring is presumed to be trans. | 1H-NMR (DMSO-D6) δ: 0.87 (4H, s), 0.94-1.16 (4H, m), 1.23 (1H, m), 1.48-1.54 (2H, m), 1.72-1.82 (4H, m), 3.30-3.35 (1H, m), 3.42 (2H, s), 3.62-3.66 (2H, m), 4.48 (1H, d, J = 4.4 Hz), 7.75-7.82 (1H, m), 7.75-7.82 (1H, m), 8.10 (1H, s), 8.14 (1H, s) | 423 | N.D. | 0.0592 |
|---|---|---|---|---|---|---|
| 126 | 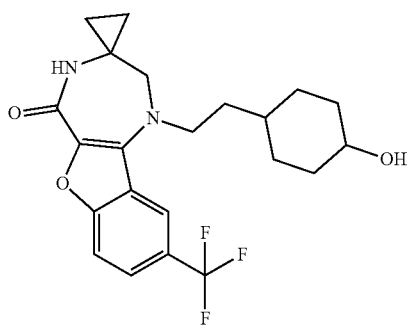 [SMILES: O=C1NC2(CC2)CN(CCC2CCC(O)CC2)c2c1oc1ccc(C(F)(F)F)cc21] | mixture of cis/trans isomers | 1H-NMR (DMSO-D6) δ: 0.88 (4H, s), 0.94-1.23 (0.85H, m), 1.40-1.56 (9.47H, m), 1.70-1.85 (0.68H, m), 3.41-3.43 (2H, m), 3.63-3.67 (2H, m), 3.70-3.75 (1H, m), 4.27 (0.83 H, d, J = 3.2 Hz), 4.49 (0.17 H, d, J = 3.2 Hz), 7.76-7.81 (1H, m), 7.76-7.81 (1H, m), 8.11 (1H, s), 8.14 (1H, s) | 423 | N.D. | 0.4640 |

TABLE 1-19

| 127 | 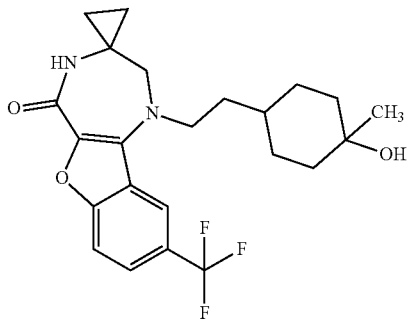 [SMILES: CC1(O)CCC(CCN2CC3(CC3)NC(=O)c3oc4ccc(C(F)(F)F)cc4c32)CC1] | The relative configuration of the substituents on the cyclohexane ring is cis or trans. stereoisomer of Example 128 | 1H-NMR (DMSO-D6) δ: 0.88 (4H, s), 1.08 (3H, s), 1.20-1.26 (3H, m), 1.32-1.53 (8H, m), 3.43 (2H, s), 3.63-3.67 (2H, m), 3.90 (1H, s), 7.75-7.81 (1H, m), 7.75-7.81 (1H, m), 8.12 (1H, s), 8.14 (1H, s) | 437 | N.D. | 0.0532 |
|---|---|---|---|---|---|---|
| 128 | 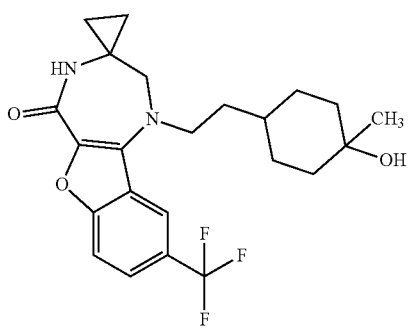 [SMILES: CC1(O)CCC(CCN2CC3(CC3)NC(=O)c3oc4ccc(C(F)(F)F)cc4c32)CC1] | The relative configuration of the substituents on the cyclohexane ring is cis or trans. stereoisomer of Example 127 | 1H-NMR (DMSO-D6) δ: 0.86 (4H, s), 1.02-1.11 (5H, m), 1.22-1.35 (3H, m), 1.48-1.57 (4H, m), 1.65-1.68 (2H, m), 3.41 (2H, s), 3.60-3.65 (2H, m), 4.20 (1H, s), 7.74-7.79 (1H, m), 7.74-7.79 (1H, m), 8.09 (1H, s), 8.12 (1H, s) | 437 | N.D. | 0.0310 |

TABLE 1-19-continued

| | | | | | |
|---|---|---|---|---|---|
| 129 | (structure) | racemate. The relative configuration of the substituents on the dioxane ring is trans. | 1H-NMR (DMSO-D6) δ: 1.53-1.64 (1H, m), 1.86-1.97 (1H, m), 2.66 (1H, dd, J = 17.0, 7.0 Hz), 2.81 (1H, dd, J = 17.0, 4.3 Hz) 3.25-3.35 (4H, m), 3.35-3.69 (5H, m), 3.69-3.77 (1H, m), 3.79-3.87 (2H, m), 7.76-7.82 (2H, m), 8.05 (1H, t, J = 4.5 Hz), 8.37 (1H, s). | 424 | 422 | 1.1843 |
| 130 | (structure) | racemate. The relative configuration of the substituents on the dioxane ring is trans. | 1H-NMR (DMSO-D6) δ: 1.55-1.66 (1H, m), 1.91 (1H, s), 2.99 (3H, s), 3.21-3.48 (8H, m), 3.51-3.67 (3H, m), 3.78-3.89 (2H, m), 3.89-3.98 (1H, m), 7.76-7.82 (2H, m), 8.04 (1H, t, J = 4.6 Hz), 8.37 (1H, s). | 477 | 475 | 1.1630 |
| 131 | (structure) | racemate. The relative configuration of the substituents on the dioxane ring is cis. | 1H-NMR (DMSO-D6) δ: 1.83-1.91 (2H, m), 3.24-3.36 (3H, m), 3.42-3.78 (8H, m), 3.79-3.89 (1H, m), 4.56 (1H, ddd, J = 46.3, 10.0, 4.5 Hz), 4.74 (1H, ddd, J = 48.2, 10.0, 7.4 Hz), 7.76-7.81 (2H, m), 8.06 (1H, t, J = 4.3 Hz), 8.37 (1H, s). | 417 | 415 | 0.1408 |
| 132 | (structure) | racemate. The relative configuration of the substituents on the dioxane ring is cis. | 1H-NMR (DMSO-D6) δ: 1.57-1.68 (1H, m), 1.78-1.89 (1H, m), 3.07-3.17 (2H, m), 3.22-3.35 (3H, m), 3.35-3.46 (3H, m), 3.47-3.56 (2H, m), 3.57-3.65 (1H, m), 3.65-3.81 (3H, m), 4.65 (1H, t, J = 5.5 Hz), 7.75-7.80 (2H, m), 7.97-8.02 (1H, m), 8.12 (1H, s). | 415 | 413 | 3.5933 |
| 133 | (structure) | racemate. The relative configuration of the substituents on the dioxane ring is trans. | 1H-NMR (DMSO-D6) δ: 1.77-1.87 (2H, m), 3.25-3.50 (6H, m), 3.52-3.70 (7H, m), 3.78-3.86 (1H, m), 4.64 (1H, t, J = 5.4 Hz), 7.74-7.81 (2H, m), 7.98-8.06 (1H, m), 8.33 (1H, s). | 415 | 413 | 1.5817 |

TABLE 1-20

| | | | | | | |
|---|---|---|---|---|---|---|
| 134 | (structure with HCl) | racemate The relative configuration of the substituents on the dioxane ring is cis. | 1H-NMR (DMSO-D6) δ: 1.62-1.73 (1H, m), 1.82-1.92 (1H, m), 3.11-3.44 (6H, m), 3.49-3.58 (1H, m), 3.62-3.81 (5H, m), 4.30 (1H, d, J = 3.7 Hz), 4.42 (1H, d, J = 3.7 Hz), 7.77-7.79 (2H, m), 7.99-8.03 (1H, m), 8.13 (1H, s). | 417 | 415 | 0.7533 |
| 135 | (structure with HCl) | racemate The relative configuration of the substituents on the dioxane ring is trans. | 1H-NMR (DMSO-D6) δ: 1.83-1.91 (2H, m), 3.25-3.46 (5H, m), 3.53-3.60 (3H, m), 3.64-3.73 (2H, m), 3.90-4.01 (2H, m), 4.42-4.71 (2H, m), 7.76-7.78 (2H, m), 8.01-8.05 (1H, m), 8.33 (1H, s). | 417 | 415 | 0.6605 |
| 136 | (structure) | racemate The relative configuration of the substituents on the dioxane ring is cis. | 1H-NMR (DMSO-D6) δ: 1.63-1.77 (1H, m), 1.78-1.90 (1H, m), 2.95 (3H, s), 3.11-3.25 (4H, m), 3.25-3.37 (3H, m), 3.42-3.54 (2H, m), 3.68-3.80 (4H, m), 3.98-4.06 (1H, m), 7.75-7.83 (2H, m), 7.97-8.03 (1H, m), 8.07 (1H, s). | 477 | 475 | 16.0465 |
| 137 | (structure) | racemate The relative configuration of the substituents on the dioxane ring is trans. | 1H-NMR (DMSO-D6) δ: 1.80-1.95 (2H, m), 2.97 (3H, s), 3.24-3.59 (8H, m), 3.65-3.78 (1H, m), 3.90-4.00 (1H, m), 4.25-4.32 (1H, m), 7.74-7.81 (2H, m), 7.95-8.03 (1H, m), 8.23 (1H, s). | 477 | 475 | 5.3557 |
| 138 | (structure) | mixture of cis/trans isomers | 1H-NMR (DMSO-D6) δ: 0.91-0.97 (1H, m), 1.24-1.45 (4H, m), 1.50-1.70 (1H, m), 1.81-1.94 (4H, m), 3.21-3.24 (2H, m), 3.32-3.36 (2H, m), 3.52-3.54 (2H, m), 4.06-4.14 (2H, m), 4.42 (1H, t, J = 5.2 Hz), 7.79 (1H, m), 7.79 (1H, m), 8.09 (1H, t, J = 4.8 Hz), 8.16 (1H, s) | 447 | 445 | 0.0151 |

TABLE 1-20-continued

| | | | | | | |
|---|---|---|---|---|---|---|
| 139 | | racemate The relative configuration of the substituents on the dioxane ring is cis. | 1H-NMR (DMSO-D6) δ: 1.62-1.74 (1H, m), 1.83-1.94 (1H, m), 2.53-2.74 (2H, m), 3.11-3.19 (2H, m), 3.26-3.38 (3H, m), 3.42-3.56 (2H, m), 3.67-3.82 (5H, m), 7.75-7.81 (2H, m), 7.99-8.04 (1H, m), 8.11 (1H, s). | 424 | 422 | 3.6933 |
| 140 | | racemate The relative configuration of the substituents on the dioxane ring is trans. | 1H-NMR (DMSO-D6) δ: 1.79-1.92 (2H, m), 2.77-2.84 (1H, m), 2.99-3.07 (1H, m) 3.27-3.51 (7H, m), 3.64-3.79 (3H, m), 3.86-3.93 (1H, m), 4.03-4.09 (1H, m), 7.74-7.79 (2H, m), 7.98-8.03 (1H, m), 8.30 (1H, s). | 424 | 422 | 5.7971 |

TABLE 1-21

| | | | | | | |
|---|---|---|---|---|---|---|
| 141 | | racemate The relative configuration of the substituents on the dioxane ring is cis. | 1H-NMR (CDCl3) δ: 1.80-1.90 (1H, m), 1.95-2.07 (1H, m), 3.00 (3H, s), 3.06-3.12 (1H, m), 3.42-3.54 (4H, m,), 3.56-3.88 (8H, m), 4.31- 4.38 (1H, m), 6.96 (1H, br s), 7.59-7.68 (2H, m), 8.29 (1H, s). | 477 | 475 | 10.3016 |
| 142 | | racemate The relative configuration of the substituents on the dioxane ring is cis. | 1H-NMR (CDCl3) δ: 1.80-2.00 (2H, m), 2.68-2.77 (1H, m), 2.88-2.99 (1H, m), 3.39-3.54 (4H, m), 3.56-3.71 (3H, m), 3.73-3.87 (4H, m), 4.00-4.08 (1H, m), 6.61 (1H, s), 7.59-7.70 (2H, m), 8.32 (1H, s). | 424 | 422 | 4.4031 |
| 143 | | racemate | 1H-NMR (DMSO-D6) δ: 1.59-1.78 (6H, m), 1.83-1.89 (1H, m), 1.98-2.06 (2H, m), 2.12-2.22 (3H, m), 3.28-3.40 (8H, m), 4.37 (1H, t, J = 5.3 Hz), 7.80-7.81 (2H, m), 8.02-8.05 (2H, m). | 423 | 421 | 0.9474 |

TABLE 1-21-continued

| | Structure | Notes | 1H-NMR | MS1 | MS2 | Val |
|---|---|---|---|---|---|---|
| 144 | 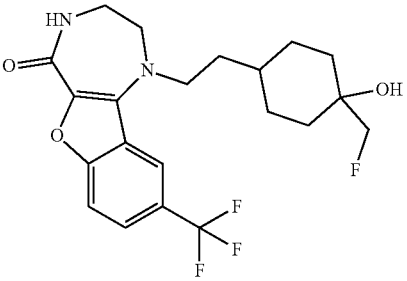 [SMILES: O=C1NCCN(CCC2CCC(O)(CF)CC2)c2c1oc1ccc(C(F)(F)F)cc21] | The relative configuration of the substituents on the cyclohexane ring is cis or trans. | 1H-NMR (DMSO-D6) δ: 1.32-1.41 (5H, m), 1.51-1.65 (6H, m), 3.29-3.32 (2H, m), 3.40-3.41 (2H, m), 3.55 (2H, t, J = 8.2 Hz), 4.02 (1H, s), 4.14 (1H, s), 4.44 (1H, s), 7.79-7.81 (2H, m), 8.01 (1H, t, J = 4.9 Hz), 8.06 (1H, s). | 429 | 427 | 0.8007 |
| 145 | 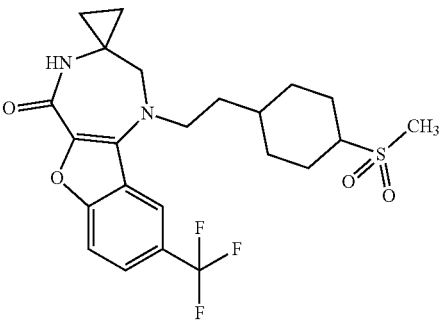 [SMILES: CS(=O)(=O)C1CCC(CCN2CC3(CC3)NC(=O)c3oc4ccc(C(F)(F)F)cc4c32)CC1] | The relative configuration of the substituents on the cyclohexane ring is presumed to be trans. | 1H-NMR DMSO-D6 δ: 0.88 (4H, s), 0.98-1.11 (2H, m), 1.32-1.43 (3H, m), 1.51-1.57 (2H, m), 1.85-1.93 (2H, m) 2.07-2.10 (2H, m) 2.90 (3H, s), 2.97-3.05 (1H, m), 3.43 (2H, s), 3.65-3.69 (2H, m), 7.76-7.82 (1H, m), 7.76-7.82 (1H, m), 8.10 (1H, s), 8.15 (1H, s) | 485 | 483 | 0.4793 |
| 146 | 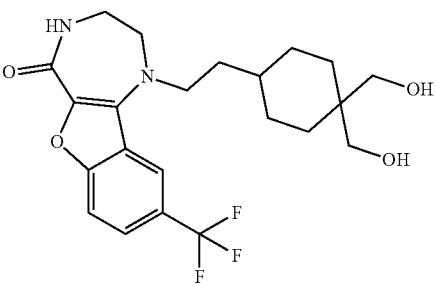 [SMILES: O=C1NCCN(CCC2CCC(CO)(CO)CC2)c2c1oc1ccc(C(F)(F)F)cc21] | | 1H-NMR (DMSO-D6) δ: 1.04-1.17 (4H, m), 1.22-1.31 (1H, m), 1.44-1.50 (2H, m), 1.54-1.64 (4H, m), 3.16 (2H, t, J = 5.6 Hz), 3.28-3.35 (4H, m), 3.39-3.41 (2H, m), 3.51-3.55 (2H, m), 4.21 (1H, t, J = 5.2 Hz), 4.27 (1H, t, J = 5.2 Hz), 7.79-7.80 (2H, m), 8.00 (1H, t, J = 4.7 Hz), 8.05 (1H, s). | 441 | 439 | 0.0231 |
| 147 | 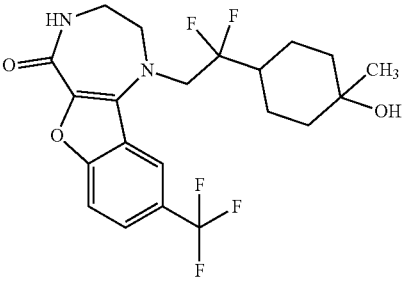 [SMILES: CC1(O)CCC(C(F)(F)CN2CCNC(=O)c3oc4ccc(C(F)(F)F)cc4c32)CC1] | The relative configuration of the substituents on the cyclohexane ring is cis or trans. stereoisomer of Example 148 | 1H-NMR (DMSO-D6) δ: 1.11 (3H, s), 1.23-1.33 (2H, m), 1.59-1.69 (6H, m), 1.85 (1H, m), 3.34-3.36 (2H, m), 3.52-3.54 (2H, m), 4.04-4.12 (1H, m), 4.04-4.12 (2H, m), 7.79 (1H, m), 7.79 (1H, m), 8.09 (1H, t, J = 5.2 Hz), 8.15 (1H, s) | 447 | 445 | 0.2129 |

TABLE 1-22

| | Structure | Notes | 1H-NMR | MS1 | MS2 | Val |
|---|---|---|---|---|---|---|
| 148 | 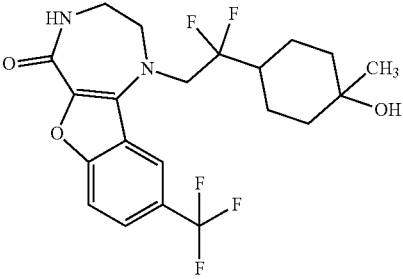 [SMILES: CC1(O)CCC(C(F)(F)CN2CCNC(=O)c3oc4ccc(C(F)(F)F)cc4c32)CC1] | The relative configuration of the substituents on the cyclohexane ring is cis or trans. stereoisomer of Example 147 | 1H-NMR (DMSO-D6) δ: 1.11 (3H, s), 1.29-1.43 (4H, m), 1.60-1.62 (2H, m), 1.80-1.82 (2H, m), 1.92 (1H, m), 3.32-3.36 (2H, m), 3.51-3.53 (2H, m), 4.07-4.15 (2H, m), 4.41 (1H, s), 7.79 (1H, m), 7.79 (1H, m), 8.10 (1H, t, J = 4.8 Hz), 8.15 (1H, s) | 447 | 445 | 0.1143 |

TABLE 1-22-continued

| | | | | | | |
|---|---|---|---|---|---|---|
| 149 | 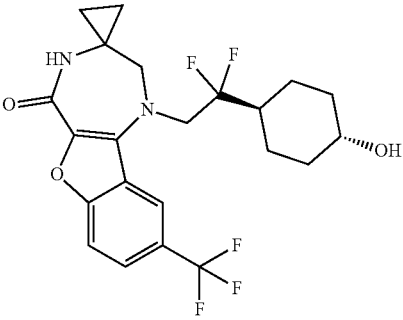 [SMILES: O=C1NC2(CC2)CN(CC(F)(F)[C@H]2CC[C@H](O)CC2)c2c1oc1ccc(C(F)(F)F)cc21] | The relative configuration of the substituents on the cyclohexane ring is presumed to be trans. | 1H-NMR (DMSO-D6) δ: 0.84-0.93 (4H, m), 1.08-1.20 (2H, m), 1.21-1.35 (2H, m), 1.83-1.93 (4H, m), 3.30-3.38 (2H, m), 3.50-3.55 (2H, m), 4.13-4.27 (2H, m), 4.61 (1H, d, J = 4.4 Hz), 7.73-7.79 (2H, m), 8.12 (1H, s), 8.26 (1H, s). | 459 | 457 | 0.0337 |
| 150 | 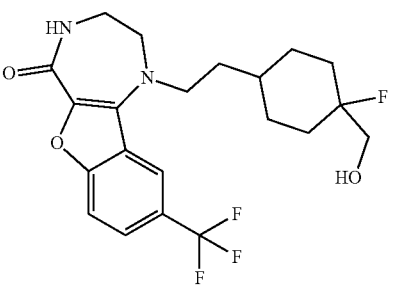 [SMILES: O=C1NCCN(CCC2CCC(F)(CO)CC2)c2c1oc1ccc(C(F)(F)F)cc21] | The relative configuration of the substituents on the cyclohexane ring is cis or trans. | 1H-NMR (DMSO-D6) δ: 1.22-1.45 (5H, m), 1.65-1.90 (6H, m), 3.29-3.32 (2H, m), 3.40-3.53 (6H, m), 4.82-4.88 (1H, m), 7.79-7.81 (2H, m), 8.01-8.06 (2H, m). | 429 | 427 | 0.1299 |
| 151 | 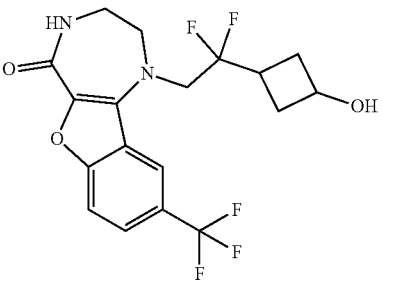 [SMILES: O=C1NCCN(CC(F)(F)C2CC(O)C2)c2c1oc1ccc(C(F)(F)F)cc21] | The relative configuration of the substituents on the cyclobutane ring is cis or trans. | 1H-NMR (DMSO-D6) δ: 1.79-1.91 (2H, m), 2.23-2.39 (3H, m), 3.29-3.38 (2H, m), 3.48-3.55 (2H, m), 3.90-4.03 (3H, m), 5.22 (1H, d, J = 6.2 Hz), 7.80 (2H, br s), 8.11 (1H, t, J = 4.6 Hz), 8.15 (1H, br s). | 405 | N.D. | 0.9573 |
| 152 | 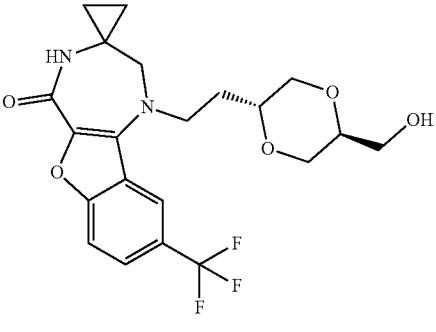 [SMILES: O=C1NC2(CC2)CN(CC[C@@H]2CO[C@@H](CO)CO2)c2c1oc1ccc(C(F)(F)F)cc21] | | 1H-NMR (DMSO-D6) δ: 0.80-0.95 (4H, m), 1.52-1.62 (1H, m), 1.76-1.86 (1H, m), 3.23-3.31 (3H, m), 3.36-3.52 (5H, m), 3.58-3.74 (2H, m), 3.78-3.87 (2H, m), 4.71 (1H, br s), 7.73-7.81 (2H, m), 8.15 (1H, s), 8.50 (1H, s). | 441 | 439 | 0.0929 |
| 153 | 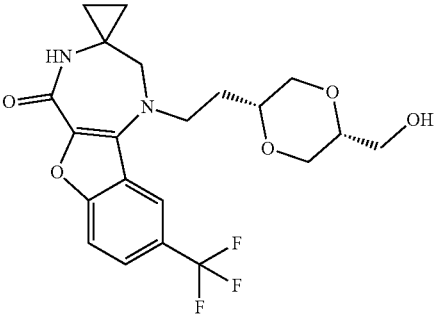 [SMILES: O=C1NC2(CC2)CN(CC[C@@H]2CO[C@H](CO)CO2)c2c1oc1ccc(C(F)(F)F)cc21] | | 1H-NMR (DMSO-D6) δ: 0.82-0.95 (4H, m), 1.75-1.83 (2H, m), 3.41 (2H, s), 3.45-3.80 (10H, m), 4.64 (1H, t, J = 5.4 Hz), 7.73-7.81 (2H, m), 8.17 (1H, s), 8.42 (1H, s). | 441 | 439 | 0.3020 |

TABLE 1-22-continued
| 154 | 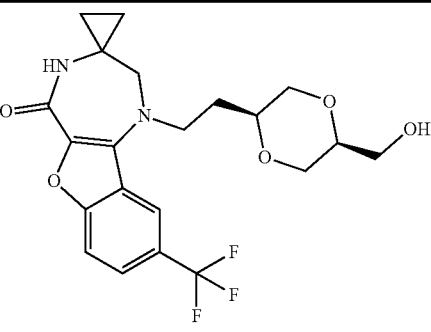 | 1H-NMR (DMSO-D6) δ: 0.82-0.95 (4H, m), 1.75-1.83 (2H, m), 3.41 (2H, s), 3.45-3.80 (10H, m), 4.64 (1H, t, J = 5.4 Hz), 7.73-7.81 (2H, m), 8.17 (1H, s), 8.42 (1H, s). | 441 | 439 | 0.3024 |
TABLE 1-23
| 155 | 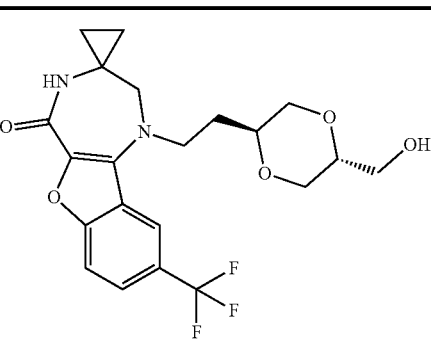 | 1H-NMR (DMSO-D6) δ: 0.80-0.95 (4H, m), 1.52-1.62 (1H, m), 1.76-1.86 (1H, m), 3.23-3.31 (3H, m), 3.36-3.52 (5H, m), 3.58-3.74 (2H, m), 3.78-3.87 (2H, m), 4.71 (1H, br s), 7.73-7.81 (2H, m), 8.15 (1H, s), 8.50 (1H, s). | 441 | 439 | 0.2210 |
| 156 | 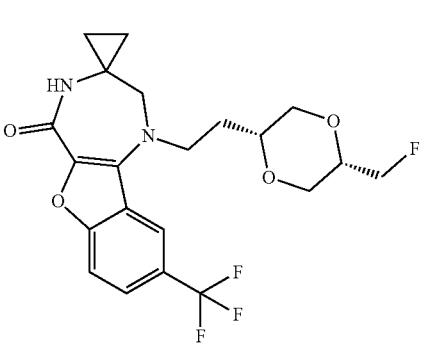 [SMILES: O=C1NC2(CC2)CN(CC[C@@H]2CO[C@H](CF)CO2)c2c1oc1ccc(C(F)(F)F)cc21] | 1H-NMR (DMSO-D6) δ: 0.82-0.95 (4H, m), 1.75-1.85 (2H, m), 3.37-3.46 (2H, m), 3.52-3.88 (8H, m), 4.55 (1H, ddd, J = 46.2, 10.0, 4.5 Hz), 4.75 (1H, ddd, J = 48.3, 10.0, 7.5 Hz), 7.75 (1H, d, J = 3.8 Hz), 7.79 (1H, dd, J = 8.8, 1.5 Hz), 8.17 (1H, s), 8.43 (1H, d, J = 1.5 Hz). | 443 | 441 | 0.0103 |
| 157 | 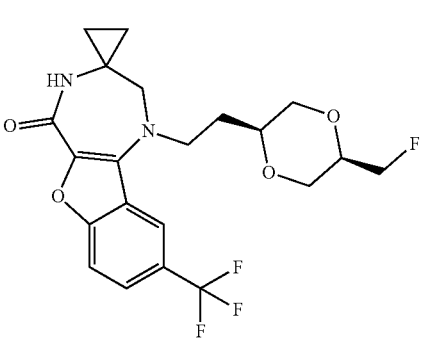 [SMILES: O=C1NC2(CC2)CN(CC[C@H]2CO[C@@H](CF)CO2)c2c1oc1ccc(C(F)(F)F)cc21] | 1H-NMR (DMSO-D6) δ: 0.82-0.95 (4H, m), 1.75-1.85 (2H, m), 3.37-3.46 (2H, m), 3.52-3.88 (8H, m), 4.55 (1H, ddd, J = 46.2, 10.0, 4.5 Hz), 4.75 (1H, ddd, J = 48.3, 10.0, 7.5 Hz), 7.75 (1H, d, J = 8.8 Hz), 7.79 (1H, dd, J = 8.8, 1.5 Hz), 8.17 (1H, s), 8.43 (1H, d, J = 1.5 Hz). | 443 | 441 | 0.2345 |

TABLE 1-23-continued
| | | | | | |
|---|---|---|---|---|---|
| 158 | 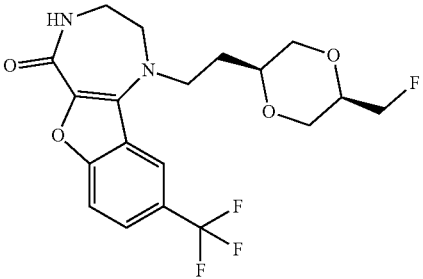 [SMILES: O=C1NCCN(CC[C@H]2CO[C@@H](CF)CO2)c2c1oc1ccc(C(F)(F)F)cc21] | 1H-NMR (CDCl3) δ: 1.80-1.91 (1H, m), 1.94-2.06 (1H, m), 3.42-3.58 (4H, m), 3.59-3.85 (6H, m), 3.86-3.96 (2H, m), 4.60 (1H, ddd, J = 46.4, 9.8, 4.5 Hz), 4.76 (1H, ddd, J = 47.6, 9.8, 6.8 Hz), 6.76 (1H, br s), 7.63 (1H, d, J = 8.5 Hz), 7.67 (1H, dd, J = 8.5, 1.4 Hz), 8.34 (1H, d, J = 1.4 Hz). | 417 | N.D. | 1.3598 |
| 159 | 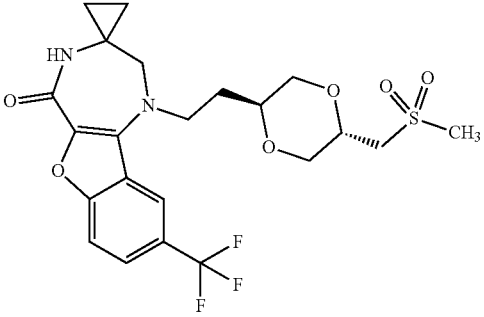 [SMILES: CS(=O)(=O)C[C@@H]1CO[C@@H](CCN2CC3(CC3)NC(=O)c3oc4ccc(C(F)(F)F)cc4c32)CO1] | 1H-NMR (DMSO-D6) δ: 0.80-0.95 (4H, m), 1.53-1.64 (1H, m), 1.77-1.88 (1H, m), 2.99 (3H, s), 3.21-3.46 (6H, m), 3.50-3.57 (1H, m), 3.59-3.68 (1H, m), 3.74-3.87 (3H, m), 3.88-3.96 (1H, m), 7.72-7.81 (2H, m), 8.16 (1H, s), 8.46 (1H, s). | 503 | 501 | 0.1638 |
| 160 | 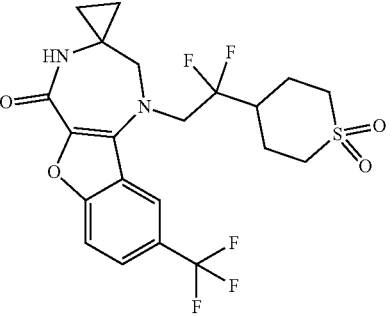 [SMILES: O=C1NC2(CC2)CN(CC(F)(F)C2CCS(=O)(=O)CC2)c2c1oc1ccc(C(F)(F)F)cc21] | 1H-NMR (DMSO-D6) δ: 0.86-0.96 (4H, m), 1.93 (2H, q, J = 12.4 Hz), 2.21-2.46 (3H, m), 3.10-3.33 (4H, m), 3.56 (2H, s), 4.30 (2H, t, J = 16.9 Hz), 7.75-7.82 (2H, m), 8.12 (1H, br s), 8.31 (1H, br s). | 493 | 491 | 0.0982 |
| 161 | 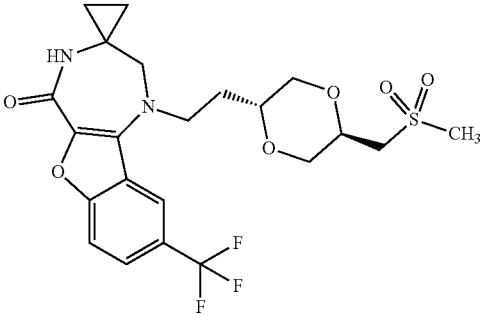 [SMILES: CS(=O)(=O)C[C@H]1CO[C@H](CCN2CC3(CC3)NC(=O)c3oc4ccc(C(F)(F)F)cc4c32)CO1] | 1H-NMR (DMSO-D6) δ: 0.80-0.95 (4H, m), 1.53-1.64 (1H, m), 1.77-1.88 (1H, m), 2.99 (3H, s), 3.21-3.46 (6H, m), 3.50-3.57 (1H, m), 3.59-3.68 (1H, m), 3.74-3.87 (3H, m), 3.88-3.96 (1H, m), 7.72-7.81 (2H, m), 8.16 (1H, s), 8.46 (1H, s). | 503 | 501 | 0.1882 |
TABLE 1-24
| | | | | | |
|---|---|---|---|---|---|
| 162 | 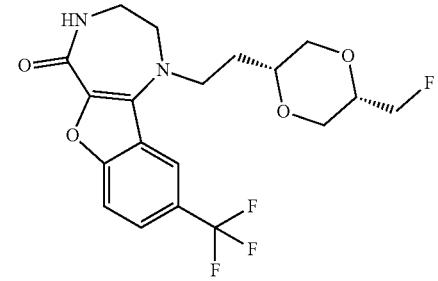 | 1H-NMR (DMSO-D6) δ: 1.83-1.91 (2H, m), 3.24-3.36 (3H, m), 3.42-3.78 (8H, m), 3.79-3.89 (1H, m), 4.56 (1H, ddd, J = 46.3, 10.0, 4.5 Hz), 4.74 (1H, ddd, J = 48.2, 10.0, 7.4 Hz), 7.76-7.81 (2H, m), 8.06 (1H, t, J = 4.3 Hz), 8.37 (1H, s). | 417 | 415 | 0.0917 |

TABLE 1-24-continued

| | Structure | Notes | NMR | MS1 | MS2 | Val |
|---|---|---|---|---|---|---|
| 163 | 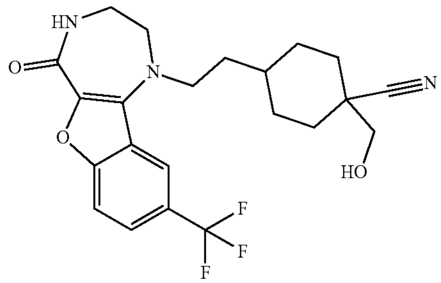 [SMILES: N#CC1(CO)CCC(CCN2CCNC(=O)c3oc4ccc(C(F)(F)F)cc4c32)CC1] | mixture of cis/trans isomers | 1H-NMR (DMSO-D6) δ: 1.21-1.28 (4.2H, m), 1.64-1.66 (3.8H, m), 1.83-1.88 (3H, m), 3.26-3.29 (2H, m), 3.39-3.41 (3.3H, m), 3.47-3.56 (2.7H, m), 5.31 (0.3H, t, J = 5.5 Hz), 5.35 (0.7H, t, J = 5.7 Hz), 7.77-7.80 (2H, m), 7.99-8.03 (2H, m). | 436 | 434 | 0.0445 |
| 164 | 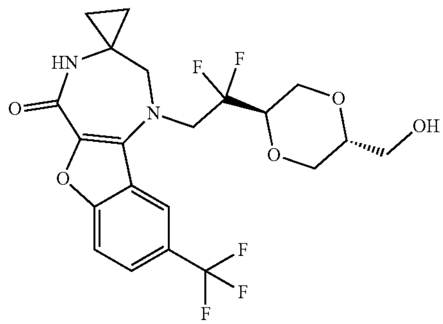 [SMILES: O=C1NC2(CC2)CN(CC(F)(F)[C@H]2CO[C@H](CO)CO2)c2c1oc1ccc(C(F)(F)F)cc21] | | 1H-NMR (DMSO-D6) δ: 0.90-0.91 (4H, m), 3.34-3.37 (1H, m), 3.43-3.66 (6H, m), 3.92-3.94 (3H, m), 4.16-4.43 (2H, m), 4.81 (1H, s), 7.75-7.80 (2H, m), 8.29 (1H, s), 8.41 (1H, s). | 477 | 475 | 0.0193 |
| 165 | 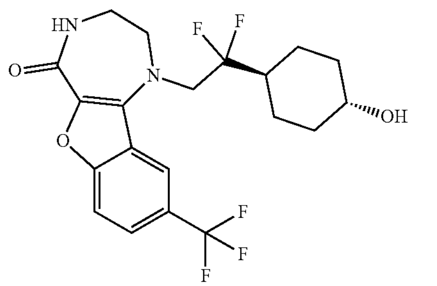 [SMILES: O=C1NCCN(CC(F)(F)[C@H]2CC[C@H](O)CC2)c2c1oc1ccc(C(F)(F)F)cc21] | | 1H-NMR (DMSO-D6) δ: 1.40-1.46 (2H, m), 1.57-1.78 (6H, m), 1.91-1.97 (1H, s), 3.32-3.36 (2H, m), 3.57-3.54 (2H, m), 3.83-3.87 (1H, m), 4.08 (2H, t, J = 16.8 Hz), 4.38 (1H, d, J = 2.8 Hz), 7.79-7.80 (2H, m), 8.09 (1H, t, J = 5.2 Hz), 8.16 (1H, s). | 433 | 431 | 0.1040 |
| 166 | 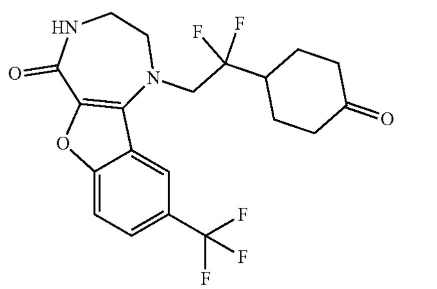 [SMILES: O=C1CCC(C(F)(F)CN2CCNC(=O)c3oc4ccc(C(F)(F)F)cc4c32)CC1] | | 1H-NMR (DMSO-D6) δ: 1.64-1.80 (2H, m), 2.10-2.34 (4H, m), 2.40-2.59 (3H, m), 3.29-3.41 (2H, m), 3.50-3.61 (2H, m), 4.17 (2H, t, J = 16.8 Hz), 7.80 (2H, br s), 8.11 (1H, t, J = 5.1 Hz), 8.16 (1H, br s). | 431 | 429 | 0.1890 |
| 167 | 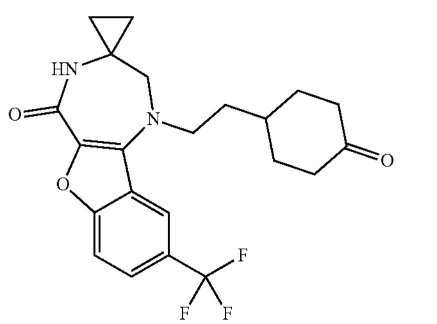 [SMILES: O=C1CCC(CCN2CC3(CC3)NC(=O)c3oc4ccc(C(F)(F)F)cc4c32)CC1] | | 1H-NMR (DMSO-D6) δ: 0.887 (4H, s), 1.36-1.46 (2H, m), 1.60-1.66 (2H, m), 1.77-1.83 (1H, m), 2.00-2.04 (2H, m), 2.16-2.20 (2H, m), 2.31-2.41 (2H, m), 3.44 (2H, s), 3.67-3.72 (2H, m), 7.74-7.80 (1H, m), 7.74-7.80 (1H, m), 8.10 (1H, s), 8.14 (1H, s) | 421 | 419 | N.T. |

TABLE 1-25

| Ex. No. | Structure | Notes | 1H-NMR (400 MHz) | MS M + H | MS M − H | hPim1 Ki (nM) |
|---|---|---|---|---|---|---|
| 2-01 | 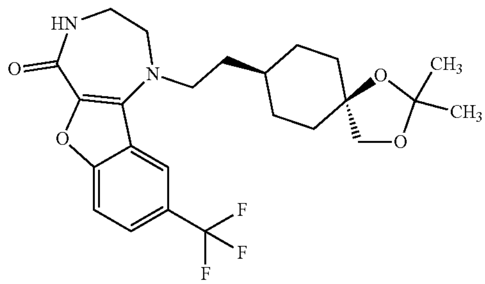 [SMILES: CC1(C)OC[C@]2(CC[C@H](CCN3CCNC(=O)c4oc5ccc(C(F)(F)F)cc5c43)CC2)O1] | | 1H-NMR (DMSO-D6) δ: 1.25-1.45 (11H, m), 1.60-1.70 (6H, m), 3.27-3.35 (2H, m), 3.37-3.42 (2H, m), 3.50-3.57 (2H, m), 3.65 (2H, s), 7.78-7.81 (2H, m), 8.01 (1H, t, J = 4.6 Hz), 8.06 (1H, s). | 467 | 465 | 1.602 |
| 2-02 | 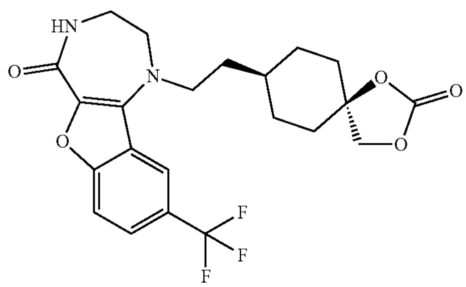 [SMILES: O=C1OC[C@]2(CC[C@H](CCN3CCNC(=O)c4oc5ccc(C(F)(F)F)cc5c43)CC2)O1] | | 1H-NMR (DMSO-D6) δ: 1.20-1.50 (3H, m), 1.58-1.76 (6H, m), 1.90-2.0 (2H, m), 3.28-3.32 (2H, m), 3.40-3.42 (2H, m), 3.54-3.58 (2H, m), 4.19 (2H, s), 7.78-7.81 (2H, m), 8.01 (1H, t, J = 4.9 Hz), 8.06 (1H, s). | 453 | 451 | 0.43 |
| 2-03 | 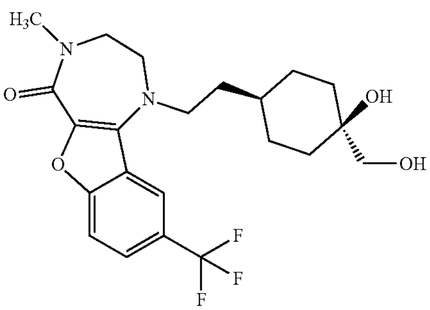 [SMILES: CN1CCN(CC[C@H]2CC[C@](O)(CO)CC2)c2c(oc3ccc(C(F)(F)F)cc23)C1=O] | | 1H-NMR (DMSO-D6) δ: 1.17-1.48 (7H, m), 1.50-1.60 (4H, m), 3.04 (3H, s), 3.12 (2H, d, J = 5.8 Hz), 3.44-3.48 (2H, m), 3.53-3.60 (4H, m), 3.79 (1H, s), 4.44 (1H, t, J = 5.8 Hz), 7.78-7.81 (2H, m), 8.08 (1H, s). | 441 | N.D. | 0.414 |
| 2-04 | 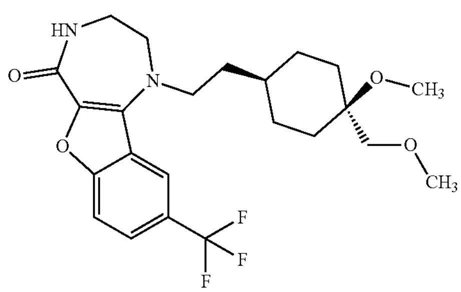 [SMILES: COC[C@]1(OC)CC[C@@H](CCN2CCNC(=O)c3oc4ccc(C(F)(F)F)cc4c32)CC1] | | 1H-NMR (DMSO-D6) δ: 1.18-1.32 (5H, m), 1.50-1.65 (4H, m), 1.72-1.80 (2H, m), 3.09 (3H, s), 3.21 (2H, s), 3.25 (3H, s), 3.28-3.34 (2H, m), 3.38-3.42 (2H, m), 3.51-3.55 (2H, m), 7.78-7.81 (2H, m), 7.99 (1H, t, J = 4.4 Hz), 8.05 (1H, s). | 455 | 453 | 1.25 |
| 2-05 | 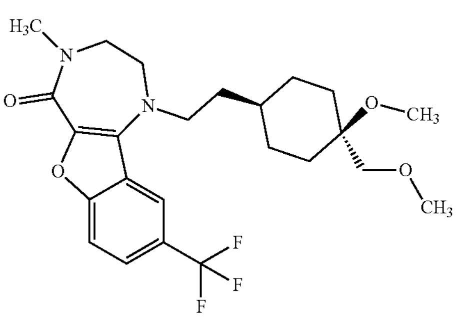 [SMILES: COC[C@]1(OC)CC[C@@H](CCN2CCN(C)C(=O)c3oc4ccc(C(F)(F)F)cc4c32)CC1] | | 1H-NMR (DMSO-D6) δ: 1.16-1.30 (5H, m), 1.50-1.60 (4H, m), 1.70-1.80 (2H, m), 3.03 (3H, s), 3.09 (3H, s), 3.21 (2H, s), 3.25 (3H, s), 3.45-3.48 (2H, m), 3.53-3.60 (4H, m), 7.78-7.80 (2H, m), 8.07 (1H, s). | 469 | N.D. | 13.24 |

TABLE 1-25-continued

| Ex. No. | Structure | Notes | 1H-NMR (400 MHz) | MS M + H | MS M − H | hPim1 Ki (nM) |
|---|---|---|---|---|---|---|
| 2-06 | (structure) | | 1H-NMR (DMSO-D6) δ: 1.19-1.44 (10H, m), 1.50-1.65 (4H, m),. 3.13 (2H, d, J = 5.8 Hz), 3.19-3.24 (1H, m), 3.41-3.44 (1H, m), 3.48-3.52 (1H, m), 3.62-3.67 (2H, m), 3.79 (1H, s), 4.43 (1H, t, J = 5.8 Hz), 7.76-7.81 (2H, m), 7.86 (1H, d, J = 3.7 Hz), 8.08 (1H, s). | 441 | 439 | 0.074 |
| 2-07 | (structure) | | 1H-NMR (DMSO-D6) δ: 1.19-1.44 (10H, m), 1.50-1.65 (4H, m), 3.13 (2H, d, J = 5.3 Hz), 3.19-3.24 (1H, m), 3.41-3.44 (1H, m), 3.48-3.53 (1H, m), 3.60-3.67 (2H , m), 3.80 (1H, s), 4.44 (1H, t, J = 5.4 Hz), 7.76-7.81 (2H, m), 7.86 (1H, d, J = 3.7 Hz), 8.08 (1H, s). | 441 | 439 | 0.136 |

The formulation examples of the present invention include the following formulations. However, the present invention is not limited by such formulation examples.

Formulation Example 1 (Production of Capsule)

| | | |
|---|---|---|
| 1) | Compound of Example 1 | 30 mg |
| 2) | Microcrystalline cellulose | 10 mg |
| 3) | Lactose | 19 mg |
| 4) | Magnesium stearate | 1 mg |

1), 2), 3) and 4) are mixed and filled in a gelatin capsule.

Formulation Example 2 (Production of Tablet)

| | | |
|---|---|---|
| 1) | Compound of Example 1 | 10 g |
| 2) | Lactose | 50 g |
| 3) | Corn starch | 15 g |
| 4) | Carmellose calcium | 44 g |
| 5) | Magnesium stearate | 1 g |

The total amount of 1), 2), 3) and 30 g of 4) are kneaded with water, vacuum dried and then granulated. The granulated powder is mixed with 14 g of 4) and 1 g of 5), and the mixture is tableted by a tableting machine. In this way, 1000 tablets containing 10 mg of the compound of Example 1 per tablet are obtained.

INDUSTRIAL APPLICABILITY

Since the compound of Formula [I] or a pharmaceutically acceptable salt thereof has a Pim-1 inhibitory activity, it may be useful for the treatment or prophylaxis of a disease selected from the group consisting of pulmonary arterial hypertension, cancer, psoriasis and systemic lupus erythematosus.

The invention claimed is:
1. A compound of Formula [I], or a pharmaceutically acceptable salt thereof:

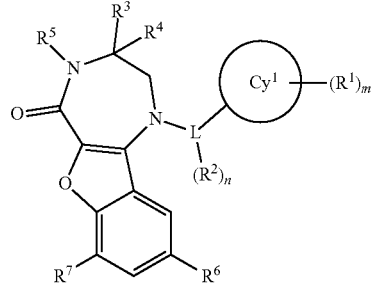

wherein
$Cy^1$ is
(1) $C_{3-7}$ cycloalkyl,
(2) 4 to 7-membered heterocycloalkyl containing one or two heteroatoms independently selected from the group consisting of oxygen and optionally oxidized sulfur, as a ring constituting atom besides carbon atom(s),
(3) $C_{5-8}$ bridged cycloalkyl,
(4) 7 to 9-membered bridged heterocycloalkyl containing one oxygen atom as a ring constituting atom besides carbon atom(s),
(5) $C_{7-11}$ spirocycloalkyl, or (6) 7 to 11-membered spiroheterocycloalkyl containing one to three oxygen atoms as a ring constituting atom besides carbon atom(s);

$R^1$ in the number of m are each independently (1) halogen,
(2) hydroxy,
(3) $C_{1-6}$ alkyl wherein the alkyl is optionally substituted by
  (a) hydroxy,
  (b) $C_{1-4}$ alkoxy,
  (c) cyano,
  (d) $OCOR^{11}$ wherein $R^{11}$ is phenyl, or
  (e) $SO_2R^{12}$ wherein $R^{12}$ is $C_{1-4}$ alkyl,
(4) $C_{1-4}$ haloalkyl wherein the haloalkyl is optionally substituted by hydroxy,
(5) $C_{1-4}$ alkoxy wherein the alkoxy is optionally substituted by 1 to 3 halogen,
(6) $COR^{13}$ wherein $R^{13}$ is
  (a) hydroxy, or
  (b) $NR^{14}R^{15}$ wherein $R^{14}$ and $R^{15}$ are each independently hydrogen or $C_{1-4}$ alkyl,
(7) cyano,
(8) $SO_2R^{16}$ wherein $R^{16}$ is $C_{1-4}$ alkyl,
(9) $C_{3-4}$ cycloalkyl wherein the cycloalkyl is optionally substituted by hydroxy, or
(10) triazolyl, or two $R^1$ bonded to the same carbon atom are taken together to form oxo;

$R^2$ in the number of n are each independently (1) halogen, or
(2) $C_{1-4}$ alkoxy, or two $R^2$ bonded to the same carbon atom are taken together to form $C_{3-4}$ cycloalkane with the carbon atom to which they are bonded;

$R^3$ and $R^4$ are each independently (1) hydrogen, or
(2) $C_{1-4}$ alkyl, or $R^3$ and $R^4$ are taken together to form $C_{3-4}$ cycloalkane with the carbon atom to which they are bonded;

$R^5$ is hydrogen or $C_{1-4}$ alkyl;

$R^6$ is $C_{1-4}$ haloalkyl;

$R^7$ is hydrogen or halogen;

L is linear $C_{1-4}$ alkylene;

m is 0, 1, 2, 3 or 4; and n is 0, 1, 2 or 3.

2. The compound according to claim 1 or a pharmaceutically acceptable salt thereof, wherein $R^5$ is hydrogen.

3. The compound according to claim 1 or a pharmaceutically acceptable salt thereof, wherein L is ethylene or trimethylene.

4. The compound according to claim 1 or a pharmaceutically acceptable salt thereof, wherein $R^7$ is hydrogen.

5. The compound according to claim 1 or a pharmaceutically acceptable salt thereof, wherein $R^2$ in the number of n are each independently halogen, or two $R^2$ bonded to the same carbon atom are taken together to form $C_{3-4}$ cycloalkane with the carbon atom to which they are bonded.

6. The compound according to claim 1 or a pharmaceutically acceptable salt thereof, which is represented by Formula [III]:

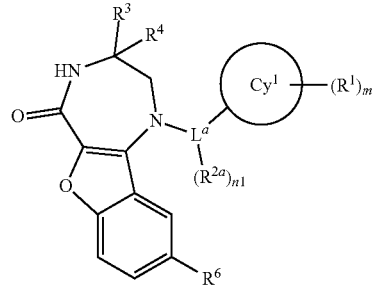

wherein
$R^{2a}$ in the number of n1 are each independently halogen;
$L^a$ is ethylene or trimethylene; and
n1 is 0, 1 or 2.

7. The compound according to claim 1 or a pharmaceutically acceptable salt thereof, wherein
$Cy^1$ is
(1) $C_{3-7}$ cycloalkyl,
(2) 4 to 7-membered heterocycloalkyl containing one or two heteroatoms independently selected from the group consisting of oxygen and sulfur atoms (the sulfur atom may be oxidized), as a ring constituting atom besides carbon atom(s),
(3) $C_{7-11}$ spirocycloalkyl, or
(4) 7 to 11-membered spiroheterocycloalkyl containing one to three oxygen atoms as a ring constituting atom besides carbon atom(s).

8. The compound according to claim 1 or a pharmaceutically acceptable salt thereof, wherein $R^6$ is
(1) monofluoromethyl,
(2) difluoromethyl, or
(3) trifluoromethyl.

9. The compound according to claim 1 or a pharmaceutically acceptable salt thereof, wherein $R^3$ and $R^4$ are each independently
(1) hydrogen, or
(2) methyl, or
$R^3$ and $R^4$ are taken together to form cyclopropane with the carbon atom to which they are bonded.

10. The compound according to claim 1 or a pharmaceutically acceptable salt thereof, wherein $R^1$ in the number of m are each independently
(1) halogen,
(2) hydroxy,
(3) $C_{1-6}$ alkyl wherein the alkyl is optionally substituted by
  (a) hydroxy,
  (b) $C_{1-4}$ alkoxy,
  (c) cyano, or
  (d) $SO_2R^{12}$ wherein $R^{12}$ is $C_{1-4}$ alkyl,
(4) $C_{1-4}$ haloalkyl wherein the haloalkyl is optionally substituted by hydroxy,
(5) $C_{1-4}$ alkoxy wherein the alkoxy is optionally substituted by 1 to 3 halogen,
(6) $COR^{13}$ wherein $R^{13}$ is
  (a) hydroxy, or
  (b) $NR^{14}R^{15}$ wherein $R^{14}$ and $R^{15}$ are each independently hydrogen or $C_{1-4}$ alkyl,
(7) cyano,
(8) $SO_2R^{16}$ wherein $R^{16}$ is $C_{1-4}$ alkyl, or
(9) $C_{3-4}$ cycloalkyl wherein the cycloalkyl is optionally substituted by hydroxy, or two $R^1$ bonded to the same carbon atom are taken together to form oxo.

11. A compound selected from the group consisting of:
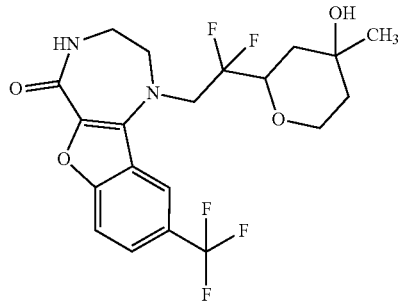
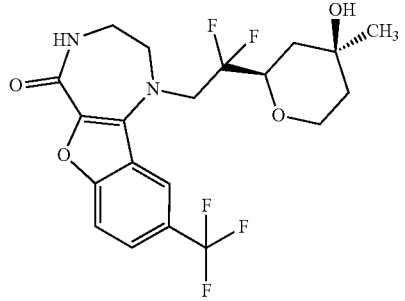
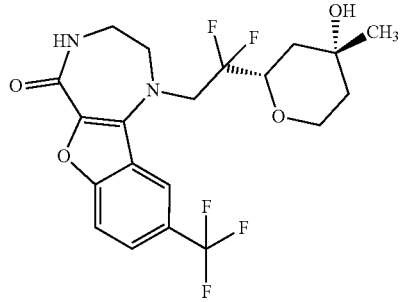
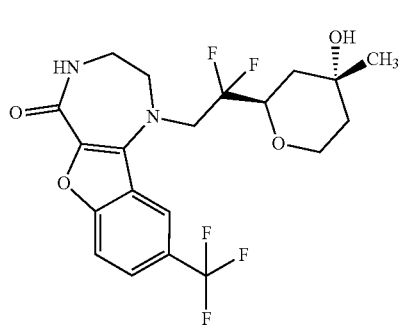
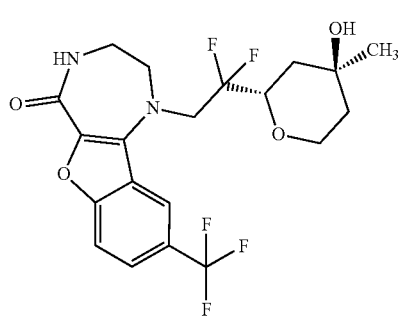
-continued
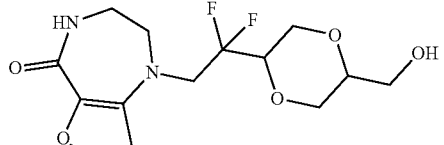
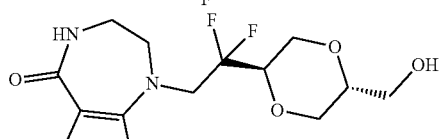
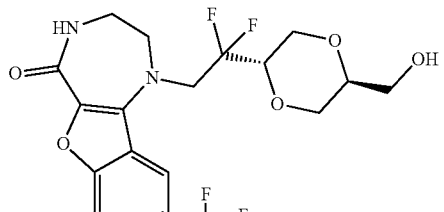
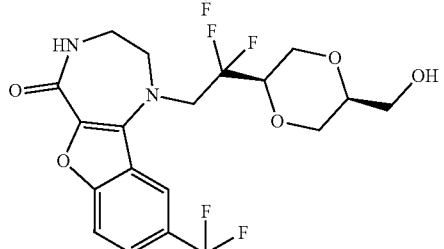
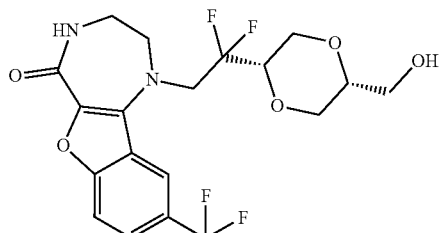
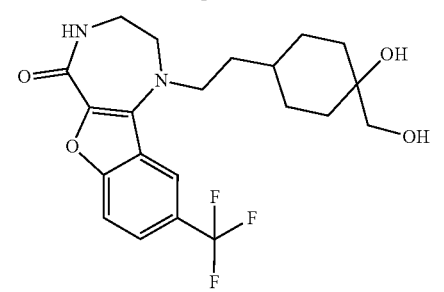

-continued

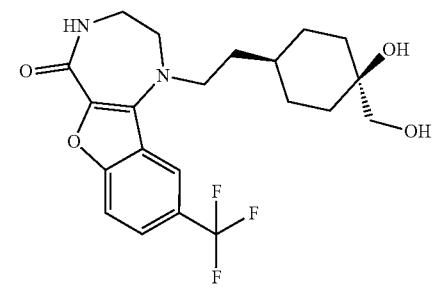

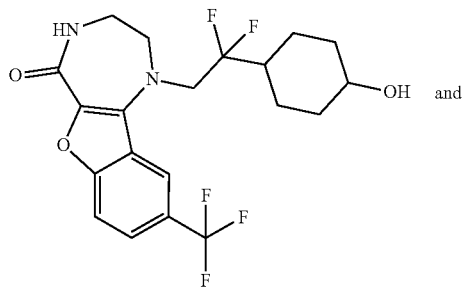

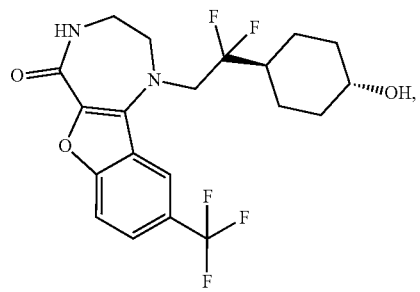

or a pharmaceutically acceptable salt thereof.

12. A pharmaceutical composition comprising the compound according to claim 1 or a pharmaceutically acceptable salt thereof, and a pharmaceutically acceptable carrier.

13. A method for treating a disease selected from the group consisting of pulmonary arterial hypertension, psoriasis and systemic lupus erythematosus in a mammal, which comprises administering a therapeutically effective amount of the compound according to claim 1 or a pharmaceutically acceptable salt thereof to the mammal.

14. A compound of the following formula or a pharmaceutically acceptable salt thereof:

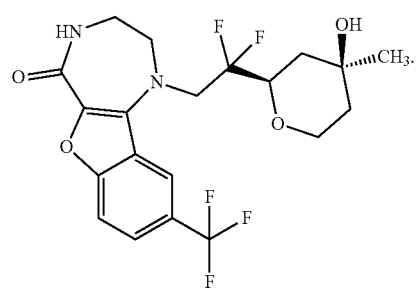 [SMILES: C[C@]1(O)CCO[C@@H](C(F)(F)CN2CCNC(=O)c3oc4ccc(C(F)(F)F)cc4c32)C1]

15. A compound of the following formula or a pharmaceutically acceptable salt thereof:

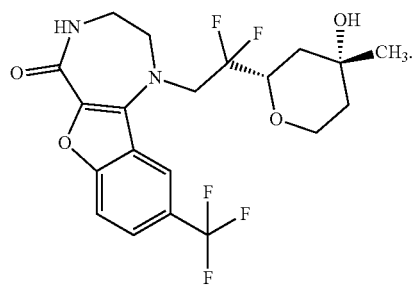 [SMILES: C[C@@]1(O)CCO[C@H](C(F)(F)CN2CCNC(=O)c3oc4ccc(C(F)(F)F)cc4c32)C1]

16. A compound of the following formula or a pharmaceutically acceptable salt thereof:

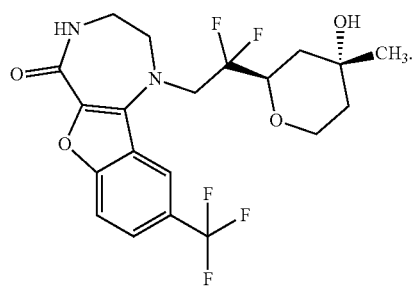 [SMILES: C[C@@]1(O)CCO[C@@H](C(F)(F)CN2CCNC(=O)c3oc4ccc(C(F)(F)F)cc4c32)C1]

17. A compound of the following formula or a pharmaceutically acceptable salt thereof:

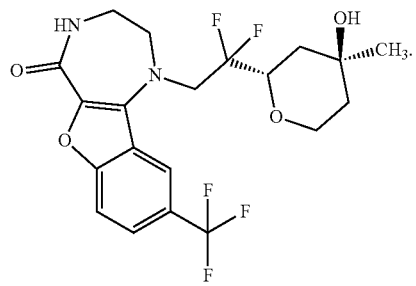 [SMILES: C[C@]1(O)CCO[C@H](C(F)(F)CN2CCNC(=O)c3oc4ccc(C(F)(F)F)cc4c32)C1]

18. A compound of the following formula or a pharmaceutically acceptable salt thereof:

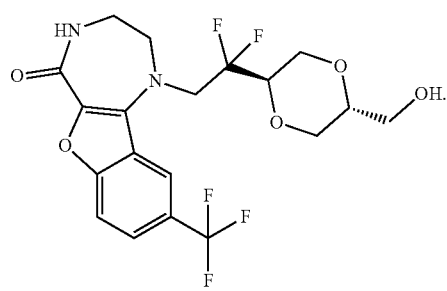 [SMILES: O=C1NCCN(CC(F)(F)[C@H]2CO[C@H](CO)CO2)c2c1oc1ccc(C(F)(F)F)cc21]

19. A compound of the following formula or a pharmaceutically acceptable salt thereof:

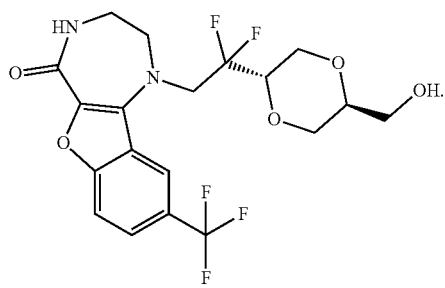 [SMILES: O=C1NCCN(CC(F)(F)[C@@H]2CO[C@@H](CO)CO2)c2c1oc1ccc(C(F)(F)F)cc21]

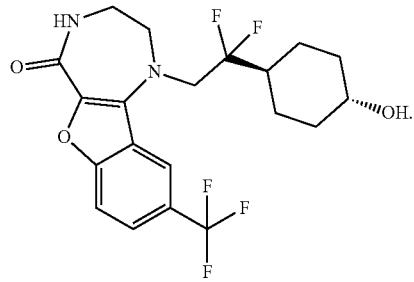

20. A compound of the following formula or a pharmaceutically acceptable salt thereof:

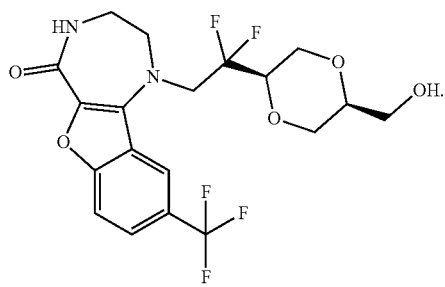 [SMILES: O=C1NCCN(CC(F)(F)[C@H]2CO[C@@H](CO)CO2)c2c1oc1ccc(C(F)(F)F)cc21]

21. A compound of the following formula or a pharmaceutically acceptable salt thereof:

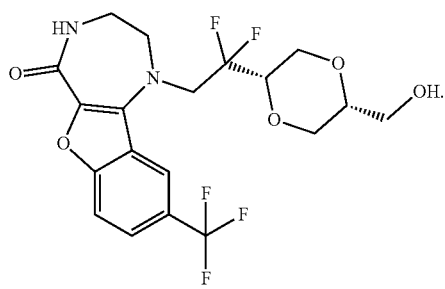 [SMILES: O=C1NCCN(CC(F)(F)[C@@H]2CO[C@H](CO)CO2)c2c1oc1ccc(C(F)(F)F)cc21]

22. A compound of the following formula or a pharmaceutically acceptable salt thereof:

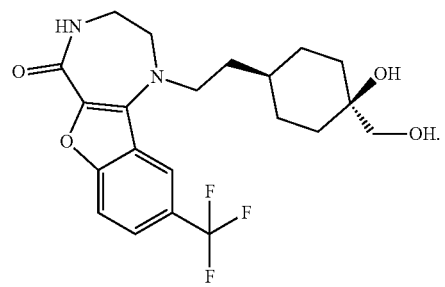 [SMILES: O=C1NCCN(CC[C@H]2CC[C@](O)(CO)CC2)c2c1oc1ccc(C(F)(F)F)cc21]

23. A compound of the following formula or a pharmaceutically acceptable salt thereof:

24. A compound of the following formula:

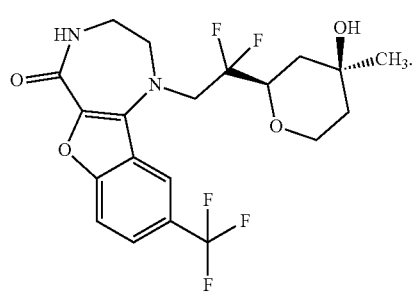 [SMILES: C[C@]1(O)CCO[C@@H](C(F)(F)CN2CCNC(=O)c3oc4ccc(C(F)(F)F)cc4c32)C1]

25. A compound of the following formula:

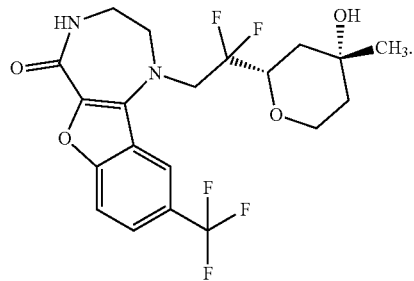 [SMILES: C[C@@]1(O)CCO[C@H](C(F)(F)CN2CCNC(=O)c3oc4ccc(C(F)(F)F)cc4c32)C1]

26. A compound of the following formula:

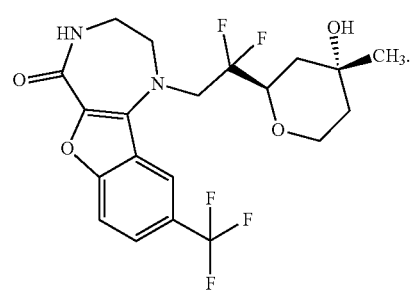 [SMILES: C[C@@]1(O)CCO[C@@H](C(F)(F)CN2CCNC(=O)c3oc4ccc(C(F)(F)F)cc4c32)C1]

27. A compound of the following formula:

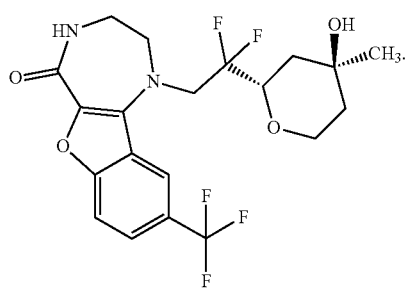 [SMILES: C[C@]1(O)CCO[C@H](C(F)(F)CN2CCNC(=O)c3oc4ccc(C(F)(F)F)cc4c32)C1]

28. A compound of the following formula:

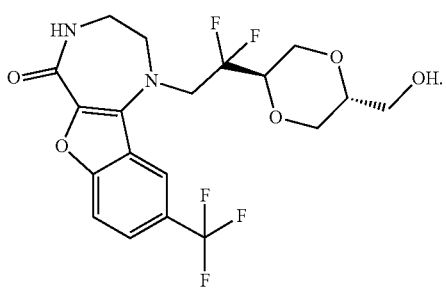 [SMILES: O=C1NCCN(CC(F)(F)[C@H]2CO[C@H](CO)CO2)c2c1oc1ccc(C(F)(F)F)cc21]

29. A compound of the following formula:

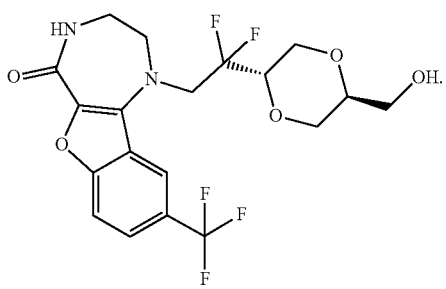 [SMILES: O=C1NCCN(CC(F)(F)[C@@H]2CO[C@@H](CO)CO2)c2c1oc1ccc(C(F)(F)F)cc21]

30. A compound of the following formula:

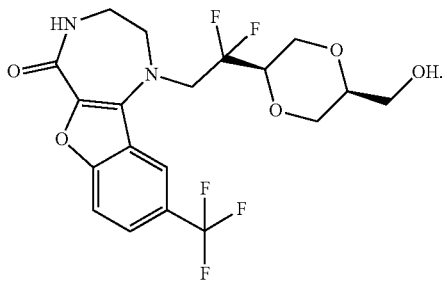 [SMILES: O=C1NCCN(CC(F)(F)[C@H]2CO[C@@H](CO)CO2)c2c1oc1ccc(C(F)(F)F)cc21]

31. A compound of the following formula:

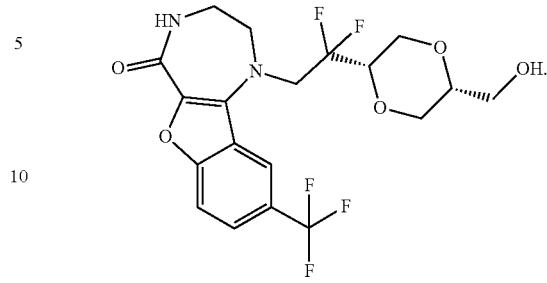

32. A compound of the following formula:

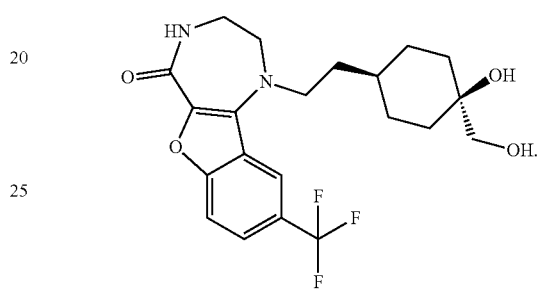

33. A compound of the following formula:

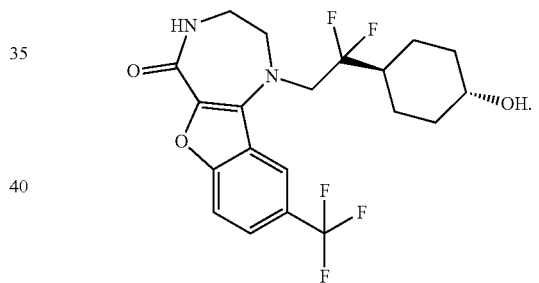

34. A pharmaceutical composition comprising the compound according to any one of claims 14-23 or a pharmaceutically acceptable salt thereof, and a pharmaceutically acceptable carrier.

35. A method for treating a disease selected from the group consisting of pulmonary arterial hypertension, psoriasis and systemic lupus erythematosus in a mammal, which comprises administering a therapeutically effective amount of the compound according to any one of claims 14-23 or a pharmaceutically acceptable salt thereof to the mammal.

36. A pharmaceutical composition comprising the compound according to any one of claims 24-33 and a pharmaceutically acceptable carrier.

37. A method for treating a disease selected from the group consisting of pulmonary arterial hypertension, psoriasis and systemic lupus erythematosus in a mammal, which comprises administering a therapeutically effective amount of the compound according to any one of claims 24-33 to the mammal.

38. A method for treating a disease selected from the group consisting of acute myeloid leukemia, colon cancer, pancreatic cancer, osteosarcoma, breast cancer, chronic myelogenous leukemia, multiple myeloma, diffuse large B-cell lymphoma and myeloproliferative neoplasm in a mammal, which comprises administering a therapeutically effective amount of the compound according to claim 1 or a pharmaceutically acceptable salt thereof to the mammal.

39. A method for treating a disease selected from the group consisting of acute myeloid leukemia, colon cancer, pancreatic cancer, osteosarcoma, breast cancer, chronic myelogenous leukemia, multiple myeloma, diffuse large B-cell lymphoma and myeloproliferative neoplasm in a mammal, which comprises administering a therapeutically effective amount of the compound according to any one of claims 14-23 or a pharmaceutically acceptable salt thereof to the mammal.

40. A method for treating a disease selected from the group consisting of acute myeloid leukemia, colon cancer, pancreatic cancer, osteosarcoma, breast cancer, chronic myelogenous leukemia, multiple myeloma, diffuse large B-cell lymphoma and myeloproliferative neoplasm in a mammal, which comprises administering a therapeutically effective amount of the compound according to any one of claims 24-33 to the mammal.

* * * * *